United States Patent
Maue et al.

(10) Patent No.: US 8,946,234 B2
(45) Date of Patent: Feb. 3, 2015

(54) HALOGEN-SUBSTITUTED COMPOUNDS

(75) Inventors: Michael Maue, Langenfeld (DE); Isabelle Adelt, Haan (DE); Wolfgang Giencke, Hofheim (DE); Markus Heil, Leichlingen (DE); Peter Jeschke, Bergisch Gladbach (DE); Bernd-Wieland Krüger, Bergisch Gladbach (DE); Friedrich August Mühlthau, Bad Soden am Taunus (DE); Alexander Sudau, Leichlingen (DE); Klaus Raming, Leverkusen (DE); Ulrich Ebbinghaus-Kintscher, Dortmund (DE); Martin Adamczewski, Köln (DE); Arnd Voerste, Köln (DE); Ulrich Görgens, Ratingen (DE); Tobias Kapferer, Düsseldorf (DE); Mark Wilhelm Drewes, Langenfeld (DE); Angela Becker, Düsseldorf (DE); Eva-Maria Franken, Leverkusen (DE)

(73) Assignee: Bayer CropScience AG, Monheim (DE)

( * ) Notice: Subject to any disclaimer, the term of this patent is extended or adjusted under 35 U.S.C. 154(b) by 98 days.

(21) Appl. No.: 13/127,917

(22) PCT Filed: Oct. 27, 2009

(86) PCT No.: PCT/EP2009/007668
§ 371 (c)(1),
(2), (4) Date: Jul. 19, 2011

(87) PCT Pub. No.: WO2010/051926
PCT Pub. Date: May 14, 2010

(65) Prior Publication Data
US 2011/0301181 A1    Dec. 8, 2011

(30) Foreign Application Priority Data

Nov. 5, 2008   (EP) .................................... 08168405

(51) Int. Cl.
| | | |
|---|---|---|
| A01N 43/54 | (2006.01) | |
| C07D 239/42 | (2006.01) | |
| C07D 401/04 | (2006.01) | |
| C07D 231/14 | (2006.01) | |
| C07D 213/81 | (2006.01) | |
| C07D 239/28 | (2006.01) | |
| C07D 239/34 | (2006.01) | |

(52) U.S. Cl.
CPC ............ *C07D 231/14* (2013.01); *C07D 213/81* (2013.01); *C07D 239/28* (2013.01); *C07D 239/34* (2013.01)
USPC ............ 514/256; 514/341; 514/350; 514/406

(58) Field of Classification Search
None
See application file for complete search history.

(56) References Cited

U.S. PATENT DOCUMENTS

| | | | |
|---|---|---|---|
| 4,766,219 A | 8/1988 | Orvik et al. | |
| 5,547,967 A | 8/1996 | Kehrbach et al. | |
| 5,753,471 A | 5/1998 | Pressler et al. | |
| 2006/0069132 A1* | 3/2006 | Armel et al. | 514/359 |
| 2006/0069270 A1 | 3/2006 | Shapiro et al. | |
| 2008/0108686 A1 | 5/2008 | Gewehr et al. | |

FOREIGN PATENT DOCUMENTS

| | | |
|---|---|---|
| DE | 196 23 744 A1 | 12/1997 |
| EP | 1 714 958 A1 | 10/2006 |
| EP | 1 911 751 A1 | 4/2008 |
| WO | WO 96/33270 A1 | 10/1996 |
| WO | WO 00/07980 A1 | 2/2000 |
| WO | WO 01/74788 A1 | 10/2001 |
| WO | WO 01/83459 A2 | 11/2001 |
| WO | WO 2004/035545 A2 | 4/2004 |

(Continued)

OTHER PUBLICATIONS

Adams, E.S. and Rinehart, K., "Directed Biosynthesis of 5"-Fluoropactamycin in *Streptomyces pactum*," *The Journal of Antibiotics* 47(12):1456-1465, Japan Antibiotics Research Association, Japan (1994).

Anderson, G.W., et al., "A Reinvestigation of the Mixed Carbonic Anhydride Method of Peptide Synthesis," *Journal of the American Chemical Society* 89(19):5012-5017, American Chemical Society, United States (1967).

Arya, D.P. and Jebaratnam, D.J., "Towards the Development of Non-Enediyne Approaches for Mimicking Enediyne Chemistry: Design, Synthesis and Activity of a 1,4-Bisdiazonium Compound," *Tetrahedron Letters* 36(25):4639-4372, Elsevier Science Ltd., England (1995).

(Continued)

*Primary Examiner* — Wu-Cheng Winston Shen
*Assistant Examiner* — Jean Cornet
(74) *Attorney, Agent, or Firm* — Sterne, Kessler, Goldstein & Fox P.L.L.C.

(57) ABSTRACT

The invention relates to compounds of the general formula (I),

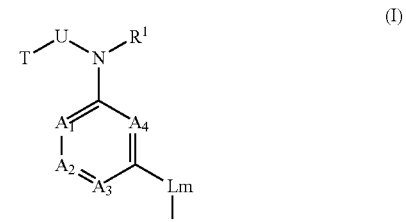

in which the radicals $A_1$, $A_2$, $A_3$, $A_4$, Lm, Q, $R^1$, T and U have the meaning given in the description and to the use of the compounds for controlling animal pests. In addition, the invention relates to processes and intermediates for the preparation of the compounds according to formula (I).

5 Claims, No Drawings

(56) References Cited

FOREIGN PATENT DOCUMENTS

| WO | WO 2004/099156 A1 | 11/2004 |
|---|---|---|
| WO | WO 2004/106324 A1 | 12/2004 |
| WO | WO 2005/060749 A1 | 7/2005 |
| WO | WO 2005/079801 A1 | 9/2005 |
| WO | WO 2005/095351 A1 | 10/2005 |
| WO | WO 2006/050506 A1 | 5/2006 |
| WO | WO 2007/024782 A2 | 3/2007 |
| WO | WO 2007/027777 A2 | 3/2007 |
| WO | WO 2007/034278 A2 | 3/2007 |
| WO | WO 2007/052843 A1 | 5/2007 |
| WO | WO 2007/071900 A1 | 6/2007 |
| WO | WO 2008/029084 A1 | 3/2008 |
| WO | WO 2008/059214 A1 | 5/2008 |

OTHER PUBLICATIONS

Aujard, I., et al., "Tetrahedral Onsager Crosses for Solubility Improvement and Crystallization Bypass," *J. Am. Chem. Soc.* 123:8177-8188, American Chemical Society, United States (2001).

Bargamova, M.D., et al., "5-Fluoro-Substituted Pyrazoles," 2338-2344, *Ivenstiya Akademii Nauk USSR Seriya Khimicheskaya*, Plenum Publishing Corporation, Russian (1991).

Bergbreiter, D.E., et al., "Synthesis and characterization of electronically varied XCX palladacycles with functional arene groups," *Inorganica Chimica Acta* 359:1912-1922, Elsevier B.V., Netherlands (2006).

Boyarskii, V.P., et al., "Synthesis of Heteroaromatic Carboxylic Acids by Carbonylation of Hetaryl Halides with Catalysts Based on Cobalt Carbonyl Modified with Epoxides," *Russian Journal of Applied Chemistry* 80(4):571-575, Pleiades Publishing, Ltd., Russia (2007).

Collins, J.C., "Dipyridine-Chromium(VI) Oxide Oxidation of Alcohols in Dichloromethane," *Tetrahedron Letters* 30:3363-3366, Pergamon Press, England (1968).

Correa, A., et al., "Iron-Catalyzed N-Arylations of Amices," *Chem. Eur. J.* 14:3527-3529, Wiley-VCH Verlag GmbH & Co. KGaA Weinheim, Germany 2008).

Cottet, F. and Schlosser, M., "Three Chloro(trifluoromentyl)pyridines as Model Substrates for Regioexhaustive Functionalization," *Eur. J. Org. Chem.* 3793-3798, Wiley-VCH Verlag GmbH & Co. KGaA Weinheim, Germany (2004).

Elguero, J., et al., "Palladium(0)-Catalyzed Preparation of 4-Arylpyrazols," *Synthesis* 563-566, Thieme Stuttgart New York, Germany (1997).

Fustero, S., et al., "Improved Regioselectivity in Pyrazole formation through the Use of Fluorinated Alcohols as Solvents: Synthesis and Biological Activity of Fluorinated Tebufenpyrad Analogs," *J. Org. Chem.* 73(9):3523-3529, American Chemical Society, United States (2008).

German, L.S., et al., "Synthesis of fluorinated pyrimidines by the reaction of perfluoro-2-methylpent-2-ene with amidines," *Russian Chemical Bulletin* 46(11):1920-1923, Plenum Publishing Corporation, United States (1997).

Gehre, A., et al., "A convenient synthesis of 2,2'-bipyridine derivatives," *Tetrahedron Letters* 48:6974-6976, Elsevier Ltd., England (2007).

Gorbunova, M.G., et al., "Synthesis and Properties of β-Ethoxyvinyl Polyfluoroalkyl Ketones," *Synthesis* 5:738-742, Thieme Stuttgart New York, Germany (2000).

Gupton, J.T., et al., "Regioselective fluoroalkoxylation and polyfluoroalkoxylation of aromatic and heteroaromatic polyhalides," *Can. J. Chem.* 63:3037-3042, Canadian Science Publishing, Canada (1985).

Höglund, I.P.J., et al., "Structure—Activity Relationship of Quinoline Derivatives as Potent and Selective $\alpha_{2c}$-Adrenoceptor Antagonists," *J. Med. Chem.* 49:6351-6363, American Chemical Society, United States (2006).

Hutchins, R.O., et al., "Orange Benene. Neutral Dichromate Oxidations in Organic Solvents," *Tetrahedron Letters* 48:4167-4170, Pergamon Press, England (1977).

Ichikawa, H., et al., "Synthesis of 4-Arylpyrazoles via $PdCl_2$(dppf)-Catalyzed Cross Coupling Reaction With Grignard Reagents," *Heterocycles* 68(11):2247-2252, The Japan Institute of Heterocyclic Chemistry, Japan (2006).

Karabelas, K. and Hallberg, A., "Synthesis of (E)-2(-Arylethenyl)silanes by Palladium-Catalyzed Arylation of Vinylsilanes in the Presence of Silver Nitrate," *J. Org. Chem.* 51:5286-5290, American Chemical Society, United States (1986).

Kimball, F.S., et al., "Optimization of α-Ketooxazole Inhibitors of Fatty Acid Amide Hydrolase," *J. Med. Chem.* 51:937-947, American Chemical Society, United States (2008).

Kirby, N.V., et al., "Synthesis and fungicidal activity of a series of novel aryloxylepidines," *Pest. Manage. Sci.* 57:844-851, Society of Chemical Industry, England (2001).

Khodakovskiy, P.V., et al., "2-(Trifluoroacetyl)imidazoles, 2-Trifluoroacetyl-1,3-thiazoles, and 2-Trifluoroacetyl-1,3-oxazoles," *Synthesis* 6:948-9556, Georg Thieme Verlag Stuttgart New York, Germany (2008).

König, W. and Geiger, R., "Eine neue Methode zur Synthese von Peptiden: Aktivierung der Carboxylgruuppe mit Dicyclohexylcarbodiimid unter Zusatz von 1-Hydroxybenzotriazolen," *Chem. Ber.* 103:788-798, VCH Verlagsgesellschaft mbH, Germany (1970) (Abstract only in English).

Kwok, T.J. and Virgilio, J., "A Preparative Route to Methyl 3-(Heteroaryl)acrylates Using Heck Methodology," *Organic Process Research and Development* 9(5):694-696, American Chemical Society, United States (2006).

Lahm, G.P., et al., "Rynaxypyre™: A new insecticidal anthranilic diamide that acts as a potent and selective ryanodine receptor activator," *Bioorg. Med. Chem. Lett.* 17:6274-6279, Elsevier Ltd., England (2007).

Lahm, G.P., et al., "Insecticidal anthranilic diamides: A new class of potent ryanodine receptor activators," *Bioorg. Med. Chem. Lett.* 15:4898-4906, Elsevier Ltd., England (2005).

Leslie, C.P., et al., "Novel carbazole derivatives as NPY Y1 antagonists," *Bioorg. Med. Chem. Lett.* 17:1043-1046, Elslevier Ltd., England (2006).

Lesma, G., et al., "Palladium-Catalyzed Hydroxycarbonylation of Aryl and Vinyl Triflates by in situ Generated Carbon Monoxide under Microwave Irradiation," *Synthesis* 4:594-596, Georg Thieme Verlag Stuttgart New York, Germany (2006).

Liu, C-L., et al., "Synthesis and biological activity of novel 2-methyl-4-trifluoromethyl-thiazole-5-carboxamide derivatives," *Journal of Fluorine Chemistry* 125:1287-1290, Elsevier B.V., Netherlands (2004).

Maugeri, C., et al., "New anti-viral drugs for the treatment of the common cold,"*Bioorg. Med. Chem.* 16:3091-3107, Elsevier Ltd., England (2008) (Available online Dec. 23, 2007).

Naito, H., et al., "Synthesis and Antitumor Activity of Novel Pyrimidinyl Pyrazole Derivatives. III.) Synthesis and Antitumor Activity of 3-Phenylpiperazinyl-1-*trans*-propenes," *Chem. Pharm. Bull.* 53(2):153-163, Pharmaceutical Society of Japan, Japan (2005).

Nielsen, N.M. and Bundgaard, H., "Prodrugs as drug delivery systems. 68. Chemical and plasma-catalyzed hydrolysis of various esters of benzoic acid: a reference system for designingg prodrug esters of carboxylic acid agents," *International Journal of Pharmaceutics* 39:75-85, Elsevier Science Publishers B.V., Netherlands (1987).

Parlow. J.J., et al., "Utility of Complementary Molecular Reactivity and Molecular Recognition (CMR/R) Technology and Polymer-Supported Reagents in the Solution-Phase Synthesis of Heterocyclic Carboxamides," *J. Org. Chem.* 62(17):5908-5919, American Chemical Society, United States (1997).

Parlow, J.J., "Synthesis of Pyrazolecarbonylaminopyridinecarboxamides as Herbicides," *J. Heterocyclic Chem.* 35:1493-1499, Journal of Heterocyclic Chemistry, United States (1998).

Perlow, D.S., et al., "Use of N-Fmoc Amino Acid Chlorides and Activated 2-(Fluorenylmethoxy)-5(4H)-oxazolones in Solid-Phase Peptide Synthesis. Efficient Syntheses of Highly N-Alkylated Cyclic

(56) References Cited

OTHER PUBLICATIONS

Hexapeptide Oxytocin Antagonists Related to L-365,209," *J. Org. Chem.* 57(16):4394-4400, American Chemical Society, United Sa(1992).

Fort-Sanchis, E., et al., "Indium-Mediated Synthesis of Heterobiaryls," *J. Org. Chem.* 72(9):3589-3591, American Chemical Society, United States (2007).

Schwetlick, K., "D.5. Substitutionen an Aromaten," *Organikum* 22:358-361, Wiley-VCH, Weinheim (2004).

Schwetlick, K., "D.7. Reaktionen von Carbonylverbindungen," *Organikum* 22:496-498, Wiley-VCH, Weinheim (2004).

Siedle, A.R., et al., "Solvolyis reactions of perfluoro-5-aza-4-nonene, $C_3F_7$—Cf=N—$C_4F_9$," *Journal of Fluorine Chemistry* 122:175-182, Elsevier Science B.V., Netherlands (2003).

Šmejkal, T. and Breit, B., "A Supramolecular Catalyst for Regioselective Hydroformylation of Unsaturated Carboxylic Acids," *Agnew. Chem. Int. Ed.* 47:311-315, Wiley-VCH Verlag GmbH & Co. KGaA Weinheim, Germany (2008).

Spalding, D.P., et al., "Heterocyclic Basic Compounds. XV. Benzacridine Derivatives," *J. Org. Chem* 19(3):357-364, American Chemical Society, United States (1954).

Spivey, A.C., et al., "Solid-Phase Synthesis of an A—B Loop Mimetic of the Cε 3 Domain of Human IgE: Macrocyclization by Sonogashira Coupling," *J. Org. Chem.* 68(5):1843-1851, American Chemical Society, United States (2003).

Tamura, O., et al., "Asymmetric Synthesis of (1*R*,2*S*)-2-Fluorocyclopropylamine, the Key Intermediate of the New Generation of Quinolonecarboxylic Acid, DU-6859," *Tetrahedron Letters* 33(24):3487-3490, Pergamon Press Ltd., England (1992).

Terrett, N.K., et al.,"Sildenafil (Viagra), a Potent and Selective Inhibitor of Type 5 CGMP Phosphodiesterase With Utility for the Treatment of Male Erectile Dysfunction," *Bioorganic & Medicinal Chemistry Letters* 6(15):1819-1824, Elsevier Science Ltd., England (1996).

Treibs, A. and Reitsam, F., "Über Dipyrryläthylene und Tripyrylmethane Pyrrol-Austausch-Reaktionen," *Justus Liebigs Ann, Chem.* 611(1):194-205, Wiley-VCH Verlag GmbH & Co. KGaA Weinheim, Germany (1958).

Williams, P.D., et al., "Development of a Novel Class of Cyclic Hexapeptide Oxytocin Antagonists Based on a Natural Product," *J. Med. Chem.* 35(21):3905-3918, American Chemical Society, United States (1992).

Yamakawi, J., et al., "Ultrasonic Acceleration of Oxidation With Solid Potassium Permanganate," *Chemistry Letters*:379-380, The Chemical Society of Japan, Japan (1983).

Yin, J. and Buchwald, S.L., "Pd-Catalyzed Intermolecular Amidation of Aryl Halides: The Discovery that Xantphos Can Be Trans-Chelating in a Palladium Complex," *J. Am. Chem. Soc.* 124(21):6043-6048, American Chemical Society, United States (2002).

Zheng, N. and Buchwald, S.L., "Copper-Catalyzed Regiospecific Synthesis of *N*-Alkylbenzimidazoles," *Org. Lett.* 9(23):4749-4751, American Chemical Society, United States (2007).

International Search Report for International Application No. PCT/EP2009/007668, European Patent Office, Netherlands, mailed Mar. 21, 2011.

International Application Report on Patentability with Written Opinion for International Application No. PCT/EP2009/007668, The International Bureau of WIPO, Switzerland, date of issuance Jun. 7, 2011.

English language abstract for International Application No. WO 2007/052843 A1, European Patent Office, espacenet database—Worldwide (2007).

English language abstract for German Application No. DE 196 23 744 A1, European Patent Office, espacenet databases—Worldwide (1997).

\* cited by examiner

HALOGEN-SUBSTITUTED COMPOUNDS

The present application relates to novel halogen-substituted compounds, to processes for their preparation and to their use for controlling animal pests, especially arthropods and in particular insects, arachnids and nematodes.

It is known that certain halogen-substituted compounds are herbicidally effective (cf. J. Org. Chem. 1997, 62(17), 5908-5919, J. Heterocycl. Chem. 1998, 35(6), 1493-1499, WO 2004/035545, WO 2004/106324, US 2006/069132, WO 2008/029084).

In addition, it is known that certain halogen-substituted compounds have cytokine-inhibitory activities (WO 00/07980).

However, nothing is known about the use of such halogen-substituted compounds for controlling animal pests, in particular as crop protection compositions.

Modern crop protection compositions have to satisfy many requirements, for example with regard to level, duration and scope of their effect and possible use. Questions of toxicity, of combinability with other active ingredients or formulation auxiliaries play a role, as does the question of complexity which is required for the synthesis of an active ingredient. Furthermore, resistances may occur. For all of these reasons, the search for novel crop protection compositions can never be considered complete and there is a continuing need for novel compounds with improved properties compared with the known compounds at least with regard to individual aspects.

It was an object of the present invention to provide compounds through which the spectrum of the pest control compositions is broadened from various aspects.

Surprisingly, it has now been found that certain halogen-substituted compounds, and their N-oxides and salts, have biological properties and are particularly suitable for controlling animal pests, and can therefore be used particularly well in the agrochemical sector and in the field of animal health.

This invention provides the use of the described compounds for controlling animal pests in agriculture and in animal health. In addition, this invention also provides novel compounds which have the uses described above and also processes for their preparation.

The halogen-substituted compounds according to the invention are defined by the formula (I)

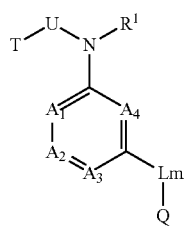

(I)

in which
$R^1$ is hydrogen, optionally substituted $C_1$-$C_6$-alkyl, $C_2$-$C_6$-alkenyl, $C_2$-$C_6$-alkynyl, $C_3$-$C_7$-cycloalkyl, $C_1$-$C_6$-alkylcarbonyl, $C_1$-$C_6$-alkoxycarbonyl, cyano-$C_1$-$C_2$-alkyl, aryl($C_1$-$C_3$)-alkyl, heteroaryl($C_1$-$C_3$)-alkyl,
the chemical group
$A_1$ is $CR^2$ or nitrogen,
$A_2$ is $CR^3$ or nitrogen,
$A_3$ is $CR^4$ or nitrogen, and
$A_4$ is $CR^5$ or nitrogen, where, however, not more than three of the chemical groups $A_1$ to $A_4$ are nitrogen at the same time;
$R^2$, $R^3$, $R^4$ and $R^5$, independently of one another, are hydrogen, halogen, CN, $NO_2$, optionally substituted $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, N,N-di-$C_2$-$C_6$-alkylamino, N—$C_2$-$C_7$-alkylaminocarbonyl, N—$C_2$-$C_7$-cycloalkylaminocarbonyl or $C_2$-$C_4$-alkoxycarbonyl;
if none of the groups $A_2$ and $A_3$ is nitrogen, $R^3$ and $R^4$, together with the carbon atom to which they are bonded, can form a 5- or 6-membered ring which comprises 0, 1 or 2 nitrogen atoms and/or 0 or 1 oxygen atom and/or 0 or 1 sulphur atom, or
if none of the groups $A_1$ and $A_2$ is nitrogen, $R^2$ and $R^3$, together with the carbon atom to which they are bonded, can form a 6-membered ring which comprises 0, 1 or 2 nitrogen atoms;
U is a group C(=W), SO or $SO_2$,
where
W is oxygen or sulphur;
L is a bivalent chemical group which is selected from the groups —NHC(=W)—, —$NR^6$C(=W)—, —$CH_2$NHC(=W)—, —$CH_2NR^6$C(=W)—, —C(=W)NH—, —C(=W)$NR^6$, —C(=W)$NHCH_2$—, —C(=W)$NR^6CH_2$—, —CH=N—$OCH_2$C(=W)NH—, —CH=N—$OCH_2$C(=W)$NR^6$—, —$CH_2$NHC(=W)NH—, —$CH_2$NHC(=W)$NR^6$—, —NH(C=W)NH—, —NH(=W)$NR^6$—, —$NR^6$(C=W)NH—, —$NR^6$(=W)$NR^6$—, —C(=W)—, —C(=W)O—, —C(=W)$OCH_2$C(=W)—, —C(=W)$OCH_2$C(=W)$NR^6$—, —C(=W)$OCH_2$C(=W)NHC(=W)NH—, —C(=W)$OCH_2$C(=W)NH—, —$CH_2$—, —($CH_2$)$_2$—, —($CH_2$)$_3$—, —Si—, —O—, —S(O)$_p$—, and —$CH_2$S(O)$_p$—, —SO(=N—CN)— and —S(=N—CN)—, —C(=W)$NHSO_2$—, where
p can assume the values 0, 1 or 2;
$R^6$ is hydrogen, optionally substituted $C_1$-$C_6$-alkyl, aryl($C_1$-$C_3$)-alkyl, heteroaryl($C_1$-$C_3$)-alkyl, $C_2$-$C_6$-alkenyl, $C_2$-$C_6$-alkynyl, $C_3$-$C_6$-cycloalkyl, $C_4$-$C_7$-alkylcycloalkyl and $C_4$-$C_7$-cycloalkylalkyl, $C_2$-$C_7$-alkylcarbonyl, $C_2$-$C_7$-alkoxycarbonyl;
m can assume the values 0 or 1;
Q is hydrogen or one of the optionally substituted groups $C_1$-$C_6$-alkyl, $C_2$-$C_6$-alkenyl, $C_2$-$C_6$-alkynyl, $C_3$-$C_6$-cycloalkyl, cyano-$C_1$-$C_2$-alkyl, $C_1$-$C_5$-heterocycloalkyl, $C_1$-$C_4$-alkoxy, $C_4$-$C_7$-alkylcycloalkyl, $C_4$-$C_7$-cycloalklylalkyl, $C_2$-$C_7$-alkylcarbonyl, $C_1$-$C_6$-alkylaldehyde, $C_1$-$C_6$-hydroxyalkyl, $C_2$-$C_7$-alkoxycarbonyl, $C_1$-$C_6$-haloalkyl, is formyl, hydroxy, halogen, cyano, aryl($C_1$-$C_3$)-alkyl, heteroaryl($C_1$-$C_3$)-alkyl or a group $OR^7$, $NR^6R^8$;
$R^7$ is selected from the optionally substituted groups $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl and $C_4$-$C_7$-cycloalkylalkyl;
$R^8$ is selected from hydrogen or the optionally $R^9$-substituted groups $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl and $C_4$-$C_7$-cycloalkylalkyl;
$R^9$ is selected from hydrogen or the groups $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl and $C_4$-$C_7$-cycloalkylalkyl optionally substituted by $R^{10}$;
$R^{10}$ is selected from halogen, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, —CN, —$NO_2$;

T is an optionally Z-polysubstituted saturated or unsaturated 5- or 6-membered ring, or is an optionally Z-polysubstituted 5- or 6-membered heterocyclic ring;

Z is hydrogen, halogen, cyano, nitro, optionally substituted $C_1$-$C_6$-alkyl, $C_1$-$C_4$-alkenyl, $C_1$-$C_4$-alkynyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, N,N-di($C_1$-$C_6$)alkylamino, —CN, —$NO_2$, —C(=W)$NR^{11}R^5$, —C(=W)$OR^{12}$, —S(O)$_2$$NR^{13}R^{14}$, —S(O)$_p$$R^{15}$, —S(O)(=$NR^{16}$)$R^{17}$ and optionally $R^{18}$-substituted phenyl and pyridinyl;

$R^{11}$ is selected from hydrogen or the optionally substituted groups $C_1$-$C_6$-alkyl, $C_2$-$C_6$-alkenyl, $C_2$-$C_6$-alkynyl, $C_3$-$C_6$-cycloalkyl, $C_2$-$C_7$-alkylcarbonyl and $C_2$-$C_7$-alkoxycarbonyl;

$R^{12}$ is selected from hydrogen or the optionally $R^6$-substituted group $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_3$-$C_6$-cycloalkyl, $C_3$-$C_6$-halocycloalkyl, $C_4$-$C_7$-alkylcycloalkyl and $C_4$-$C_7$-cycloalkylalkyl;

$R^{13}$ is selected from hydrogen or the optionally substituted groups $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_4$-$C_7$-alkylcycloalkyl, $C_4$-$C_7$-cycloalkylalkyl, $C_2$-$C_7$-alkylcarbonyl and $C_2$-$C_7$-alkoxycarbonyl;

$R^{14}$ is selected from hydrogen or the optionally $R^{19}$-substituted groups $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl and $C_4$-$C_7$-cycloalkylalkyl;

$R^{15}$ is selected from the optionally $R^{20}$-substituted groups $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl and $C_4$-$C_7$-cycloalkylalkyl, $C_1$-$C_4$-haloalkyl;

$R^{16}$ is selected from hydrogen, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_4$-$C_7$-alkylcycloalkyl, $C_4$-$C_7$-cycloalkylalkyl, $C_2$-$C_7$-alkylcarbonyl and $C_2$-$C_7$-alkoxycarbonyl;

$R^{17}$ is selected from hydrogen or the optionally $R^{20}$-substituted groups $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl and $C_4$-$C_7$-cycloalkylalkyl;

$R^{18}$ is selected from halogen, —OH, —$NH_2$, —COOH, —CN, —$NO_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, N,N-di($C_1$-$C_6$)-alkylamino, $C_2$-$C_6$-alkylcarbonyl, $C_2$-$C_6$-alkoxycarbonyl, $C_2$-$C_7$-alkylaminocarbonyl and N,N-di($C_1$-$C_6$)-alkylaminocarbonyl;

$R^{19}$ is selected from hydrogen or the optionally $R^{21}$-substituted groups $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, —CN, —$NO_2$ and optionally $R^{20}$-substituted phenyl or pyridyl;

$R^{20}$ is selected from halogen, —CN, —$NO_2$, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_2$-$C_7$-alkylcarbonyl, $C_2$-$C_7$-alkoxycarbonyl, $C_2$-$C_7$-alkylaminocarbonyl, or optionally $R^{22}$-substituted phenyl or pyridyl;

$R^{21}$ is selected from halogen, —OH, —$NH_2$, —COOH, —CN, —$NO_2$ or the optionally substituted groups $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, N,N-di($C_1$-$C_6$)-alkylamino, $C_2$-$C_4$-alkylcarbonyl, $C_2$-$C_4$-alkoxycarbonyl, $C_2$-$C_7$-alkylaminocarbonyl, and N,N-di($C_1$-$C_6$)-alkylaminocarbonyl, where $R^{22}$ is selected from halogen, —OH, —$NH_2$, —COOH, —CN, —$NO_2$, —CH=N—O—$CH_3$, —C($CH_3$)=N—O—$CH_3$, $C_1$-$C_6$-alkyl, $C_2$-$C_6$-alkenyl, $C_1$-$C_6$-haloalkyl, $C_2$-$C_6$-haloalkenyl, $C_2$-$C_3$-alkynyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, N,N-di($C_1$-$C_6$)-alkylamino, $C_2$-$C_4$-alkylcarbonyl, $C_2$-$C_4$-alkoxycarbonyl, $C_2$-$C_7$-alkylaminocarbonyl, N,N-di($C_1$-$C_6$)-alkylaminocarbonyl; or L, Q and $R^4$, together with the carbon atoms to which they are bonded, form an optionally substituted 5- or 6-membered ring which optionally comprises 0, 1 or 2 nitrogen atoms and/or 0 or 1 oxygen atom and/or 0 or 1 sulphur atom.

Preference is given to compounds of the formula (I)

in which $R^1$ is hydrogen or the optionally substituted groups $C_1$-$C_6$-alkyl, $C_2$-$C_6$-alkenyl, $C_2$-$C_6$-alkynyl, $C_3$-$C_7$-cycloalkyl, $C_1$-$C_6$-alkylcarbonyl, $C_1$-$C_6$-alkoxycarbonyl, cyano-$C_1$-$C_2$-alkyl, aryl($C_1$-$C_3$)-alkyl, heteroaryl($C_1$-$C_3$)-alkyl;

$A_1$ is $CR^2$ or nitrogen, $A_2$ is $CR^3$ or nitrogen, $A_3$ is $CR^4$ or nitrogen, and $A_4$ is $CR^5$ or nitrogen, where, however, at most three of the chemical groups $A_1$ to $A_4$ are nitrogen at the same time, and where $R^2$, $R^3$, $R^4$ and $R^5$, independently of one another, are hydrogen, halogen, CN, $NO_2$, optionally substituted $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, N,N-di($C_2$-$C_6$) alkylamino, N—$C_2$-$C_7$-alkylaminocarbonyl, N—$C_2$-$C_7$-cycloalkylaminocarbonyl or $C_2$-$C_4$-alkoxycarbonyl, if none of the groups $A_2$ and $A_3$ is nitrogen, $R^3$ and $R^4$, together with the carbon to which they are bonded, can form a 5- or 6-membered ring which comprises 0, 1 or 2 nitrogen atoms and/or 0 or 1 oxygen atom and/or 0 or 1 sulphur atom, or if none of the groups $A_1$ and $A_2$ is nitrogen, $R^2$ and $R^3$, together with the carbon to which they are bonded, can form a 6-membered ring which comprises 0, 1 or 2 nitrogen atoms;

U is a group C(=W), SO or $SO_2$;

W is oxygen or sulphur;

L is a bivalent chemical group which is selected from the groups —NHC(=W)—, —$NR^6$C(=W)—, —$CH_2$NHC(=W)—, —$CH_2NR^6$C(=W)—, —C(=W)NH, —C(=W)$NR^6$, —C(=W)NHCH$_2$—, —C(=W)$NR^6CH_2$—, —$CH_2$NHC(=W)NH—, —$CH_2$NHC(=W)$NR^6$—, —NH(C=W)NH—, —NH(=W)$NR^6$—, —$NR^6$ —(C=W)NH—, —NR$^6$(=W)NR$^6$—, —C(=W)—, —C(=W)O—, —C(=W)OCH$_2$C(=W)—, —C(=W)OCH$_2$C(=W)NR$^6$—, —C(=W)OCH$_2$C(=W)NHC(=W)NH—, —C(=W)OCH$_2$C(=W)NH—, —CH$_2$—, —(CH$_2$)$_2$—, —(CH$_2$)$_3$—, —Si—, —O—, —S(O)$_p$—, and —CH$_2$—S(O)$_p$—, —SO(=N—CN)— and —S(=N—CN)—, —C(=W)NHSO$_2$—;

p can assume the values 0, 1 or 2;

$R^6$ is hydrogen or the optionally substituted groups $C_1$-$C_6$-alkyl, aryl($C_1$-$C_3$)-alkyl, heteroaryl($C_1$-$C_3$)-alkyl, $C_2$-$C_6$-alkenyl, $C_2$-$C_6$-alkynyl, $C_3$-$C_6$-cycloalkyl, $C_4$-$C_7$-alkylcycloalkyl and $C_4$-$C_7$-cycloalkylalkyl, $C_2$-$C_7$-alkylcarbonyl, $C_2$-$C_7$-alkoxycarbonyl;

m can assume the values 0 or 1;

Q is hydrogen or the optionally substituted groups $C_1$-$C_6$-alkyl, $C_2$-$C_6$-alkenyl, $C_2$-$C_6$-alkynyl, $C_3$-$C_6$-cycloalkyl, cyano-$C_1$-$C_2$-alkyl, $C_1$-$C_5$-heterocycloalkyl, $C_1$-$C_4$-alkoxy, $C_4$-$C_7$-alkylcycloalkyl, $C_4$-$C_7$-cycloalkylalkyl, $C_2$-$C_7$-alkylcarbonyl, $C_1$-$C_6$-alkylaldehyde, $C_1$-$C_6$-hydroxyalkyl, $C_2$-$C_7$-alkoxycarbonyl, $C_1$-$C_6$-haloalkyl, is formyl, hydroxy, halogen, cyano, aryl($C_1$-$C_3$)-alkyl, heteroaryl($C_1$-$C_3$)-alkyl or is a group $OR^7$, $NR^6R^8$;

$R^7$ is selected from optionally substituted $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl and $C_4$-$C_7$-cycloalkylalkyl;

$R^8$ is selected from hydrogen or optionally $R^9$-substituted $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl and $C_4$-$C_7$-cycloalkylalkyl;

$R^9$ is selected from hydrogen or optionally $R^{10}$-substituted $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl and $C_4$-$C_7$-cycloalkylalkyl;

$R^{10}$ is selected from halogen, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, —CN, —NO$_2$;

the chemical group T is one of the radicals (T-1) to (T-90), shown below, which may be optionally Z-polysubstituted:

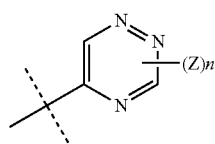 (T-1)

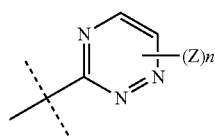 (T-2)

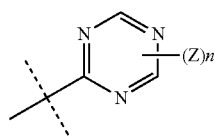 (T-3)

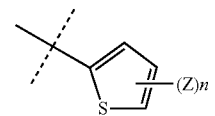 (T-4)

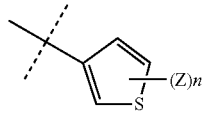 (T-5)

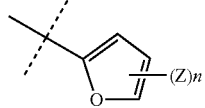 (T-6)

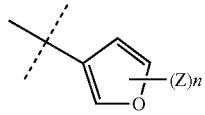 (T-7)

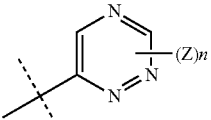 (T-8)

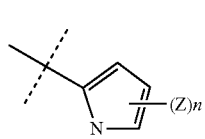 (T-9)

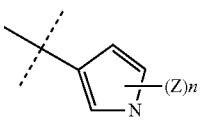 (T-10)

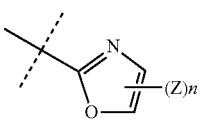 (T-11)

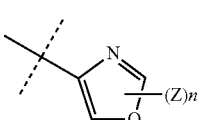 (T-12)

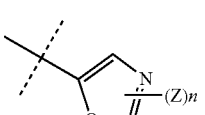 (T-13)

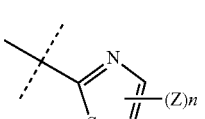 (T-14)

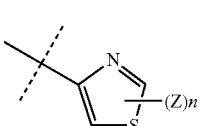 (T-15)

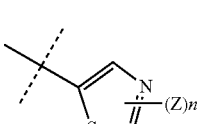 (T-16)

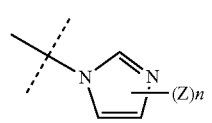 (T-17)
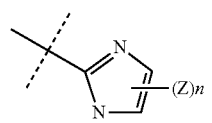 (T-18)
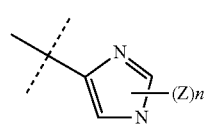 (T-19)
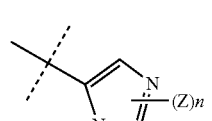 (T-20)
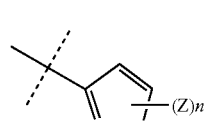 (T-21)
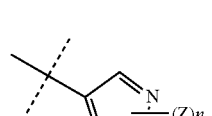 (T-22)
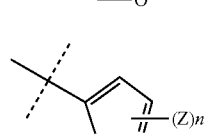 (T-23)
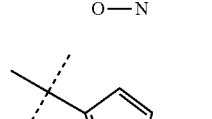 (T-24)
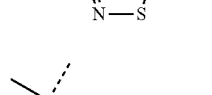 (T-25)
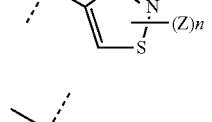 (T-26)
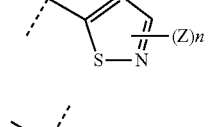 (T-27)
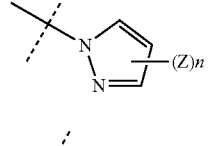 (T-28)
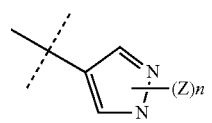 (T-29)
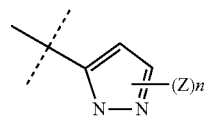 (T-30)
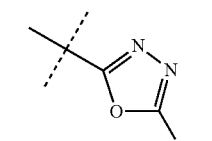 (T-31)
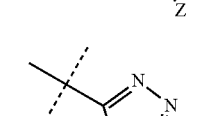 (T-32)
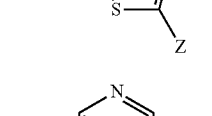 (T-33)
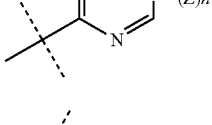 (T-34)
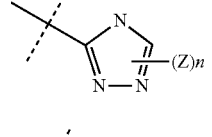 (T-35)
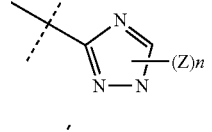 (T-36)
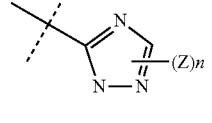 (T-37)
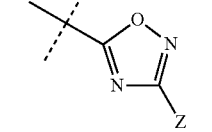 (T-38)
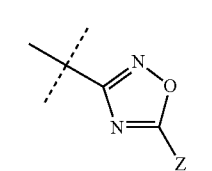 (T-39)

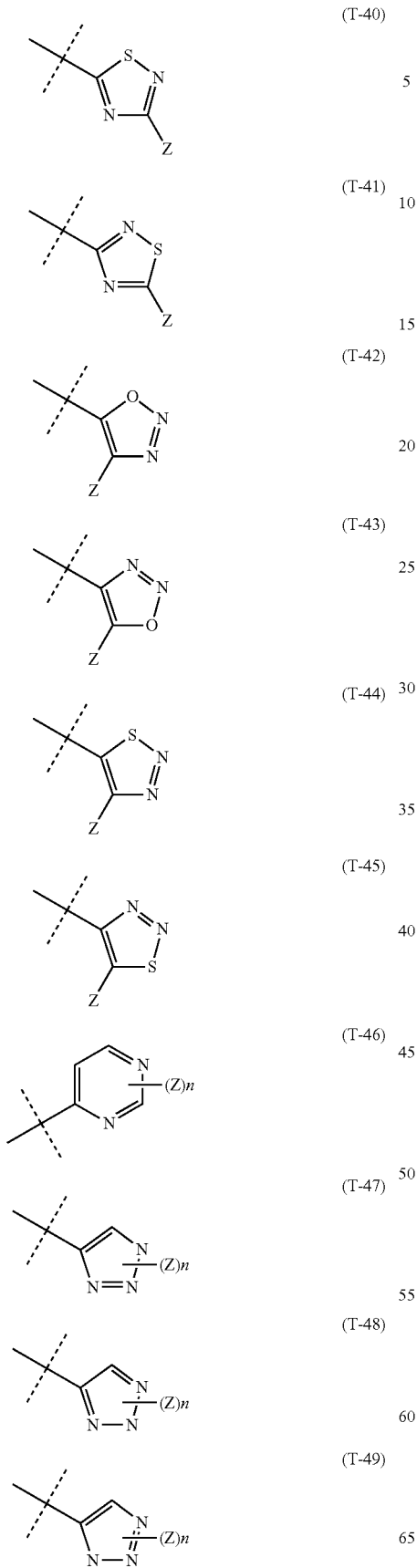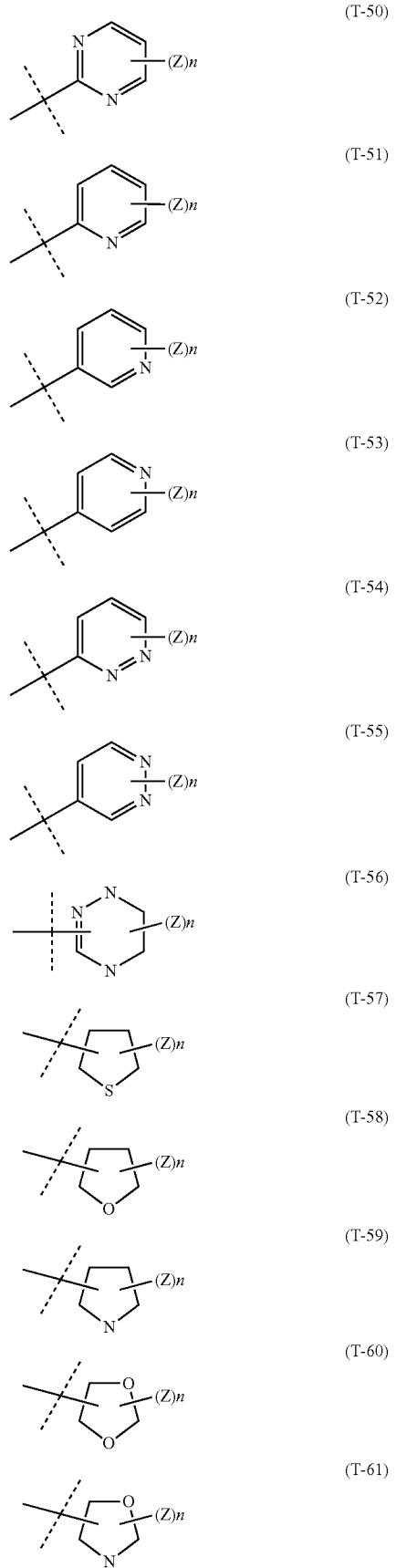

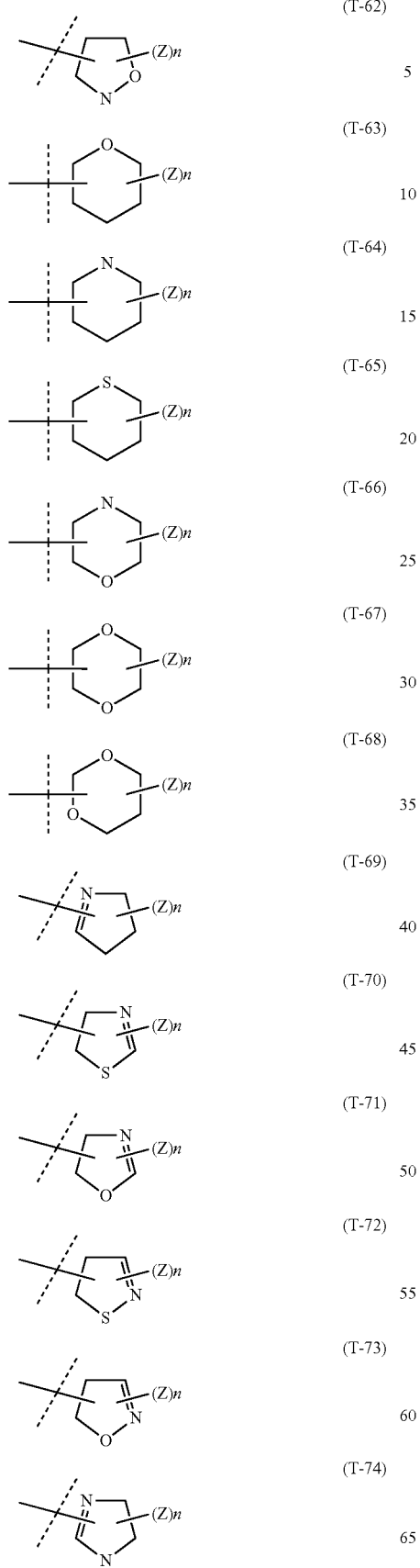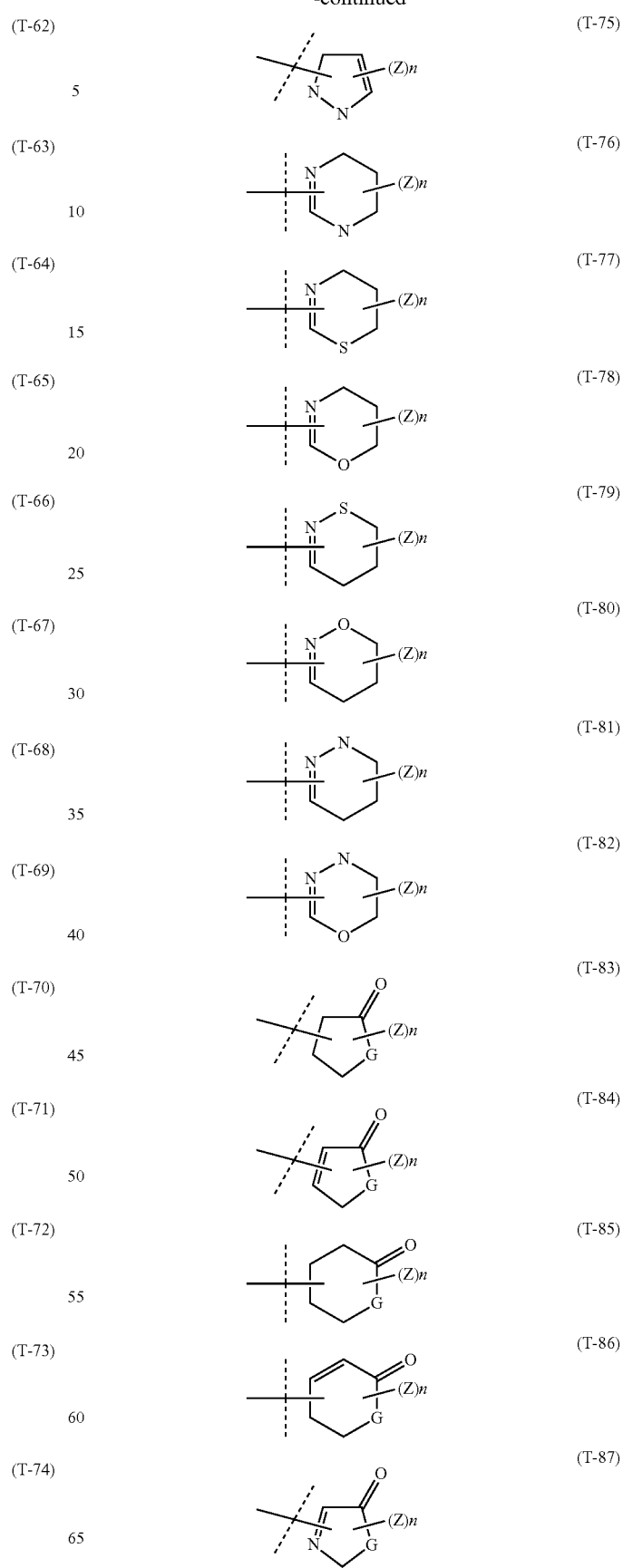

-continued

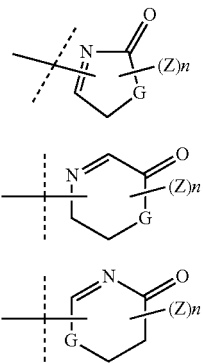

(T-88)

(T-89)

(T-90)

where
G is oxygen, sulphur or Z-substituted nitrogen,
n can assume values from 0 to 4,
Z is hydrogen, halogen, cyano, nitro or the optionally substituted groups $C_1$-$C_6$-alkyl, $C_1$-$C_4$-alkenyl, $C_1$-$C_4$-alkynyl, $C_1$-$C_6$-haloalkyl, $C_3$-$C_6$-Cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, N,N-di($C_1$-$C_6$)-alkylamino, —CN, —$NO_2$, —$S(O)_2NR^{13}R^{14}$, —$S(O)_pR^{15}$, —$S(O)(=NR^{16})$ $R^{17}$ or optionally is $R^{18}$-substituted phenyl or pyridinyl;
$R^{13}$ is selected from hydrogen or one of the optionally substituted groups $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_4$-$C_7$-alkylcycloalkyl, $C_4$-$C_7$-cycloalkylalkyl, $C_2$-$C_7$-alkylcarbonyl and $C_2$-$C_7$-alkoxycarbonyl;
$R^{14}$ is selected from hydrogen or one of the optionally $R^{19}$-substituted groups $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl and $C_4$-$C_7$-cycloalkylalkyl;
$R^{15}$ is selected from optionally $R^{20}$-substituted $C_1$-$C_6$-alkyl, $C_2$-$C_6$-alkenyl, $C_2$-$C_6$-alkynyl, $C_3$-$C_6$-Cycloalkyl, $C_4$-$C_7$-alkylcycloalkyl and $C_4$-$C_7$-cycloalkylalkyl, $C_1$-$C_4$-haloalkyl;
$R^{16}$ is selected from hydrogen, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_4$-$C_7$-alkylcycloalkyl, $C_4$-$C_7$-cycloalkylalkyl, $C_2$-$C_7$-alkylcarbonyl and $C_2$-$C_7$-alkoxycarbonyl;
$R^{17}$ is selected from hydrogen, optionally $R^{20}$-substituted $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl and $C_4$-$C_7$-cycloalkylalkyl;
$R^{18}$ is selected from halogen, —OH, —$NH_2$, —COOH, —CN, —$NO_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, N,N-di($C_1$-$C_6$)-alkylamino, $C_2$-$C_6$-alkylcarbonyl, $C_2$-$C_6$-alkoxycarbonyl, $C_2$-$C_7$-alkylaminocarbonyl and N,N-di($C_1$-$C_6$)-alkylaminocarbonyl;
$R^{19}$ is selected from hydrogen, optionally $R^{21}$-substituted $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, —CN, —$NO_2$, optionally $R^{19}$-substituted phenyl or pyridyl;
$R^{20}$ is selected from halogen, —CN, —$NO_2$, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_2$-$C_7$-alkylcarbonyl, $C_2$-$C_7$-alkoxycarbonyl, $C_2$-$C_7$-alkylaminocarbonyl, or optionally $R^{22}$-substituted phenyl or pyridyl;

$R^{21}$ is selected from halogen, —OH, —$NH_2$, —COOH, —CN, —$NO_2$, or optionally substituted $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, N,N-di($C_1$-$C_6$)-alkylamino, $C_2$-$C_4$-alkylcarbonyl, $C_2$-$C_4$-alkoxycarbonyl, $C_2$-$C_7$-alkylaminocarbonyl, and N,N-di($C_1$-$C_6$)-alkylaminocarbonyl;
$R^{22}$ is selected from halogen, —OH, —$NH_2$, —COOH, —CN—$NO_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_1$-$C_6$-alkylamino, N,N-di($C_1$-$C_6$)-alkylamino, $C_2$-$C_4$-alkylcarbonyl, $C_2$-$C_4$-alkoxycarbonyl, $C_2$-$C_7$-alkylaminocarbonyl, N,N-di($C_1$-$C_6$)-alkylaminocarbonyl.
In addition
L, Q and $R^4$, together with the carbon atoms to which they are bonded, can form an optionally substituted 5- or 6-membered ring which optionally comprises 0, 1 or 2 nitrogen atoms and/or 0 or 1 oxygen atom and/or 0 or 1 sulphur atom.
Particular preference is given to compounds of the formula (I)

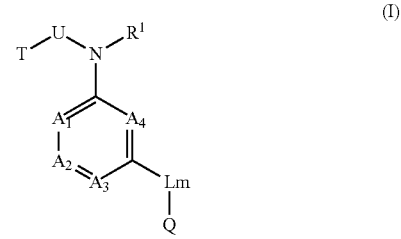

(I)

in which
$R^1$ is hydrogen or the optionally substituted groups $C_1$-$C_6$-alkyl, $C_2$-$C_6$-alkenyl, $C_2$-$C_6$-alkynyl, $C_3$-$C_7$-cycloalkyl, $C_1$-$C_6$-alkylcarbonyl, $C_1$-$C_6$-alkoxycarbonyl, cyano-$C_1$-$C_2$-alkyl, aryl($C_1$-$C_3$)-alkyl, heteroaryl($C_1$-$C_3$)-alkyl;
$A_1$ is $CR^2$ or nitrogen,
$A_2$ is $CR^3$ or nitrogen,
$A_3$ is $CR^4$ or nitrogen and
$A_4$ is $CR^5$ or nitrogen, where, however, at most three of the chemical groups $A_1$ to $A_4$ are nitrogen at the same time, and where
$R^2$, $R^3$, $R^4$ and $R^5$, independently of one another, are hydrogen, halogen, CN, $NO_2$, optionally substituted $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, N—$C_2$-$C_7$-alkylaminocarbonyl, N—$C_2$-$C_7$-cycloalkylaminocarbonyl,
if none of the groups $A_2$ and $A_3$ is nitrogen, $R^3$ and $R^4$, together with the carbon atom to which they are bonded, can form a 5- or 6-membered ring which comprises 0, 1 or 2 nitrogen atoms and/or 0 or 1 oxygen atom and/or 0 or 1 sulphur atom, or
if none of the groups $A_1$ and $A_2$ is nitrogen, $R^2$ and $R^3$, together with the carbon atom to which they are bonded, can form a 6-membered ring which comprises 0, 1 or 2 nitrogen atoms;

U is C(=W), SO or SO₂;

W is oxygen or sulphur;

L is a bivalent chemical group which is selected from the groups —CH₂NHC(=W)—, —CH₂NR⁶C(=W)—, —C(=W)NH, —C(=W)NR⁶, —NH(C=W)NH—, —NH(C=W)NR⁶—, —NR⁶(C=W)NH—, —NR⁶(=W)NR⁶—, —C(=W)—, —C(=W)O—, —C(=W)OCH₂C(=W)—, —C(=W)OCH₂C(=W)NR⁶—, —C(=W)OCH₂C(=W)NHC(=W)NH—, —C(=W)OCH₂C(=W)NH—, —O—, —S(O)$_p$—, and —CH₂—S(O)$_p$—, —SO(=N—CN)— and —S(=N—CN)—, —C(=W)NHSO₂—, where p can assume the values 0, 1 or 2 and R⁶ is hydrogen, C₁-C₆-alkyl, aryl(C₁-C₃)-alkyl, heteroaryl(C₁-C₃)-alkyl, C₂-C₇-alkylcarbonyl, C₂-C₇-alkoxycarbonyl;

m can assume the values 0 or 1;

Q is hydrogen or the optionally substituted groups C₁-C₆-alkyl, C₂-C₆-alkenyl, C₂-C₆-alkynyl, C₃-C₆-cycloalkyl, cyano-C₁-C₂-alkyl, C₁-C₅-heterocycloalkyl, C₁-C₄-alkoxy, C₄-C₇-alkylcycloalkyl, C₄-C₇-cycloalkylalkyl, C₂-C₇-alkylcarbonyl, C₁-C₆-alkylaldehyde, C₁-C₆-hydroxyalkyl, C₂-C₇-alkoxycarbonyl, C₁-C₆-haloalkyl, cyano, aryl(C₁-C₃)-alkyl, heteroaryl(C₁-C₃)-alkyl, or is a group NR⁶R⁸, where R⁸ is selected from hydrogen, C₁-C₆-alkyl, C₂-C₆-alkenyl, C₂-C₆-alkynyl, C₃-C₆-cycloalkyl, C₄-C₇-alkylcycloalkyl and C₄-C₇-cycloalkylalkyl;

T is one of the optionally Z-mono- or -polysubstituted heterocycles (T-5), (T-7), (T-9), (T-10), (T-12), (T-13), (T-15), (T-16), (T-19), (T-20), (T-23), (T-26), (T-28), (T-29), (T-34), (T-35), (T-36), (T-30), (T-33), (T-37), (T-46), (T-51), (T-52), (T-53), where n can assume values from 0 to 4 and Z is hydrogen, chlorine, bromine, iodine, cyano, nitro or the optionally substituted groups C₁-C₄-alkyl, C₁-C₄-alkenyl, C₁-C₄-alkynyl, C₁-C₄-haloalkyl, C₃-C₆-Cycloalkyl, C₃-C₆-halocycloalkyl, C₁-C₄-alkoxy, C₁-C₄-haloalkoxy, C₁-C₄-alkylthio, C₁-C₄-haloalkylthio, C₁-C₄-alkylsulphinyl, C₁-C₄-haloalkylsulphinyl, C₁-C₄-alkylsulphonyl, C₁-C₄-haloalkylsulphonyl, N,N-di(C₁-C₄)-alkylamino, and optionally R¹⁸-substituted phenyl and pyridinyl;

R¹⁸ is selected from halogen, —OH, —NH₂, —COOH, —CN, —NO₂, C₁-C₄-alkyl, C₁-C₄-haloalkyl, C₁-C₄-alkoxy, C₁-C₄-haloalkoxy, C₁-C₄-alkylthio, C₁-C₄-haloalkylthio, C₁-C₄-alkylsulphinyl, C₁-C₄-haloalkylsulphinyl, C₁-C₄-alkylsulphonyl, C₁-C₄-haloalkylsulphonyl, C₁-C₄-alkylamino, N,N-di(C₁-C₄)-alkylamino, C₁-C₄-alkylcarbonyl, C₁-C₄-alkoxycarbonyl, C₁-C₄-alkylaminocarbonyl and N,N-di(C₁-C₄)-alkylaminocarbonyl.

In addition,

L, Q and R⁴, together with the carbon atoms to which they are bonded, can form an optionally substituted 5- or 6-membered ring which optionally comprises 0, 1 or 2 nitrogen atoms and/or 0 or 1 oxygen atom and/or 0 or 1 sulphur atom.

Very particular preference is given to compounds of the formula (I)

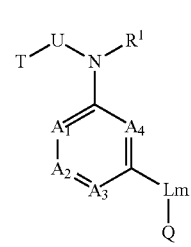

(I)

in which

R¹ is hydrogen, methyl, ethyl, n-propyl, isopropyl, n-butyl, 2-butynyl, isobutyl, sec-butyl, tert-butyl, methoxymethyl, ethoxymethyl, propoxymethyl, methylcarbonyl, ethylcarbonyl, n-propylcarbonyl, allyl, propargyl, isopropylcarbonyl, sec-butylcarbonyl, tert-butylcarbonyl, methoxycarbonyl, ethoxycarbonyl, n-propoxycarbonyl, isopropoxycarbonyl, sec-butoxycarbonyl, tert-butoxycarbonyl, cyanomethyl, 2-cyanoethyl;

A₁ is CR² or nitrogen,

A₂ is CR³ or nitrogen,

A₃ is CR⁴ or nitrogen and

A₄ is CR⁵ or nitrogen, where, however, at most three of the chemical groups A₁ to A₄ are nitrogen at the same time, and where R² and R⁵, independently of one another, are hydrogen, methyl, fluorine and chlorine and R³ and R⁴, independently of one another, are hydrogen, fluorine, chlorine, bromine, CN, NO₂, methyl, ethyl, fluoromethyl, difluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, methylsulphonyl, methylsulphinyl, trifluoromethylsulphonyl, trifluoromethylsulphinyl and N-cyclopropylaminocarbonyl; where U is C(=W), SO₂, W is oxygen, L is a bivalent chemical group which is selected from the groups —C(=O)NH, —C(=O)NR⁶, —C(=O)O—, —C(=O)OCH₂C(=O)—, —C(=O)OCH₂C(=O)NR⁶—, —C(=O)OCH₂C(=O)NHC(=O)NH—, —C(=O)OCH₂C(=O)NH—, —C(=W)NHSO₂—, where R⁶ is hydrogen, methyl, ethyl, n-propyl, isopropyl, n-butyl, isobutyl, sec-butyl, tert-butyl, methoxymethyl, ethoxymethyl, propoxymethyl, methylcarbonyl, ethylcarbonyl, n-propylcarbonyl, isopropylcarbonyl, sec-butylcarbonyl, tert-butylcarbonyl, methoxycarbonyl, ethoxycarbonyl, n-propoxycarbonyl, isopropoxycarbonyl, sec-butoxycarbonyl, tert-butoxycarbonyl, cyanomethyl, 2-cyanoethyl;

m assumes the value 1;

Q is hydrogen, methyl, ethyl, n-propyl, 1-methylethyl, 1,1-dimethylethyl, 1-methylpropyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 2,2-dimethyl-3-fluoropropyl, cyclopropyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloro-1,1-dimethylprop-2-enyl, oxetan-3-yl, isoxazol-3-ylmethyl, 1,2,4-triazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenyl ethyl, 4-chlorophenylethyl, 2-trifluoromethylphenylethyl, 1-pyridin-2-ylethyl, pyridin-2-ylmethyl, 5-fluoropyridin-2-ylmethyl, pyrimidin-2-ylmethyl, methoxy, 2-ethoxyethyl, 2-(methylsulphanyl)ethyl, 1-methyl-2-(ethylsulphanyl)ethyl, methoxycarbonyl, methoxycarbonylmethyl, $NH_2$, N-ethylamino, N-allylamino, N,N-dimethylamino, N,N-diethylamino; or Q is hydrogen, methyl, ethyl, n-propyl, 1-methylethyl, 1,1-dimethylethyl, 1-methylpropyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 2,2-dimethyl-3-fluoropropyl, cyclopropyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, oxetan-3-yl, isoxazol-3-ylmethyl, 1,2,4-triazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, 1-pyridin-2-ylethyl, pyridin-2-ylmethyl, 5-fluoropyridin-2-ylmethyl, pyrimidin-2-ylmethyl, methoxy, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, $NH_2$, N-ethylamino, N-allylamino, N,N-dimethylamino, N,N-diethylamino;

T is one of the optionally Z-polysubstituted heterocycles (T-12), (T-13), (T-15), (T-16), (T-19), (T-20), (T-23), (T-26), (T-30), (T-33), (T-37), (T-46), (T-51), (T-52), (T-53); where n can assume values from 0 to 3 and Z is hydrogen, chlorine, bromine, iodine, cyano, nitro, methyl, ethyl, n-propyl, isopropyl, n-butyl, isobutyl, sec-butyl, tert-butyl, ethenyl, 1-propenyl, 2-propenyl, ethynyl, 1-propynyl, 1-butynyl, difluoromethyl, trichloromethyl, chlorodifluoromethyl, dichlorofluoromethyl, trifluoromethyl, chloromethyl, bromomethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, trifluoromethoxy-1,1,2,2-tetrafluoroethoxydifluoromethyl, trifluoromethylthio, trifluoromethylsulphinyl, trifluoromethylsulphonyl, methoxy, ethoxy, n-propoxy, trifluoromethoxy, difluoromethoxy, cyclopropyl, cyclobutyl, 2,2,2-trifluoroethoxy, 1-trifluoromethylethoxy, 3,3,3,2,2-pentafluoropropoxy, 4-fluorophenyl, 4-chlorphenyl, 4-trifluoromethylphenyl, 2,2,2-trifluoroethyl, 2,2-difluoro-1-methylcyclopropyl; or Z is hydrogen, chlorine, bromine, iodine, cyano, nitro, methyl, ethyl, n-propyl, isopropyl, n-butyl, isobutyl, sec-butyl, tert-butyl, ethenyl, 1-propenyl, 2-propenyl, ethynyl, 1-propynyl, 1-butynyl, difluoromethyl, trichloromethyl, chlorodifluoromethyl, dichlorofluoromethyl, trifluoromethyl, chloromethyl, bromomethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, trifluoromethoxy-1,1,2,2-tetrafluoroethoxy-difluoromethyl, trifluoromethylthio, trifluoromethylsulphinyl, trifluoromethylsulphonyl, methoxy, ethoxy, n-propoxy, trifluoromethoxy, difluoromethoxy, cyclopropyl, cyclobutyl, 2,2,2-trifluoroethoxy, 1-trifluoromethylethoxy, 3,3,3,2,2-pentafluoropropoxy, 4-fluorophenyl, 4-chlorophenyl, 4-trifluoromethylphenyl, 2,2,2-trifluoroethyl, 2,2-difluoro-1-methylcyclopropyl, phenyl, methoxymethyl, cyclopropyl(fluoro)methyl, 2,4-dichlorophenyl, 4-trifluoromethoxyphenyl, 2-chlorophenyl, 3,5-bis(trifluoromethyl)phenyl, (1,1,1,3,3,3-hexafluoropropan-2-yl)oxy.

In addition,

L, Q and $R^4$, together with the carbon atoms to which they are bonded, can form an optionally substituted 5- or 6-membered ring which optionally comprises 0, 1 or 2 nitrogen atoms and/or 0 or 1 oxygen atom and/or 0 or 1 sulphur atom.

According to the invention "alkyl"—on its own or as part of a chemical group—is straight-chain or branched hydrocarbons, preferably having 1 to 6 carbon atoms, such as, for example, methyl, ethyl, n-propyl, isopropyl, n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Is also preferably alkyls having 1 to 4 carbon atoms such as, inter alia, methyl, ethyl, n-propyl, isopropyl, n-butyl, isobutyl, sec-butyl or tert-butyl. The alkyls according to the invention can be substituted by one or more identical or different radicals.

According to the invention, "alkenyl"—on its own or as part of a chemical group—is straight-chain or branched hydrocarbons, preferably having 2 to 6 carbon atoms and at least one double bond, such as, for example, vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. Is also preferably alkenyls having 2 to 4 carbon atoms, such as, inter alia, 2-propenyl, 2-butenyl or 1-methyl-2-propenyl. The alkenyls according to the invention can be substituted by one or more identical or different radicals.

According to the invention, "alkynyl"—on its own or as part of a chemical group—is straight-chain or branched hydrocarbons, preferably having 2 to 6 carbon atoms and at least one triple bond, such as, for example, 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexinyl, 3-hexinyl, 4-hexinyl, 5-hexinyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl, 1-ethyl-1-methyl-2-propynyl and 2,5-hexadiynyl. Is also preferably alkynyls having 2 to 4 carbon atoms, such as, inter alia, ethynyl, 2-propynyl or 2-butynyl-2-propenyl. The alkynyls according to the invention can be substituted by one or more identical or different radicals.

According to the invention, "cycloalkyl"—on its own or as part of a chemical group—is mono-, bi- or tricyclic hydrocarbons, preferably having 3 to 10 carbons, such as, for example, cyclopropyl, cyclobutyl, cyclopentyl, cyclohexyl, cycloheptyl, cyclooctyl, bicyclo[2.2.1]heptyl, bicyclo[2.2.2]octyl or adamantyl. Is also preferably cycloalkyls having 3, 4, 5, 6 or 7 carbon atoms, such as, inter alia, cyclopropyl or cyclobutyl. The cycloalkyls according to the invention can be substituted by one or more identical or different radicals.

According to the invention, "alkylcycloalkyl" is mono-, bi- or tricyclic alkylcycloalkyl, preferably having 4 to 10 or 4 to 7 carbon atoms, such as, for example, ethylcyclopropyl, isopropylcyclobutyl, 3-methylcyclopentyl and 4-methylcyclohexyl. Is also preferably alkylcycloalkyls having 4, 5 or 7 carbon atoms, such as, inter alia, ethylcyclopropyl or 4-methylcyclohexyl. The alkylcycloalkyls according to the invention can be substituted by one or more identical or different radicals.

According to the invention, "cycloalkylalkyl" is mono-, bi- or tricyclic cycloalkylalkyl, preferably having 4 to 10 or 4 to 7 carbon atoms, such as, for example, cyclopropylmethyl, cyclobutylmethyl, cyclopentylmethyl, cyclohexylmethyl and cyclopentylethyl. Is also preferably cycloalkylalkyls having 4, 5 or 7 carbon atoms such as, inter alia, cyclopropylmethyl or cyclobutylmethyl. The cycloalkylalkyls according to the invention can be substituted by one or more identical or different radicals.

According to the invention, "halogen" is fluorine, chlorine, bromine or iodine, in particular fluorine, chlorine or bromine.

The halogen-substituted chemical groups according to the invention, such as, for example, haloalkyl, halocycloalkyl, haloalkyloxy, haloalkylthio, haloalkylsulphinyl or haloalkylsulphonyl are substituted by halogen one or more times up to the maximum possible substituent number. In the case of polysubstitution by halogen, the halogen atoms may be identical or different and may all be bonded to one or more carbon atoms. Here, halogen is in particular fluorine, chlorine, bromine or iodine, preferably fluorine, chlorine or bromine and particularly preferably fluorine.

According to the invention, "halocycloalkyl" is mono-, bi- or tricyclic halocycloalkyl, preferably having 3 to 10 carbon atoms, such as, inter alia, 1-fluorocyclopropyl, 2-fluorocyclopropyl or 1-fluorocyclobutyl. Is also preferably halocycloalkyl having 3, 5 or 7 carbon atoms. The halocycloalkyls according to the invention can be substituted by one or more identical or different radicals.

According to the invention, "haloalkyl", "haloalkenyl" or "haloalkynyl" is halogen-substituted alkyls, alkenyls or alkynyls having preferably 1 to 9 identical or different halogen atoms, such as, for example, monohaloalkyl such as $CH_2CH_2Cl$, $CH_2CH_2F$, $CHClCH_3$, $CHFCH_3$, $CH_2Cl$, $CH_2F$; perhaloalkyl, such as $CCl_3$ or $CF_3$ or $CF_2CF_3$; polyhaloalkyl such as $CHF_2$, $CH_2F$, $CH_2CHFCl$, $CHCl_2$, $CF_2CF_2H$, $CH_2CF_3$. The same applies for haloalkenyl and other halogen-substituted radicals. Haloalkoxy is e.g. $OCF_3$, $OCHF_2$, $OCH_2F$, $OCF_2CF_3$, $OCH_2CF_3$ and $OCH_2CH_2Cl$.

Further examples of haloalkyls are trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl and pentafluoro-tert-butyl. Preference is given to haloalkyls having 1 to 4 carbon atoms and 1 to 9, preferably 1 to 5, identical or different halogen atoms which are selected from fluorine, chlorine or bromine. Particular preference is given to haloalkyls having 1 or 2 carbon atoms and having 1 to 5 identical or different halogen atoms which are selected from fluorine or chlorine, such as, inter alia, difluoromethyl, trifluoromethyl or 2,2-difluoroethyl.

According to the invention, "hydroxyalkyl" is straight-chain or branched alcohol, preferably having 1 to 6 carbon atoms, such as, for example, methanol, ethanol, n-propanol, isopropanol, n-butanol, isobutanol, sec-butanol and tert-butanol. Is also preferably hydroxyalkyl groups having 1 to 4 carbon atoms. The hydroxyalkyl groups according to the invention can be substituted by one or more identical or different radicals.

According to the invention, "alkoxy" is straight-chain or branched O-alkyl, preferably having 1 to 6 carbon atoms, such as, for example, methoxy, ethoxy, n-propoxy, isopropoxy, n-butoxy, isobutoxy, sec-butoxy and tert-butoxy. Is also preferably alkoxy groups having 1 to 4 carbon atoms. The alkoxy groups according to the invention can be substituted by one or more identical or different radicals.

According to the invention, "haloalkoxy" is halogen-substituted straight-chain or branched O-alkyl, preferably having 1 to 6 carbon atoms, such as, inter alia, difluoromethoxy, trifluoromethoxy, 2,2-difluoroethoxy, 1,1,2,2-tetrafluoroethoxy, 2,2,2-trifluoroethoxy and 2-chloro-1,1,2-trifluoroethoxy. Is also preferably haloalkoxy groups having 1 to 4 carbon atoms. The haloalkoxy groups according to the invention can be substituted by one or more identical or different radicals.

According to the invention, "alkylthio" is straight-chain or branched S-alkyl, preferably having 1 to 6 carbon atoms, such as, for example, methylthio, ethylthio, n-propylthio, isopropylthio, n-butylthio, isobutylthio, sec-butylthio and tert-butylthio. Is also preferably alkylthio groups having 1 to 4 carbon atoms. The alkylthio groups according to the invention can be substituted by one or more identical or different radicals.

Examples of haloalkylthioalkyls, i.e. halogen-substituted alkylthio groups, are, inter alia, difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio or 2-chloro-1,1,2-trifluoroethylthio.

According to the invention, "alkylsulphinyl" is straight-chain or blanched alkylsulphinyl, preferably having 1 to 6 carbon atoms, such as, for example, methylsulphinyl, ethylsulphinyl, n-propylsulphinyl, isopropylsulphinyl, n-butylsulphinyl, isobutylsulphinyl, sec-butylsulphinyl and tert-butylsulphinyl. Is also preferably alkylsulphinyl groups having 1 to 4 carbon atoms. The alkylsulphinyl groups according to the invention can be substituted by one or more identical or different radicals.

Examples of haloalkylsulphinyl groups, i.e. halogen-substituted alkylsulphinyl groups, are, inter alia, difluoromethylsulphinyl, trifluoromethylsulphinyl, trichloromethylsulphinyl, chlorodifluoromethylsulphinyl, 1-fluoroethylsulphinyl, 2-fluoroethylsulphinyl, 2,2-difluoroethylsulphinyl, 1,1,2,2-tetrafluoroethylsulphinyl, 2,2,2-trifluoroethylsulphinyl and 2-chloro-1,1,2-trifluoroethylsulphinyl.

According to the invention, "alkylsulphonyl" is straight-chain or branched alkylsulphonyl, preferably having 1 to 6 carbon atoms, such as, for example, methylsulphonyl, ethylsulphonyl, n-propylsulphonyl, isopropylsulphonyl, n-butylsulphonyl, isobutylsulphonyl, sec-butylsulphonyl and tert-butylsulphonyl. Is also preferably alkylsulphonyl groups having 1 to 4 carbon atoms. The alkylsulphonyl groups according to the invention can be substituted by one or more identical or different radicals.

Examples of haloalkylsulphonyl groups, i.e. halogen-substituted alkylsulphonyl groups are, inter alia, difluoromethylsulphonyl, trifluoromethylsulphonyl, trichloromethylsulphonyl, chlorodifluoromethylsulphonyl, 1-fluoroethylsulphonyl, 2-fluoroethylsulphonyl, 2,2-difluoroethylsulphonyl, 1,1,2,2-tetrafluoroethylsulphonyl, 2,2,2-trifluoroethylsulphonyl and 2-chloro-1,1,2-trifluoroethylsulphonyl.

According to the invention, "alkylcarbonyl" is a straight-chain or branched alkyl-C(=O), preferably having 2 to 7 carbon atoms, such as methylcarbonyl, ethylcarbonyl, n-propylcarbonyl, isopropylcarbonyl, sec-butylcarbonyl and tert-butylcarbonyl. Is also preferably alkylcarbonyls having 1 to 4 carbon atoms. The alkylcarbonyls according to the invention can be substituted by one or more identical or different radicals.

According to the invention, "cycloalkylcarbonyl" is straight-chain or branched cycloalkylcarbonyl, preferably having 3 to 10 carbon atoms in the cycloalkyl moiety, such as, for example, cyclopropylcarbonyl, cyclobutylcarbonyl, cyclopentylcarbonyl, cyclohexylcarbonyl, cycloheptylarbonyl, cyclooctylcarbonyl, bicyclo[2.2.1]heptyl, bicyclo[2.2.2]octylcarbonyl and adamantylcarbonyl. Is also preferably cycloalkylcarbonyl having 3, 5 or 7 carbon atoms in the cycloalkyl moiety. The cycloalkylcarbonyl groups according to the invention can be substituted by one or more identical or different radicals.

According to the invention, "alkoxycarbonyl"—on its own or as part of a chemical group—is straight-chain or branched alkoxycarbonyl, preferably having 1 to 6 carbon atoms or 1 to 4 carbon atoms in the alkoxy moiety, such as, for example, methoxycarbonyl, ethoxycarbonyl, n-propoxycarbonyl, isopropoxycarbonyl, sec-butoxycarbonyl and tert-butoxycarbonyl. The alkoxycarbonyl groups according to the invention can be substituted by one or more identical or different radicals.

According to the invention, "alkylaminocarbonyl" is straight-chain or branched alkylaminocarbonyl having preferably 1 to 6 carbon atoms or 1 to 4 carbon atoms in the alkyl moiety, such as, for example, methylaminocarbonyl, ethylaminocarbonyl, n-propylaminocarbonyl, isopropylaminocarbonyl, sec-butylaminocarbonyl and tert-butylaminocarbonyl. The alkylaminocarbonyl groups according to the invention can be substituted by one or more identical or different radicals.

According to the invention, "N,N-dialkylaminocarbonyl" is straight-chain or branched N,N-dialkylaminocarbonyl having preferably 1 to 6 carbon atoms or 1 to 4 carbon atoms in the alkyl moiety, such as, for example, N,N-dimethylaminocarbonyl, N,N-diethylaminocarbonyl, N,N-di(n-propylamino)carbonyl, N,N-di(isopropylamino)carbonyl and N,N-di(sec-butylamino)carbonyl. The N,N-dialkylaminocarbonyl groups according to the invention can be substituted by one or more identical or different radicals.

According to the invention, "aryl" is a mono-, bi- or polycyclic aromatic system having preferably, 6 to 14, in particular 6 to 10, ring carbon atoms, such as, for example, phenyl, naphthyl, anthryl, phenanthrenyl, preferably phenyl. Aryl is also polycyclic systems, such as tetrahydronaphthyl, indenyl, indanyl, fluorenyl, biphenyl, where the bonding side is on the aromatic system. The aryl groups according to the invention can be substituted by one or more identical or different radicals.

Examples of substituted aryls are the arylalkyls which may likewise be substituted by one or more identical or different radicals in the alkyl and/or aryl moiety. Examples of such arylalkyls are, inter alia, benzyl and 1-phenylethyl.

According to the invention, "heterocycle", "heterocyclic ring" or "heterocyclic ring system" is a carbocyclic ring system with at least one ring in which at least one carbon atom is replaced by a heteroatom, preferably by a heteroatom from the group consisting of N, O, S, P, B, Si, Se and which is saturated, unsaturated or heteroaromatic and may be unsubstituted or substituted by a substituent Z, where the bonding site is localized on a ring atom. Unless defined otherwise, the heterocyclic ring comprises preferably 3 to 9 ring atoms, in particular 3 to 6 ring atoms, and one or more, preferably 1 to 4, in particular 1, 2 or 3, heteroatoms in the heterocyclic ring, preferably from the group consisting of N, O and S, where, however, two oxygen atoms should not be directly adjacent. The heterocyclic rings usually comprise not more than 4 nitrogen atoms, and/or not more than 2 oxygen atoms and/or not more than 2 sulphur atoms. If the heterocyclyl radical or the heterocyclic ring is optionally substituted, it can be fused with other carbocyclic or heterocyclic rings. In the case of optionally substituted heterocyclyl, the invention also encompasses polycyclic systems such as, for example, 8-azabicyclo[3.2.1]octanyl or 1-azabicyclo[2.2.1]heptyl. In the case of optionally substituted heterocyclyl, the invention also encompasses spirocyclic systems, such as, for example, 1-oxa-5-azaspiro[2.3]hexyl.

Heterocyclyl groups according to the invention are, for example, piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl.

A particular meaning is given to heteroaryls, i.e. heteroaromatic systems. According to the invention, the expression heteroaryl stands for heteroaromatic compounds, i.e. completely unsaturated aromatic heterocyclic compounds which fall within the above definition of heterocycles. Preferably for 5- to 7-membered rings having 1 to 3, preferably 1 or 2, identical or different heteroatoms from the aforementioned group. Heteroaryls according to the invention are, for example, furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl. The heteroaryl groups according to the invention can also be substituted via one or more identical or different radicals.

Substituted groups, such as a substituted alkyl, alkenyl, alkynyl, cycloalkyl, aryl, phenyl, benzyl, heterocyclyl and heteroaryl radical, are, for example, a substituted radical derived from the unsubstituted parent substances, where the substituents are, for example, one or more, preferably 1, 2 or 3, radicals from the group consisting of halogen, alkoxy, alkylthio, hydroxy, amino, nitro, carboxy or a group equivalent to the carboxy group, cyano, isocyano, azido, alkoxycarbonyl, alkylcarbonyl, formyl, carbamoyl, mono- and N,N-dialkylaminocarbonyl, substituted amino, such as acylamino, mono- and N,N-dialkylamino, trialkylsilyl and optionally substituted cycloalkyl, optionally substituted aryl, optionally substituted heterocyclyl, where each of the last-mentioned cyclic groups may also be bonded via heteroatoms or divalent functional groups as in the case of the specified alkyl radicals, and alkylsulphinyl, where both enantiomers of the alkylsulphonyl group are encompassed, alkylsulphonyl, alkylphosphinyl, alkylphosphonyl and, in the case of cyclic radicals (="cyclic parent substance"), also alkyl, haloalkyl, alkylthioalkyl, alkoxyalkyl, optionally substituted mono- and N,N-dialkylaminoalkyl and hydroxyalkyl.

In the term "substituted groups" such as substituted alkyl etc., in addition to the specified saturated hydrocarbon-containing radicals, encompassed substituents are corresponding unsaturated aliphatic and aromatic radicals, such as optionally substituted alkenyl, alkynyl, alkenyloxy, alkynyloxy, alkenylthio, alkynylthio, alkenyloxycarbonyl, alkynyloxycarbonyl, alkenylcarbonyl, alkynylcarbonyl, mono- and N,N-dialkenylaminocarbonyl, mono- and dialkynylaminocarbonyl, mono- and N,N-dialkenylamino, mono- and N,N-dialkynylamino, trialkenylsilyl, trialkynylsilyl, optionally substituted cycloalkenyl, optionally substituted cycloalkynyl, phenyl, phenoxy etc. In the case of substituted cyclic radicals with aliphatic fractions in the ring, cyclic systems with substituents which are bonded to the ring with a double bond, e.g. with an alkylidene group such as methylidene or ethylidene or an oxo group, imino group, and a substituted imino group are also encompassed.

If two or more radicals form one or more rings, then these may be carbocyclic, heterocyclic, saturated, partially saturated, unsaturated, for example also aromatic and further substituted.

The substituents mentioned by way of example ("first substituent level") may, if they comprise hydrocarbon-containing fractions, be optionally further substituted there ("second substituent level"), for example by one of the substituents as defined for the first substituent level. Corresponding further substituent levels are possible. Preferably, the term "substituted radical" encompasses only one or two substituent levels.

Preferred substituents for the substituent levels are, for example,
amino, hydroxy, halogen, nitro, cyano, isocyano, mercapto, isothiocyanato, carboxy, carboxamide, $SF_5$, aminosulphonyl, alkyl, cycloalkyl, alkenyl, cycloalkenyl, alkynyl, N-monoalkylamino, N,N-dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulphenyl and alkylsulphinyl, where both enantiomers of the alkylsulphinyl group are encompassed, alkylsulphonyl, N-monoalkylaminosulphonyl, N,N-dialkylaminosulphonyl, alkylphosphinyl, alkylphosphonyl, where both enantiomers are encompassed for alkylphosphinyl and alkylphosphonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino, benzylamino, heterocyclyl and trialkylsilyl.

Substituents which are composed of two or more substituent levels are preferably alkoxyalkyl, alkylthioalkyl, alkylthioalkoxy, alkoxyalkoxy, phenethyl, benzyloxy, haloalkyl, halocycloalkyl, haloalkoxy, haloalkylthio, haloalkylsulphinyl, haloalkylsulphonyl, halogenalkanoyl, haloalkylcarbonyl, haloalkoxycarbonyl, haloalkoxyalkoxy, haloalkoxyalkylthio, haloalkoxyalkanoyl, haloalkoxyalkyl.

For radicals with carbon atoms, preference is given to those having 1 to 6 carbon atoms, preferably 1 to 4 carbon atoms, in particular 1 or 2 carbon atoms. As a rule preference is given to substituents from the group consisting of halogen, e.g. fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given here to the substituents methyl, methoxy, fluorine and chlorine.

Substituted amino such as mono- or disubstituted amino means a radical from the group of the substituted amino radicals which are N-substituted, for example, by one or two identical or different radicals from the group consisting of alkyl, hydroxy, amino, alkoxy, acyl and aryl; preferably N-mono- and N,N-dialkylamino, (e.g. methylamino, ethylamino, N,N-dimethylamino, N,N-diethylamino, N,N-di-n-propylamino, N,N-diisopropylamino or N,N-dibutylamino), N-mono- or N,N-dialkoxyalkylamino groups (e.g. N-methoxymethylamino, N-methoxyethylamino, N,N-di(methoxymethyl)amino or N,N-di(methoxyethyl)amino), N-mono- and N,N-diarylamino, such as optionally substituted anilines, acylamino, N,N-diacylamino, N-alkyl-N-arylamino, N-alkyl-N-acylamino and saturated N-heterocycles; here, preference is given to alkyl radicals having 1 to 4 carbon atoms; here, aryl is preferably phenyl or substituted phenyl; for acyl, the definition given below applies, preferably $(C_1-C_4)$-alkanoyl. The same applies accordingly for substituted hydroxylamino or hydrazino.

According to the invention, the term "cyclic amino groups" encompasses heteroaromatic or aliphatic ring systems with one or more nitrogen atoms. The heterocycles are saturated or unsaturated, consist of one or more, optionally condensed ring systems and include optionally further heteroatoms, such as, for example, one or two nitrogen, oxygen, and/or sulphur atoms. In addition, the term also encompasses those groups which have a spiro ring or bridged ring system. The number of atoms which form the cyclic amino group is arbitrary and may consist, for example, in the case of a one-ring system, of 3 to 8 ring atoms and, in the case of a two-ring system, of 7 to 11 atoms.

Examples of cyclic amino groups with saturated and unsaturated monocyclic groups with one nitrogen atom as heteroatom which may be specified are 1-azetidinyl, pyrrolidino, 2-pyrrolidin-1-yl, 1-pyrrolyl, piperidino, 1,4-dihydropyrazin-1-yl, 1,2,5,6-tetrahydropyrazin-1-yl, 1,4-dihydropyridin-1-yl, 1,2,5,6-tetrahydropyridin-1-yl, homopiperidinyl; examples of cyclic amino groups with saturated and unsaturated monocyclic groups having two or more nitrogen atoms as heteroatoms which may be mentioned are 1-imidazolidinyl, 1-imidazolyl, 1-pyrazolyl, 1-triazolyl, 1-tetrazolyl, 1-piperazinyl, 1-homopiperazinyl, 1,2-dihydropiperazin-1-yl, 1,2-dihydropyrimidin-1-yl, perhydropyrimidin-1-yl, 1,4-diazacycloheptan-1-yl; examples of cyclic amino groups with saturated and unsaturated monocyclic groups having one or two oxygen atoms and one to three nitrogen atoms as heteroatoms, such as, for example, oxazolidin-3-yl, 2,3-dihydroisoxazol-2-yl, isoxazol-2-yl, 1,2,3-oxadiazin-2-yl, morpholino; examples of cyclic amino groups with saturated and unsaturated monocyclic groups having one to three nitrogen atoms and one to two sulphur atoms as heteroatoms which may be mentioned are thiazolidin-3-yl, isothiazolin-2-yl, thiomorpholino, or dioxothiomorpholino; examples of cyclic amino groups with saturated and unsatured condensed cyclic groups which may be mentioned are indol-1-yl, 1,2-dihydrobenzimidazol-1-yl, perhydropyrrolo[1,2-a]pyrazin-2-yl; an example of cyclic amino groups with spirocyclic groups that may be mentioned is 2-azaspiro[4.5]decan-2-yl; an example of cyclic amino groups with bridged heterocyclic groups that may be mentioned is 2-azabicyclo[2.2.1]heptan-7-yl.

Substituted amino also includes quaternary ammonium compounds (salts) with four organic substituents on the nitrogen atom.

Optionally substituted phenyl is preferably phenyl which is unsubstituted or substituted one or more times, preferably up to three times, by identical or different radicals from the group consisting of halogen, $(C_1-C_4)$-alkyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_1-C_4)$-haloalkyl, $(C_1-C_4)$-haloalkoxy, $(C_1-C_4)$-alkylthio, $(C_1-C_4)$-haloalkylthio, cyano, isocyano and nitro, e.g. o-, m- and p-tolyl, dimethylphenyls, 2-, 3- and 4-chlorophenyl, 2-, 3- and 4-fluorophenyl, 2-, 3- and 4-trifluoromethyl- and -trichloromethylphenyl, 2,4-, 3,5-, 2,5- and 2,3-dichlorophenyl, o-, m- and p-methoxyphenyl.

Optionally substituted cycloalkyl is preferably cycloalkyl which is unsubstituted or substituted one or more times, preferably up to three times, by identical or different radicals from the group consisting of halogen, cyano, $(C_1-C_4)$-alkyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_1-C_4)$-haloalkyl and $(C_1-C_4)$-haloalkoxy, in particular is substituted by one or two $(C_1-C_4)$-alkyl radicals.

Optionally substituted heterocyclyl is preferably heterocyclyl which is unsubstituted or substituted one or more times, preferably up to three times, by identical or different radicals from the group consisting of halogen, cyano, $(C_1-C_4)$-alkyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_1-C_4)$-haloalkyl, $(C_1-C_4)$-haloalkoxy, nitro and oxo, in particular is substituted one or more times by radicals from the group consisting of halogen, $(C_1-C_4)$-alkyl, $(C_1-C_4)$-alkoxy, $(C_1-C_4)$-haloalkyl and oxo, very particularly by one or two $(C_1-C_4)$-alkyl radicals.

Examples of alkyl-substituted heteroaryls are furylmethyl, thienylmethyl, pyrazolylmethyl, imidazolylmethyl, 1,2,3- and 1,2,4-triazolylmethyl, isoxazolylmethyl, thiazolylmethyl, isothiazolylmethyl, 1,2,3-, 1,3,4-, 1,2,4- and 1,2,5-oxadiazolylmethyl, azepinylmethyl, pyrrolylmethyl, pyridylmethyl, pyridazinylmethyl, pyrimidinylmethyl, pyrazinylmethyl, 1,3,5-, 1,2,4- and 1,2,3-triazinylmethyl, 1,2,4-, 1,3,2-, 1,3,6- and 1,2,6-oxazinylmethyl, oxepinylmethyl, thiepinylmethyl and 1,2,4-diazepinylmethyl.

Salts of the compounds according to the invention that are suitable according to the invention, for example salts with bases or acid addition salts, are all customary nontoxic salts, for example agriculturally and/or physiologically acceptable salts, for example, salts with bases or acid addition salts. Preference is given to salts with inorganic bases, such as, for example, alkali metal salts (e.g. sodium, potassium or caesium salts), alkaline earth metal salts (e.g. calcium or magnesium salts), ammonium salts or salts with organic bases, in particular with organic amines, such as, for example, triethylammonium salts, dicyclohexylammonium salts, N,N'-dibenzylethylenediammonium salts, pyridinium salts, picolinium salts or ethanolammonium salts, salts with inorganic acids (e.g. hydrochlorides, hydrobromides, dihydrosulphates, trihydrosulphates, or phosphates), salts with organic carboxylic acids or organic sulphonic acids (e.g. formates, acetates, trifluoroacetates, maleates, tartrates, methanesulphonates, benzenesulphonates or 4-toluenesulphonates). As is known, tert-amines, such as, for example, some of the compounds according to the invention, can form N-oxides, which likewise constitute salts according to the invention.

In addition, preferred embodiments of the invention are the compounds of the general formulae (Ia) to (Iv).

In the general formulae (Ia) to (Iv) below, the groups and substituents $A_1$, $A_2$, $A_3$, $A_4$, U, L, m, Q and $R^1$ have the meanings given above. The radicals $Z^1$, $Z^2$ and $Z^3$ are described by the aforementioned radical definition of Z.

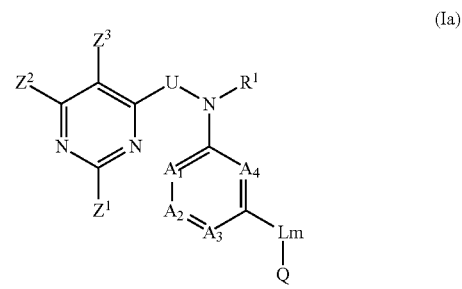

(Ia)

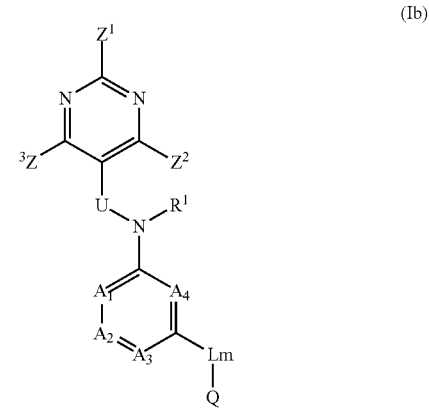

(Ib)

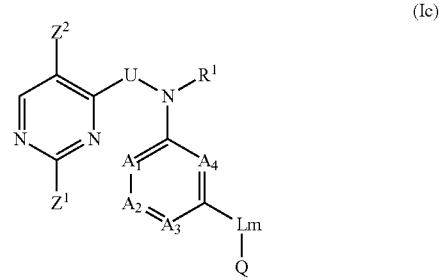

(Ic)

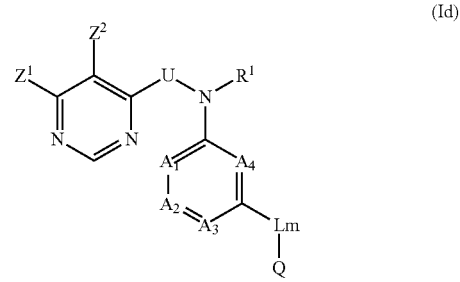

(Id)

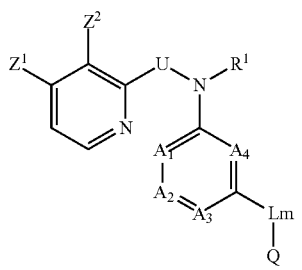
(Ie)
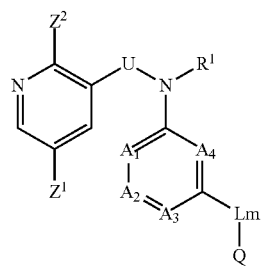
(If)
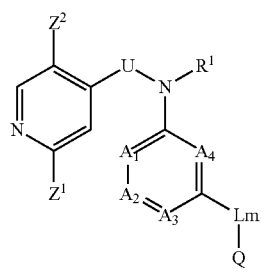
(Ig)
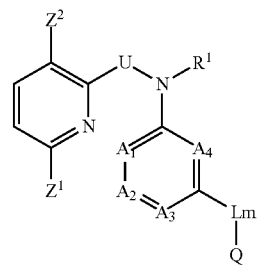
(Ih)
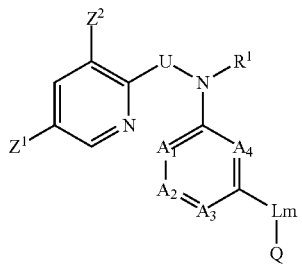
(Ii)
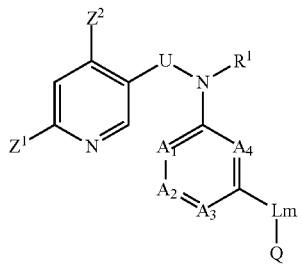
(Ij)
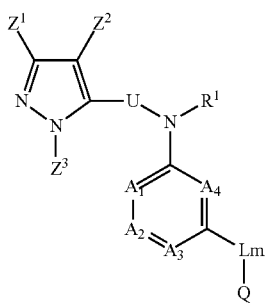
(Ik)
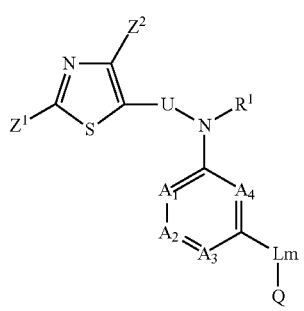
(Il)
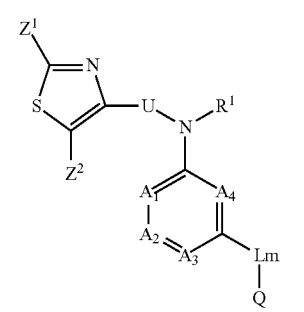
(Im)
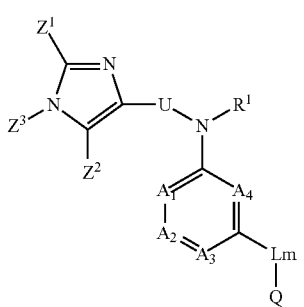
(In)
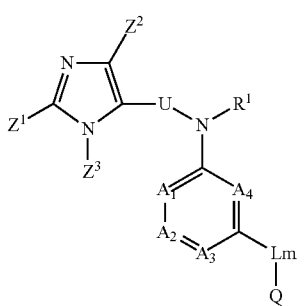
(Io)

(Ip) 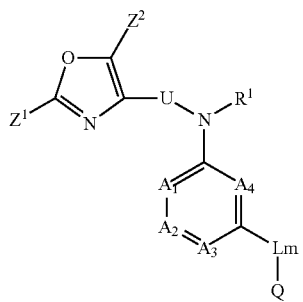

(Iq) 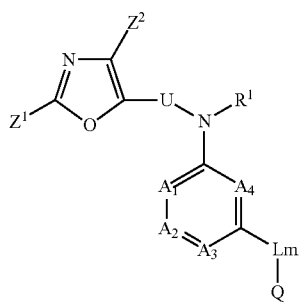

(Ir) 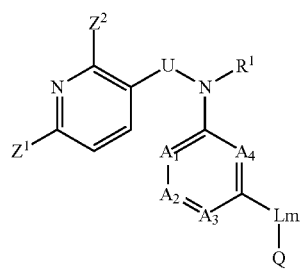

(Is) 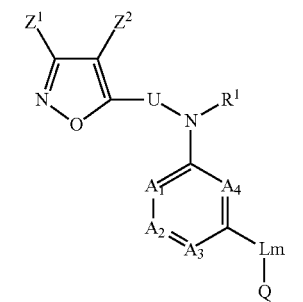

(It) 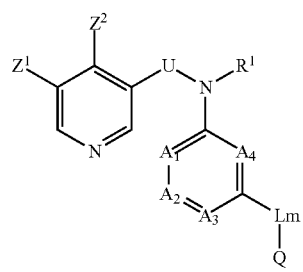

(Iu) 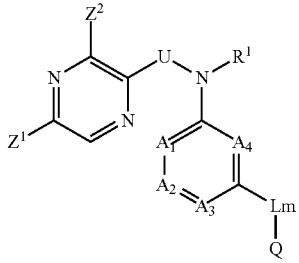

(Iv) 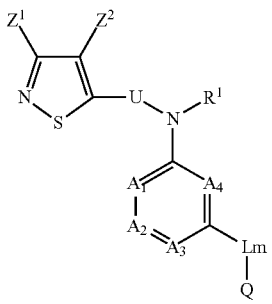

The compounds (Ia) to (Iv) are suitable for controlling animal pests in agriculture and in animal health.

The invention also provides the compounds (Ia), (Ib), (Ic), (Id), (Ie), (If), (Ig), (Ih), (Ii), (Ij), (Im), (In), (Io), (Ip), (Iq), (Ir), (Is), (It), (Iu), (Iv).

The compounds according to the invention can be present as geometric and/or as optically active isomers or corresponding isomer mixtures in varying composition depending on the nature of the substituents. These stereoisomers are, for example, enantiomers, diastereomers, atropisomers or geometric isomers. The invention thus encompasses pure stereoisomers and also any desired mixtures of these isomers.

The compounds according to the invention can, if appropriate, be present in various polymorphic forms or as a mixture of different polymorphic forms. Both the pure polymorphs and also the polymorph mixtures are provided by the invention can be used according to the invention.

Finally, it has been found that the novel compounds of the formula (I), coupled with good plant compatibility, favourable toxicity to warm-blooded animals and good environmental compatibility, are suitable in particular for controlling animal pests, in particular arthropods, insects, arachnids, helminths, nematodes and molluscs, which are encountered in agriculture, in forestry, in the protection of stored products and of materials, and also in the hygiene sector or in the area of animal health. The compounds according to the invention can likewise be used in the field of animal health, for example for controlling endo- and/or ectoparasites.

The compounds according to the invention can be used as compositions for controlling animals pests, preferably as crop protection compositions. They are effective against normally sensitive and resistant species and against all or some stages of development.

The compounds according to the invention can be converted to generally known formulations. Such formulations generally comprise from 0.01 to 98% by weight of active ingredient, preferably from 0.5 to 90% by weight.

The compounds according to the invention can be present in their standard commercial formulations and in application forms prepared from these formulations in a mixture with other active ingredients or synergists. Synergists are compounds through which the effect of the active ingredients is increased without the added synergist itself having to be actively effective.

The active ingredient content of the application forms prepared from the standard commercial formulations can vary within wide ranges. The active ingredient concentration of the application forms can be from 0.00000001 to 95% by weight of active ingredient, preferably from 0.00001 to 1% by weight.

The application takes place in a customary manner appropriate for the application forms.

According to the invention, all plants and plant parts can be treated. Here, plants are to be understood as meaning all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or non-protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits and seed material and also roots, tubers and rhizomes. The plant parts also include harvested material, and vegetative and generative propagation material, for example cuttings, tubers, rhizomes, offshoots and seed material.

Treatment according to the invention of the plants and plant parts with the active ingredients takes place directly or by allowing the compounds to act on their surroundings, habitat or storage space by the customary treatment methods, e.g. by immersion, spraying, evaporation, fogging, scattering, painting on, injecting and, in the case of propagation material, in particular in the case of seed material, also by applying one or more coats.

As already mentioned above, it is possible to treat all plants and their parts according to the invention. In a preferred embodiment wild plant species and plant cultivars, or those obtained by conventional biological breeding methods, such as hybridizing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof, are treated. The terms "parts" or "parts of plants" or "plant parts" have been explained above.

Particularly preferably, plants of the plant cultivars which are in each case commercially available or in use are treated according to the invention. Plant cultivars are to be understood as meaning plants having new properties ("traits") which have been cultivated by conventional breeding, by mutagenesis or by recombinant DNA techniques. These can be cultivars, bio- or genotypes.

In the field of animal health, i.e. in the field of veterinary medicine, the active ingredients according to the present invention are effective against animal parasites, in particular ectoparasites or endoparasites. The term endoparasites includes in particular helminths, such as cestodes, nematodes or trematodes, and protozoa, such as coccidia. Ectoparasites are typically and preferably arthropods, in particular insects such as flies (stinging and licking), parasitic fly larvae, lice, hair lice, bird lice, fleas and the like; or acarids, such as ticks, for example hard ticks or soft ticks, or mites, such as scab mites, harvest mites, bird mites and the like.

Moreover, it has been found that the compounds according to the invention exhibit a high insecticidal effect against insects which destroy industrial materials. In the present context, industrial materials are to be understood as meaning inanimate materials, such as, preferably, plastics, adhesives, sizes, papers and cardboards, leather, wood and processed wood products and coating compositions.

Furthermore, the compounds according to the invention can be used alone or in combinations with other active ingredients as antifouling compositions.

The active ingredients are also suitable for controlling animal pests in domestic, hygiene and stored-product protection, in particular insects, arachnids and mites, which are found in enclosed spaces such as, for example, dwellings, factory halls, offices, vehicle cabins and the like. For controlling these pests, they can be used alone or in combination with other active ingredients and auxiliaries in domestic insecticide products. They are effective against sensitive and resistant species and also against all developmental stages.

Plants are to be understood as meaning all plant species, plant cultivars and plant populations such as desired and undesired wild plants or crop plants. Crop plants to be treated according to the invention are plants which occur naturally, or those which have been obtained by conventional breeding and optimization methods or by biotechnological and genetic engineering methods or by combinations of the aforementioned methods. The term crop plant of course also encompasses transgenic plants.

Plant cultivars are understood as meaning plants with new properties, so-called traits, which have been cultivated either by conventional breeding, by mutagenesis or by recombinant DNA techniques or a combination thereof. These can be cultivars, strains, bio- and genotypes.

Plant parts are to be understood as meaning all parts and organs of the plants above and below the ground, such as shoot, leaf, flower and root, in particular leaves, needles, stalks, stems, flowers, fruit bodies, fruits, seeds, roots, tubers and rhizomes. Furthermore, the term plant parts encompasses harvested material and also vegetative and generative propagation material, such as, for example, cuttings, tubers, rhizomes, offshoots and seeds or seed material.

In one embodiment of the invention, plant species and plant cultivars which are naturally occurring or have been obtained by conventional breeding and optimization methods (e.g. hybridization or protoplast fusion), and plant parts thereof, are treated.

In a further embodiment according to the invention, transgenic plants which have been obtained by genetic engineering methods, optionally in combination with conventional methods, and parts thereof, are treated.

The treatment method according to the invention is preferably used on genetically modified organisms, such as, for example, plants or plant parts.

Genetically modified plants, so-called transgenic plants, are plants in which a heterologous gene has been stably integrated into the genome.

The term "heterologous gene" essentially means a gene which is provided or assembled outside of the plant and, when introduced into the nuclear, chloroplastic or hypochondrial genome, gives the transformed plant new or improved agronomic or other properties by expressing a protein or polypeptide of interest or by downregulating or silencing other gene(s) which is/are present in the plant (using, for example, antisense technology, cosuppression technology or RNAi technology [RNA interference]). A heterologous gene which is present in the genome is likewise called a transgene. A transgene that is defined by its specific presence in the plant genome is called a transformation or transgenic event.

Depending on the plant species or plant cultivars, their location and their growth conditions (soils, climate, vegetation period, diet), the treatment according to the invention may also lead to superadditive ("synergistic") effects. Thus, for example, the following effects, which exceed the effects which are actually to be expected, are possible: reduced application rates and/or extended activity spectrum and/or increased effectiveness of the active ingredients and compositions which can be used according to the invention, better plant growth, increased tolerance to high or low temperatures, increased tolerance to dryness or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration in the fruits, better storability and/or processability of the harvested products.

At certain application rates, the active ingredient combinations according to the invention may also have a strengthening effect in plants. They are therefore suitable for mobilizing the defence system of the plant against attack by undesired phytopathogenic fungi and/or microorganisms and/or viruses. This may, if appropriate, be one of the reasons for the increased effectiveness of the combinations according to the invention, for example in respect of fungi. Plant-strengthening (resistance-inducing) substances are to be understood as meaning in the present context also those substances or substance combinations which are capable of stimulating the defence system of plants in such a way that, when subsequently inoculated with undesired phytopathogenic fungi and/or microorganisms and/or viruses, the treated plants have a considerable degree of resistance to these undesired phytopathogenic fungi and/or microorganisms and/or viruses. In the present case, undesired phytopathogenic fungi and/or microorganisms and/or viruses are to be understood as meaning phytopathogenic fungi, bacteria and viruses. The substances according to the invention can therefore be used for protecting plants against attack by the mentioned pathogens within a certain period of time after treatment. The period of time over which a protective effect is achieved extends generally from 1 to 10 days, preferably 1 to 7 days, following treatment of the plants with the active ingredients.

Plants which are also preferably treated according to the invention are resistant to one or more biotic stress factors, i.e. these plants have an improved defence against animal and microbial pests, such as nematodes, insects, mites, phytopathogenic fungi, bacteria, viruses and/or viroids.

Besides the aforementioned plants and plant cultivars, according to the invention, it is also possible to treat those which are resistant to one or more abiotic stress factors.

Abiotic stress conditions can include, for example, drought, cold temperature conditions, heat conditions, osmotic stress, flooding, increased soil salt content, increased mineral exposure, ozone conditions, bright light conditions, limited availability of nitrogen nutrients, limited availability of phosphorus nutrients or shade avoidance.

Plants and plant cultivars which may likewise be treated according to the invention are those plants characterized by enhanced yield characteristics. Enhanced yield in said plants can be the result, for example, of improved plant physiology, improved plant growth and improved plant development, such as water use efficiency, water retention efficiency, improved nitrogen use, enhanced carbon assimilation, improved photosynthesis, increased germinating power and accelerated maturation. The yield can moreover be influenced by improving plant architecture (under stress and nonstress conditions), including early flowering, flowering control for the production of hybrid seed material, seedling vigour, plant size, internode number and distance, root growth, seed size, fruit size, pod size, pod or ear number, number of seeds per shoot or ear, seed mass, enhanced seed filling, reduced seed dispersal, reduced pod dehiscence and lodging resistance. Further yield features include seed composition such as carbohydrate content, protein content, oil content and oil composition, nutritional value, reduction in antinutritional compounds, improved processability and better storability.

Plants which can be treated according to the invention are hybrid plants that already express the properties of heterosis or the hybrid effect, which results in generally higher yield, greater vigour, better health and better resistance to biotic and abiotic stress factors. Such plants are typically produced by crossing an inbred male-sterile parent line (the female hybridization partner) with another inbred pollen-fertile parent line (the male hybridization partner). The hybrid seed material is typically harvested from the male-sterile plants and sold to growers. Male-sterile plants can sometimes (e.g. in the case of corn) be produced by detasseling (i.e. mechanically removing the male reproductive organs or the male flowers); however, it is more usual for the male sterility to be based on genetic determinants in the plant genome. In this case, and especially when the desired product to be harvested from the hybrid plants is seeds, it is typically favourable to ensure that the pollen fertility in hybrid plants which contain the genetic determinants responsible for the male sterility, is fully restored. This can be accomplished by ensuring that the male hybridization partners have corresponding fertility restorer genes which are capable of restoring the male fertility in hybrid plants that contain the genetic determinants responsible for the male sterility. Genetic determinants for male sterility can be localized in the cytoplasm. Examples of cytoplasmic male sterility (CMS) has been described, for example, for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396, where for example, a ribonuclease such as barnase is selectively expressed in the tapetum cells in the stamens. Fertility can then be restored by expression in the tapetum cells of a ribonuclease inhibitor such as barstar.

Plants or plant cultivars (which are obtained using plant biotechnology methods, such as genetic engineering), which can be treated according to the invention are herbicide-tolerant plants, i.e. plants made tolerant to one or more given herbicides. Such plants can be obtained either by genetic transformation or by selection of plants containing a mutation imparting such herbicide tolerance.

Herbicide-tolerant plants are, for example, glyphosate-tolerant plants, i.e. plants made tolerant to the herbicide glyphosate or salts thereof. Thus, for example, glyphosate-tolerant plants can be obtained by transforming the plant with a gene encoding for the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes which encode a petunia EPSPS, a tomato EPSPS or an *Eleusine* EPSPS. It may also be a mutated EPSPS. Glyphosate-tolerant plants can also be obtained by expressing a gene that encodes a glyphosate oxidereductase enzyme. Glyphosate-tolerant plants can also be obtained by expressing a gene that encodes a glyphosate acetyl transferase enzyme. Glyphosate-tolerant plants can also be obtained by selecting plants which naturally occurring mutations of the aforementioned genes.

Other herbicide-resistant plants are, for example, plants which have been rendered tolerant to herbicides which inhibit the enzyme glutamine synthase, such as bialaphos, phosphinothricin or glufosinate. Such plants can be obtained by expressing an enzyme which detoxifies the herbicide or a mutant of the enzyme glutamine synthase that is resistant to inhibition. One such effective detoxifying enzyme is, for example, an enzyme encoding a phosphinothricin acetyl transferase (such as, for example, the bar or pat protein from *Streptomyces* species). Plants which express an exogenous phosphinothricin acetyl transferase have been described.

Further herbicide-tolerant plants are also plants which have been rendered tolerant to the herbicides which inhibit the enzyme hydroxyphenylpyruvatedioxygenase (HPPD). Hydroxyphenylpyruvate-dioxygenases are enzymes which catalyse the reaction in which para-hydroxyphenylpyruvate (HPP) is converted to homogentisate. Plants which are tolerant to HPPD inhibitors can be transformed with a gene which encodes a naturally occurring resistant HPPD enzyme or a gene which encodes a mutated HPPD enzyme. Tolerance to HPPD inhibitors can also be attained by transforming plants with genes encoding certain enzymes which permit the formation of homogentisate despite inhibition of the native HPPD enzyme by the HPPD inhibitor. Tolerance of plants to HPPD inhibitors can also be improved by transforming plants with a gene encoding a prephenate dehydrogenase enzyme in addition to a gene encoding an HPPD-tolerant enzyme.

Further herbicide-resistant plants are plants which have been rendered tolerant to acetolactate synthase (ALS) inhibitors. Known ALS inhibitors include, for example, sulphonylurea, imidazolinone, triazolopyrimidines, pyrimidinyloxy(thio)benzoates and/or sulphonylaminocarbonylthiazolinone herbicides. It is known that different mutations in the ALS enzyme (also known as acetohydroxy acid synthase, AHAS) confer tolerance to different herbicides and groups of herbicides. The production of sulphonylurea-tolerant plants and imidazolinone-tolerant plants is described in the international publication WO 1996/033270. Further sulphonylurea- and imidazolinone-tolerant plants are also described in, for example, WO 2007/024782.

Further plants which are tolerant to imidazolinone and/or sulphonylurea can be obtained by induced mutagenesis, selection in cell cultures in the presence of the herbicide or by mutation breeding.

Plants or plant cultivars (which have been obtained by plant biotechnology methods, such as genetic engineering) which can likewise be treated according to the invention are insect-resistant transgenic plants, i.e. plants rendered resistant to attack by certain target insects. Such plants can be obtained by genetic transformation or by selection of plants containing a mutation which imparts such insect resistance.

In the present context, the term "insect-resistant transgenic plant" encompasses any plant containing at least one transgene which includes a coding sequence encoding the following:

1) an insecticidal crystal protein from *Bacillus thuringiensis* or an insecticidal portion thereof, such as the insecticidal crystal proteins which are described online at: http://www.lifesci.sussex.ac.uk/Home/Neil_Crickmore/Bt/, has been listed, or insecticidal portions thereof, e.g. proteins of the Cry protein classes Cry1Ab, Cry1Ac, Cry1F, Cry2Ab, Cry3Ae or Cry3Bb or insecticidal portions thereof;
2) a crystal protein comprising *Bacillus thuringiensis* or a portion thereof which has an insecticidal effect in the presence of a second crystal protein other than *Bacillus thuringiensis* or a portion thereof, such as the binary toxin which consists of the crystal proteins Cy34 and Cy35; or
3) an insecticidal hybrid protein which comprises portions of two different insecticidal crystal proteins from *Bacillus thuringiensis*, such as, for example, a hybrid of the proteins from 1) above or a hybrid of the proteins from 2) above, e.g. the protein Cry1A.105, which is produced by the maize event MON98034 (WO 2007/027777); or
4) a protein according to any one of points 1) to 3) above wherein some, in particular 1 to 10, amino acids have been replaced by another amino acid in order to achieve higher insecticidal effectiveness in respect of a target insect species and/or in order to expand the spectrum of the corresponding target insect species and/or because of changes which have been induced in the encoding DNA during cloning or transformation, such as the Cry3Bb1 protein in the maize event MON863 or MON88017 or the Cry3A protein in the maize event MIR 604;
5) an insecticidal secreted protein from *Bacillus thuringiensis* or *Bacillus cereus* or an insecticidal portion thereof, such as the vegetative insecticidal proteins (VIP), which are listed at http://www.lifesci.sussex.ac.uk/Home/Neil_Crickmore/Bt/vip.html e.g. proteins from the VIP3Aa protein class; or
6) a secreted protein from *Bacillus thuringiensis* or *Bacillus cereus*, which has an insecticidal effect in the presence of a second secreted protein from *Bacillus thuringiensis* or *B. cereus*, such as the binary toxin which consists of the proteins VIP1A and VIP2A;
7) an insecticidal hybrid protein comprising portions from different secreted proteins from *Bacillus thuringiensis* or *Bacillus cereus*, such as a hybrid of the proteins in 1) or a hybrid of the proteins in 2) above; or
8) a protein according to one of points 1) to 3) above, in which some, in particular 1 to 10, amino acids have been replaced by another amino acid in order to obtain higher insecticidal effectiveness in respect of a target insect species, and/or in order to expand the spectrum of the corresponding target insect species, and/or because of charges which have been induced in the encoding DNA during cloning or transformation (the encoding for an insecticidal protein being retained), such as the VIP3Aa protein in the cotton event COT 102.

The insect-resistant transgenic plants in the present context naturally also include those plants comprising a combination of genes encoding the proteins of one of the aforementioned classes 1 to 8. In one embodiment, an insect-resistant plant contains more than one transgene encoding a protein of any of the aforementioned classes 1 to 8 in order to expand the spectrum of the corresponding target insect species or in order to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which can likewise be treated according to the invention are tolerant to abiotic stress factors. Such plants can be obtained by genetic transformation or by selection of plants containing a mutation which imparts such stress resistance. Particularly useful plants with stress tolerance include the following:

a. plants which contain a transgene which is able to reduce the expression and/or activity of the gene for the poly (ADP-ribose)polymerase (PARP) in the plant cells or plants.

b. plants which contain a stress tolerance-enhancing transgene which is able to reduce the expression and/or activity of the PARG encoding genes of the plants or plant cells;
c. plants which contain a stress tolerance-enhancing transgene encoding a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which can likewise be treated according to the invention have an altered amount, quality and/or storability of the harvested product and/or modified properties of certain constituents of the harvested products, such as, for example:
1) Transgenic plants which synthesize a modified starch which, in respect of its chemicophysical properties, in particular the amylose content or the amylose/amylopectin ratio, the degree of branching, average chain length, the side chain distribution, the viscosity behaviour, the gelling strength, the starch grain size and/or starch grain morphology, is altered compared to the synthesized starch in wild type plant cells or plants, such that this modified starch is better suited for certain applications.
2) Transgenic plants which synthesize non-starch carbohydrate polymers or non-starch carbohydrate polymers with altered properties compared to wild type plants without genetic modification. Examples are plants which produce polyfructose, in particular of the inulin and levan type, plants which produce alpha-1,4-glucans, plants which produce alpha-1,6-branched alpha-1,4-glucans and plants which produce alternan.
3) Transgenic plants which produce hyaluronan.

Plants or plant cultivars (which have been obtained by plant biotechnology methods such as genetic engineering) which can likewise be treated according to the invention are plants such as cotton plants with altered fibre properties. Such plants can be obtained by genetic transformation or by selection of plants containing a mutation imparting such modified fibre properties and include:
a) plants such as cotton plants, which contain a modified form of cellulose synthase genes;
b) plants such as cotton plants which contain a modified form of rsw2 or rsw3 homologous nucleic acids;
c) plants such as cotton plants with an increased expression of sucrose phosphate synthase;
d) plants such as cotton plants with an increased expression of sucrose synthase;
e) plants such as cotton plants in which the time point of the plasmodesmatal gating at the base of the fibre cell is altered, e.g. through downregulation of fibre-selective β-1,3-glucanase;
f) plants such as cotton plants with fibres with altered reactivity, e.g. through expression of the N-acetylglucosaminetransferase gene including nodC, and chitin synthase genes.

Plants or plant cultivars (which have been obtained by plant biotechnology methods such as genetic engineering) which can likewise be treated according to the invention are plants such as oilseed rape or related *brassica* plants having modified properties of the oil composition. Such plants can be obtained by genetic transformation or by selection of plants containing a mutation which imparts such modified oil properties and include:

a) plants such as oilseed rape plants which produce oil with a high oleic acid content;
b) plants such as oilseed rape plants which produce oil with a low linolenic acid content;
c) plants such as oilseed rape plants which produce oil with a low saturated fatty acid content.

Particularly useful transgenic plants which can be treated according to the invention are plants with one or more genes encoding one or more toxins are the transgenic plants which are supplied under the following trade names. YIELD GARD® (for example maize, cotton, soybeans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Herbicide-tolerant plants which may be mentioned are, for example, maize varieties, cotton varieties and soybean varieties which are supplied under the following trade names: Roundup Ready® (glyphosate tolerance, for example maize, cotton, soybeans), Liberty Link® (phosphinothricin tolerance, for example oilseed rape), IMI® (imidazolinone tolerance) and SCS® (sulphonylurea tolerance), for example maize. Herbicide-resistant plants (plants traditionally cultivated for herbicide tolerance) which may be mentioned include the varieties supplied under the name Clearfield® (for example maize).

Particularly useful transgenic plants which can be treated according to the invention are plants which contain transformation events or a combination of transformation events and which are listed, for example, in the databases of various national or regional authorities (see, for example, http://gmoinfojrc.it/gmp_browse.aspx and http://www.agbios.com/dbase.php).

The treatment according to the invention of the plants and plant parts with the active ingredient combinations is carried out directly or through action on their environment, habitat or storage space by the customary treatment methods, for example by dipping, spraying, vaporizing, misting, scattering, painting on and, in the case of propagation material, in particular in the case of seed material, also by coating with one or more layers.

In particular, the mixtures according to the invention are suitable for treating seed material. In this connection, the combinations according to the invention specified above as preferred or particularly preferred are preferably to be mentioned. Thus, a large part of the damage to crop plants which is caused by pests occurs as early as when the seed material is infested during storage and after the seed material is introduced into the soil, as well as during and directly after germination of the plants. This phase is particularly critical since the roots and shoots of the growing plant are particularly sensitive and even minor damage can lead to the death of the whole plant. Protecting the seed material and the germinating plant through the use of suitable compositions is therefore of particularly great interest.

The control of pests by treating the seed material of plants has been known for a long time and is the subject of continual improvements. Nevertheless, the treatment of seed material entails a series of problems which cannot always be solved satisfactorily. Thus, it is desirable to develop methods for protecting the seed material and the germinating plant which dispense with the additional application of crop protection products after planting or after emergence of the plants. It is furthermore desirable to optimize the amount of active ingredient used in such a way as to provide optimum protection for the seed material and the germinating plant from attack by pests, but without damaging the plant itself by the active ingredient used. In particular, methods for the treatment of seed material should also take into consideration the intrinsic insecticidal properties of transgenic plants in order to achieve optimum protection of the seed material and of the germinating plant with a minimum of crop protection products being used.

The present invention therefore relates in particular also to a method for the protection of seed material and germinating plants from attack by pests, by treating the seed material with a composition according to the invention. The invention likewise relates to the use of the compositions according to the invention for the treatment of seed material for protecting the seed material and the plants resulting therefrom from pests. Furthermore, the invention relates to seed material which has been treated with a composition according to the invention for protection against pests.

It is one of the advantages of the present invention that the particular systemic properties of the compositions according to the invention mean that treatment of the seed material with these compositions not only protects the seed material itself, but also the resulting plants after emergence, from pests. In this manner, the immediate treatment of the crop at the time of sowing or shortly thereafter can be dispensed with.

A further advantage is the synergistic increase in the insecticidal effectiveness of the compositions according to the invention compared with the insecticidal individual active ingredient, which exceeds the expected effectiveness of the two active ingredients applied individually. The synergistic increase in the fungicidal effectiveness of the compositions according to the invention compared with the fungicidal individual active ingredient, which exceeds the expected effectiveness of the active ingredient applied individually, is also advantageous. This makes it possible to optimize the amount of active ingredients used.

It is likewise considered advantageous that the mixtures according to the invention can also be used in particular in transgenic seed material, in which case the plants resulting from this seed material are capable of expressing a protein directed against pests. By treating such seed material with the compositions according to the invention, certain pests can be controlled merely through the expression of the, for example, insecticidal protein, and additionally through the compositions according to the invention are protected against damage.

The compositions according to the invention are suitable for protecting seed material of any plant variety as already mentioned above which is used in agriculture, in a greenhouse, in forests or in horticulture. In particular, it is seed material from maize, peanut, canola, oilseed rape, poppy, soybean, cotton, beet (e.g. sugarbeet and fodder beet), rice, millet, wheat, barley, oats, rye, sunflower, tobacco, potatoes or vegetables (e.g. tomatoes, cabbage plants). The compositions according to the invention are likewise suitable for treating the seed material of fruit plants and vegetables as already specified above. The treatment of the seed material of maize, soybeans, cotton, wheat and canola or oilseed rape is of particular importance.

As already mentioned above, the treatment of transgenic seed material with a composition according to the invention is also of particular importance. In this connection, the seed material is that of plants which generally comprise at least one heterologous gene which controls the expression of a polypeptide with in particular insecticidal properties. In this connection, the heterologous genes in transgenic seed material can originate from microorganisms such as *Bacillus, Rhizobium, Pseudomonas, Serratia, Trichoderma, Clavibacter, Glomus* or *Gliocladium*. The present invention is particularly suitable for the treatment of transgenic seed material which comprises at least one heterologous gene originating from *Bacillus* sp. and whose gene product exhibits effectiveness against the European corn borer and/or the corn root worm. Here, it is particularly preferably a heterologous gene which originates from *Bacillus thuringiensis*.

Within the context of the present invention, the composition according to the invention is applied to the seed material alone or in a suitable formulation. Preferably, the seed material is treated in a state in which it is stable enough to avoid damage during treatment. In general, the seed material can be treated at any time between harvest and sowing. The seed material usually used has been separated from the plant and freed from cobs, shells, stalks, coats, hairs or fruit flesh.

When treating the seed material, care must generally be taken that the amount of the composition according to the invention applied to the seed material and/or further additives is selected in such a way that the termination of the seed material is not adversely affected, or that the resulting plant is not damaged. This must be ensured particularly in the case of active ingredients which can exhibit phytotoxic effects at certain application rates.

Moreover, the compounds according to the invention can be used for controlling a large number of different pests including, for example, harmful sucking insects, biting insects and other plant-parasitic pests, stored grain pests, pests which destroy industrial materials, and hygiene pests including parasites in the field of animal health and can be used for their control, like, for example, their eradication and extermination. The present invention therefore also encompasses a method for controlling pests.

In the field of animal health, i.e. in the field of veterinary medicine, the active ingredients according to the present invention are effective against animal parasites, in particular ectoparasites or endoparasites. The term endoparasites includes in particular helminths, such as cestodes, nematodes or trematodes, and protozoa, such as coccidia. Ectoparasites are typically and preferably arthropods, in particular insects such as fleas (stinging and licking), parasitic fly larvae, lice, hair lice, bird lice, fleas and the like; or acarids, such as ticks, for example hard ticks or soft ticks, or mites, such as scab mites, harvest mites, bird mites and the like.

These parasites include:

From the order of the Anoplurida, e.g. *Haematopinus* spp., *Linognathus* spp., *Pediculus* spp., *Phtirus* spp., *Solenopotes* spp.; specific examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;*

From the order of the Mallophagida and the suborders Amblycerina and Ischnocerina, e.g. *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; specific examples are: *Bovicola bovis, Bovicola ovis, Bovicola limbata, Damalina bovis, Trichodectes canis, Felicola subrostratus, Bovicola caprae, Lepikentron ovis, Werneckiella equi;*

From the order of the Diptera and the suborders Nematocerina and Brachycerina, e.g. *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calli-*

*phora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; specific examples are: *Aedes aegypti*, *Aedes albopictus*, *Aedes taeniorhynchus*, *Anopheles gambiae*, *Anopheles maculipennis*, *Calliphora erythrocephala*, *Chrysozona pluvialis*, *Culex quinquefasciatus*, *Culex pipiens*, *Culex tarsalis*, *Fannia canicularis*, *Sarcophaga carnaria*, *Stomoxys* calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricomis, Gasterophilus pecorum, Braula coeca;

From the order of the Siphonapterida, e.g. *Pulex* spp., *Ctenocephalides* spp., *Tunga* spp., *Xenopsylla* spp., *Ceratophyllus* spp.; specific examples are: *Ctenocephalides canis*, *Ctenocephalides felis*, *Pulex irritans*, *Tunga penetrans*, *Xenopsylla cheopis*;

From the order of the Heteropterida, e.g. *Cimex* spp., *Triatoma* spp., *Rhodnius* spp., *Panstrongylus* spp.;

From the order of the Blattarida, e.g. *Blatta orientalis*, *Periplaneta americana*, *Blattela germanica*, *Supella* spp. (e.g. *Suppella longipalpa*);

From the subclass of the Acari (Acarina) and the orders of the Meta- and Mesostigmata, e.g. *Argas* spp., *Ornithodorus* spp., *Otobius* spp., *Ixodes* spp., *Amblyomma* spp., *Rhipicephalus* (*Boophilus*) spp., *Dermacentor* spp., *Haemaphysalis* spp., *Hyalomma* spp., *Dermanyssus* spp., *Rhipicephalus* spp. (the original genus of multi-host ticks), *Ornithonyssus* spp., *Pneumonyssus* spp., *Raillietia* spp., *Pneumonyssus* spp., *Sternostoma* spp., *Varroa* spp., *Acarapis* spp.; specific examples are: *Argas persicus*, *Argas reflexus*, *Ornithodorus moubata*, *Otobius megnini*, *Rhipicephalus* (*Boophilus*) *microplus*, *Rhipicephalus* (*Boophilus*) *decoloratus*, *Rhipicephalus* (*Boophilus*) *annulatus*, *Rhipicephalus* (*Boophilus*) *calceratus*, *Hyalomma anatolicum*, *Hyalomma aegypticum*, *Hyalomma marginatum*, *Hyalomma transiens*, *Rhipicephalus evertsi*, *Ixodes ricinus*, *Ixodes hexagons*, *Ixodes canisuga*, *Ixodes pilosus*, *Ixodes rubicundus*, *Ixodes scapularis*, *Ixodes holocyclus*, *Haemaphysalis concinna*, *Haemaphysalis punctata*, *Haemaphysalis cinnabarina*, *Haemaphysalis otophila*, *Haemaphysalis leachi*, *Haemaphysalis longicorni*, *Dermacentor marginatus*, *Dermacentor reticulatus*, *Dermacentor pictus*, *Dermacentor albipictus*, *Dermacentor andersoni*, *Dermacentor variabilis*, *Hyalomma mauritanicum*, *Rhipicephalus sanguineus*, *Rhipicephalus bursa*, *Rhipicephalus appendiculatus*, *Rhipicephalus capensis*, *Rhipicephalus turanicus*, *Rhipicephalus zambeziensis*, *Amblyomma americanum*, *Amblyomma variegatum*, *Amblyomma maculatum*, *Amblyomma hebraeum*, *Amblyomma cajennense*, *Dermanyssus gallinae*, *Ornithonyssus bursa*, *Ornithonyssus sylviarum*, *Varroa jacobsoni*;

From the order of the Actinedida (Prostigmata) and Acaridida (Astigmata), e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; specific examples are: *Cheyletiella yasguri*, *Cheyletiella blakei*, *Demodex cards*, *Demodex bovis*, *Demodex ovis*, *Demodex caprae*, *Demodex equi*, *Demodex caballi*, *Demodex suis*, *Neotrombicula autumnalis*, *Neotrombicula desaleri*, *Neoschöngastia xerothermobia*, *Trombicula akamushi*, *Otodectes cynotis*, *Notoedres cati*, *Sarcoptis canis*, *Sarcoptes bovis*, *Sarcoptes ovis*, *Sarcoptes rupicaprae* (=*S. caprae*), *Sarcoptes equi*, *Sarcoptes suis*, *Psoroptes ovis*, *Psoroptes cuniculi*, *Psoroptes equi*, *Chorioptes bovis*, *Psoergates ovis*, *Pneumonyssoidic mange*, *Pneumonyssoides caninum*, *Acarapis woodi*.

The active ingredients according to the invention are also suitable for controlling arthropods, helminths and protozoa which attack animals. The animals include agricultural livestock such as, for example, cattle, sheep, goats, horses, pigs, donkeys, camels, buffaloes, rabbits, chickens, turkeys, ducks, geese, cultured fish, honeybees. Moreover, the animals include domestic animals—which are also referred to as companion animals—such as, for example, dogs, cats, cage birds, aquarium fish and so-called experimental animals such as, for example, hamsters, guinea pigs, rats and mice.

By controlling these arthropods, helminths and/or protozoa, the intention is to reduce deaths and improve performance (in the case of meat, milk, wool, hides, eggs, honey etc.) and the health of the host animal, so that more economical and simpler animal keeping is made possible through the usde of the active ingredients according to the invention.

For example, it is thus desirable to prevent or interrupt the uptake of blood by the parasites from the host (where applicable). Moreover, controlling the parasites can contribute to preventing the transmission of infectious substances.

The term "controlling" as used herein with regard to the field of animal health means that the active ingredients are effective in reducing the incidence of the respective parasite in an animal infected with such parasites to innocuous levels. More specifically, "controlling", as used herein, means that the active ingredient kills the respective parasite, inhibits its growth or inhibits its proliferation.

In general, the active ingredients according to the invention can be applied directly when used for the treatment of animals. They are preferably applied in the form of pharmaceutical compositions which may contain pharmaceutically acceptable excipients and/or auxiliaries known in the prior art.

In the field of animal health and in animal keeping, the active ingredients are applied (=administered) in a known manner by enteral administration in the form of, for example, tablets, capsules, drinks, drenches, granules, pastes, boli, the feed-through method, suppositories, by parenteral administration, such as, for example, by injections (intramuscular, subcutaneous, intravenous, intraperitoneal and the like), implants, by nasal application, by dermal application in the form of, for example, dipping or bathing, spraying, pouring-on and spotting-on, washing, dusting, and with the help of active-ingredient-containing shaped articles, such as collars, ear tags, tail tags, limb bands, halters, marking devices and the like. The active ingredients can be formulated as shampoo or as suitable formulations that can be used in aerosols or unpressurized sprays, e.g. pump sprays and atomizer sprays.

When used for livestock, poultry, domestic animals etc., the active ingredients according to the invention can be applied as formulations (for example powders, wettable powders ["WP"], emulsions, emulsifiable concentrates ["EC"], flowable compositions, homogeneous solutions and suspension concentrates ["SC"]) which comprise the active ingredients in an amount of from 1 to 80% by weight, either directly or after dilution (e.g. 100- to 10 000-fold dilution), or they can be used as a chemical bath.

When used in the field of animal health, the active ingredients according to the invention can be used in combination with suitable synergists or other active ingredients, such as, for example, acaricides, insecticides, anthelmintics, anti-protozoal compositions.

The compounds according to the invention can be prepared by customary methods known to the person skilled in the art.

Reaction scheme 1 depicts the general synthesis process A for the compounds (I-1) according to the invention.

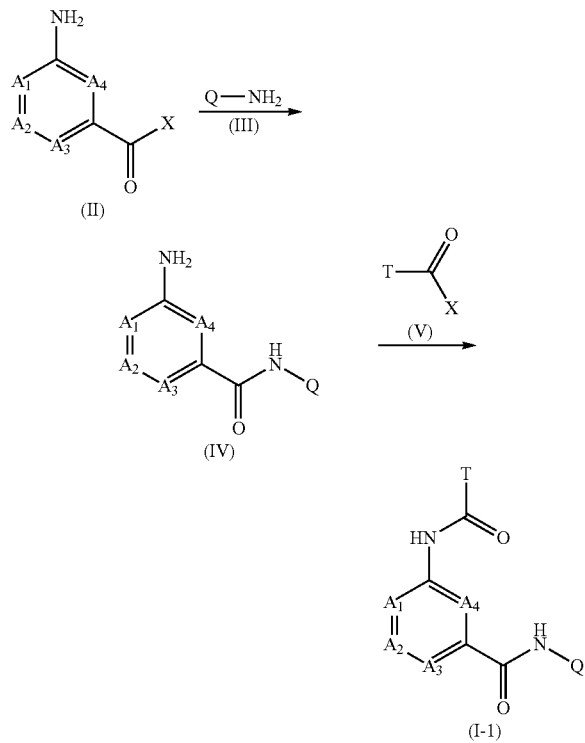

The radicals $A_1$-$A_4$, Q and T have the meanings described above. X is any desired leaving group.

Compounds according to the invention of the type (I-1) can be synthesized by reacting amines of the general structure (IV) with activated carboxylic acid derivatives of the general structure (V). The reaction can be carried out with or without solvents. In this step, a suitable base can likewise be used.

In general, it is advantageous to carry out the first reaction step of the synthesis method A according to the invention, if appropriate, in the presence of a suitable diluent and, if appropriate, in the presence of suitable basic reaction auxiliary.

Diluents are advantageously used in an amount such that the reaction mixture remains readily stirrable throughout the entire process.

The solvent which may be used is any solvent which does not adversely affect the reaction, such as, for example, water. Of suitability are aromatic hydrocarbons such as benzene or toluene; halogenated hydrocarbons such as dichloromethane, chloroform or tetrachloromethane, open-chain or cyclic ethers such as diethyl ether, dioxane, tetrahydrofuran or 1,2-dimethoxyethane; esters such as ethyl acetate and butyl acetate; ketones such as, for example, acetone, methyl isobutyl ketone and cyclohexanone; amides such as dimethylformamide and dimethylacetamide; nitriles such as acetonitrile; and other inert solvents such as 1,3-dimethyl-2-imidazolidinone; the solvents can be used alone or in combination of two or more.

The base used can be an organic base such as triethylamine, ethyldiisopropylamine, tri-n-butylamine, pyridine and 4-dimethylaminopyridine; furthermore, the following bases can, for example, be used alkali metal hydroxides, such as, for example, sodium hydroxide and potassium hydroxide; carbonates such as sodium hydrogencarbonate and potassium carbonate; phosphates such as dipotassium hydrogenphosphate and disodium phosphate; alkali metal hydrides, such as sodium hydride; alkali metal alcoholates, such as sodium methanolate and sodium ethanolate. These bases can be used in ratios of from 0.01 to 5.0 mole equivalents based on (IV) and (V).

Furthermore, silver(I) cyanide can also be used as base and activator [Journal of Organic Chemistry. 1992, 57, 4394-4400; Journal of Medicina Chemistry 1992, 35, 3905-3918; Journal of Organic Chemistry 2003, 68, 1843-1851].

The suitable reaction temperature is in the range from −20° C. up to the boiling point of the particular solvent and the reaction time is between a few minutes and 96 hours depending on the choice of reactants, solvents and reaction temperature.

Cyclic carboxylic acid halides, as are represented by the general structure (V), can be prepared simply by reacting a heterocyclic carboxylic acid with halogenating reagents such as thionyl chloride, thionyl bromide, phosphoryl chloride, oxalyl chloride, phosphorus trichloride, etc. [Houben-Weyl, 1952, vol. VIII, p. 463 ff.]

The synthesis of carboxamides represented by the formula (I-1) can, however, also be carried out using coupling reagents such as dicyclohexylcarbodiimide and additives such as 1-hydroxybenzotriazole [Chem. Ber. 1970, 788]. It is also possible to use coupling reagents such as 1-ethyl-3-(3-dimethylaminopropyl)carbodiimide, 1,1'-carbonyl-1H-imidazole and similar compounds.

Coupling reagents which are used for carrying out the synthesis process are all those which are suitable for the preparation of an ester or amide bond (cf. e.g. Bodansky et al., Peptide Synthesis, 2nd ed., Wiley & Sons, New York, 1976; Gross, Meienhofer, The Peptide: Analysis, Synthesis, Biology (Academic Press, New York, 1979).

Furthermore, mixed anhydrides can also be used for the synthesis of (I-1) [J. Am. Chem. Soc 1967, 5012]. In this process it is possible to use various chloroformates, such as, for example, isobutyl chloroformate, isopropyl chloroformate. Similarly, diethylacetyl chloride, trimethylacetyl chloride and the like can be used for this.

Compounds of the general structure (IV) can be synthesized by reacting an amine of the general structure (III) with activated carboxylic acid derivatives of the general structure (II). In this connection, the same conditions apply for the choice of solvent, the reaction conditions, the reaction time and the reagents as for the synthesis of (I-1) described above.

Reaction scheme 2 shows the general synthesis process B for the synthesis of the compounds (I-1) according to the invention.

Reaction scheme 2

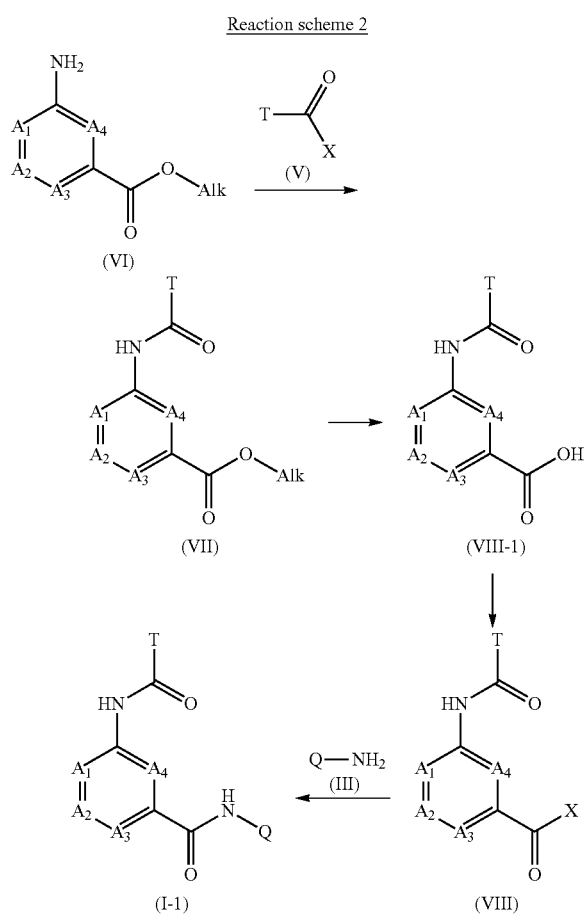

The radicals $A_1$-$A_4$, Q and T have the meanings described above. X is any desired leaving group and Alk is an alkyl radical, such as, for example, methyl or ethyl.

Compounds according to the invention of the type (I-1) can be synthesized by reacting an amine of the general structure (III) with activated carboxylic acid derivatives of the general structure (VIII). Here, the same conditions apply for the choice of solvent, the reaction conditions, the reaction time and the reagents as for the reaction of (IV) and (V) to give (I-1) described in synthesis process A.

The synthesis of activated carboxylic acid derivatives of the general structure (VIII) can take place by a two-stage synthesis from the corresponding carboxylic acid esters of the general structure (VII). In the first step, the carboxylic acid function (O-Alk), protected in the form of an ester, of the compound (VII) is deprotected depending on the alkyl ester used with a suitable reagent [Greene's protective groups in organic synthesis, 4th edition, P. G. M. Wuts, T. W. Greene, John Wiley & Sons, Inc., Hoboken, N.J.] and the resulting free hydroxy group of the acid function of (VIII-1) is converted to a leaving group X. In this connection, the same processes can be used as have already been described in the synthesis of (V). Compounds of the general structure (VII) can be synthesized by reacting amines of the general structure (VI) with activated carboxylic acid derivatives of the general structure (V). Here, the same conditions apply for the selection of the solvent, the reaction conditions, the reaction time, and the reagents as for the synthesis of (I-1) described in synthesis process A.

If the compounds (I) according to the invention are compounds of the general structures (I-2) and (I-3), the synthesis can take place via synthesis process C (reaction scheme 3).

Reaction scheme 3

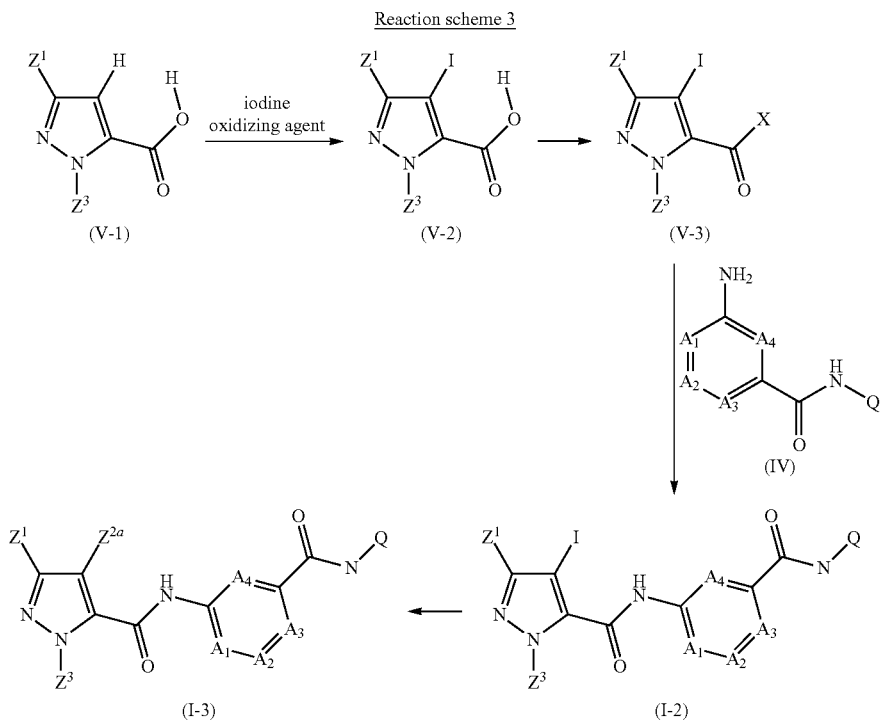

The radicals $Z^1$, $Z^3$ and Q have the meanings described above. $Z^{2a}$ is optionally substituted aryl or heteroaryl, optionally substituted alkenyl or alkynyl or perfluoroalkyl, X is any desired leaving group.

Compounds according to the invention of the general structure (I-3) can be synthesized from the compounds according to the invention of the general structure (I-2). Here, the iodine atom in the compounds of type (I-2) is replaced, via metal mediation, inter alia by perfluoroalkyl [PCT Int. Appl., 2005095351], aryl [Journal of Organic Chemistry 2007, 72(9), 3589-3591; Synthesis 1997, (5), 563-566; Heterocycles 2006, 68(11), 2247-2252] and alkenyl [PCT Int. Appl., 2005060749; Organic Process Research & Development 2005, 9(5), 694-696; Chemical & Pharmaceutical Bulletin 2005, 53(2), 153-163; Journal of Organic Chemistry 1986, 51(26), 5286-90].

The compounds according to the invention of the general structure (I-2) can be synthesized by reacting activated carboxylic acid derivatives of the general structure (V-3) with amines of the general structure (IV). The reaction conditions for this reaction have already been described in synthesis process A for the synthesis of (I-1).

The compounds of the general structure (V-3) can be synthesized in a two-stage process starting from pyrazolecarboxylic acids of the type (V-1) which can be prepared by processes known in the literature [Journal of Organic Chemistry 2008, 73(9), 3523-3529; Bioorganic & Medicinal Chemistry Letters 2005, 15(22), 4898-4906; US2006069270]. Here, in the first step, compounds of the formula (V-1) are iodized in the 4-position with iodine and an oxidizing agent, such as, for example cerium(IV) ammonium nitrate. The hydroxy function of (V-2) is then converted into the leaving group X by those methods already described in synthesis process A for the preparation of (V).

Reaction scheme 4 shows the general synthesis process D for the synthesis of the compounds (I-4) according to the invention.

Reaction scheme 4

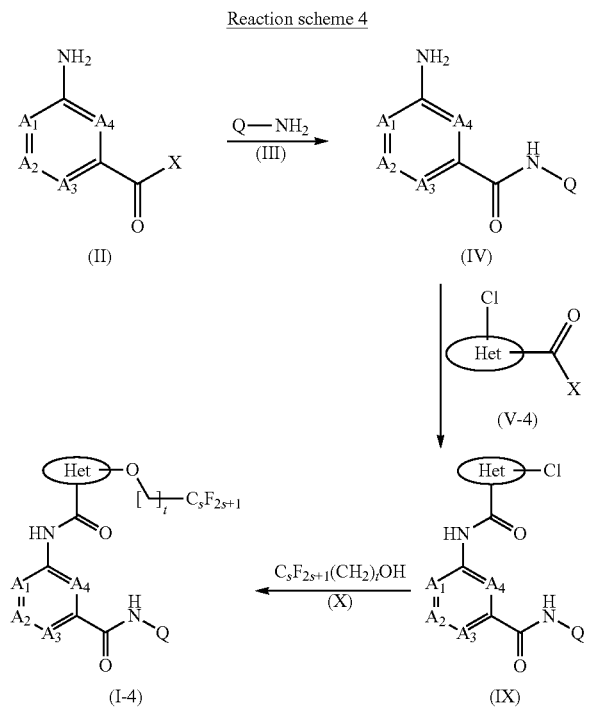

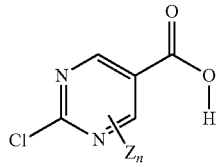

(V-4a)

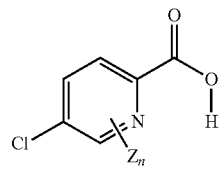

(V-4b)

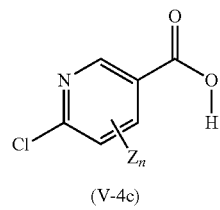

(V-4c)

(V-4c)

Compounds of the general formula (V-4) represent here special N-heterocyclic carboxylic acids, for example these may be the carboxylic acids of the type (V-4-a)-(V-4-ac). It is common to all of these carboxylic acids that the chlorine atom, on account of its position relative to the nitrogen atoms, is activated for a nucleophilic substitution. The radicals $A_1$-$A_4$ and Q have the meanings described above. X is any desired leaving group. "n", "t" and "s", independently of one another, are 0-3, where the sum of "s" and "t" is ≤4.

The compounds according to the invention of the general structure (I-4) can be synthesized by the reaction of perfluorinated alcohols of the general structure (X) with chlorine compounds of the general structure (IX). This substitution reaction can be carried out by processes known in the literature [Pest Management Science 2001; 57(9), 844-851; Canadian Journal of Chemistry 1985, 63(11), 3037-42].

The compounds of the general structure (IX) can be synthesized by reacting amines of the general structure (IV) with activated heterocyclic carboxylic acid derivatives of the general structure (V-4). The reaction conditions for this reaction have already been described in synthesis process A for the synthesis of (I-1).

The preparation of amines of the general structure (IV) takes place according to the method described in synthesis process A by reacting amines of the general structure (III) with activated carboxylic acid derivatives of the general structure (II).

Reaction scheme 5 shows the general synthesis process E for the synthesis of the compounds according to the invention of the general structure (I-5).

Reaction scheme 5

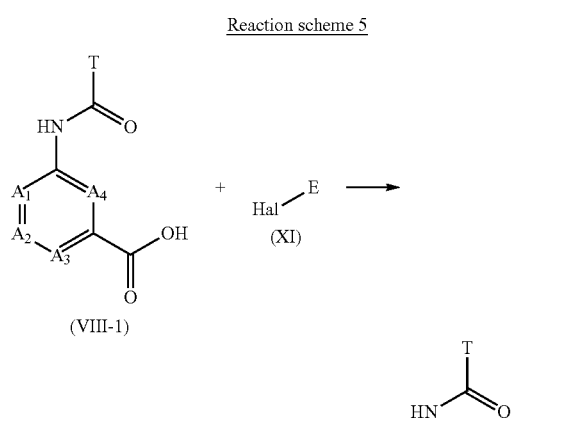

The radicals $A_1$-$A_4$ and T have the meanings described above. E is optionally substituted primary and secondary alkyl radicals. Hal represents a halogen atom, preferably chlorine or bromine.

The compounds according to the invention of the general structure (I-5) can be prepared by a substitution reaction between carboxylic acid of the general structure (VIII-1) and halogen compounds of the general structure (XI). The reaction can be carried out analogously to procedures known in the literature [Tetrahedron Letters 2007, 48 (39), 6974-6976; International Journal of Pharmaceutics 1987, 39 (1), 75-85].

Reaction scheme 6 shows the general synthesis process F for the synthesis of the compounds according to the invention of the general structure (I-6).

Reaction scheme 6

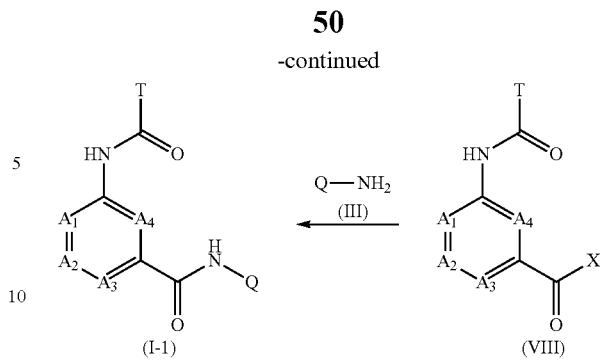

The radicals $A_1$-$A_4$, Q and T have the meanings described above. Y is bromine, iodine or triflate. X is any desired leaving group and Alk is an alkyl radical, such as, for example, methyl or ethyl.

Compounds according to the invention of the type (I-1) can be synthesized starting from compounds of the general structure (VII) by the process described in synthesis process B. Compounds of the general structure (VII) can be synthesized, inter alia, by a metal-mediated coupling of compounds of the general structure (XII) with carboxamides of the general structure (V-5). The reaction can be carried out analogously to known literature procedures [Chemistry—A European Journal 2008, 14(12), 3527-3529; Organic Letters 2007, 9(23), 4749-4751; Journal of the American Chemical Society 2002, 124(21), 6043-6048; Bioorganic & Medicinal Chemistry 2008, 16(6), 3091-3107].

Activated carboxylic acid derivatives of the general formula (II) are accessible from cyclic aminocarboxylic acids of the general formula (II-1) by methods already described in synthesis process A for the synthesis of (V). Substances of the general formula (II-1) are generally known compounds in organic chemistry which can be obtained by established synthesis processes. Possible synthesis routes of the cyclic aminocarboxylic acids of the general formula (II-1) are depicted in reaction scheme 7.

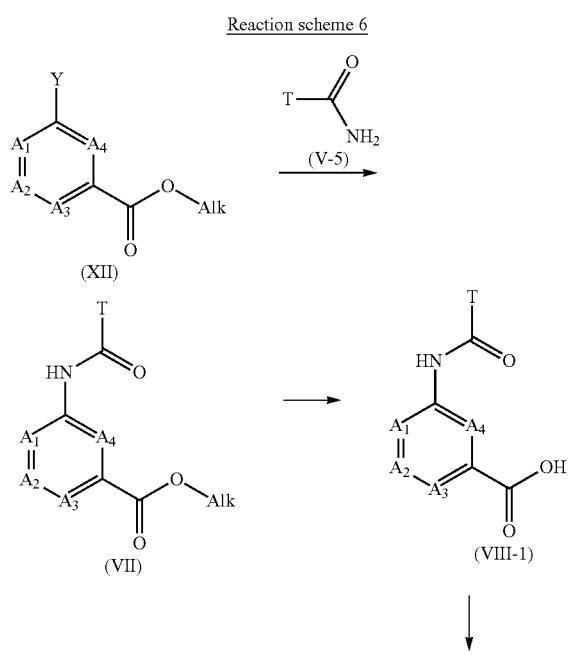

Reaction scheme 7

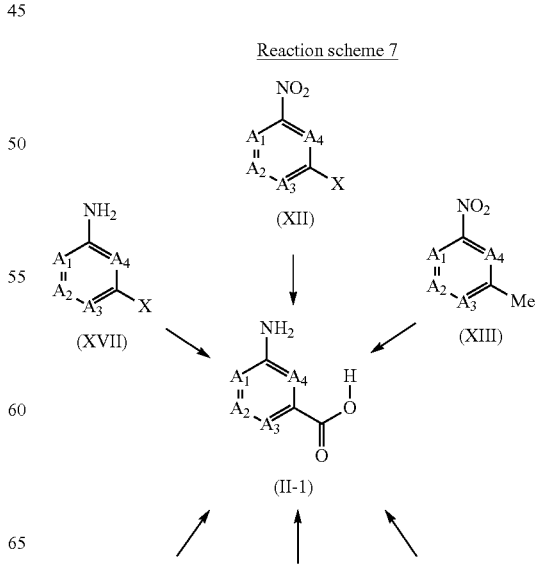

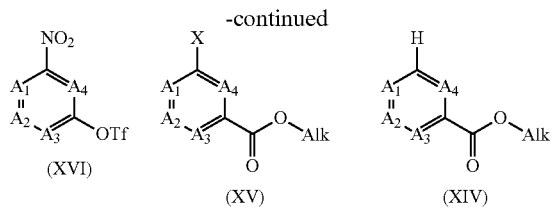

Starting materials for the synthesis of aminocarboxylic acids of the general structure (II-1) that may be used are, for example, halogenated (hetero)aromatic nitro and amino compounds, as are represented by the formulae (XII) and (XVII). Here, the leaving group X is replaced by a cyano group and this is then acid- or base-hydrolysed. The halogen-cyano exchange can take place, for example, by a nucleophilic substitution on the aromatic with a cyanide species such as, for example, sodium cyanide [U.S. Pat. No. 4,766,219] or else via a copper-mediated reaction [Journal of Antibiotics 1994, 47(12), 1456-65].

In the case of the nitro compounds (XVII), a reduction of the nitro function into an amino function can then also take place. Suitable processes for such reactions are hydrogenations and metal-mediated reactions such as, for example, tin(II) chloride, iron powder, zinc powder and compounds similar to these.

Hydrogenations can take place in a suitable solvent in the presence of a catalyst under a hydrogen atmosphere (atmospheric pressure or increased pressure). Catalysts which can be used are palladium catalysts, such as, for example, palladium on carbon, nickel catalysts such as Raney nickel, cobalt catalysts, ruthenium catalysts, rhodium catalysts, platinum catalysts and compounds similar to these. Suitable solvents are water, alcohols such as methanol and ethanol, aromatic hydrocarbons such as benzene and toluene, open-chain or cyclic ethers, such as diethyl ether, dioxane and tetrahydrofuran, and also esters such as ethyl acetate. The reductions can be carried out in a pressure range from 1 bar to 100 bar, and the temperature can vary between −20° C. and the boiling point of the solvent used. Depending on the reaction conditions, the reaction times are between a few minutes and 96 hours.

The metal-mediated reductions such as, for example, with tin(II) chloride, can be carried out by a process described in Organic Syntheses Coll. Vol. (III), 453.

Furthermore, (hetero)aromatic aminocarboxylic acids of the general structure (II-1) can also be synthesized from the corresponding methyl precursors of the type (XIII) by oxidation. Oxidizing agents suitable for such oxidations are, for example, potassium permanganate, sodium dichromate, chromium trioxide and compounds similar to these [Tetrahedron Letters 1995, 36(25), 4369-72; Bioorganic & Medicinal Chemistry Letters 2007, 17(4), 1043-1046]. Enzymatic processes can likewise also be used for such oxidations [PCT Int. Appl., 9502061]. The subsequently required reduction of the nitro function can be carried out analogously to the processes described above.

A further method for synthesizing (hetero)aromatic aminocarboxylic acids of the general structure (II-1) is the nitration of carboxylic acid precursors represented by the formula (XIV) or (XV) and the subsequent reduction of the nitro function. The nitrations can be carried out by processes in the literature [Justus Liebigs Annalen der Chemie [Annals of chemistry] 1958, 611, 194-205; Organikum [Organic chemistry], Wiley-VCH, 22nd edition, 358 ff]. The subsequently required reduction of the nitro function can be carried out analogously to the processes described above.

Furthermore, (hetero)aromatic aminocarboxylic acids of the general structure (II-1) can be prepared from the corresponding (hetero)aryl triflates of the type (XVI) with the help of a palladium-catalyzed process [Synthesis 2006, (4), 594-596].

Possible syntheses of the heterocyclic carboxylic acid derivatives of the general formula (V) are depicted in reaction scheme 8.

Reaction scheme 8

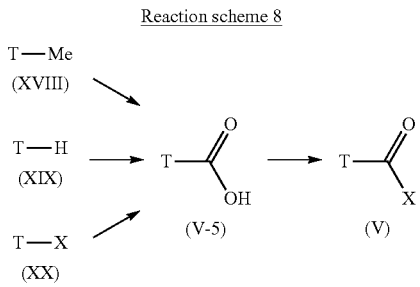

Heterocyclic carboxylic acids of the general structure (V-5) can be synthesized, inter alia, from methyl derivatives of the general formula (XVIII) by oxidation of the methyl function. Here, the processes already mentioned for the oxidation of methyl groups of the compounds of the general structure (XIII) can be used.

Heterocyclic carboxylic acids of the general structure (V-5) can be synthesized from precursors of the general structure (XIX) by deprotonation with a suitable base and by scavenging the corresponding carbanion with carbon dioxide [Journal of Medicinal Chemistry 2008, 51(4), 937-947; Bioorganic & Medicinal Chemistry Letters 2007, 17(22), 6274-6279]. Suitable bases are, for example, lithium diisopropylamide, n-butyllithium, sec-butyllithium and compounds similar to these.

For the above-described process for the synthesis of heterocyclic carboxylic acids of the general structure (V-5), the corresponding halogenated heterocycles (XX) are likewise suitable. However, the carbanion here is not generated by deprotonation, but by a metalation reaction [Angewandte Chemie, International Edition 2008, 47(2), 311-315]. Of suitability for these metalation reactions are preferably n-butyllithium, tert-butyllithium and isopropylmagnesium chloride.

Heterocyclic carboxylic acids of the general structure (V-5) can likewise be converted from halogenated precursors of the general structure (XX) with the help of palladium-catalysed reactions known in the literature into the corresponding heterocyclic carboxylic acid esters [Russian Journal of Applied Chemistry 2007, 80(4), 571-575].

Furthermore, heterocyclic carboxylic acids of the general structure (V-5) can be synthesized from halogenated compounds of the general structure (XX) by a substitution reaction of the halogens with cyanides and subsequent hydrolysis of the nitrile function with strong acid or bases [WO 2005079801].

Heterocyclic activated carboxylic acid derivatives, such as, for example, carboxylic acid halides, as are represented by the general structure V, can be prepared by reacting a cyclic carboxylic acid represented by the formula (V-5) with halogenating reagents such as thionyl chloride, thionyl bromide, phosphoryl chloride, oxalyl chloride, phosphorus trichloride, etc. [Organikum [Organic chemistry], Wiley-VCH, 22nd edition, 496ff].

Activated carboxylic acid derivatives of the general structure (II) can be synthesized by generally known literature processes from carboxylic acids of the formula (II-1) [Organikum (Organic chemistry), Wiley-VCH, 22nd edition, 496ff; Chem. Ber. 1970, 788; J. Am. Chem. Soc 1967, 5012]. The compounds of the formula (II-1) are commercially available or can be prepared by known literature processes [Synthesis 2006, (4), 594-596; Tetrahedron Letters 1995, 36(25), 4369-72; Bioorganic & Medicinal Chemistry Letters 2007, 17(4), 1043-1046; PCT Int. Appl., 9502061, Journal of Organic Chemistry 1954, 19, 357-64; WO 2001083459].

Compounds of the general structure III are commercially available and/or can be prepared by processes generally known in the specialist literature [Houben-Weyl (1992), Vol. E, 16d, 646ff; Tetrahedron Letters, 33(24), 3487-90; 1992].

Compounds of the general structure (V) are generally commercially available and/or can be synthesized by known literature processes [Journal of Medicinal Chemistry 2008, 51(4), 937-947; Bioorganic & Medicinal Chemistry Letters 2007, 17(22), 6274-6279; Russian Journal of Applied Chemistry 2007, 80(4), 571-575; WO 2005079801; Journal of Organic Chemistry 2008, 73(9), 3523-3529; Bioorganic & Medicinal Chemistry Letters 2005, 15(22), 4898-4906; US2006069270].

The pyrazolecarboxylic acids of the formula (V-6) are novel and likewise provided by the invention.

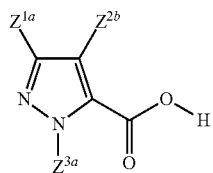

(V-6)

where, independently of one another, $Z^{1a}$ is 1,2,2,2-tetrafluoroethyl, 1-chloro-1,2,2,2-tetrafluoroethyl, 2,2,2-trichloroethyl, 2-chloro-2,2-difluoroethyl, pentafluoroethyl, 1,1-difluoroethyl, pentafluoro-tert-butyl, heptafluoro-n-propyl, heptafluoro-isopropyl, nonafluoro-n-butyl, trifluoromethoxy-1,1,2,2-tetrafluoroethoxydifluoromethyl, trifluoromethoxy, difluoromethoxy, chlorodifluoromethyl, dichlorofluoromethyl, difluoromethyl, 2,2,2-trifluoromethyl, 2,2-difluoro-1-methyl-cyclopropyl, $Z^{2b}$ is fluorine, chlorine, bromine, iodine, cyano, nitro, methyl, ethyl, n-propyl, isopropyl, cyclopropyl, trifluoromethyl, pentafluoroethyl, heptafluoro-n-propyl, ethenyl, 1-propenyl, 2-propenyl, ethynyl, 1-propynyl, 1-butynyl, 4-fluorophenyl and $Z^{3a}$ is methyl, ethyl, n-propyl, isopropyl, n-butyl, isobutyl, sec-butyl, tert-butyl, 1-fluoro-1-methylethyl, 1-fluoroethyl, 2-(ethoxy)ethyl, 2-(methoxy)ethyl, cyclobutyl, cyclopentyl.

With the exception of the compounds according to the invention of the formula (V-6), compounds with the combinations are 1.) $Z^{1a}$=1,1-difluoroethyl; $Z^{2b}$=chlorine; $Z^{3a}$=methyl or
2.) $Z^{1a}$=pentafluoroethyl; $Z^{2b}$=chlorine; $Z^{3a}$=methyl.

The compounds of the general structure (VI) can be synthesized by processes known in the literature from the compounds of the general structure (II) [Journal of the American Chemical Society 2001, 123(34), 8177-8188; Inorganica Chimica Acta 2006, 359(6), 1912-1922].

Compounds of the general structures (X) to XX are commercially available and/or known from the relevant specialist literature.

Oxidizing agents for the oxidation of alcoholic groups are known (cf. e.g. oxidation reagents in Organic Synthesis by Oxidation with Metal Compounds, Mijs, de Jonge, Plenum Verlag, New York, 1986; Manganese Compounds as Oxidizing Agens in Organic Chemistry, Arndt, Open Court Publishing Company, La Salle, Ill., 1981; The Oxidation of Organic Compounds by Permanganate Ion and Hexavalent Chromium, Lee, Open Court Publishing Company, La Salle, Ill., 1980). An oxidation can be carried out, for example, in the presence of permanganates (e.g. potassium permanganate), metal oxides (e.g. manganese dioxide, chromium dioxides which are used, for example, in dipyridine-chromium(VI) oxide as Collins reagent (cf. J. C. Collins et al., Tetrahedron Lett. 30, 3363-3366, 1968)). Likewise in the presence of pyridinium chlorochromate (e.g. Corey's reagent) (cf. also R. O. Hutchins et al., Tetrahedron Lett. 48, 4167-4170, 1977; D. Landini et al. Synthesis 134-136, 1979) or ruthenium tetroxide (cf. S.-I. Murahashi, N. Komiya Ruthenium-catalyzed Oxidation of Alkenes, Alcohols, Amines, Amides, β-Lactams, Phenols and Hydrocarbons, in: Modern Oxidation Methods, Baeckvall, Jan-Erling (Eds.), Wiley-VCH-Verlag GmbH & Co. KGaA, 2004). Likewise suitable are ultrasound-induced oxidation reactions, and the use of potassium permanganate (cf. J. Yamawaki et al., Chem. Lett. 3, 379-380, 1983).

For the deblocking/elimination of the protective group PG, all known suitable acidic or basic reaction auxiliaries can be used in accordance with the process method described in the literature. When using protective groups for amino groups of the carbamate type, preference is given to using acidic reaction auxiliaries. When using the tert-butylcarbamate protective group (BOC group), mixtures of mineral acids such as hydrochloric acid, hydrobromic acid, nitric acid, sulphuric acid, phosphoric acid or organic acids such as benzoic acid, formic acid, acetic acid, trifluoroacetic acid, methanesulphonic acid, benzenesulphonic acid or toluenesulphonic acid and a suitable diluent such as water and/or an organic solvent such as tetrahydrofuran, dioxane, dichloromethane, chloroform, ethyl acetate, ethanol or methanol, for example, are used. Preference is given to mixtures of hydrochloric acid or acetic acid with water and/or an organic solvent such as ethyl acetate.

It is known that some reactions and preparation processes can be carried out particularly well in the presence of diluents or solvents and basic or acidic reaction auxiliaries. Mixtures of the diluents and solvents can likewise be used. The diluents or solvents are advantageously used in an amount such that the reaction mixture is readily stirrable through the entire process.

Suitable diluents and solvents for carrying out the process according to the invention are in principle all organic solvents that are inert under the specific reaction conditions. Examples to be mentioned are: halogenated hydrocarbons (e.g. chlorinated hydrocarbons, such as tetraethylene, tetrachloroethane, dichloropropane, methylene chloride, dichlorobutane, chloroform, tetrachloromethane, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), ethers (e.g. ethyl propyl ether, methyl-tert-butyl ether, n-butyl ether, anisole, phenetol, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide), amines (e.g. trimethyl-, triethyl-, tripropyl-, tributylamine, n-methylmorpholine, pyridine and tetramethylenediamine), nitrohydrocarbons (e.g. nitromethane, nitroethane, nitropropane, nitrobenzene, chloronitrobenzene, o-nitrotoluene; nitriles, such as acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzylmethyl sulphoxide, diisobutyl sulphoxide, dibutyl sulphoxide, diisoamyl sulphoxide, sulphones (e.g. dimethyl sulphone, diethyl sulphone, dipropyl sulphone, dibutyl sulphone, diphenyl sulphone, dihexyl sulphone, methylethyl sulphone, ethylpropyl sulphone, ethylisobutyl sulphone and pentamethylene sulphone), aliphatic, cycloaliphatic or aromatic hydrocarbons (e.g. pentane, hexane, heptane, octane, nonane and technical-grade hydrocarbons), also so-called "white spirits" with components having boiling points in the range of, for example, 40° C. to 250° C., cymene, benzine fractions within the boiling interval from 70° C. to 190° C., cyclohexane, methylcyclohexane, petroleum ether, ligroin, octane, benzene, toluene, chlorobenzene, bromobenzene, nitrobenzene, xylene, esters (e.g. methyl acetate, ethyl acetate, butyl acetate, isobutyl acetate, dimethyl carbonate, dibutyl carbonate, ethylene carbonate); amides (e.g. hexamethylenephosphoramide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine) and ketones (e.g. acetone, acetophenone, methyl ethyl ketone, methyl butyl ketone).

Basic reaction auxiliaries for carrying out the process according to the invention that may be used are all suitable acid binders. Examples to be mentioned are: alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo(4.4.0)dec-5-ene (MTBD); diazabicyclo(4.3.0)nonene (DBN), diazabicyclo(2.2.2)octane (DABCO), 1,8-diazabicyclo(5.4.0)undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, in particular tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, α-picoline, β-picoline, isoquinoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethyldiamine).

Acidic reaction auxiliaries for carrying out the processes according to the invention that may be used are all mineral acids (e.g. halohydric acids such as hydrofluoric acid, hydrochloric acid, hydrobromic acid or hydroiodic acid, and also sulphuric acid, phosphoric acid, phosphorus acid, nitric acid), Lewis acids (e.g. aluminium(III) chloride, boron trifluoride or its etherate, titanium(V) chloride, tin(V) chloride, and organic acids (e.g. formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesulphonic acid.

If protective groups are provided in the reaction schemes, all generally known protective groups can be used. In particular those which are described by Greene T. W., Wuts P. G. W. in Protective Groups in Organic Synthesis; John Wiley & Sons, Inc. 1999, "Protection for the hydroxyl group including 1,2- and 1,3-diols".

Also suitable are protective groups
of the substituted methyl ether type (e.g. methoxymethyl ether (MOM), methyl thiomethyl ether (MTM), (phenyldimethylsilyl)methoxymethyl ether (SNOM-OR), benzyloxymethyl ether (BOM-OR), para-methoxybenzyloxymethyl ether (PMBM-OR), para-nitrobenzyloxymethyl ether, ortho-nitrobenzyloxymethyl ether (NBOM-OR), (4-methoxyphenoxy)methyl ether (p-AOM-OR), guaiacol methyl ether (GUM-OR), tert-butoxymethyl ether, 4-pentyloxymethyl ether (POM-OR), silyloxymethyl ether, 2-methoxyethoxymethyl ether (MEM-OR), 2,2,2-trichloroethoxymethyl ether, bis(2-chloroethoxy)methyl ether, 2-(trimethylsilyl)ethoxymethyl ether (SEM-OR), methoxymethyl ether (MM-OR));
of the substituted ethyl ether type (e.g. 1-ethoxyethyl ether (EE-OR), 1-(2-chloroethoxy)ethyl ether (CEE-OR), 1-[2-(trimethylsilyl)ethoxy]ethyl ether (SEE-OR), 1-methyl-1-methoxyethyl ether (MIP-OR), 1-methyl-1-benzyloxyethyl ether (MBE-OR), 1-methyl-1-benzyloxy-2-fluoroethyl ether (MIP-OR), 1-methyl-1-phenoxyethyl ether, 2,2-trichloroethyl ether, 1,1-dianisyl-2,2,2-trichloroethyl ether (DATE-OR), 1,1,1,3,3,3-hexafluoro-2-phenylisopropyl ether (HIP-OR), 2-trimethylsilylethyl ether, 2-(benzylthio)ethyl ether, 2-(phenylselenyl)ethyl ether), of an ether type (e.g. tetrahydropyranyl ether (THP-OR), 3-bromotetrahydropyranyl ether (3-BrTHP-OR), tetrahydrothiopyranyl ether, 1-methoxycyclohexyl ether, 2- and 4-picolyl ether, 3-methyl-2-picolyl N-oxido ether, 2-quinolinylmethyl ether (Qm-OR), 1-pyrenylmethyl ether, diphenylmethyl ether (DPM-OR), para,para'-dinitrobenzhydryl ether (DNB-OR), 5-dibenzosuberyl ether, triphenylmethyl ether (Tr-OR), alpha-naphthyldiphenylmethyl ether, para-methoxyphenyldiphenylmethyl ether (MMTrOR), di(para-methoxyphenyl) phenylmethyl ether (DMTr-OR), tri(para-methoxyphenyl) phenylmethyl ether (TMTr-OR), 4-(4'-bromophenacyloxy) phenyldiphenylmethyl ether, 4,4',4"-tris(4,5-dichlorophthalimidophenyl)methyl ether (CPTr-OR), 4,4',4"-tris(benzoyloxyphenyl)methyl ether (TBTr-OR), 4,4'-dimethoxy-3"-N-(imidazolylmethyl)trityl ether (IDTr-OR), 4,4'-dimethoxy-3"-[N-(imidazolylethyl)carbamoyl]trityl ether (IETr-OR), 1,1-bis(4-methoxyphenyl)-1'-pyrenylmethyl ether (Bmpm-OR), 9-anthryl ether, 9-(9-phenyl)xanthenyl ether (Pixyl-OR), 9-(9-phenyl-10-oxo)anthryl (tritylon ether), 4-methoxytetrahydropyranyl ether (MTHP-OR), 4-methoxytetrahydrothiopyranyl ether, 4-methoxytetrahydrothiopyranyl S,S-dioxide, 1-[(2-chloro-4-methyl)phenyl]-4-methoxypiperidin-4-yl ether (CTMP-OR), 1-(2-fluorophenyl)-4-methoxypiperidin-4-yl ether (Fpmp-OR), 1,4-dioxan-2-yl ether, tetrahydrofuranyl ether, tetrahydrothiofuranyl ether, 2,3,3a,4,5,6,7,7a-octahydro-7,8,8-trimethyl-4,7-methanebenzofuran-2-yl ether (MBF-OR), tert-butyl ether, allyl ether, propargyl ether, parachlorophenyl ether, para-methoxyphenyl ether, para-nitrophenyl ether, para-2,4-dinitrophenyl ether (DNP-OR), 2,3,5,6-tetrafluoro-4-(trifluoromethyl)phenyl ether, benzyl ether (Bn-OR));
of the substituted benzyl ether type (e.g. para-methoxybenzyl ether (MPM-OR), 3,4-dimethoxybenzyl ether (DMPM-OR), orthonitrobenzyl ether, para-nitrobenzyl ether, para-halobenzyl ether, 2,6-dichlorobenzyl ether, para-aminoacylbenzyl ether (PAB-OR), para-azidobenzyl ether (Azb-OR), 4-azido-3-chlorobenzyl ether, 2-trifluoromethylbenzyl ether, para-(methylsulphinyl)benzyl ether (Msib-OR));

of the silyl ether type (e.g. trimethylsilyl ether (TMS-OR), triethylsilyl ether (TES-OR), triisopropylsilyl ether (TIPS-OR), dimethylisopropylsilyl ether (IPDMS-OR), diethylisopropylsilyl ether (DEIPS-OR), dimethylhexylsilyl ether (TDS-OR), tert-butyldimethylsilyl ether (TBDMS-OR), tert-buyldiphenylsilyl ether (TBDPS-OR), tribenzylsilyl ether, tri-para-xylylsilyl ether, triphenylsilyl ether (TPS-OR), diphenylmethylsilyl ether (DPMS-OR), di-tert-butylmethylsilyl ether (DTBMS-OR), tris(trimethylsilyl)silyl ether (sisyl ether), di-tert-butylmethylsilyl ether (DTBMS-OR), tris(trimethylsilyl)silyl ether (sisyl ether), (2-hydroxystyryl)dimethylsilyl ether (HSDMS-OR), (2-hydroxystyryl)diisopropylsilyl ether (HSDIS-OR), tert-butylmethoxyphenylsilyl ether (TBMPS-OR), tert-butoxydiphenylsilyl ether (DPTBOS-OR));

of the ester type (e.g. formate ester, benzoylformate ester, acetate ester (Ac-OR), chloroacetate ester, dichloroacetate ester, trichloroacetate ester, trifluoracetate ester, (TFA-OR), methoxyacetate ester, triphenylmethoxyacetate ester, phenoxyacetate ester, para-chlorophenoxyacetate ester, phenylacetate ester, diphenylacetate ester (DPA-OR), nicotinate ester, 3-phenylpropionate ester, 4-pentoate ester, 4-oxopentoate ester (levulinate) (Lev-OR) 4,4-(ethylenedithio)pentanoate ester (LevS-OR), 5-[3-bis(4-methoxyphenyl)hydroxymethoxyphenoxy]levulinate ester, pivaloate ester (Pv-OR), 1-adamantanoate ester, crotonate ester, 4-methoxycrotonate ester, benzoate ester (Bz-OR), para-phenylbenzoate ester, 2,4,6-trimethylbenzoate ester (mesitoate), 4-(methylthiomethoxy)butyrate ester (MTMB-OR), 2-(methylthiomethoxymethyl)benzoate ester (MTMT-OR), of the ester type (e.g. methyl carbonate, methoxymethyl carbonate, 9-fluorenylmethyl carbonate (Fmoc-OR), ethyl carbonate, 2,2,2-trichloroethyl carbonate (Troc-OR), 1,1-dimethyl-2,2,2-trichloroethyl carbonate (TCBOC-OR), 2-(trimethylsilyl)ethyl carbonate (TMSEC-OR), 2-(phenylsulphonyl)ethyl carbonate (Psec-OR), 2-(triphenylphosphonio)ethyl carbonate (Peoc-OR), tert-butyl carbonate (Boc-OR), isobutyl carbonate, vinyl carbonate, allyl carbonate (Alloc-OR), para-nitrophenyl carbonate, benzyl carbonate (Z-OR), para-methoxybenzyl carbonate, 3,4-dimethoxybenzyl carbonate, ortho-nitrobenzyl carbonate, para-nitrobenzyl carbonate, 2-dansylethyl carbonate (Dnseoc-OR), 2-(4-nitrophenyl)ethyl carbonate (Npeoc-OR), 2-(2,4-dinitrophenyl)ethyl carbonate (Dnpeoc)), and of the sulphate type (e.g. allylsulphonate (Als-OR), methanesulphonate (Ms-OR), benzylsulphonate, tosylate (Ts-OR), 2-[(4-nitrophenyl)ethyl]sulphonate (Npes-OR)).

Suitable catalysts for carrying out a catalytic hydrogenation in the process according to the invention are all customary hydrogenation catalysts, such as, for example, platinum catalysts (e.g. platinum plate, platinum sponge, platinum black, colloidal platinum, platinum oxide, platinum wire), palladium catalysts (e.g. palladium sponge, palladium black, palladium oxide, palladium-carbon, colloidal palladium, palladium-barium sulphate, palladium-barium carbonate, palladium hydroxide), nickel catalysts (e.g. reduced nickel, nickel oxide, Raney nickel), ruthenium catalysts, cobalt catalysts (e.g. reduced cobalt, Raney cobalt), copper catalysts (e.g. reduced copper, Raney copper, Ullmann copper). Preference is given to using noble metal catalysts (e.g. platinum and palladium or ruthenium catalysts), which are optionally applied to a suitable support (e.g. carbon or silicon), rhodium catalysts (e.g. tris(triphenylphosphine)rhodium(I) chloride in the presence of triphenylphosphine). In addition, "chiral hydrogenation catalysts" (e.g. those which contain chiral diphosphine ligands, such as (2S,3S)-(−)-2,3-bis(diphenylphosphino)butane [(S,S)-chiraphos] or (R)-(+)-2,2'- or (S)-(−)-2,2'-bis(diphenylphosphino)-1,1'-binaphthalene [R(+)-BINAP and S(−)-BINAP]) can be used, as the result of which the fraction of one isomer in the isomer mixture is increased and the appearance of another isomer is almost completely suppressed.

The preparation of salts of the compounds according to the invention takes place by standard processes. Representative acid addition salts are, for example, those which are formed by reaction with inorganic acids, such as, for example, sulphuric acid, hydrochloric acid, hydrobromic acid, phosphoric acid or organic carboxylic acids such as acetic acid, trifluoroacetic acid, citric acid, succinic acid, butyric acid, lactic acid, formic acid, fumaric acid, maleic acid, malonic acid, camphoric acid, oxalic acid, phthalic acid, propionic acid, glycolic acid, glutaric acid, stearic acid, salicylic acid, sorbic acid, tartaric acid, cinnamic acid, valeric acid, picric acid, benzoic acid or organic sulphonic acids such as methanesulphonic acid and 4-toluenesulphonic acid.

Also representative are salts of compounds according to the invention which are formed from organic bases, such as, for example, pyridine or triethylamines, or those which are formed from inorganic bases, such as, for example, hydrides, hydroxides or carbonates of sodium, lithium, calcium, magnesium or barium if the compound of the general formula (I) has a structural element suitable for this salt formation.

Synthesis methods for the synthesis of heterocyclic N-oxides and tert-amines are known. They can be obtained with peroxy acids (e.g. peracetic acid and meta-chloroperbenzoic acid (MCPBA), hydrogen peroxide), alkyl hydroperoxides (e.g. tert-butyl hydroperoxide), sodium perborate and dioxiranes (e.g. dimethyldioxirane). These methods are described, for example, by T. L. Gilchrist, in Comprehensive Organic Synthesis, Vol. 7, p. 748-750, 1992, S. V. Ley, (Ed.), Pergamon Press; M. Tisler, B. Stanovnik, in Comprehensive Heterocyclic Chemistry, Vol. 3, p. 18-20, 1984, A. J. Boulton, A. McKillop, (Eds.), Pergamon Press; M. R. Grimmett, B. R. T. Keene in Advances in Heterocyclic Chemistry, Vol. 43, p. 149-163, 1988, A. R. Katritzky, (Ed.), Academic Press; M. Tisler, B. Stanovnik, in Advances in Heterocyclic Chemistry, Vol. 9, p. 285-291, 1968, A. R. Katritzky, A. J. Boulton (Eds.), Academic Press; G. W. H. Cheeseman, E. S. G. Werstiuk in Advances in Heterocyclic Chemistry, Vol. 22, p. 390-392, 1978, A. R. Katritzky, A. J. Boulton, (Eds.), Academic Press.

EXPERIMENTAL SECTION

Synthesis Process A

Example (Ik-1)

N-[4-Chloro-3-(cyclopropylcarbamoyl)phenyl]-1-methyl-3-(pentafluoroethyl)-4-(trifluoromethyl)-1H-pyrazole-5-carboxamide

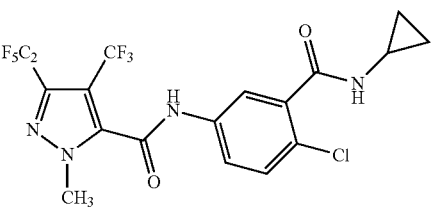

560 mg (1.79 mmol) of 1-methyl-3-pentafluoroethyl-4-trifluoromethylpyrazole-5-carboxylic acid are suspended in 10 ml of dichloromethane. The suspension is cooled to 0° C. and then subsequently admixed with 0.02 ml of N,N-dimethylformamide and 188 µl (2.15 mmol) of oxalyl chloride. The reaction mixture is stirred firstly for 0.5 h at 0° C. and then for 3 hours at room temperature. The solvent is removed under reduced pressure on a rotary evaporator. The resulting 1-methyl-3-(pentafluoroethyl)-4-(trifluoromethyl)-1H-pyrazole-5-carbonyl chloride is used for the subsequent synthesis step without further work-up.

95.3 mg (0.45 mmol) of 5-amino-2-chloro-N-cyclopropylbenzamide, 3.7 mg (0.03 mmol) of N,N-dimethylpyridine-4-amine are dissolved in 2.5 ml of ethyl acetate. The solution is cooled to 0° C. using an ice bath and admixed with 158 µl (0.91 mmol) of N-ethyldiisopropylamine. 100 mg (0.30 mmol) of 1-methyl-3-(pentafluoroethyl)-4-(trifluoromethyl)-1H-pyrazole-5-carbonyl chloride are suspended in 2.5 ml of ethyl acetate and then added to the cooled reaction solution. The reaction mixture is heated for four hours at 50° C. and then stirred for 16 hours at room temperature. The reaction solution is diluted with 10.0 ml of ethyl acetate. The organic phase is washed three times with 1M hydrochloric acid, twice with 1M sodium hydroxide solution and once with saturated sodium chloride solution. The organic phase is dried over sodium sulphate and filtered and solvent is removed under reduced pressure on a rotary evaporator. This gives 151 mg of N-[4-chloro-3-(cyclopropylcarbamoyl)phenyl]-1-methyl-3-(pentafluoroethyl)-4-(trifluoromethyl)-1H-pyrazole-5-carboxamide (97%) as white solid.

$^1$H-NMR (400 MHz, d$_3$-acetonitrile): δ=9.35 (br. s, 1H), 7.71 (d, 1H), 7.65 (dd, 1H), 7.45 (d, 1H), 6.94 (br. s, 1H), 3.98 (s, 3H), 2.82 (m, 1H), 0.76 (m, 2H), 0.58 (m, 2H) ppm.

HPLC-MS$^{a)}$: log P=3.34; mass (m/z)=505 [M+H]$^+$.

Example (Ib-27)

N-[4-Chloro-3-(cyclopropylcarbamoyl)phenyl]-4-(difluoromethyl)-2-(pentafluoroethyl)pyrimidine-5-carboxamide

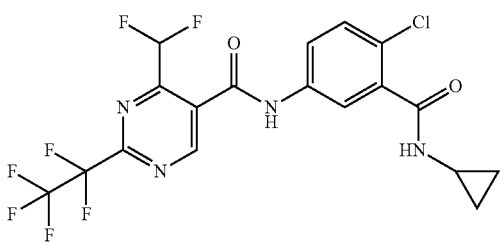 [SMILES: O=C(NC1CC1)c1cc(NC(=O)c2cnc(C(F)(F)C(F)(F)F)nc2C(F)F)ccc1Cl]

In 10 ml of dichloromethane, 467 mg of 4-(difluoromethyl)-2-(pentafluoroethyl)pyrimidine-5-carboxylic acid are admixed with two drops of N,N-dimethylformamide and cooled to 0° C. Following the dropwise addition of 167 µl of oxalyl chloride, the reaction mixture is stirred at room temperature for three hours and then concentrated by evaporation. This gives the crude product 4-(difluoromethyl)-2-(pentafluoroethyl)pyrimidine-5-carbonyl chloride.

63 mg (0.3 mmol) of 5-amino-2-chloro-N-cyclopropylbenzamide, 3.1 mg (0.025 mmol) of N,N-dimethylpyridine-4-amine are dissolved in 2 ml of ethyl acetate. The solution is cooled to 0° C. using an ice bath and admixed with 96.9 mg (750 mmol) of N-ethyldiisopropylamine. 77.6 mg (0.25 mmol) of 4-(difluoromethyl)-2-(pentafluoroethyl)pyrimidine-5-carbonyl chloride (is used as crude product) are dissolved or suspended in 2 ml of absolute ethyl acetate and then added to the cooled reaction solution. The reaction mixture is heated for four hours at 50° C. and then further stirred for 16 hours at room temperature. The reaction solution is diluted with 8 ml of ethyl acetate. The organic phase is washed twice with 1M hydrochloric acid, once with 1M sodium hydroxide solution and once with saturated sodium chloride solution. The organic phase is dried over sodium sulphate and filtered and solvent is removed under reduced pressure on a rotary evaporator.

This gives 112 mg of N-[4-chloro-3-(cyclopropylcarbamoyl)phenyl]-4-(difluoromethyl)-2-(pentafluoroethyl)pyrimidine-5-carboxamide (92%) as white solid.

$^1$H-NMR (400 MHz, D$_6$-DMSO): δ=10.91 (br. s, 1H), 9.56 (s, 1H), 8.33 (m, 1H), 7.70 (s, 1H), 7.67 (dd, 1H), 7.33 (t, 1H), 2.84 (m, 1H), 0.70 (m, 2H), 0.53 (m, 2H) ppm.

HPLC-MS$^{a)}$: log P=2.92 mass (m/z)=485 [M+H]$^+$.

Example (Ik-124)

N-{4-Chloro-3-[(2,2,2-trifluoroethyl)carbamoyl]phenyl}-3-(pentafluoroethyl)-4-(trifluoromethyl)-1H-pyrazole-5-carboxamide

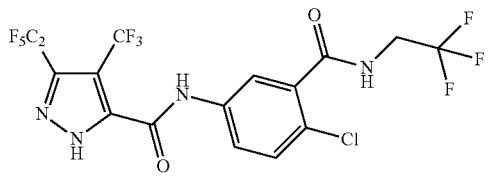

250 mg (0.84 mmol) of 3-(pentafluoroethyl)-4-(trifluoromethyl)-1H-pyrazole-5-carboxylic acid are suspended in 5.0 ml of dichloromethane and, in succession, admixed with one drop of N,N-dimethylformamide and 219 µl (2.52 mmol) of oxalyl chloride. The reaction mixture is stirred for 30 minutes at room temperature and for 30 minutes under reflux. The solvent is removed under reduced pressure on a rotary evaporator. The resulting product 3-(pentafluoroethyl)-4-(trifluoromethyl)-1H-pyrazole-5-carbonyl chloride is used for the following synthesis step without further purification.

A suspension of 212 mg (0.84 mmol) of 5-amino-2-chloro-N-(2,2,2-trifluoroethyl)benzamide and 168 mg (1.26 mmol) of silver(I) cyanide in 5.0 ml of dichloromethane is admixed with a solution of 265 mg (0.84 mmol) of 3-(pentafluoroethyl)-4-(trifluoromethyl)-1H-pyrazole-5-carbonyl chloride in 3.0 ml of dichloromethane and stirred for 16 h at room temperature. The suspension is then filtered over silica gel and the product is eluted with a mixture of dichloromethane and methanol (1:1). The solvents are removed under reduced pressure on a rotary evaporator and the resulting crude product is taken up in ethyl acetate. The organic phase is washed successively twice with 1M hydrochloric acid and once with saturated sodium chloride solution. The organic phase is then dried over magnesium sulphate, filtered and concentrated by evaporation under reduced pressure on a rotary evaporator. The crude product is then triturated with a mixture of dichloromethane, methyl tert-butyl ether and cyclohexane (1:1:1). The crude product obtained from the mother liquor is then purified by means of preparative HPLC. In this way, 49 mg of N-{4-chloro-3-[(2,2,2-trifluoroethyl)carbamoyl]phenyl}-3-(pentafluoroethyl)-4-(trifluoromethyl)-1H-pyrazole-5-carboxamide (11%) were obtained as a colourless solid.

$^1$H-NMR (400 MHz, d$_3$-acetonitrile): δ=9.09 (br. 5, 1H), 7.78 (d, 1H), 7.68 (dd, 1H), 7.48 (d, 1H), 7.23 (br. s, 1H), 4.03-4.12 (m, 2H) ppm.

HPLC-MS$^{a)}$: log P=3.26 mass (m/z)=533 [M+H]$^+$.

Example (Ik-125)

N-{4-Chloro-3-[(2,2,2-trifluoroethyl)carbamoyl]-phenyl}-1-methyl-3,4-bis(trifluoromethyl)-1H-pyrazole-5-carboxamide

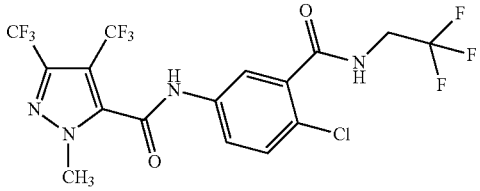 [SMILES: Cn1nc(C(F)(F)F)c(C(F)(F)F)c1C(=O)Nc1ccc(Cl)c(C(=O)NCC(F)(F)F)c1]

50 mg (0.19 mmol) of 1-methyl-3,4-bis(trifluoromethyl)-1H-pyrazole-5-carboxylic acid are suspended in 5.0 ml of dichloromethane and, in succession, admixed with one drop of N,N-dimethylformamide and 50 µl (2.52 mmol) of oxalyl chloride. The reaction mixture is stirred for 30 minutes at room temperature and for 30 minutes under reflux. The solvent is removed under reduced pressure on a rotary evaporator. The resulting product 1-methyl-3,4-bis(trifluoromethyl)-1H-pyrazole-5-carbonyl chloride is used for the subsequent synthesis step without further purification.

A suspension of 53 mg (0.21 mmol) of 5-amino-2-chloro-N-(2,2,2-trifluoroethyl)benzamide and 38 mg (0.29 mmol) of silver(I) cyanide in 5.0 ml of dichloromethane is admixed with a solution of 53 mg (0.19 mmol) of 3-(pentafluoroethyl)-4-(trifluoromethyl)-1H-pyrazole-5-carbonyl chloride in 3.0 ml of dichloromethane and stirred for 16 h at room temperature. The suspension is then filtered over silica gel and the product is eluted with a mixture of cyclohexane and ethyl acetate (1:1). The organic phase is washed successively three times with 1M hydrochloric acid, twice with 1M sodium hydroxide solution and once with saturated sodium chloride solution. The organic phase is then dried over magnesium sulphate, filtered and concentrated by evaporation under reduced pressure on a rotary evaporator. The crude product is then triturated with cyclohexane, the cyclohexane is decanted and the product is dried in vacuo. In this way, 63 mg of N-{4-chloro-3-[(2,2,2-trifluoroethyl)carbamoyl]phenyl}-1-methyl-3,4-bis(trifluoromethyl)-1H-pyrazole-5-carboxamide (66%) were obtained as a beige solid.

$^1$H-NMR (400 MHz, d$_3$-acetonitrile): δ=9.10 (br. s, 1H), 7.70 (d, 1H), 7.66 (dd, 1H), 7.49 (d, 1H), 7.23 (br. s, 1H), 4.02-4.14 (m, 2H), 3.98 (s, 3H) ppm.

HPLC-MS$^{a)}$: log P=3.25 mass (m/z)=497 [M+H]$^+$.

Example (Ik-233)

N-[4-Chloro-3-(cyclopropylcarbamoyl)phenyl]-3-[cyclopropyl(fluoro)methyl]-1-methyl-4-(trifluoromethyl)-1H-pyrazole-5-carboxamide

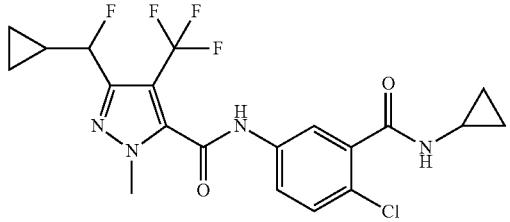 [SMILES: Cn1nc(C(F)C2CC2)c(C(F)(F)F)c1C(=O)Nc1ccc(Cl)c(C(=O)NC2CC2)c1]

515 mg (1.86 mmol) of 4-(4,6-dimethoxy-1,3,5-triazin-2-yl)-4-methylmorpholinium chloride are added to a solution of 410 mg (1.55 mmol) of 3-[cyclopropyl(hydroxy)methyl]-1-methyl-4-(trifluoromethyl)-1H-pyrazole-5-carboxylic acid and 327 mg (1.55 mmol) of 5-amino-2-chloro-N-cyclopropylbenzamide in tetrahydrofuran (10 ml) and the mixture is stirred for six hours at room temperature. The reaction mixture is concentrated by evaporation, admixed with water, extracted with dichloromethane and the combined organic phases are dried over sodium sulphate. Following concentration by evaporation in vacuo, the solid is washed with dichloromethane to give 308 mg of (N-[4-chloro-3-(cyclopropylcarbamoyl)phenyl]-3-[cyclopropyl(hydroxy)methyl]-1-methyl-4-(trifluoromethyl)-1H-pyrazole-5-carboxamide (44%).

$^1$H-NMR (400 MHz, d$_6$-DMSO): δ=11.10 (s, 1H), 8.30 (d, 1H), 7.67 (m, 2H), 7.45 (d, 1H), 5.12 (br. s, 1H), 4.02 (br. d, 1H), 3.84 (s, 3H), 2.83 (m, 1H), 1.36 (m, 1H), 0.77 (m, 2H), 0.51 (m, 3H), 0.44 (m, 2H), 0.20 (m, 1H) ppm.

HPLC-MS$^{a)}$: log P=2.00; mass (m/z) 439 [M–H$_2$O+H]$^+$.

Starting from N-[4-chloro-3-(cyclopropylcarbamoyl)phenyl]-3-[cyclopropyl(hydroxy)methyl]-1-methyl-4-(trifluoromethyl)-1H-pyrazole-5-carboxamide, N-[4-chloro-3-(cyclopropylcarbamoyl)-phenyl]-3-[cyclopropyl(fluoro)methyl]-1-methyl-4-(trifluoromethyl)-1H-pyrazole-5-carboxamide is prepared analogously to the preparation of ethyl 3-(2-fluoropropan-2-yl)-1-methyl-4-(trifluoromethyl)-1H-pyrazole-5-carboxylate.

$^1$H-NMR (400 MHz, d$_6$-DMSO): δ=11.10 (s, 1H), 8.34 (br. d, 1H), 7.66-7.68 (m, 2H), 7.47 (d, 1H), 4.87 (dd, 1H), 2.80-2.86 (m, 1H), 1.60-1.65 (m, 1H), 0.67-0.76 (m, 5H), 0.51-0.55 (m, 2H), 0.34-0.39 (m, 1H) ppm.

HPLC-MS$^{a)}$: log P=2.76; mass (m/z) 439 [M–F+H]$^+$.

Synthesis Process B

Example (Ik-2)

2-Chloro-5-({[1-methyl-3-(pentafluoroethyl)-4-(trifluoromethyl)-1H-pyrazol-5-yl]carbonyl}amino)benzoic acid

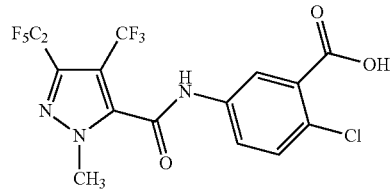

6.74 g (36.3 mmol) of methyl 5-amino-2-chlorobenzoate, 0.22 g (1.8 mmol) of 4-N,N-dimethylaminopyridine and 9.49 ml (54.4 mmol) of N-ethyldiisopropylamine are dissolved in 50.0 ml of ethyl acetate and cooled to 0° C. A solution of 6.0 g (18.1 mmol) of 1-methyl-3-(pentafluoroethyl)-4-(trifluoromethyl)-1H-pyrazole-5-carbonyl chloride in 100 ml of ethyl acetate is added over the course of an hour to this reaction mixture. When the addition is complete, the reaction mixture is stirred at room temperature for 16 hours. The reaction mixture is diluted with 250 ml of ethyl acetate and the organic phase is then washed three times with in each case 100 ml of 1M hydrochloric acid, three times with 1M sodium hydroxide solution and once with saturated sodium chloride solution.

This gives 8.0 g of a mixture of methyl 2-chloro-5-({[1-methyl-3-(pentafluoroethyl)-4-(trifluoromethyl)-1H-pyrazol-5-yl]carbonyl}amino)benzoate and methyl 5-(bis{[1- methyl-3-(pentafluoroethyl)-4-(trifluoromethyl)-1H-pyrazol-5-yl]carbonyl}amino)-2-chlorobenzoate in the ratio 6:4.

Methyl 2-chloro-5-({[1-methyl-3-(pentafluoroethyl)-4-(trifluoromethyl)-1H-pyrazol-5-yl]carbonyl}amino)benzoate
HPLC-MS[a)]: log P=4.05; mass (m/z)=480 [M+H]+.

Methyl 5-(bis{[1-methyl-3-(pentafluoroethyl)-4-(trifluoromethyl)-1H-pyrazol-5-yl]carbonyl}amino)-2-chlorobenzoate
HPLC-MS[a)]: log P=5.85; mass (m/z)=790 [M−H+H$_2$O]+.

8.0 g of the product mixture from the synthesis of methyl 2-chloro-5-({[1-methyl-3-(pentafluoroethyl)-4-(trifluoromethyl)-1H-pyrazol-5-yl]carbonyl}amino)benzoate are suspended in 150 ml of methanol and then admixed with 15.6 ml of 2M sodium hydroxide solution. The reaction mixture is stirred for 16 hours at room temperature and then slowly dripped into a mixture of 150 ml of 1M hydrochloric acid and 250 ml of ice. When the addition is complete, the mixture is stirred for a further one hour. The white precipitate which forms is filtered off and washed with cold water. After drying the solid in an oil pump vacuum, it is suspended in 50 ml of warm ethyl acetate and then precipitated out again by slowly adding 500 ml of cyclohexane. The precipitate is filtered off and dried.

This gives 4.55 g of 2-chloro-5-({[1-methyl-3-(pentafluoroethyl)-4-(trifluoromethyl)-1H-pyrazol-5-yl]carbonyl}amino)benzoic acid (54%) as white solid.

$^1$H-NMR (400 MHz, d$_3$-acetonitrile): δ=9.17 (br. s, 1H), 8.11 (d, 1H), 7.73 (dd, 1H), 7.52 (d, 1H), 3.98 (s, 3H) ppm.
HPLC-MS[a)]: log P=3.22; mass (m/z)=466 [M+H]+.

Example (Ik-3)

N-[4-Chloro-3-(prop-2-yn-1-ylcarbamoyl)phenyl]-1-methyl-3-(pentafluoroethyl)-4-(trifluoromethyl)-1H-pyrazole-5-carboxamide

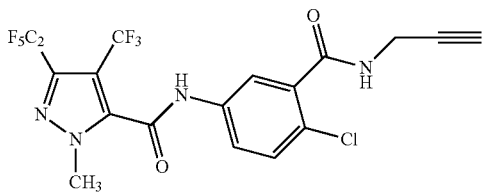

70 mg (0.15 mmol) of 2-chloro-5-({[1-methyl-3-(pentafluoroethyl)-4-(trifluoromethyl)-1H-pyrazol-5-yl]carbonyl}amino)benzoic acid are suspended in 2.0 ml of dichloromethane and then admixed in succession with 20.3 mg (0.15 mmol) of 1-hydroxybenzotriazole, 28.8 mg (0.20 mmol) of N-(3-dimethylaminopropyl)-N'-ethylcarbodiimide hydrochloride and 52.3 µL (0.30 mmol) of N-ethyldiisopropylamine. The reaction mixture is stirred for 20 minutes at room temperature and then admixed with 13.4 µL (0.20 mmol) of propargylamine. The reaction mixture is afterstirred overnight at room temperature and then concentrated under reduced pressure on a rotary evaporator. The crude product is then purified by means of preparative HPLC (C18, Saphir 110, 5 µm, 20×125 mm; gradient: 0-1.5 min 94% water, 5% acetonitrile, 1% formic acid, 1.5-6.0 min linear gradient to 4% water, 95% acetonitrile, 1% formic acid, 6.0-14.0 min 4% water, 95% acetonitrile, 1% formic acid).

This gives 57 mg of N-[4-chloro-3-(prop-2-yn-1-ylcarbamoyl)phenyl]-1-methyl-3-(pentafluoroethyl)-4-(trifluoromethyl)-1H-pyrazole-5-carboxamide (75%) as white solid.
HPLC-MS[b)]: log P=3.11; mass (m/z)=503 [M+H]+.

Example (Ik-127)

N-{3-Bromo[2-(1R,2S)-2-fluorocycloprop-1-ylcarbamoyl]pyrid-6-yl}-1-methyl-3-(pentafluoroethyl)-4-(trifluoromethyl)-1H-pyrazole-5-carboxamide

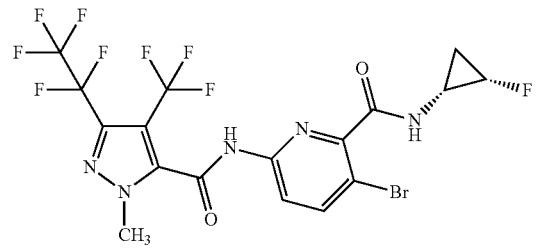 [SMILES: Cn1nc(C(F)(F)C(F)(F)F)c(C(F)(F)F)c1C(=O)Nc1ccc(Br)c(C(=O)N[C@@H]2C[C@@H]2F)n1]

528 mg (1.59 mmol) of 1-methyl-3-(pentafluoroethyl)-4-(trifluoromethyl)-1H-pyrazole-5-carbonyl chloride and a suspension of 214 mg of silver(I) cyanide in 13.4 ml of acetonitrile are added to a solution of 369 mg (1.59 mmol) of methyl 6-amino-3-bromopyridine-2-carboxylate (cf. WO 2008/084717) in 13.4 ml of dichloromethane. The reaction mixture is then stirred for 24 hours at room temperature. The reaction mixture is then filtered and the solvent mixture is stripped off in vacuo. The remaining residue is purified by means of column chromatography over silica gel using the eluent mixture cyclohexane:acetone (gradient). This gives 302 mg of methyl 3-bromo-6-({[1-methyl-3-(pentafluoroethyl)-4-(trifluoromethyl)-1H-pyrazole-5-yl]carbonyl}amino)pyridine-2-carboxylate (34%).
HPLC-MS[a)]: log P=4.06; mass (m/z)=527 [M+H]+.

425 mg (0.80 mmol) of methyl 3-bromo-6-({[1-methyl-3-(pentafluoroethyl)-4-(trifluoromethyl)-1H-pyrazol-5-yl]carbonyl}amino)pyridine-2-carboxylate are suspended in 13.4 ml of methanol and then admixed with 0.60 ml of 2M sodium hydroxide solution. The reaction mixture is stirred for 4 hours at 50° C. The reaction mixture is then taken up in ethyl acetate and shaken once against 1M hydrochloric acid. The organic phase is separated off, dried and concentrated by evaporation in vacuo. This gives 360 mg of 3-bromo-6-({[1-methyl-3-(pentafluoroethyl)-4-(trifluoromethyl)-1H-pyrazol-5-yl]carbonyl}amino)pyridine-2-carboxylic acid (65%; purity: 75% strength), which can be used without further purification for subsequent reactions.
HPLC-MS[a)]: log P=2.78; mass (m/z)=513 [M+H]+.

400 mg (783 µmol) of 3-bromo-6-({[1-methyl-3-(pentafluoroethyl)-4-(trifluoromethyl)-1H-pyrazol-5-yl]carbonyl}amino)pyridine-2-carboxylic acid are suspended in 36 ml of dichloromethane and then admixed in succession with 193 mg (783 mop of (1R,2S)-2-fluorocyclopropanaminium 4-methylbenzenesulphonate, 387 mg (1.02 mmol) of 2-(7-aza-1H-benzotriazol-1-yl)-1,1,3,3-tetramethyluronium hexafluorophosphate (HATU) and 388 µl (2.35 mmol) of N-ethyldiisopropylamine. The reaction mixture is stirred for 30 hours at room temperature. For work-up, the reaction mixture is washed in succession with 1M hydrochloric acid and sodium hydrogencarbonate solution. The organic phase is separated off, dried over sodium sulphate and concentrated by evaporation in vacuo. The remaining residue is purified by means of column chromatography on silica gel using the eluent mixture cyclohexane:acetone (gradient). This gives 228 mg of N-{3-bromo-[2-(1R,2S)-2-fluorocycloprop-1-yl-carbamoyl]pyrid-6-yl}-1-methyl-3-(pentafluoroethyl)-4-(trifluoromethyl)-1H-pyrazole-5-carboxamide (51%).

$^1$H-NMR (400 MHz, d$_6$-DMSO): δ=8.40 (d, 1H), 7.85 (d, 1H), 4.78 (m, 1H), 4.11 (s, 3H), 3.18 (br. s, 1H), 1.15-1.21 (m, 2H) ppm.

$^{13}$C-NMR (600 MHz, d$_6$-DMSO; 328K): δ=147.5; 143.9; 140.0; 121.5; 118.8; 108.8; 82.1; 69.8; 53.4; 38.9; 25.0; 11.4 ppm.

HPLC-MS[a)]: log P=3.29; mass (m/z)=568, 570 [M+1]$^+$.

Example (Ik-128)

5-Bromo-N-[(1R,2S)-2-fluorocyclopropyl]-2-({[1-methyl-3-(pentafluoroethyl)-4-(trifluoromethyl)-1H-pyrazol-5-yl]carbonyl}amino)isonicotinamide

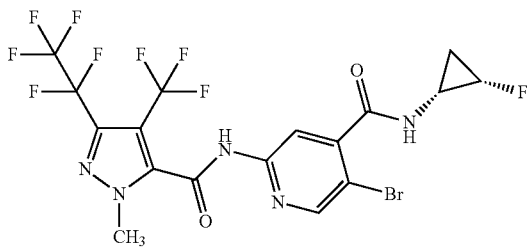 [SMILES: Cn1nc(C(F)(F)C(F)(F)F)c(C(F)(F)F)c1C(=O)Nc1cc(C(=O)N[C@@H]2C[C@@H]2F)c(Br)cn1]

The reaction with methyl 2-amino-5-bromoisonicotinate (cf. WO 2006/020830; bromination of methyl 2-aminoisonicotinate) takes place analogously to the reaction procedure in Example Ik-127 using:
738 mg (3.19 mmol) of methyl 2-amino-5-bromoisonicotinate in 26.8 ml of dichloromethane,
1056 mg (3.19 mmol) of 1-methyl-3-(pentafluoroethyl)-4-(trifluoromethyl)-1H-pyrazole-5-carbonyl chloride,
428 mg of silver(I) cyanide in
26.8 ml of acetonitrile.

The remaining residue is purified by means of column chromatography over silica gel using the eluent mixture cyclohexane:acetone (gradient). This gives 250 mg of methyl 5-bromo-2-({[1-methyl-3-(pentafluoroethyl)-4-(trifluoromethyl)-1H-pyrazol-5-yl]carbonyl}amino)-isonicotinate (15%).

HPLC-MS[a)]: log P=4.04; mass (m/z)=527 [M+H]$^+$.

The subsequent ester cleavage takes place analogously to the reaction procedure in Example (Ik-127) using:
335 mg (0.82 mmol) of methyl 5-bromo-2-({[1-methyl-3-(pentafluoroethyl)-4-(trifluoromethyl)-1H-pyrazol-5-yl]carbonyl}amino)isonicotinate,
15.2 ml of methanol,
1.24 ml of 2M sodium hydroxide solution.

This gives 380 mg of 5-bromo-2-({[1-methyl-3-(pentafluoroethyl)-4-(trifluoromethyl)-1H-pyrazol-5-yl]carbonyl}amino)isonicotinic acid (85%), which can be used without further purification for subsequent reactions.

HPLC-MS[a)]: log P=2.85; mass (m/z)=513 [M+H]$^+$.

The reaction of the 5-bromo-2-({[1-methyl-3-(pentafluoroethyl)-4-(trifluoromethyl)-1H-pyrazol-5-yl]carbonyl}amino)isonicotinic acid takes place analogously to the reaction procedure in Example (Ik-127) using:
100 mg (196 µmol) of 5-bromo-2-({[1-methyl-3-(pentafluoroethyl)-4-(trifluoromethyl)-1H-pyrazol-5-yl]carbonyl}amino)isonicotinic acid, 9.0 ml of dichloromethane, 48.3 mg (196 µmol) of (1R,2S)-2-fluorocyclopropanaminium 4-methylbenzenesulphonate, 96.6 mg (254 µmol) of HATU, 0.097 ml (587 µmol) of Hünig's base.

The remaining residue is purified by means of column chromatography on silica gel using the eluent mixture cyclohexane:acetone (gradient). This gives 89.4 mg of 5-bromo-N-[(1R,2S)-2-fluorocyclopropyl]-2-({[1-methyl-3-(pentafluoroethyl)-4-(trifluoromethyl)-1H-pyrazol-5-yl]carbonyl}amino)isonicotinamide (80%).

$^1$H-NMR (600 MHz, d$_3$-acetonitrile): δ=9.65 (br. s, 1H), 8.52 (d, 1H), 8.22 (d, 1H), 4.75 (m, 1H), 3.97 (s, 3H), 2.88 (br. s, 1H), 1.01-1.22 (m, 2H) ppm.

$^{13}$C-NMR (600 MHz, d$_3$-acetonitrile): δ=157.5; 151.8; 150.7; 148.3; 137.1; 114.2; 113.4; 111.2; 70.8; 39.6; 26.4; 12.2 ppm.

HPLC-MS[a)]: log P=3.19; mass (m/z)=568, 570 [M+1]$^+$.

Example (Ik-129)

5-Chloro-2-({[1-methyl-3-(pentafluoroethyl)-4-(trifluoromethyl)-1H-pyrazol-5-yl]carbonyl}amino)isonicotinic acid

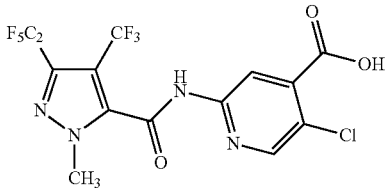

1.50 g (9.85 mmol) of methyl 2-aminoisonicotinate (commercially available) are stirred in 15 ml of dimethylformamide and admixed at a temperature of −18° C. in portions with 1.83 g (13.8 mol) of N-chlorosuccinimide. The mixture is then stirred for a further hour at −18° C. For work-up, the total reaction mixture is taken up in ethyl acetate and shaken against an aqueous sodium thiosulphate solution. The organic phase is then washed with water, dried over sodium sulphate and concentrated by evaporation in vacuo. The remaining residue is purified by means of column chromatography on silica gel using the eluent mixture cyclohexane:acetone (gradient). This gives 383 mg of methyl 2-amino-5-chloroisonicotinate (16%).

$^1$H-NMR (400 MHz, d$_6$-DMSO): δ=8.00 (s, 1H), 6.78 (s, 1H), 6.25 (br. s, 2H), 3.85 (s, 3H) ppm.

HPLC-MS[a)]: log P=1.30; mass (m/z)=187 [M+H]$^+$.

Moreover, 500 mg of methyl 2-amino-3,5-dichloroisonicotinate (23%) were also isolated as by-product.

$^1$H-NMR (400 MHz, d$_6$-DMSO): δ=8.04 (s, 1H), 6.62 (br. s, 2H), 3.92 (s, 3H) ppm.

HPLC-MS[a)]: log P=1.75; mass (m/z)=221 [M+1]$^+$.

The reaction with methyl 2-amino-5-chloroisonicotinate takes place analogously to the reaction procedure in Example (Ik-127) using:
601 mg (3.21 mmol) of methyl 2-amino-5-chloroisonicotinate in 28.0 ml of dichloromethane,
1064 mg (3.21 mmol) of 1-methyl-3-(pentafluoroethyl)-4-(trifluoromethyl)-1H-pyrazole-5-carbonyl chloride,
431 mg of silver(I) cyanide in 28.0 ml of acetonitrile.

The remaining residue is purified by means of column chromatography on silica gel using the eluent mixture cyclohexane:acetone (gradient). This gives 563 mg of methyl 5-chloro-2-({[1-methyl-3-(pentafluoroethyl)-4-(trifluoromethyl)-1H-pyrazol-5-yl]carbonyl}amino)-isonicotinate (36%).

The subsequent ester cleavage takes place analogously to the reaction procedure in Example (Ik-127) using:
563 mg (1.17 mmol) of methyl 5-chloro-2-({[1-methyl-3-(pentafluoroethyl)-4-(trifluoromethyl)-1H-pyrazol-5-yl]carbonyl}amino)isonicotinate,
15.3 ml of methanol,
1.57 ml of 2M sodium hydroxide solution.

This gives 542 mg of 5-chloro-2-({[1-methyl-3-(pentafluoroethyl)-4-(trifluoromethyl)-1H-pyrazol-5-yl]carbonyl}amino)isonicotinic acid (97%; purity: 98% strength), which can be used for subsequent reactions without further purification.

HPLC-MS[a)]: log P=2.82; mass (m/z)=467 [M+1]$^+$.

Example (Ik-130)

N-[2-(2,2-Difluorocycloprop-1-ylcarbamoyl)pyrid-4-yl]-1-methyl-3-(pentafluoroethyl)-4-(trifluoromethyl)-1H-pyrazole-5-carboxamide

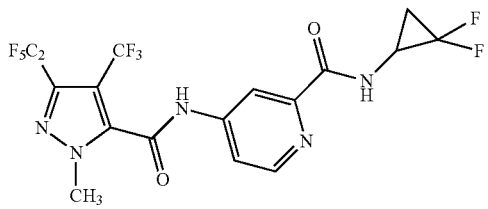

The reaction with methyl 4-aminopyridine-2-carboxylate (cf. WO 2001/074788) takes place analogously to the reaction procedure in Example (Ik-127) using:
486 mg (3.19 mmol) of methyl 4-aminopyridine-2-carboxylate in 26.8 ml of dichloromethane,
1056 mg (3.19 mmol) of 1-methyl-3-(pentafluoroethyl)-4-(trifluoromethyl)-1H-pyrazole-5-carbonyl chloride,
428 mg of silver(I) cyanide in
26.8 ml of acetonitrile.

The remaining residue is purified by means of column chromatography on silica gel using the eluent mixture cyclohexane:acetone (gradient). This gives 984 mg of methyl 4-({[1-methyl-3-(pentafluoroethyl)-4-(trifluoromethyl)-1H-pyrazol-5-yl]carbonyl}amino)pyridine-2-carboxylate (69%).

$^1$H-NMR (400 MHz, d$_6$-DMSO): δ=8.67 (d, 1H), 8.31 (s, 1H), 7.80 (d, 1H), 4.03 (s, 3H), 3.90 (s, 3H) ppm.
HPLC-MS[a)]: log P=3.01; mass (m/z)=447 [M+H]$^+$.

The subsequent ester cleavage takes place analogously to the reaction procedure in Example (Ik-127) using:
900 mg (2.01 mmol) of methyl 4-({[1-methyl-3-(pentafluoroethyl)-4-(trifluoromethyl)-1H-pyrazol-5-yl]carbonyl}amino)pyridine-2-carboxylate,
25.0 ml of methanol,
1.51 ml of 2M sodium hydroxide solution.

This gives 807 mg of 4-({[1-methyl-3-(pentafluoroethyl)-4-(trifluoromethyl)-1H-pyrazol-5-yl]carbonyl}amino)pyridine-2-carboxylic acid (58%; purity: 63%), which can be used for subsequent reactions.

HPLC-MS[a)]: log P=2.06; mass (m/z)=433 [M+H]$^+$.

The reaction of 4-({[1-methyl-3-(pentafluoroethyl)-4-(trifluoromethyl)-1H-pyrazol-5-yl]carbonyl}-amino)pyridine-2-carboxylic acid takes place analogously to the reaction procedure in Example (Ik-127) using:

150 mg (347 µmol) of 4-({[1-methyl-3-(pentafluoroethyl)-4-(trifluoromethyl)-1H-pyrazol-5-yl]carbonyl}amino)pyridine-2-carboxylic acid,
13.5 ml of dichloromethane,
85.8 mg (1.50 mmol) of 2,2-difluorocyclopropylamine,
171.4 mg (451 µmol) of HATU,
172 µl (587 µmol) of Hünig's base.

The remaining residue is purified firstly by means of column chromatography on silica gel using the eluent mixture cyclohexane:acetone (gradient) and then by means of preparative HPLC using the eluent mixture acetone:water (neutral). This gives 68 mg of N-[2-(2,2-difluorocycloprop-1-ylcarbamoyl)pyrid-4-yl]-1-methyl-3-(pentafluoroethyl)-4-(trifluoromethyl)-1H-pyrazole-5-carboxamide (38%).

$^1$H-NMR (600 MHz, d$_3$-acetonitrile): δ=9.55 (br. s, 1H), 8.31 (br. s, 1H), 8.56 (d, 1H), 8.27 (d, 1H), 7.81 (dd, 1H), 3.99 (s, 3H), 3.47 (br. s, 1H), 1.64-1.93 (m, 2H) ppm.
$^{13}$C-NMR (600 MHz, d$_3$-acetonitrile): δ=166.0; 157.8; 151.6; 150.9; 146.6; 140.4; 137.2; 121.8; 119.6; 117.2; 112.8; 112.7; 111.2; 109.6; 39.8; 31.3; 18.1 ppm.
HPLC-MS[a)]: log P=3.59; mass (m/z)=508 [M+H]$^+$.

Example (Ik-131)

2-Chloro-5-({[1-methyl-3-(pentafluoroethyl)-4-(trifluoromethyl)-1H-pyrazol-5-yl]carbonyl}amino)nicotinic acid

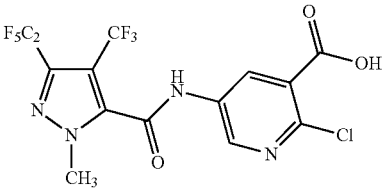

The reaction with methyl 5-amino-2-chloronicotinate (cf. WO 2006/050506) takes place analogously to the reaction procedure in Example (Ik-127) using:
601 mg (3.21 mmol) of methyl 5-amino-2-chloronicotinate in 28.0 ml of dichloromethane,
1.06 g (3.19 mmol) of 1-methyl-3-(pentafluoroethyl)-4-(trifluoromethyl)-1H-pyrazole-5-carbonyl chloride,
431 mg of silver(I) cyanide in
28.0 ml of acetonitrile.

The remaining residue is purified by means of column chromatography on silica gel using the eluent mixture cyclohexane:acetone (gradient). This gives 980 mg of methyl 2-chloro-5-({[1-methyl-3-(pentafluoroethyl)-4-(trifluoromethyl)-1H-pyrazol-5-yl]carbonyl}amino)nicotinate (62%).

$^1$H-/$^{13}$C-correlation (HMQC) NMR (600 MHz, d$_3$-acetonitrile): δ=8.75 (s, 1H), 8.57 (s, 1H), 4.04 (s, 3H), 3.91 (s, 3H) ppm.
$^{13}$C-NMR (600 MHz, d$_3$-acetonitrile): δ=164.2; 156.3; 143.5; 143.3; 140.2; 135.5; 134.0; 131.0; 126.6; 120.8; 118.3; 110.1; 109.6; 53.4; 39.3 ppm.
HPLC-MS[a)]: log P=3.70; mass (m/z)=481 [M+H]$^+$.

The subsequent ester cleavage takes place analogously to the reaction procedure in Example (Ik-127) using:
940 mg (1.95 mmol) of methyl 2-chloro-5-({[1-methyl-3-(pentafluoroethyl)-4-(trifluoromethyl)-1H-pyrazol-5-yl]carbonyl}amino)nicotinate,
32.8 ml of methanol,
2.93 ml of 2M sodium hydroxide solution.

This gives 912 mg of 2-chloro-5-({[1-methyl-3-(pentafluoroethyl)-4-(trifluoromethyl)-1H-pyrazol-5-yl]

carbonyl}amino)pyridine-3-carboxylic acid (96%; purity: 96% strength), which can be used for subsequent reactions without further purification.

HPLC-MS$^{a)}$: log P=2.27; mass (m/z)=467 [M+H]$^+$.

Synthesis Process C

Example (Ik-4)

N-[4-Chloro-3-(cyclopropylcarbamoyl)phenyl]-1-methyl-3-(pentafluoroethyl)-4-iodo-1H-pyrazole-5-carboxamide

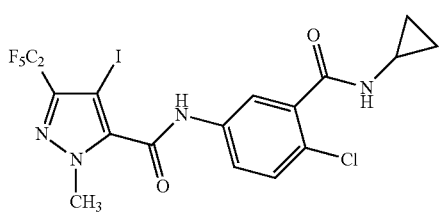

0.49 g (2.34 mmol) of 4-chloro-3-(cyclopropylcarbamoyl) aniline dissolved in 0.5 ml of dioxane are added dropwise to a solution of 1.28 g (2.34 mmol) of 4-iodo-1-methyl-3-pentafluoroethyl-1H-pyrazolecarboxylic acid and 0.54 g (2.81 mmol) of 1-ethyl-3-[3-dimethylaminopropyl]carbodiimide hydrochloride in 20 ml of dioxane and the reaction mixture is stirred for three days at room temperature. The majority of the dioxane is distilled off at reduced pressure on a rotary evaporator and the residue is admixed with 20 ml of water. The aqueous phase is extracted three times with ethyl acetate and the organic phase is then washed three times with saturated sodium chloride solution. After drying over sodium sulphate, the solvent is distilled off at reduced pressure on a rotary evaporator and the residue is purified by means of flash chromatography on silica gel (eluent: cyclohexane/ethyl acetate). This gives 0.70 g of N-[4-chloro-3-(cyclopropylcarbamoyl) phenyl]-1-methyl-3-(pentafluoroethyl)-4-iodo-1H-pyrazole-5-carboxamide (53%) as an oil.

$^1$H-NMR (400 MHz, d$_3$-acetonitrile): δ=8.84 (br. s, 1H), 7.68 (d, 1H), 7.66 (dd, 1H), 7.45 (d, 1H), 6.80 (br. s, 1H), 4.04 (s, 3H), 2.85 (m, 1H), 0.91 (m, 2H), 0.77 (m, 2H) ppm.

HPLC-MS$^{a)}$: log P=3.16; mass (m/z)=563 [M+H]$^+$.

Example (Ik-5)

N-[4-Chloro-3-(cyclopropylcarbamoyl)phenyl]-1-methyl-3-(pentafluoroethyl)-4-ethenyl-1H-pyrazol-5-carboxamide

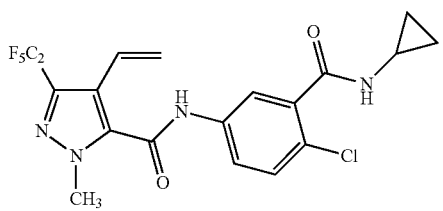

In succession, 18.5 mg (0.016 mmol) of tetrakis(triphenylphosphine)palladium, 0.044 g (0.320 mmol) of potassium carbonate in 1 ml of water, and 0.077 g (320 μmol of 2,4,6-trivinylcyclotriboroxane pyridine complex are added to a solution of 180 mg (0.32 mmol) of N-[4-chloro-3-(cyclopropylcarbamoyl)phenyl]-1-methyl-3-(pentafluoroethyl)-4-iodo-1H-pyrazole-5-carboxamide from Example Ik-4 in 3 ml of dimethoxyethane, and the reaction mixture is heated under reflux for 20 hours. The solvent is completely distilled off at reduced pressure on a rotary evaporator and the residue is purified by means of flash chromatography on silica gel (eluent: cyclohexane/ethyl acetate; gradient: 2 hours, from 0% to 100% ethyl acetate). This gives 0.107 g of N-[4-chloro-3-(cyclopropylcarbamoyl)phenyl]-1-methyl-3-(pentafluoroethyl)-4-ethenyl-1H-pyrazole-5-carboxamide (70%) as an oil.

$^1$H-NMR (400 MHz, d$_3$-acetonitrile): δ=8.78 (br. s, 1H), 7.68 (d, 1H), 7.62 (dd, 1H), 7.42 (d, 1H), 6.79 6.71 (m, 2H), 5.46 (m, 1H), 5.43 (m, 1H) 3.99 (s, 3H), 2.85 (m, 1H), 0.92 (m, 2H), 0.77 (m, 2H) ppm.

HPLC-MS$^{a)}$: log P=3.11, mass (m/z)=463 [M+H]$^+$.

Example (Ik-126)

N-{4-Chloro-3-[(2,2,2-trifluoroethyl)carbamoyl] phenyl}-3-(difluoromethoxy)-1-methyl-4-(trifluoromethyl)-1H-pyrazole-5-carboxamide

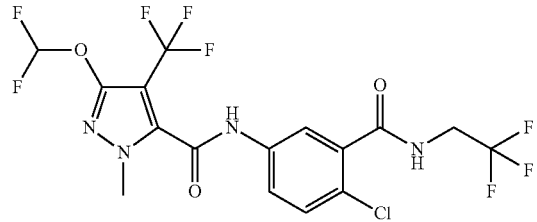 [SMILES: Cn1nc(OC(F)F)c(C(F)(F)F)c1C(=O)Nc1ccc(Cl)c(C(=O)NCC(F)(F)F)c1]

36.2 mg (0.19 mmol) of copper(I) iodide and 8.8 mg (0.15 mmol) of potassium fluoride are initially introduced in a heat-dried vial under argon, and 4 ml of N,N-dimethylformamide and 70.0 mg (0.12 mmol) of N-{4-chloro-3-[(2,2,2-trifluoroethyl)carbamoyl]phenyl}-3-(difluoromethoxy)-4-iodo-1-methyl-1H-pyrazole-5-carboxamide and 36.0 mg (254 μmol) of trifluoromethyltrimethylsilane are added. The reaction mixture is degassed in the ultrasound, flushed with argon and the closed vial is heated at 80° C. for two hours. The reaction solution is poured onto water and extracted with ethyl acetate. The organic phase is dried over sodium sulphate, filtered and concentrated by evaporation on a rotary evaporator. Chromatographic purification on silica gel gives 8.00 mg of N-{4-chloro-3-[(2,2,2-trifluoroethyl)carbamoyl] phenyl}-3-(difluoromethoxy)-1-methyl-4-(trifluoromethyl)-1H-pyrazole-5-carboxamide (13%).

$^1$H-NMR (400 MHz, d$_6$-DMSO): δ=11.18 (s, 1H), 9.02 (m, 1H), 7.71 (m, 2H), 7.53 (d, 1H), 7.38 (t, 1H), 4.03 (m, 2H), 3.84 (s, 3H) ppm.

HPLC-MS$^{a)}$: log P=3.01; mass (m/z) 495 [M+H]$^+$.

Synthesis Process D

Example (Ib-2)

N-[4-Chloro-3-(cyclopropylcarbamoyl)phenyl]-2-(2,2,2-trifluoroethoxy)-4-trifluoromethyl)pyrimidine-5-carboxamide

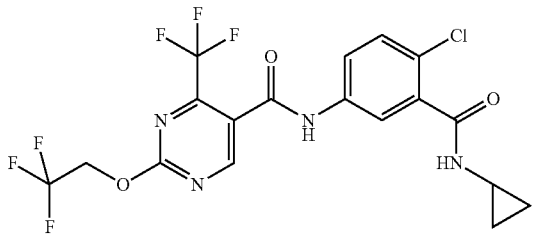 [SMILES: O=C(NC1CC1)c1cc(NC(=O)c2cnc(OCC(F)(F)F)nc2C(F)(F)F)ccc1Cl]

2-Chloro-4-trifluoromethyl-5-pyrimidinecarboxylic acid and 5-amino-2-chloro-N-cyclopropylbenzamide are coupled by the method described in synthesis process A. This gives 2-chloro-N-[4-chloro-3-(cyclopropylcarbamoyl)phenyl]-4-(trifluoromethyl)pyrimidine-5-carboxamide.

$^1$H-NMR (400 MHz, $d_6$-DMSO): δ=9.35 (s, 1H), 8.32 (d, 1H), 7.67 (m, 1H), 7.64 (s, 1H), 7.47 (dd, 1H), 2.83 (m, 1H), 0.69 (m, 2H), 0.55 (m, 2H) ppm.

HPLC-MS$^{a)}$: log P=2.36; mass (m/z)=419 [M+H]$^+$.

105 mg (250 µmol) of 2-chloro-N-[4-chloro-3-(cyclopropylcarbamoyl)phenyl]-4-(trifluoromethyl)-pyrimidine-5-carboxamide and 67.5 mg (675 µmol) of trifluoroethanol are dissolved in 5 ml of acetonitrile. At −5° C., 64.5 mg (575 µmol) are added in portions. The reaction mixture is stirred overnight at room temperature and then admixed with 5 ml of 1M hydrochloric acid. The aqueous phase is extracted twice with 5 ml of ethyl acetate, then dried over sodium sulphate and filtered and the solvent is removed under reduced pressure on a rotary evaporator. The residue is purified by means of flash chromatography over silica gel (eluent: cyclohexane/ethyl acetate: 2/1).

This gives 60 mg of N-[4-chloro-3-(cyclopropylcarbamoyl)phenyl]-2-(2,2,2-trifluoroethoxy)-4-trifluoromethyl)pyrimidine-5-carboxamide (50%) as a white solid.

$^1$H-NMR (400 MHz, $d_6$-DMSO): δ=10.78 (s, 1H), 9.22 (s, 1H), 8.31 (d, 1H), 7.66 (m, 2H), 7.45 (dd, 1H), 2.83 (m, 1H), 0.70 (m, 2H), 0.53 (m, 2H) ppm.

HPLC-MS$^{a)}$: log P=2.76; mass (m/z)=483 [M+H]$^+$.

The following were obtained in the same way:

Example (Ii-7)

N-[4-Chloro-3-(cyclopropylcarbamoyl)phenyl]-5-(2,2,2-trifluoroethoxy)-3-(trifluoromethyl)pyridine-2-carboxamide

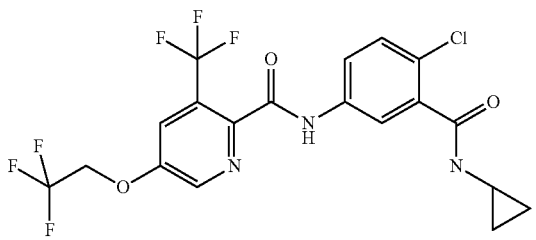 [SMILES: O=C(NC1CC1)c1cc(NC(=O)c2ncc(OCC(F)(F)F)cc2C(F)(F)F)ccc1Cl]

5-Chloro-3-trifluoromethylpyridine-2-carboxylic acid and 5-amino-2-chloro-N-cyclopropylbenzamide are coupled by the method described in preparation process A. This gives 5-chloro-N-[4-chloro-3-(cyclopropylcarbamoyl)phenyl]-3-(trifluoromethyl)pyridine-2-carboxamide.

$^1$H-NMR (400 MHz, $d_6$-DMSO): δ=10.80 (s, 1H), 8.99 (s, 1H), 8.53 (s, 1H), 8.31 (d, 1H), 7.72 (m, 2H), 7.44 (dd, 1H), 2.83 (m, 1H), 0.69 (m, 2H), 0.53 (m, 2H) ppm.

HPLC-MS$^{a)}$: log P=2.55; mass (m/z)=418 [M+H]$^+$.

Analogously to the preparation of (Ib-2), N-[4-chloro-3-(cyclopropylcarbamoyl)phenyl]-5-(2,2,2-trifluoroethoxy)-3-(trifluoromethyl)pyridine-2-carboxamide is synthesized from 5-chloro-N-[4-chloro-3-(cyclopropylcarbamoyl)phenyl]-3-(trifluoromethyl)pyridine-2-carboxamide and 2,2,2-trifluoroethanol with the addition of 0.2 equivalents of 18-crown-6.

$^1$H-NMR (400 MHz, $d_3$-acetonitrile): δ=9.78 (s, 1H), 8.57 (d, 1H), 7.87 (d, 1H), 7.81 (s, 1H), 7.77 (dd, 1H), 7.42 (dd, 1H), 6.90 (bs, 1H), 4.77 (q, 2H), 2.83 (m, 2H), 0.75 (m, 1H), 0.58 (m, 2H) ppm.

HPLC-MS$^{a)}$: log P=2.90; mass (m/z)=482 [M+H]$^+$.

Example (Ij-1)

N-[4-Chloro-3-(cyclopropylcarbamoyl)phenyl]-6-(2,2,2-trifluoroethoxy)-4-(trifluoromethyl)pyridine-3-carboxamide

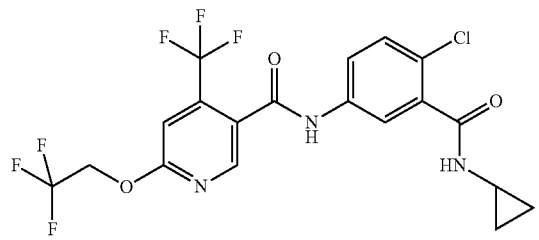 [SMILES: O=C(NC1CC1)c1cc(NC(=O)c2cnc(OCC(F)(F)F)cc2C(F)(F)F)ccc1Cl]

2-Chloro-4-trifluoromethylpyridine-5-carboxylic acid and 5-amino-2-chloro-N-cyclopropylbenzamide are coupled by the method described in preparation process A. This gives 2-chloro-N-[4-chloro-3-(cyclopropylcarbamoyl)phenyl]-4-(trifluoromethyl)pyridine-5-carboxamide.

$^1$H-NMR (400 MHz, $d_6$-DMSO): δ=10.80 (s, 1H), 8.85 (s, 1H), 8.30 (d, 1H), 8.05 (s, 1H), 7.67 (m, 2H), 7.45 (m, 1H), 2.83 (m, 1H), 0.69 (m, 2H), 0.53 (m, 2H) ppm.

HPLC-MS$^{a)}$: log P=2.35; mass (m/z)=418 [M+H]$^+$.

Analogously to the preparation of (Ib-2), N-[4-chloro-3-(cyclopropylcarbamoyl)phenyl]-5-(2,2,2-trifluoroethoxy)-3-(trifluoromethyl)pyridine-2-carboxamide is synthesized from 2-chloro-N-[4-chloro-3-(cyclopropylcarbamoyl)phenyl]-4-(trifluoromethyl)pyridine-5-carboxamide and 2,2,2-trifluoroethanol.

$^1$H-NMR (400 MHz, $d_6$-DMSO): δ=8.62 (s, 1H), 8.30 (d, 1H), 7.68 (m, 2H), 7.45 (m, 2H), 5.13 (q, 2H), 2.83 (m, 1H), 0.69 (m, 2H), 0.53 (m, 2H) ppm.

HPLC-MS$^{a)}$: log P=3.02; mass (m/z)=482 [M+H]$^+$.

Synthesis Process E

Example (Ia-1)

N-[4-Chloro-3-(cyclopropylcarbamoyl)phenyl]-2-methyl-6-(pentafluoroethyl)-5-(trifluoromethyl)pyrimidine-4-carboxamide

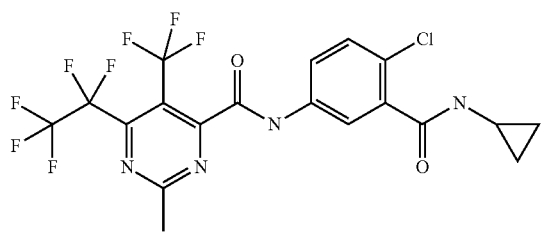 [SMILES: Cc1nc(C(=O)Nc2ccc(Cl)c(C(=O)NC3CC3)c2)c(C(F)(F)F)c(C(F)(F)C(F)(F)F)n1]

In a heat-dried flask, 975 mg (3.02 mmol) of 2-methyl-6-(pentafluoroethyl)-5-(trifluoromethyl)pyrimidine-4-carboxamide, 833 mg (6.03 mmol) of potassium carbonate, 287 mg (1.51 mmol) of copper iodide and molecular sieve are initially introduced under argon. Then, 795 mg (3.02 mmol) of ethyl 5-bromo-2-chlorobenzoate, 429 mg (3.02 mmol) of N,N'-dimethylcyclohexane-1.2-diamine and 5 ml of toluene are added dropwise. The reaction mixture is stirred at 100° C. in a microwave for 45 min and then diluted with ethyl acetate, filtered over Celite and concentrated by evaporation on a rotary evaporator. The residue is purified by means of flash chromatography on silica gel (eluent: cyclohexane/ethyl acetate 1/5). This gives 0.16 g of ethyl 2-chloro-5-({[2-methyl-6-(pentafluoroethyl)-5-(trifluoromethyl)pyrimidin-4-yl]-carbonyl}amino)benzoate (10%) as a beige solid.

$^1$H-NMR (400 MHz, d$_6$-DMSO): δ=8.05 (d, 1H), 7.81-7.78 (m, 1H), 7.59-7.52 (m, 1H), 4.36 (q, 2H), 2.88 (s, 3H), 1.33 (t, 3H) ppm.

HPLC-MS$^{a)}$: log P=4.55; mass (m/z)=506 [M+H]$^+$.

32 mg (1.22 mmol) of lithium hydroxide are added to a solution of 142 mg (0.28 mmol) of ethyl 2-chloro-5-({[2-methyl-6-(pentafluoroethyl)-5-(trifluoromethyl)pyrimidin-4-yl]carbonyl}amino)-benzoate in a 1:1 tetrahydrofuran/water mixture. The reaction mixture is stirred overnight at room temperature, acidified and evaporated. The residue is taken up in ethyl acetate, washed with 1M hydrochloric acid, dried and concentrated by evaporation. This gives 94 mg of 2-chloro-5-({[2-methyl-6-(pentafluoroethyl)-5-(trifluoromethyl)pyrimidin-4-yl]carbonyl}amino)benzoic acid (70%).

$^1$H-NMR (400 MHz, d$_3$-acetonitrile): δ=9.36 (br. s, 1H), 8.20 (m, 1H), 7.81-7.77 (m, 1H), 7.54-7.51 (m, 1H), 2.87 (s, 3H) ppm.

HPLC-MS$^{a)}$: log P=3.30; mass (m/z)=478 [M+H]$^+$.

In 10 ml of dichloromethane, 94 mg (0.19 mmol) of 2-chloro-5-({[2-methyl-6-(pentafluoroethyl)-5-(trifluoromethyl)pyrimidin-4-yl]carbonyl}amino)benzoic acid are admixed with two drops of N,N-dimethylformamide and cooled to 0° C. After adding 0.05 ml of oxalyl dichloride, the reaction mixture is stirred at room temperature for three hours and then concentrated by evaporation.

$^{a)}$ Note regarding the determination of the log P values and mass detection: The log P values given were determined in accordance with EEC Directive 79/831 Annex V.A8 by HPLC (High Performance Liquid Chromatography) on a phase inversion column (C18). Agilent 1100 LC system; 50*4.6 Zorbax Eclipse Plus C18 1.8 micron; eluent A: acetonitrile (0.1% formic acid); eluent B: water (0.09% formic acid); linear gradient from 10% acetonitrile to 95% acetonitrile in 4.25 min, then 95% acetonitrile for a further 1.25 min; oven temperature 55° C.; flow: 2.0 ml/min. The mass detection is carried out via an Agilend MSD system.

$^{b)}$ Note regarding the determination of the log P values and mass detection: The log P values given were determined in accordance with EEC Directive 79/831 Annex V.A8 by HPLC (High Performance Liquid Chromatography) on a phase inversion column (C18). HP1100; 50*4.6 Zorbax Eclipse Plus C18 1.8 micron; eluent A: acetonitrile (0.1% formic acid); eluent B: water (0.08% formic acid); linear gradient from 5% acetonitrile to 95% acetonitrile in 1.70 min, then 95% acetonitrile for a further 1.00 min; oven temperature 55° C.; flow: 2.0 ml/min. The mass detection is carried out via the mass detector Micromass ZQ2000 from Waters.

The compounds listed in Tables 1-6 were synthesized with the help of the above-described synthesis processes A to E.

Preparation of the Starting Compounds

Ethyl 4-(difluoromethyl)-2-(pentafluoroethyl)pyrimidine-5-carboxylate

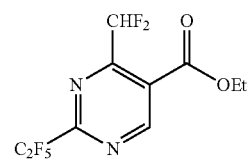

A mixture of 1.62 g (10 mmol) of 2,2,3,3,3-pentafluoropropanimidamide and 2.22 g (10 mmol) of ethyl 2-(ethoxymethylene)-4,4-difluoro-3-oxobutanoate (for preparation see WO 2005/123690) in 10 ml of ethanol is stirred under reflux for 4 days after adding 0.68 g (10 mmol) of sodium ethylate. Concentration by evaporation in vacuo is then carried out and the residue is taken up in 10 ml of water and extracted twice with 10 ml of ethyl acetate. The organic phases are washed successively with 5 ml of water and 5 ml of saturated sodium chloride solution, dried over sodium sulphate, filtered and concentrated by evaporation in vacuo. Chromatographic purification with a mixture of cyclohexane and ethyl acetate gives 1.26 g of ethyl 4-(difluoromethyl)-2-(pentafluoroethyl)pyrimidine-5-carboxylate (40%) as a white solid.

$^1$H-NMR (400 MHz, d$_6$-DMSO): δ=9.58 (s, 1H), 7.49 (t, 1H), 4.45 (q, 2H), 1.38 (t, 3H) ppm.

HPLC-MS$^{a)}$: log P=3.42; mass (m/z)=321 [M+H]$^+$.

The following were obtained in the same way:

Ethyl 2-(pentafluoroethyl)-4-(trifluoromethyl)pyrimidine-5-carboxylate from ethyl 2-(ethoxymethylene)-4,4,4-trifluoro-3-oxobutanoate and 2,2,3,3,3-pentafluoropropanimidamide

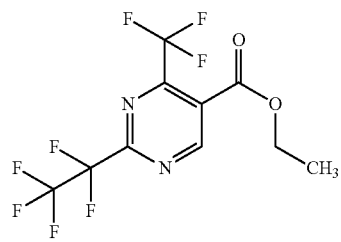 [SMILES: CCOC(=O)c1cnc(C(F)(F)C(F)(F)F)nc1C(F)(F)F]

¹H-NMR (400 MHz, d₆-DMSO): δ=9.66 (s, 1H), 4.45 (q, 2H), 1.36 (t, 3H) ppm.

HPLC-MS$^{a)}$: log P=3.86; mass (m/z)=339 [M+H]⁺.

Ethyl 2-(heptafluoropropyl)-4-(trifluoromethyl)pyrimidine-5-carboxylate from ethyl 2-(ethoxymethylene)-4,4,4-trifluoro-3-oxobutanoate and 2,2,3,3,4,4,4-heptafluorobutanimidamide

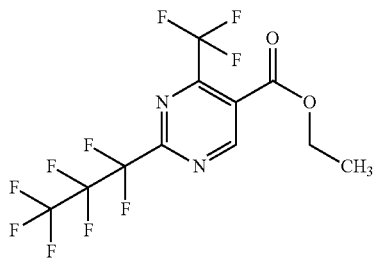 [SMILES: CCOC(=O)c1cnc(C(F)(F)C(F)(F)C(F)(F)F)nc1C(F)(F)F]

¹H-NMR (400 MHz, d₆-DMSO): δ=9.68 (s, 1H), 4.46 (q, 2H), 1.36 (t, 3H) ppm.

HPLC-MS$^{a)}$: log P=4.32; mass (m/z)=389 [M+H]⁺.

Ethyl 4,6-dimethyl-2-(pentafluoroethyl)pyrimidine-5-carboxylate from ethyl (2E)-2-acetyl-3-ethoxybut-2-enoate (for preparation see Journal of Medicinal Chemistry 2006, 49, 6351) and 2,2,3,3,3-pentafluoropropanimidamide

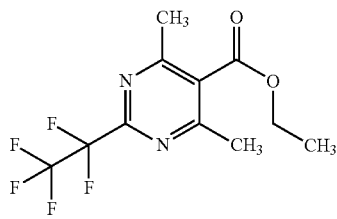 [SMILES: CCOC(=O)c1c(C)nc(C(F)(F)C(F)(F)F)nc1C]

¹H-NMR (400 MHz, d₆-DMSO): δ=4.46 (q, 2H), 3.10 (s, 6H), 1.36 (t, 3H) ppm.

HPLC-MS$^{a)}$: log P=3.68; mass (m/z)=299 [M+H]⁺.

Ethyl 2,4-bis(pentafluoroethyl)pyrimidine-5-carboxylate from ethyl 2-(ethoxymethylene)-4,4,5,5,5-pentafluoro-3-oxopentanoate (preparation analogous to WO 2005/123690) and 2,2,3,3,3-pentafluoropropanimidamide

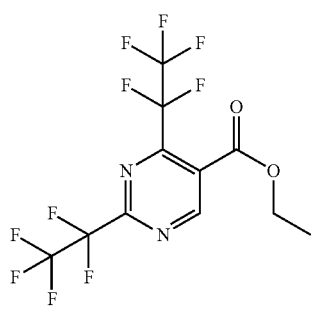 [SMILES: CCOC(=O)c1cnc(C(F)(F)C(F)(F)F)nc1C(F)(F)C(F)(F)F]

¹H-NMR (400 MHz, d₆-DMSO): δ=9.68 (s, 1H), 4.46 (q, 2H), 1.35 (t, 3H) ppm.

HPLC-MS: log P=4.41; mass (m/z)=389 [M+H]⁺.

Ethyl 4-(pyridin-2-yl)-2-(trifluoromethyl)pyrimidine-5-carboxylate from ethyl 3-ethoxy-2-(pyridin-2-ylcarbonyl)acrylate (preparation analogous to WO 2005/123690) and 2,2,2-trifluoropropanimidamide

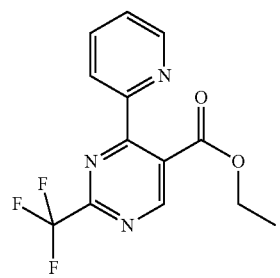 [SMILES: CCOC(=O)c1cnc(C(F)(F)F)nc1-c1ccccn1]

¹H-NMR (400 MHz, d₆-DMSO): δ=9.28 (s, 1H), 8.69-8.71 (m, 1H), 8.27-8.30 (m, 1H), 8.09 (dt, 1H), 7.61-7.64 (m, 1H), 4.31 (q, 2H), 1.18 (t, 3H) ppm.

HPLC-MS: log P=3.09; mass (m/z)=298 [M+H]⁺.

Ethyl 4-methyl-2-(pentafluoroethyl)pyrimidine-5-carboxylate can be synthesized analogously to the procedure in

*Bioorg. Med. Chem. Letters* 2005, 15, 4898.

4-(Difluoromethyl)-2-(pentafluoroethyl)pyrimidine-5-carboxylic acid

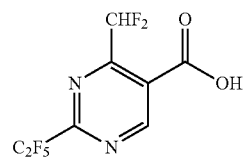

1.15 g (3.59 mmol) of ethyl 4-(difluoromethyl)-2-(pentafluoroethyl)pyrimidine-5-carboxylate are dissolved in 4 ml of ethanol. 5.39 ml (10.8 mmol) of 2M sodium hydroxide solution are added and the reaction mixture is stirred for four hours at room temperature. 2M hydrochloric acid is added to establish a pH of 2-3. The resulting solid is filtered off with suction, washed with a small amount of water and triturated with cyclohexane. This gives 870 mg of 4-(difluoromethyl)-2-(pentafluoroethyl)pyrimidine-5-carboxylic acid (83%) as a white solid.

¹H-NMR (400 MHz, d₆-DMSO): δ=9.55 (s, 1H), 7.58 (t, 1H) ppm.

HPLC-MS$^{a)}$: log P=1.80; mass (m/z)=293 [M+H]⁺.

The following were obtained in the same way:

2-(Pentafluoroethyl)-4-(trifluoromethyl)pyrimidine-5-carboxylic acid from ethyl 2-(pentafluoroethyl)-4-(trifluoromethyl)pyrimidine-5-carboxylate

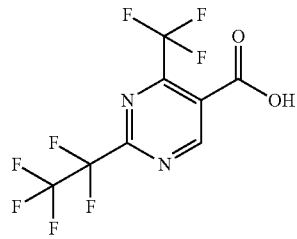 [SMILES: O=C(O)c1cnc(C(F)(F)C(F)(F)F)nc1C(F)(F)F]

¹H-NMR (400 MHz, d₆-DMSO): δ=9.40 (s, 1H) ppm.
HPLC-MS[a]: log P=1.80; mass (m/z)=311 [M+H]⁺.

2-(Heptafluoropropyl)-4-(trifluoromethyl)pyrimidine-5-carboxylic acid from ethyl 2-(heptafluoropropyl)-4-(trifluoromethyl)pyrimidine-5-carboxylate

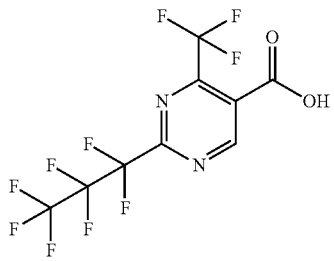 [SMILES: O=C(O)c1cnc(C(F)(F)C(F)(F)C(F)(F)F)nc1C(F)(F)F]

¹H-NMR (400 MHz, d₆-DMSO): δ=9.50 (s, 1H) ppm.
HPLC-MS[a]: log P=2.23; mass (m/z)=361 [M+H]⁺.

4-Methyl-2-(trifluoromethyl)pyrimidine-5-carboxylic acid from ethyl 4-methyl-2-(trifluoromethyl)pyrimidine-5-carboxylate

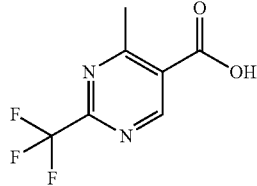

¹H-NMR (400 MHz, d₆-DMSO): δ=9.19 (s, 1H) ppm.
HPLC-MS[a]: log P=1.26; mass (m/z)=207 [M+H]⁺.

4-Methyl-2-(pentafluoroethyl)pyrimidine-5-carboxylic acid from ethyl 4-methyl-2-(pentafluoroethyl)pyrimidine-5-carboxylate

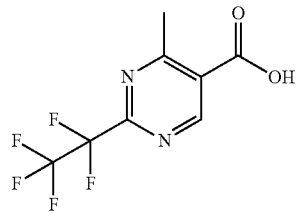 [SMILES: Cc1nc(C(F)(F)C(F)(F)F)ncc1C(=O)O]

¹H-NMR (400 MHz, d₆-DMSO): δ=9.25 (s, 1H) ppm.
HPLC-MS[a]: log P=1.97; mass (m/z)=257 [M+H]⁺.

4,6-Dimethyl-2-(pentafluoroethyl)pyrimidine-5-carboxylic acid from ethyl 4,6-dimethyl-2-(pentafluoroethyl)pyrimidine-5-carboxylate

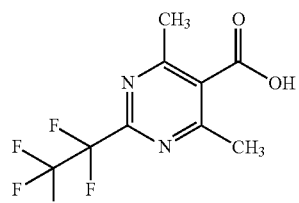

¹H-NMR (400 MHz, d₆-DMSO): δ=2.58 (s, 6H) ppm.
HPLC-MS[a]: log P=1.63; mass (m/z)=271 [M+H]⁺.

4-Chloro-3-(trifluoromethyl)pyridine-2-carboxylic acid was prepared analogously to the literature reference *European Journal of Organic Chemistry* 2004, 18, 3793 from 4-chloro-3-(trifluoromethyl)pyridine

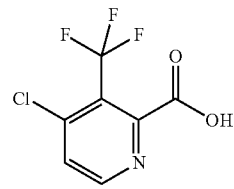 [SMILES: O=C(O)c1nccc(Cl)c1C(F)(F)F]

¹H-NMR (400 MHz, d₆-DMSO): δ=9.13 (d, 1H), 9.07 (d, 1H) ppm.
HPLC-MS: log P=1.16; mass (m/z)=226 [M+H]⁺.

2,4-Bis(pentafluoroethyl)pyrimidine-5-carboxylic acid from ethyl 2,4-bis(pentafluoroethyl)-pyrimidine-5-carboxylate

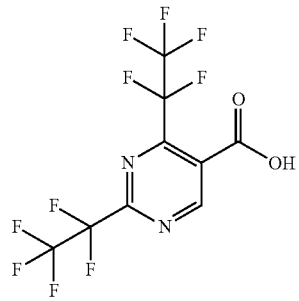 [SMILES: O=C(O)c1cnc(C(F)(F)C(F)(F)F)nc1C(F)(F)C(F)(F)F]

¹H-NMR (400 MHz, d₆-DMSO): δ=9.56 (s, 1H) ppm.
HPLC-MS: log P=2.24; mass (m/z)=361 [M+H]⁺.

4-(Pyridin-2-yl)-2-(trifluoromethyl)pyrimidine-5-carboxylic acid

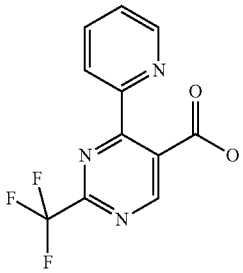

¹H-NMR (400 MHz, d₆-DMSO): δ=9.27 (s, 1H), 8.71-8.69 (m, 1H), 8.23-8.21 (m, 1H), 8.09-8.04 (m, 1H), 7.62-7.59 (m, 1H) ppm.

HPLC-MS: log P=1.50; mass (m/z)=270 [M+H]⁺.

5-Cyano-1-methyl-3-pentafluoroethyl-4-trifluoromethyl-1H-pyrazole

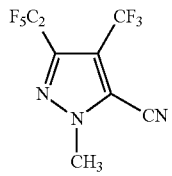

42.0 g (147 mmol) of 5-fluoro-1-methyl-3-pentafluoroethyl-4-trifluoromethylpyrazole [synthesis see Izvestiya Akademii Nauk SSSR, Seriya Khimicheskaya 1990, (11), 2583-9] and 11.5 g (235 mmol) of sodium cyanide are suspended in 150 ml of acetonitrile and then heated at reflux temperature under a protective gas atmosphere. After cooling, the reaction mixture is poured onto a mixture of 300 ml of distilled water and 300 ml of diethyl ether. The aqueous phase is extracted three times with diethyl ether. The combined organic phases are washed twice with water and once with saturated aqueous sodium chloride solution. The organic phase is dried over sodium sulphate and then filtered. The solvent is removed under reduced pressure on a rotary evaporator and the residue obtained in this way is subjected to fractional distillation in vacuo. This gives 37.0 g of 5-cyano-1-methyl-3-pentafluoroethyl-4-trifluoromethylpyrazole (82%) as a colourless liquid (b.p. 74° C./10 mbar).

¹H-NMR (400 MHz, d₃-acetonitrile): δ=4.11 (s, 3H) ppm.

GC-MS: retention time 2.67 min; mass (m/z)=224 [M]⁺.

1-Methyl-3-pentafluoroethyl-4-trifluoromethyl-1H-pyrazole-5-carboxylic acid

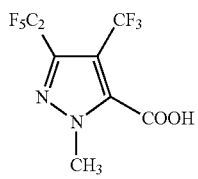

11.0 g (37.5 mmol) of 5-cyano-1-methyl-3-pentafluoroethyl-4-trifluoromethyl-1H-pyrazole, 22 ml of 50% strength sodium hydroxide solution and 7.0 ml of distilled water are heated in an oil bath until the solid has dissolved. The reaction mixture is then stirred overnight (oil bath temperature 100° C.). After cooling, the reaction mixture is poured onto a mixture of 150 ml of concentrated hydrochloric acid and 150 ml of ice. The mixture is afterstirred for 30 minutes and the solid is filtered off. The solid is washed with a small amount of water and then dried in an oil pump vacuum. This gives 11.2 g (95%) of 1-methyl-3-pentafluoroethyl-4-trifluoromethyl-1H-pyrazole-5-carboxylic acid as a white solid.00

¹H-NMR (400 MHz, d₃-acetonitrile): δ=4.08 (s, 3H) ppm.

HPLC-MS[a]: log P=1.86; mass (m/z)=313 [M+H]⁺.

3-Chloro-2-[5-fluoro-3-(pentafluoroethyl)-4-(trifluoromethyl)-1H-pyrazol-1-yl]pyridine

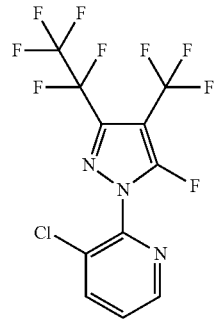

1.0 g (7.0 mmol) of 3-chloro-2-hydrazinopyridine is suspended in 2.9 ml (21 mmol) of triethylamine and 40.0 ml of acetonitrile and, at −65° C., added to 2.1 g (7 mmol) of (1,1,1,3,4,4,5,5,5-nonafluoro-2-(trifluoromethyl)pent-2-ene. The reaction mixture is slowly heated to room temperature and then stirred at room temperature for 60 hours. The solid is filtered off and afterwashed with diethyl ether. The solvent is removed under reduced pressure on a rotary evaporator. The product is extracted from the residue three times with cyclohexane. The organic phases are combined and the solvent is removed under reduced pressure on a rotary evaporator. This gives 1.95 g of 3-chloro-2-[5-fluoro-3-(pentafluoroethyl)-4-(trifluoromethyl)-1H-pyrazol-1-yl]pyridine (73%) as an orange oil.

¹H-NMR (400 MHz, d₃-acetonitrile): δ=8.58-8.62 (m, 1H), 8.12-8.18 (m, 1H), 7.62-7.68 (m, 1H) ppm.

GC-MS: retention time 5.88 min; mass (m/z)=383 [M]⁺.

3-Chloro-2-[5-cyano-3-(pentafluoroethyl)-4-(trifluoromethyl)-1H-pyrazol-1-yl]pyridine

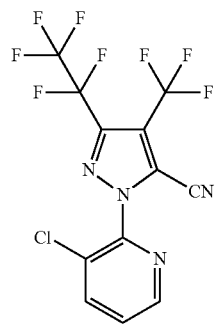 [SMILES: N#Cc1c(C(F)(F)F)c(C(F)(F)C(F)(F)F)nn1-c1ncccc1Cl]

1.95 g (5.1 mmol) of 3-chloro-2-[5-fluor-3-(pentafluoroethyl)-4-(trifluoromethyl)-1H-pyrazol-1-yl]pyridine and 0.30 g (6.1 mmol) of sodium cyanide are suspended in 20 ml of acetonitrile and the reaction mixture is then stirred under reflux for 16 hours. After cooling, the reaction mixture is poured onto a water/diethyl ether mixture. The aqueous phase is extracted three times with diethyl ether. The combined organic phases are washed twice with water and once with saturated sodium chloride solution and then dried over magnesium sulphate and filtered. The solvent is removed under reduced pressure on a rotary evaporator. The crude product is purified by means of flash chromatography on silica gel. This gives 1.7 g of 3-chloro-2-[5-cyano-3-(pentafluoroethyl)-4-(trifluoromethyl)-1H-pyrazol-1-yl]pyridine (84%) as a yellow oil.

$^1$H-NMR (400 MHz, d$_3$-acetonitrile): δ=8.61 (dd, 1H), 8.20 (dd, 1H), 7.70 (dd, 1H) ppm.

GC-MS: retention time 6.43 min; mass (m/z)=390 [M]$^+$.

3-(Pentafluoroethyl)-4-(trifluoromethyl)-1H-pyrazole-5-carboxylic acid

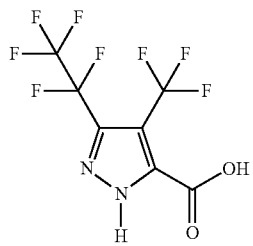 [SMILES: O=C(O)c1[nH]nc(C(F)(F)C(F)(F)F)c1C(F)(F)F]

4.9 g (12.5 mmol) of 3-chloro-2-[5-cyano-3-(pentafluoroethyl)-4-(trifluoromethyl)-1H-pyrazol-1-yl]pyridine are dissolved in 24 ml of methanol and admixed with 32.6 ml (494 mmol) of 50% strength sodium hydroxide solution (494 mmol). The reaction mixture is stirred for 7 days at room temperature. The reaction mixture is diluted with 10 ml of water and then concentrated to half the volume by evaporation. The mixture is then dripped onto concentrated hydrochloric acid with ice. The colourless solid which precipitates out is filtered off and dried in vacuo. This gives 2.95 g of 3-(pentafluoroethyl)-4-(trifluoromethyl)-1H-pyrazole-5-carboxylic acid (79%) as a colourless solid.

HPLC-MS$^{a)}$: log P=2.00; mass (m/z)=299 [M+H]$^+$.

Methyl 3-(pentafluoroethyl)-4-(trifluoromethyl)-1H-pyrazole-5-carboxylate

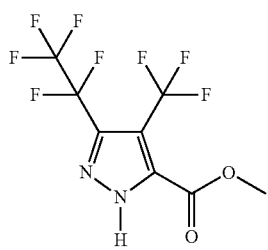 [SMILES: COC(=O)c1[nH]nc(C(F)(F)C(F)(F)F)c1C(F)(F)F]

0.8 g (2.6 mmol) of 3-(pentafluoroethyl)-4-(trifluoromethyl)-1H-pyrazol-5-carboxylic acid are dissolved in 15.0 ml of methanol and then slowly admixed dropwise with 0.58 ml (7.9 mmol) of thionyl chloride. The reaction solution is then heated under reflux for 16 hours. After cooling, the solvent is removed under reduced pressure on a rotary evaporator and the residue is taken up in ethyl acetate. The organic phase is carefully admixed with saturated sodium hydrogencarbonate solution. The organic phase is washed with saturated sodium chloride solution, dried over magnesium sulphate and filtered. The solvent is removed under reduced pressure on a rotary evaporator. This gives 0.75 g of methyl 3-(pentafluoroethyl)-4-(trifluoromethyl)-1H-pyrazole-5-carboxylate (96%) as a colourless oil.

$^1$H-NMR (400 MHz, d$_3$-acetonitrile): δ=3.92 (s, 3H) ppm.

HPLC-MS$^{a)}$: log P=3.02; mass (m/z)=313 [M+H]$^+$.

1-Ethyl-3-(pentafluoroethyl)-4-(trifluoromethyl)-1H-pyrazole-5-carboxylic acid

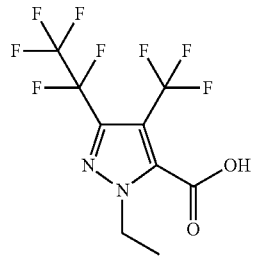 [SMILES: CCn1nc(C(F)(F)C(F)(F)F)c(C(F)(F)F)c1C(=O)O]

0.23 g (0.72 mmol) of methyl 3-(pentafluoroethyl)-4-(trifluoromethyl)-1H-pyrazole-5-carboxylate and 0.3 g (2.2 mmol) of potassium carbonate are suspended in 7.0 ml of acetone and admixed with 0.12 ml of iodoethane (1.4 mmol). The reaction mixture is stirred overnight at room temperature. 1.1 ml (2.2 mmol) of 2N sodium hydroxide solution are added to the suspension. The solution is then stirred overnight at room temperature. The reaction mixture is diluted with water and adjusted to pH 2-3 with 1M hydrochloric acid. The aqueous reaction solution is extracted three times with ethyl acetate. The combined organic phases are dried over magnesium sulphate, filtered and concentrated by evaporation under reduced pressure on a rotary evaporator. This gives 0.22 g of 1-ethyl-3-(pentafluoroethyl)-4-(trifluoromethyl)-1H-pyrazole-5-carboxylic acid (91%) as a colourless solid.

$^1$H-NMR (400 MHz, d$_3$-acetonitrile): δ=4.44 (q, 2H), 1.44 (t, 3H) ppm.

HPLC-MS$^{a)}$: log P=2.18; mass (m/z)=327 [M+H]$^+$.

1-Isopropyl-4-(pentafluoroethyl)-3-(trifluoromethyl)-1H-pyrazole-5-carboxylic acid

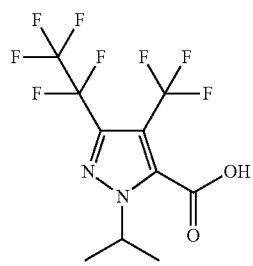 [SMILES: CC(C)n1nc(C(F)(F)C(F)(F)F)c(C(F)(F)F)c1C(=O)O]

The compound is synthesized analogously to the preparation of 1-ethyl-3-(pentafluoroethyl)-4-(trifluoromethyl)-1H-pyrazole-5-carboxylic acid from methyl 3-(pentafluoroethyl)-4-(trifluoromethyl)-1H-pyrazole-5-carboxylate and 2-iodopropane.

$^1$H-NMR (400 MHz, d$_3$-acetonitrile): δ=5.03 (sep, 1H), 1.47 (d, 6H) ppm.

HPLC-MS$^{a)}$: log P=2.55; mass (m/z)=341 [M+H]$^+$.

1-(Methoxymethyl)-4-(pentafluoroethyl)-3-(trifluoromethyl)-1H-pyrazole-5-carboxylic acid

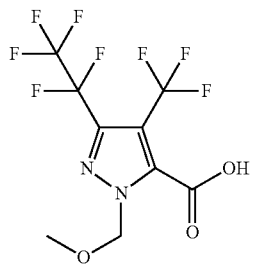 [SMILES: COCn1nc(C(F)(F)C(F)(F)F)c(C(F)(F)F)c1C(=O)O]

The compound is synthesized analogously to the preparation of 1-ethyl-3-(pentafluoroethyl)-4-(trifluoromethyl)-1H-pyrazole-5-carboxylic acid from methyl 3-(pentafluoroethyl)-4-(trifluoromethyl)-1H-pyrazole-5-carboxylate and methoxymethyl chloride.

$^1$H-NMR (400 MHz, d$_3$-acetonitrile): δ=5.03 (sep, 1H), 1.47 (d, 6H) ppm.
HPLC-MS$^{a)}$: log P=1.90; mass (m/z)=343 [M+H]$^+$.

Ethyl 3,4-bis(trifluoromethyl)-1H-pyrazole-5-carboxylate

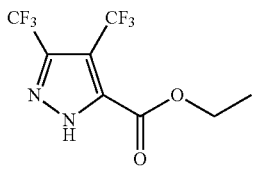 [SMILES: CCOC(=O)c1[nH]nc(C(F)(F)F)c1C(F)(F)F]

7.57 g (63.0 mmol) of diazoethyl acetate are initially introduced under protective gas into 200 ml of diethyl ether and brought to −70° C. 20.4 g (126 mmol) of hexafluorobutyne are then introduced into the cooled solution. The reaction mixture is slowly heated to room temperature and stirred for 16 hours. The solvent is then removed on a rotary evaporator. This gives 17.0 g of ethyl 3,4-bis(trifluoromethyl)-1H-pyrazole-5-carboxylate (98%) as a yellow oil.

$^1$H-NMR (400 MHz, d$_3$-acetonitrile): δ=4.42 (q, 2H), 1.38 (t, 3H) ppm.
GC-MS: retention time 3.48 min; mass (m/z)=276 [M]$^+$.

1-Methyl-3,4-bis(trifluoromethyl)-1H-pyrazole-5-carboxylic acid

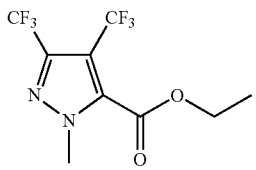 [SMILES: CCOC(=O)c1c(C(F)(F)F)c(C(F)(F)F)nn1C]

1-Methyl-3,4-bis(trifluoromethyl)-1H-pyrazole-5-carboxylic acid is synthesized analogously to the preparation of 1-ethyl-3-(pentafluoroethyl)-4-(trifluoromethyl)-1H-pyrazole-5-carboxylic acid from ethyl 3,4-bis(trifluoromethyl)-1H-pyrazole-5-carboxylate and iodomethane.

$^1$H-NMR (400 MHz, d$_3$-acetonitrile): δ=4.12 (s, 3H) ppm.
HPLC-MS$^{a)}$: log P=1.47; mass (m/z)=263 [M+H]$^+$.

1,4-Dimethyl-3-(pentafluoroethyl)-1H-pyrazole-5-amine

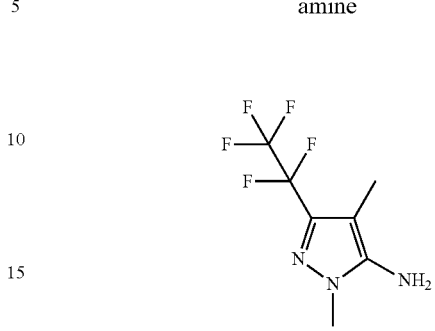

A solution of 39 g (388 mmol) of N,N-diisopropylamine in 500 ml of tetrahydrofuran is admixed at −5° C. with 232 ml (371 mmol) of a 1.6M solution of n-butyllithium in hexane. The solution is stirred for 30 minutes at 0° C. and then cooled to −78° C. 18.5 g (337 mmol) of n-propionitrile are then added dropwise. When addition is complete, the solution is stirred for 15 minutes. 30 g (169 mmol) of methyl pentafluoropropanoate are then slowly added. When addition is complete, the reaction mixture is stirred for a further 45 min at −78° C. The mixture is then heated to room temperature and stirred for one hour at room temperature. The reaction mixture is cooled to 0° C. and admixed with 700 ml of water. The pH of the solution is adjusted to 1 with conc. hydrochloric acid. The aqueous phase is extracted with ethyl acetate and the combined organic phases are dried over magnesium sulphate and concentrated by evaporation under reduced pressure on a rotary evaporator. The residue is dissolved in 200 ml of ethanol and admixed with 10.5 g (224 mmol) of methylhydrazine and 16 ml of conc. hydrochloric acid. The mixture is heated under reflux for five hours. The ethanol is removed under reduced pressure on a rotary evaporator and the pH of the aqueous phase is adjusted to 14. The aqueous phase is extracted several times with dichloromethane. The combined organic phases are dried over magnesium sulphate and concentrated by evaporation under reduced pressure on a rotary evaporator. This gives 13.0 g of 1,4-dimethyl-3-(pentafluoroethyl)-1H-pyrazole-5-amine (34%).

$^1$H-NMR (400 MHz, CDCl$_3$): δ=3.83 (s, 3H), 3.32 (br. s, 2H), 1.98 (s, 3H) ppm.

1,4-Dimethyl-3-(pentafluoroethyl)-1H-pyrazole-5-carboxylic acid

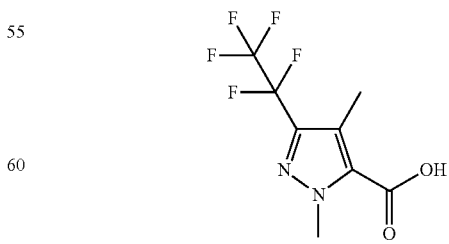

8.66 g (85.1 mmol) of tert-butyl nitrite and 6.0 g (67.4 mmol) of copper(I) cyanide are suspended in 360 ml of acetonitrile and heated to 65° C. A solution of 13.0 g (57.2 mmol)

of 1,4-dimethyl-3-(pentafluoroethyl)-1H-pyrazole-5-amine in 20 ml of acetonitrile is then slowly added. The reaction mixture is further stirred for 24 hours at 65° C. The reaction mixture is then filtered over Celite. The filtrate is concentrated by evaporation under reduced pressure on a rotary evaporator. The residue is taken up in water and acidified with conc. hydrochloric acid. The aqueous phase is extracted several times with dichloromethane. The combined organic phases are concentrated by evaporation under reduced pressure on a rotary evaporator and the residue is purified by column chromatography on silica gel (hexane:ethyl acetate=5:1). The resulting product (2.3 g, 9.7 mmol) is heated under reflux with 3.44 g (63 mmol) of potassium hydroxide in 20 ml of water. After 3 h the reaction solution is cooled to 0° C. and adjusted to pH 6 with dilute hydrochloric acid. The resulting solid is filtered and dried. This gives 0.3 g of 1,4-dimethyl-3-(pentafluoroethyl)-1H-pyrazole-5-carboxylic acid (2%) as a white solid.

$^1$H-NMR (400 MHz, CDCl$_3$): δ=4.22 (s, 3H), 2.44 (s, 3H) ppm.

1-Methyl-3-pentafluoroethyl-1H-pyrazole

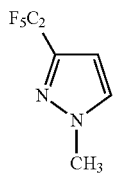

7.18 g (156 mmol) of methylhydrazine are added dropwise to a solution of 30.9 g (142 mmol) of (1E)-1-ethoxy-4,4,5,5,5-pentafluoropent-1-en-3-one (preparation: *Synthesis* 2000, 5, 738-742) in 56 ml of methanol, and the reaction mixture is heated under reflux for 18 hours. The majority of the methanol is distilled off at atmospheric pressure and the residue is poured on to ice. The aqueous phase is extracted three times with dichloromethane and the organic phase is then washed three times with saturated sodium chloride solution. After drying over sodium sulphate, the solvent is distilled off at reduced pressure on a rotary evaporator. This gives 15.8 g of 1-methyl-3-pentafluoroethyl-1H-pyrazole (52%) as an oil.

$^1$H-NMR (400 MHz, d$_3$-acetonitrile): δ=7.61 (m, 1H), 6.57 (m, 1H), 3.89 (s, 3H) ppm.
HPLC-MS$^{a)}$: log P=2.29; mass (m/z)=201 [M+H]$^+$.

The following were obtained in the same way:

1-Methyl-3-(1-chloro-1,2,2,2-tetrafluoroethyl)-1H-pyrazole from (1E)-4-chloro-1-ethoxy-4,5,5,5-tetrafluoropent-1-en-3-one

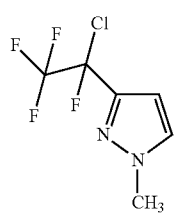

$^1$H-NMR (400 MHz, d$_3$-acetonitrile) δ=7.58 (m, 1H), 6.54 (m, 1H), 3.89 (s, 3H) ppm.
HPLC-MS$^{a)}$: log P=2.46; mass (m/z)=217 [M+H]$^+$.

1-Methyl-3-heptafluoropropyl-1H-pyrazole from (1E)-1-ethoxy-4,4,5,5,6,6,6-heptafluorohex-1-en-3-one

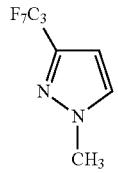

$^1$H-NMR (400 MHz, d$_3$-acetonitrile): δ=7.91 (m, 1H), 6.65 (m, 1H), 3.94 (s, 3H) ppm.
HPLC-MS$^{a)}$: log P=2.84; mass (m/z)=251 [M+H]$^+$.

1-Methyl-3-nonafluorobutyl-1H-pyrazole from (1E)-1-ethoxy-4,4,5,5,6,6,7,7,7-nonafluorohept-1-en-3-one

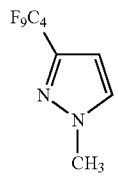

$^1$H-NMR (400 MHz, d$_3$-acetonitrile): δ=7.61 (m, 1H), 6.57 (m, 1H), 3.97 (s, 3H) ppm.
HPLC-MS$^{a)}$: log P=3.38; mass (m/z)=301 [M+H]$^+$.

3-{[Difluoro(trifluoromethoxy)methoxy](difluoro)methyl}-1-methyl-1H-pyrazole from (3E)-1-[difluoro(trifluoromethoxy)methoxy]-4-ethoxy-1,1-difluorobut-3-en-2-one

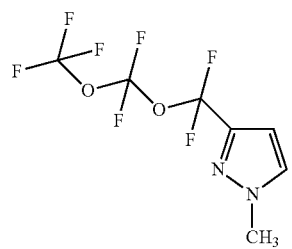

$^1$H-NMR (400 MHz, d$_3$-acetonitrile): δ=7.58 (m, 1H), 6.54 (m, 1H), 3.90 (s, 3H) ppm.
HPLC-MS$^{a)}$: log P=3.79; mass (m/z)=333 [M+H]$^+$.

4-Bromo-1-methyl-3-heptafluoropropyl-1H-pyrazole

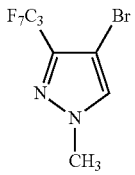

At 40° C., 3.27 g (20.5 mmol) of bromine are added dropwise to a solution of 4.65 g (18.6 mmol) of 1-methyl-3-heptafluoropropyl-1H-pyrazole in 18 ml of water and the reaction mixture is afterstirred firstly for one hour at 60° C. and then for 18 hours at room temperature. The aqueous phase is extracted three times with dichloromethane and the organic phase is dried over sodium sulphate. The dichloromethane is distilled off at reduced pressure on a rotary evaporator. This gives 5.75 g of 1-methyl-3-heptafluoropropyl-4-bromo-1H-pyrazole (78%) as an oil.

$^1$H-NMR (400 MHz, $d_3$-acetonitrile): δ=7.73 (m, 1H), 3.90 (s, 3H) ppm.

HPLC-MS$^{a)}$: log P=3.53; mass (m/z)=330 [M+H]$^+$.

The following were obtained in the same way:

4-Bromo-1-methyl-3-pentafluoroethyl-1H-pyrazole from 1-methyl-3-pentafluoroethyl-1H-pyrazole

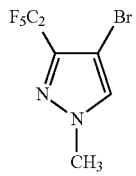

$^1$H-NMR (400 MHz, $d_3$-acetonitrile): δ=7.77 (m, 1H), 3.90 (s, 3H) ppm.

HPLC-MS$^{a)}$: log P=2.99; mass (m/z)=280 [M+H]$^+$.

4-Bromo-1-methyl-3-(1-chloro-1,2,2,2-tetrafluoroethyl)-1H-pyrazole from 1-methyl-3-(1-chloro-1,2,2,2-tetrafluoroethyl)-1H-pyrazole

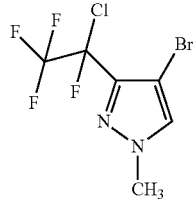

$^1$H-NMR (400 MHz, $d_3$-acetonitrile) δ=7.75 (m, 1H), 3.89 (s, 3H) ppm,

HPLC-MS$^{a)}$: log P=3.17; mass (m/z)=296 [M+H]$^+$.

1-Methyl-3-pentafluoroethyl-1H-pyrazole-5-carboxylic acid

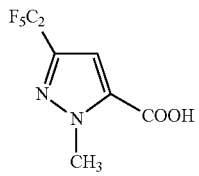

Under an argon atmosphere, 5.00 g (25.0 mmol) of 1-methyl-3-pentafluoroethyl-1H-pyrazole are initially introduced into diethyl ether and the solution is cooled to −78° C. 11.1 ml (27.7 mmol) of 2M lithium diisopropylamide solution in tetrahydrofuran/heptane are added dropwise and, at −30° C. and with vigorous stirring, 450 g of crushed dry ice are added. When the evolution of gas has stopped, the reaction mixture is admixed with 235 ml of water and adjusted to pH 11 with 1M sodium hydroxide solution. The alkaline solution is extracted three times with ethyl acetate and then adjusted to pH 2 with 1N hydrochloric acid. The aqueous phase is extracted three times with ethyl acetate and the organic phase is dried over sodium sulphate. Distilling of the solvent on a rotary evaporator under reduced pressure gives 1.20 g of 1-methyl-3-pentafluoroethyl-1H-pyrazole-5-carboxylic acid (18%) as a solid.

$^1$H-NMR (400 MHz, $d_3$-acetonitrile): δ=7.14 (m, 1H), 4.16 (s, 3H) ppm.

HPLC-MS$^{a)}$: log P=2.08; mass (m/z)=245 [M+H]$^+$.

The following were obtained in the same way:

4-Bromo-1-methyl-3-pentafluoroethyl-1H-pyrazole-5-carboxylic acid from 4-bromo-1-methyl-3-pentafluoroethyl-1H-pyrazole

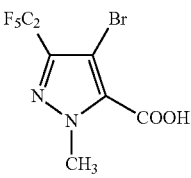

$^1$H-NMR (400 MHz, $d_3$-acetonitrile) δ=4.15 (s, 3H) ppm.

HPLC-MS$^{a)}$: log P=4.69; mass (m/z)=324 [M+H]$^+$.

4-Bromo-1-methyl-3-heptafluoropropyl-1H-pyrazole-5-carboxylic acid from 4-bromo-1-methyl-3-heptafluoropropyl-1H-pyrazole

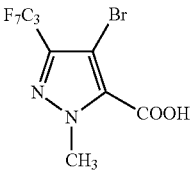

$^1$H-NMR (400 MHz, $d_3$-acetonitrile): δ=4.15 (s, 3H) ppm.

HPLC-MS$^{a)}$: log P=2.26; mass (m/z)=374 [M+H]$^+$.

4-Bromo-1-methyl-3-(1-chloro-1,2,2,2-tetrafluoroethyl)-1H-pyrazole-5-carboxylic acid from 4-bromo-1-methyl-3-(1-chloro-1,2,2,2-tetrafluoroethyl)-1H-pyrazole

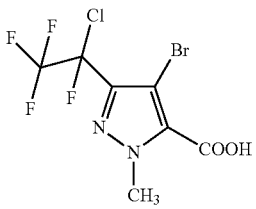

$^1$H-NMR (400 MHz, $d_3$-acetonitrile): δ=4.14 (s, 3H) ppm.

HPLC-MS$^{a)}$: log P=2.43; mass (m/z)=340 [M+H]$^+$.

1-Methyl-3-nonafluorobutyl-1H-pyrazole-5-carboxylic acid from 1-methyl-3-nonafluorobutyl-1H-pyrazole

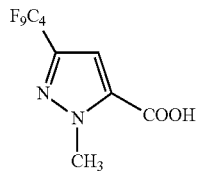

$^1$H-NMR (400 MHz, d$_3$-acetonitrile): δ=7.14 (m, 1H), 4.17 (s, 3H) ppm.
HPLC-MS$^{a)}$: log P=3.01; mass (m/z)=345 [M+H]$^+$.

3-{[Difluoro(trifluoromethoxy)methoxy](difluoro)methyl}-1-methyl-1H-pyrazole-5-carboxylic acid from 3-{[difluoro(trifluoromethoxy)methoxy](difluoro)methyl}-1-methyl-1H-pyrazole

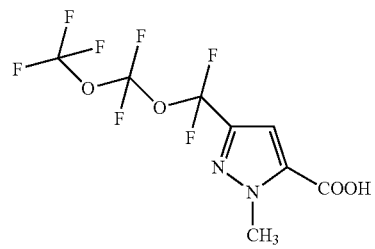 [SMILES: Cn1nc(C(F)(F)OC(F)(F)OC(F)(F)F)cc1C(=O)O]

$^1$H-NMR (400 MHz, d$_3$-acetonitrile): δ=7.11 (m, 1H), 4.16 (s, 3H) ppm.
HPLC-MS$^{a)}$: log P=3.38; mass (m/z)=377 [M+H]$^+$.

4-Bromo-1-methyl-3-nonafluorobutyl-1H-pyrazole-5-carboxylic acid

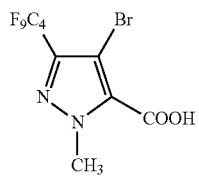

At 40° C., 255 mg (1.60 mmol) of bromine are added dropwise to a solution of 0.50 g (1.45 mmol) of 1-methyl-3-nonafluorobutyl-1H-pyrazole-5-carboxylic acid in 3.5 ml of water and the reaction mixture is afterstirred firstly for one hour at 60° C. and then for three days at room temperature. The aqueous phase is extracted three times with dichloromethane and the organic phase is dried over sodium sulphate. The dichloromethane is distilled off at reduced pressure on a rotary evaporator. This gives 0.54 g of 4-bromo-1-methyl-3-nonafluorobutyl-1H-pyrazole-5-carboxylic acid (80%) as an oil.
$^1$H-NMR (400 MHz, d$_3$-acetonitrile): δ=4.16 (s, 3H) ppm.
HPLC-MS$^{a)}$: log P=3.17; mass (m/z)=424 [M+H]$^+$.

The following were obtained in the same way:

4-Bromo-3-{[(difluoro(trifluoromethoxy)methoxy](difluoro)methyl}-1-methyl-1H-pyrazole-5-carboxylic acid from 3-{[difluoro(trifluoromethoxy)methoxy](difluoro)methyl}-1-methyl-1H-pyrazole-5-carboxylic acid

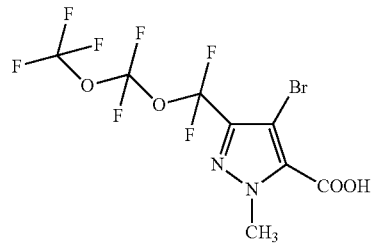

$^1$H-NMR (400 MHz, d$_3$-acetonitrile): δ=4.14 (s, 3H) ppm.
HPLC-MS$^{a)}$: log P=3.56; mass (m/z)=456 [M+H]$^+$.

1-Methyl-3-pentafluoroethyl-4-iodo-1H-pyrazole-5-carboxylic acid

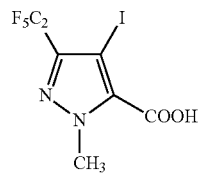

1.34 g (2.46 mmol) of ammonium cerium(IV) nitrate and then 0.75 g (2.95 mmol) of iodine are added to a solution of 1.20 g (4.91 mmol) of 1-methyl-3-pentafluoroethyl-1H-pyrazole-5-carboxylic acid in 4.3 ml of acetonitrile and the reaction mixture is heated under reflux for 18 hours. After adding 20 ml of dichloromethane, washing is carried out firstly with water, with sodium disulphite solution and finally with saturated sodium chloride solution. The organic phase is dried over sodium sulphate and the solvent is distilled off at reduced pressure on a rotary evaporator. This gives 1.28 g of 4-iodo-1-methyl-3-pentafluoroethyl-1H-pyrazole-5-carboxylic acid (47%) as an oil.
$^1$H-NMR (400 MHz, d$_3$-acetonitrile): δ=4.16 (s, 3H) ppm.
HPLC-MS: log P=2.33; mass (m/z)=371 [M+H]$^+$.

4-Fluoro-2-methyl-6-(pentafluoroethyl)-5-(trifluoromethyl)pyrimidine can be synthesized analogously to the procedures from the patent JP 07196622 and *Russ. Chem. Bull.* 1997, 46, 1920.

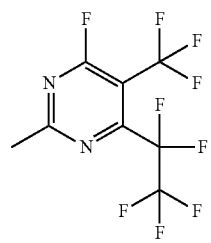 [SMILES: Cc1nc(F)c(C(F)(F)F)c(C(F)(F)C(F)(F)F)n1]

2-Methyl-6-(pentafluoroethyl)-5-(trifluoromethyl) pyrimidine-4-carbonitrile

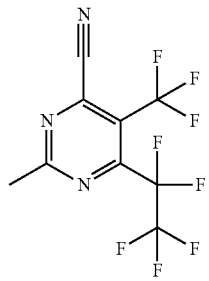 [SMILES: Cc1nc(C#N)c(C(F)(F)F)c(C(F)(F)C(F)(F)F)n1]

5.0 g (16.8 mmol) of 4-fluoro-2-methyl-6-(pentafluoroethyl)-5-(trifluoromethyl)pyrimidine are dissolved in 40 ml of acetonitrile. 986 mg (20.1 mmol) of sodium cyanide are added and the reaction mixture is stirred for 18 hours at 50° C. A further 493 mg (10.7 mmol) of sodium cyanide are added and the reaction mixture is stirred under reflux for three hours. After adding 100 ml of water and 100 ml of ethyl acetate, the organic phase is separated off. The aqueous phase is extracted three times with ethyl acetate. The combined organic phases are washed twice with water and with a saturated sodium chloride solution, then dried over sodium sulphate, filtered and the solvent is removed on a rotary evaporator. This gives 4.71 g of 2-methyl-6-(pentafluoroethyl)-5-(trifluoromethyl) pyrimidine-4-carbonitrile (92%) as a dark oil.

$^1$H-NMR (400 MHz, d$_3$-acetonitrile): δ=2.87 (s, 3H) ppm.
GC-MS: mass (m/z)=305 [M]$^+$.

2-Methyl-6-(pentafluoroethyl)-5-(trifluoromethyl) pyrimidine-4-carboxamide

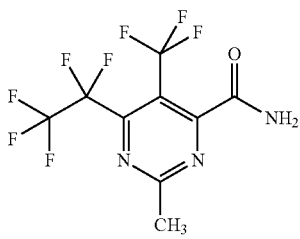 [SMILES: Cc1nc(C(N)=O)c(C(F)(F)F)c(C(F)(F)C(F)(F)F)n1]

4.70 g (15.4 mmol) of 2-methyl-6-(pentafluoroethyl)-5-(trifluoromethyl)pyrimidine-4-carbonitrile are dissolved in 80 ml of concentrated sulphuric acid. The reaction mixture is stirred for 12 hours at 100° C. and then added to 300 ml of ice water. The aqueous phase is extracted four times with ethyl acetate. The combined organic phases are dried over sodium sulphate and the solvent is concentrated by evaporation under reduced pressure on a rotary evaporator. Half of the crude product was purified by means of flash chromatography on silica gel (eluent: cyclohexane/ethyl acetate=1/1). This gives 0.63 g of 2-methyl-6-(pentafluoroethyl)-5-(trifluoromethyl) pyrimidine-4-carboxamide (13%) as a viscous oil.

$^1$H-NMR (400 MHz, d$_6$-DMSO): δ=8.16 (s, 1H), 8.13 (s, 1H), 2.83 (s, 3H) ppm.
HPLC-MS: log P=2.33; mass (m/z)=324 [M+H]$^+$.

Methyl-3-(difluoromethoxy)-1-methyl-1H-pyrazole-5-carboxylate

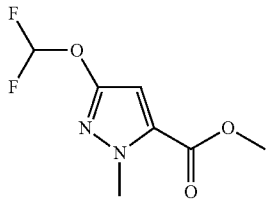

A solution of 2.00 g (12.8 mmol) of methyl 3-hydroxy-1-methyl-1H-pyrazole-5-carboxylate (preparation: Chem. Ber. 1974, 107, 1318-1328) in 28 ml of N,N-dimethylformamide is admixed with 5.09 g (32.0 mmol, 96%) of chlorodifluoroacetic acid sodium salt and 2.66 g (19.2 mmol) of potassium carbonate, and the reaction mixture is heated at 80° C. overnight. The reaction mixture is added to 300 ml of water and extracted several times with ethyl acetate. The organic phase is dried over magnesium sulphate, filtered and concentrated by evaporation in vacuo on a rotary evaporator. Chromatographic purification gives 1.07 g of methyl-3-(difluoromethoxy)-1-methyl-1H-pyrazole-5-carboxylate (40%).

$^1$H-NMR (400 MHz, d$_6$-DMSO): δ=7.19 (t, 1H), 6.55 (s, 1H), 4.00 (s, 3H), 3.55 (s, 3H) ppm.
HPLC-MS: log P=2.04; mass (m/z)=207 [M+H]$^+$.

The preparation of the ethyl ester is described in WO2007/071900A1.

3-(Difluoromethoxy)-1-methyl-1H-pyrazole-5-carboxylic acid

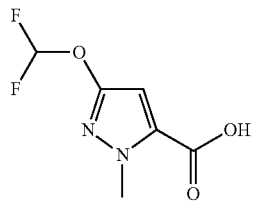

200 mg (0.97 mmol) of methyl 3-(difluoromethoxy)-1-methyl-1H-pyrazole-5-carboxylate are dissolved in 6.5 ml of methanol and 1.94 ml of 1M sodium hydroxide solution is added. The reaction mixture is stirred overnight at room temperature, then admixed with 1M hydrochloric acid and extracted with ethyl acetate. The organic phase is dried over sodium sulphate, filtered and concentrated by evaporation in vacuo. This gives 180 mg of 3-difluoromethoxy-1-methyl-1H-pyrazole-5-carboxylic acid (97%).

$^1$H-NMR (400 MHz, d$_6$-DMSO): δ=7.26 (t, 1H), 6.49 (s, 1H), 3.99 (s, 3H) ppm.
HPLC-MS: log P=1.15; mass (m/z)=193 [M+H]$^+$.

Methyl 4-chloro-3-(difluoromethoxy)-1-methyl-1H-pyrazole-5-carboxylate

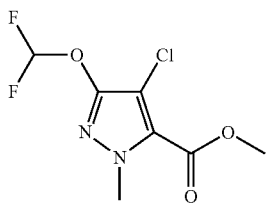

A solution of 400 mg (1.94 mmol) of methyl-3-(difluoromethoxy)-1-methyl-1H-pyrazole-5-carboxylate in 10 ml of N,N-dimethylformamide is admixed at 0° C. with 389 mg (2.91 mmol) of N-chlorosuccinimide and then stirred for 8 hours at 80° C. The reaction solution is poured onto water and extracted twice with ethyl acetate. The combined organic phases are dried over sodium sulphate and concentrated by evaporation in vacuo. This gives 466 mg of methyl 4-chloro-3-(difluoromethoxy)-1-methyl-1H-pyrazole-5-carboxylate (99%).

$^1$H-NMR (400 MHz, d$_6$-DMSO): δ=7.25 (t, 1H), 4.01 (s, 3H), 3.91 (s, 3H) ppm.

HPLC-MS: log P=2.57. mass (m/z) 241 [M+H]$^+$.

Methyl 4-bromo-3-(difluoromethoxy)-1-methyl-1H-pyrazole-5-carboxylate

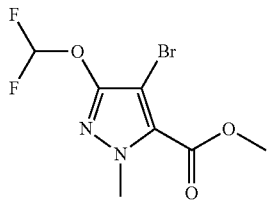

A solution of 700 mg (3.39 mmol) of methyl 3-(difluoromethoxy)-1-methyl-1H-pyrazole-5-carboxylate in 20 ml of chloroform is admixed dropwise with a solution of 570 mg (3.56 mmol) of bromine in 10 ml of chloroform and then stirred for three days at room temperature. The reaction mixture is added to 80 ml of water with some sodium bisulfite and shaken. The organic phase is separated off, dried over magnesium sulphate, filtered and concentrated by evaporation in vacuo: 792 mg of methyl 4-bromo-3-(difluoromethoxy)-1-methyl-1H-pyrazole-5-carboxylate (82%) are produced as white crystals.

$^1$H-NMR (400 MHz, d$_6$-DMSO): δ=7.24 (t, 1H), 4.01 (s, 3H), 3.90 (s, 3H) ppm.

HPLC-MS: log P=2.62; mass (m/z)=285; 287 [M+H]$^+$.

Methyl 3-(difluoromethoxy)-4-iodo-1-methyl-1H-pyrazole-5-carboxylate

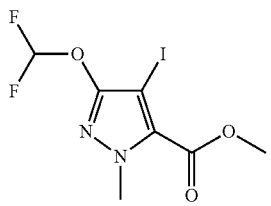

A solution of 500 mg (2.42 mmol) of methyl 3-(difluoromethoxy)-1-methyl-1H-pyrazole-5-carboxylate in 20 ml of acetonitrile is admixed with 665 mg (1.21 mmol) of ammonium cerium(IV) nitrate and 369 mg (1.45 mmol) of iodine and heated under reflux for three hours and afterstirred at room temperature overnight. The reaction mixture is diluted with water and ethyl acetate, and the organic phase is washed with saturated sodium thiosulphate solution, dried over sodium sulphate, filtered and concentrated by evaporation in vacuo. This gives 750 mg of methyl 3-(difluoromethoxy)-4-iodo-1-methyl-1H-pyrazole-5-carboxylate (93%).

$^1$H-NMR (400 MHz, d$_6$-DMSO): δ=7.22 (t, 1H), 4.02 (s, 3H), 3.88 (s, 3H) ppm.

HPLC-MS: log P=2.69; mass (m/z)=333 [M+H]$^+$.

The following acids were prepared analogously to the aforementioned saponification:

4-Chloro-3-(difluoromethoxy)-1-methyl-1H-pyrazole-5-carboxylic acid

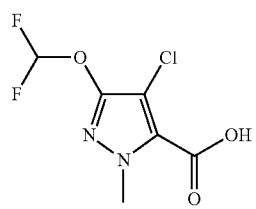

$^1$H-NMR (400 MHz, d$_6$-DMSO): δ=7.23 (t, 1H), 3.99 (s, 3H) ppm.

HPLC-MS: log P=1.50; mass (m/z)=227 [M+H]$^+$.

4-Bromo-3-(difluoromethoxy)-1-methyl-1H-pyrazole-5-carboxylic acid

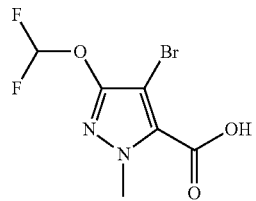

$^1$H-NMR (400 MHz, d$_6$-DMSO): δ=7.31 (t, 1H), 4.01 (s, 3H) ppm;

HPLC-MS: log P=1.52; mass (m/z)=271 [M+H]$^+$.

4-Iodo-3-(difluoromethoxy)-1-methyl-1H-pyrazole-5-carboxylic acid

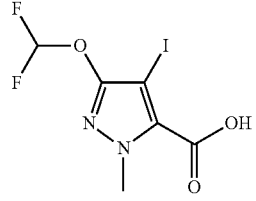

$^1$H-NMR (400 MHz, d$_6$-DMSO): δ=7.20 (t, 1H), 4.01 (s, 3H) ppm.

HPLC-MS: log P=1.64; mass (m/z)=319 [M+H]$^+$.

Methyl 1-methyl-3-(2,2,2-trifluoroethoxy)-1H-pyrazole-5-carboxylate

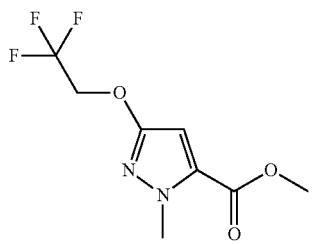 [SMILES: COC(=O)c1cc(OCC(F)(F)F)nn1C]

A solution of 200 mg (1.28 mmol) of methyl 3-hydroxy-1-methyl-5-pyrazolecarboxylate (for preparation see above) in 10 ml of N,N-dimethylformamide is admixed with 254 mg (2.56 mmol) of 2,2,2-trifluoroethyl-4-methylbenzenesulphonate and 138 mg (2.56 mmol) of potassium carbonate and the reaction mixture is heated at 100° C. for five hours and afterstirred at room temperature for two days. The reaction mixture is added to water and extracted several times with ethyl acetate. The organic phase is dried over sodium sulphate, filtered and concentrated by evaporation in vacuo on a rotary evaporator. This gives 500 mg of methyl 1-methyl-3-(2,2,2-trifluoroethoxy)-1H-pyrazole-5-carboxylate (50% strength, 82%).

$^1$H-NMR (400 MHz, $d_6$-DMSO): δ=6.41 (s, 1H), 4.77 (m, 2H), 3.94 (s, 3H), 3.83 (s, 3H) ppm.

HPLC-MS: log P=2.61; mass (m/z)=239 [M+H]$^+$.

Methyl 4-fluoro-1-methyl-3-(2,2,2-trifluoroethoxy)-1H-pyrazole-5-carboxylate

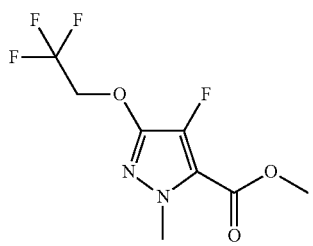

A solution of 300 mg (1.26 mmol) of methyl 1-methyl-3-(2,2,2-trifluoroethoxy)-1H-pyrazole-5-carboxylate and 404 mg (1.52 mmol) of 1-(chloromethyl)-4-fluoro-1,4-diazoniabicyclo[2.2.2]octaneditetrafluoroborate (Selectfluor) in 37.5 ml of acetonitrile is heated under reflux for five hours. After cooling, the solution is admixed with 1M hydrochloric acid and extracted twice with ethyl acetate. The organic phase is washed with saturated sodium chloride solution, dried over Na$_2$SO$_4$, filtered and concentrated by evaporation in vacuo. Chromatographic purification on silica gel gives 190 mg of methyl 4-fluoro-1-methyl-3-(2,2,2-trifluoroethoxy)-1H-pyrazole-5-carboxylate (26% strength, 15%).

HPLC-MS: log P=2.79; mass (m/z)=257 [M+H]$^+$.

The chlorination, bromination and iodination proceeds analogously to the reactions shown above:

Methyl 4-chloro-1-methyl-3-(2,2,2-trifluoroethoxy)-1H-pyrazole-5-carboxylate

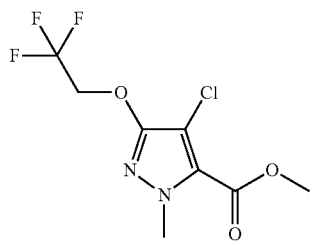 [SMILES: COC(=O)c1c(Cl)c(OCC(F)(F)F)nn1C]

$^1$H-NMR (400 MHz, $d_6$-DMSO): δ=4.83 (m, 2H), 3.95 (s, 3H), 3.89 (s, 3H) ppm.

HPLC-MS: log P=3.08; mass (m/z)=273 [M+H]$^+$.

Methyl 4-bromo-1-methyl-3-(2,2,2-trifluoroethoxy)-1H-pyrazole-5-carboxylate

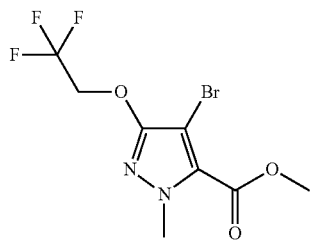 [SMILES: COC(=O)c1c(Br)c(OCC(F)(F)F)nn1C]

$^1$H-NMR (400 MHz, $d_6$-DMSO): δ=4.81 (m, 2H), 3.97 (s, 3H), 3.88 (s, 3H) ppm.

HPLC-MS: log P=3.14; mass (m/z)=317, 319 [M+H]$^+$.

Methyl 4-iodo-1-methyl-3-(2,2,2-trifluoroethoxy)-1H-pyrazole-5-carboxylate

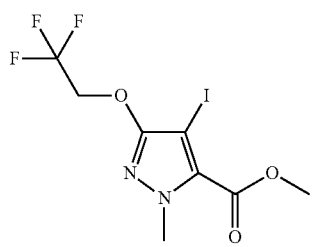

$^1$H-NMR (400 MHz, $d_6$-DMSO): δ=4.81 (m, 2H), 3.98 (s, 3H), 3.87 (s, 3H) ppm.

HPLC-MS: log P=3.17; mass (m/z)=365 [M+H]$^+$.

The following acids were prepared analogously to the aforementioned saponification:

1-Methyl-3-(2,2,2-trifluoroethoxy)-1H-pyrazole-5-carboxylic acid

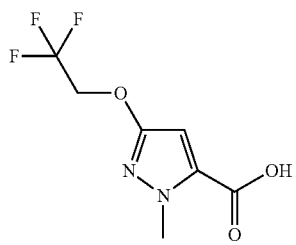

$^1$H-NMR (400 MHz, $d_6$-DMSO): δ=4.74 (m, 2H), 3.94 (s, 3H) ppm.

HPLC-MS: log P=1.65; mass (m/z)=225 [M+H]$^+$.

4-Fluoro-1-methyl-3-(2,2,2-trifluoroethoxy)-1H-pyrazole-5-carboxylic acid

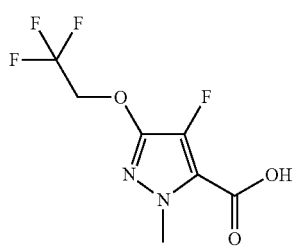 [SMILES: Cn1nc(OCC(F)(F)F)c(F)c1C(=O)O]

$^1$H-NMR (400 MHz, $d_6$-DMSO): δ=4.83 (m, 2H), 3.89 (s, 3H) ppm.

HPLC-MS: log P=1.83; mass (m/z)=243 [M+H]$^+$.

4-Chloro-1-methyl-3-(2,2,2-trifluoroethoxy)-1H-pyrazole-5-carboxylic acid

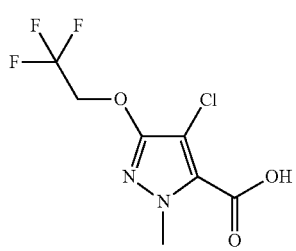 [SMILES: Cn1nc(OCC(F)(F)F)c(Cl)c1C(=O)O]

$^1$H-NMR (400 MHz, $d_6$-DMSO): δ=4.85 (m, 2H), 3.94 (s, 3H) ppm.

HPLC-MS: log P=2.00; mass (m/z)=259 [M+H]$^+$.

4-Bromo-1-methyl-3-(2,2,2-trifluoroethoxy)-1H-pyrazole-5-carboxylic acid

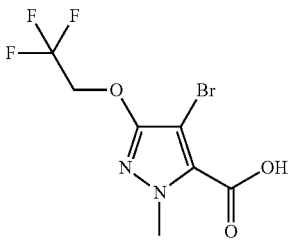 [SMILES: Cn1nc(OCC(F)(F)F)c(Br)c1C(=O)O]

$^1$H-NMR (400 MHz, $d_6$-DMSO): δ=4.84 (m, 2H), 3.96 (s, 3H) ppm.

HPLC-MS: log P=2.03; mass (m/z)=303 [M+H]$^+$.

4-Iodo-1-methyl-3-(2,2,2-trifluoroethoxy)-1H-pyrazole-5-carboxylic acid

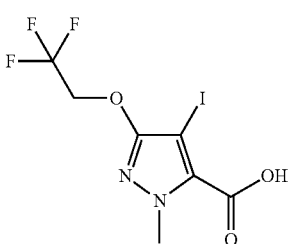

$^1$H-NMR (400 MHz, $d_6$-DMSO): δ=4.75 (m, 2H), 3.87 (s, 3H) ppm.

HPLC-MS: log P=2.11; mass (m/z)=351 [M+H]$^+$.

4-Bromo-3-cyclopropyl-1-methyl-1H-pyrazole-5-carboxylic acid

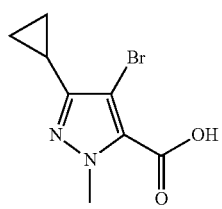

A solution, cooled to 0° C., of 100 mg (0.60 mmol) of 3-cyclopropyl-1-methyl-1H-pyrazole-5-carboxylic acid in 5 ml of acetic acid is admixed with 173 mg (1.08 mmol) of bromine and afterstirred overnight at room temperature. Acetic acid and bromine are drawn off on a rotary evaporator and the solid residue is washed with cyclohexane and a small amount of diethyl ether. This gives 69.0 mg of 4-bromo-3-cyclopropyl-1-methyl-1H-pyrazole-5-carboxylic acid (47%) as a yellowish solid.

$^1$H-NMR (400 MHz, $d_6$-DMSO): δ=3.96 (s, 3H), 1.84 (m, 1H), 0.89 (m, 2H), 0.77 (m, 2H) ppm.

HPLC-MS: log P=1.76; mass (m/z)=245 [M+H]$^+$.

Ethyl 3-cyclopropyl-4-iodo-1-methyl-1H-pyrazole-5-carboxylate

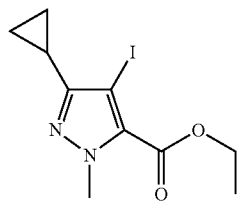

A solution of 500 mg (2.57 mmol) of ethyl-3-cyclopropyl-1-methyl-1H-pyrazole-5-carboxylate (prepared from ethyl-3-cyclopropyl-1H-pyrazole-5-carboxylate in accordance with *Bioorg. Med. Chem. Lett.* 1996, 6, 1819-1824) in 5 ml of acetonitrile is admixed with 706 mg (1.28 mmol) of ammonium cerium(IV) nitrate and 392 mg (1.53 mmol) of iodine and heated under reflux for three hours and afterstirred overnight at room temperature. The reaction mixture is diluted with water and ethyl acetate, and the organic phase is washed with saturated sodium thiosulphate solution, dried over sodium sulphate, filtered and concentrated by evaporation in vacuo. Chromatographic purification gives 506 mg of ethyl-3-cyclopropyl-4-iodo-1-methyl-1H-pyrazole-5-carboxylate (66%).

$^1$H-NMR (400 MHz, $d_6$-DMSO): δ=4.34 (m, 2H), 3.98 (s, 3H), 1.82 (m, 1H), 1.36 (m, 3H), 0.89 (m, 2H), 0.75 (m, 2H) ppm.

HPLC-MS: log P=3.56; mass (m/z)=321 [M+H]$^+$.

Ethyl 3-cyclopropyl-1-methyl-4-(trifluoromethyl)-1H-pyrazole-5-carboxylate

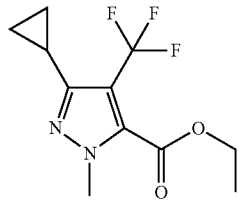 [SMILES: CCOC(=O)c1c(C(F)(F)F)c(C2CC2)nn1C]

268 mg (1.40 mmol) of copper(I) iodide and 65.3 mg (1.12 mmol) of potassium fluoride are initially introduced into a heat-dried vial under argon, and 3 ml of N,N-dimethylformamide and 300 mg (0.93 mmol) of ethyl-3-cyclopropyl-4-iodo-1-methyl-1H-pyrazole-5-carboxylate and 0.28 ml (1.87 mmol) of trimethyl(trifluoromethyl)silane are added. The reaction mixture is degassed in the ultrasound, flushed with argon and the closed via is heated at 80° C. for three hours. The cooled reaction solution is admixed with a small amount of water, diluted with ethyl acetate, filtered over silica gel (ethyl acetate) and concentrated by evaporation on a rotary evaporator. Chromatographic purification on silica gel gives 212 mg of ethyl 3-cyclopropyl-1-methyl-4-(trifluoromethyl)-1H-pyrazole-5-carboxylate (86%).

$^1$H-NMR (400 MHz, $d_6$-DMSO): δ=4.36 (m, 2H), 3.94 (s, 3H), 1.97 (m, 1H), 1.31 (m, 3H), 0.90 (m, 2H), 0.83 (m, 2H) ppm.

HPLC-MS: log P=3.66; mass (m/z)=263 [M+H]$^+$.

3-Cyclopropyl-1-methyl-4-(trifluoromethyl)-1H-pyrazole-5-carboxylic acid

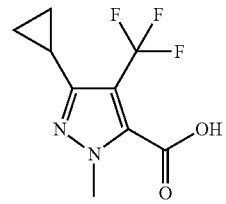 [SMILES: Cn1nc(C2CC2)c(C(F)(F)F)c1C(=O)O]

This compound is prepared analogously to the preparation of 3-(difluoromethoxy)-1-methyl-1H-pyrazole-5-carboxylic acid from ethyl 3-cyclopropyl-1-methyl-4-(trifluoromethyl)-1H-pyrazole-5-carboxylate:

$^1$H-NMR (400 MHz, $d_6$-DMSO): δ=3.92 (s, 3H), 1.94 (m, 1H), 0.89 (m, 2H), 0.82 (m, 2H) ppm;

HPLC-MS: log P=1.74; mass (m/z)=235 [M+H]$^+$.

Methyl 1-methyl-3-[4-(trifluoromethyl)phenyl]-1H-pyrazole-5-carboxylate

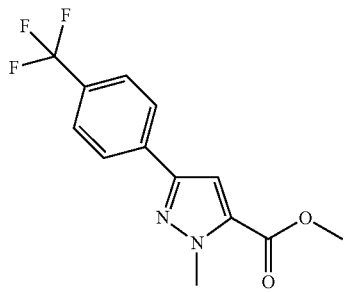 [SMILES: COC(=O)c1cc(-c2ccc(C(F)(F)F)cc2)nn1C]

1.50 g (5.36 mmol) of methyl 1-methyl-3-(4,4,5,5-tetramethyl-1,3,2-dioxaborolan-2-yl)-1H-pyrazole-5-carboxylate (for preparation see WO2007/034278A2), 1.21 g (5.36 mmol) of 1-bromo-4-(trifluoromethyl)benzene and bis(triphenylphosphine)palladium(II) chloride are initially introduced under argon and admixed with 6.69 ml of a 2M solution of sodium carbonate in water and 20 ml of dioxane. The reaction mixture is heated at 100° C. for three hours and, after cooling over Celite and sodium sulphate, is filtered. The filter cake is afterwashed with ethyl acetate and the filtrate is concentrated by evaporation on a rotary evaporator. Chromatographic purification on silica gel gives 529 mg of methyl 1-methyl-3-[4-(trifluoromethyl)phenyl]-1H-pyrazole-5-carboxylate (35%) (for preparation also see DD1984/210265).

$^1$H-NMR (400 MHz, $d_6$-DMSO): δ=8.05 (d, 2H), 7.75 (d, 2H), 7.44 (s, 1H), 4.16 (s, 3H), 3.88 (s, 3H) ppm.

HPLC-MS: log P=3.82; mass (m/z)=285 [M+H]$^+$.

Methyl 4-iodo-1-methyl-3-[4-(trifluoromethyl)phenyl]-1H-pyrazole-5-carboxylate

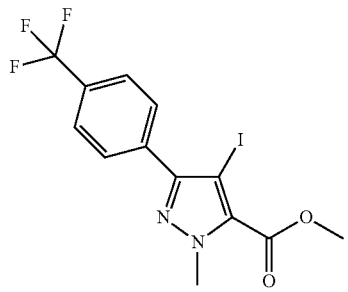 [SMILES: COC(=O)c1c(I)c(-c2ccc(C(F)(F)F)cc2)nn1C]

This compound is prepared analogously to the preparation of ethyl 3-cyclopropyl-4-iodo-1-methyl-1H-pyrazole-5-carboxylate from methyl 1-methyl-3-[4-(trifluoromethyl)phenyl]-1H-pyrazole-5-carboxylate and iodine.

$^1$H-NMR (400 MHz, d$_6$-DMSO): δ=7.97 (d, 2H), 7.82 (d, 2H), 4.16 (s, 3H), 3.92 (s, 3H) ppm.

HPLC-MS: log P=4.23; mass (m/z)=411 [M+H]$^+$.

Methyl 1-methyl-4-(trifluoromethyl)-3-[4-(trifluoromethyl)phenyl]-1H-pyrazole-5-carboxylate

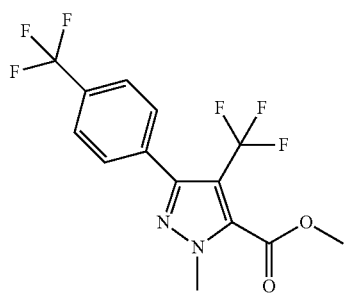 [SMILES: COC(=O)c1c(C(F)(F)F)c(-c2ccc(C(F)(F)F)cc2)nn1C]

This compound is prepared analogously to the preparation of ethyl 3-cyclopropyl-1-methyl-4-(trifluoromethyl)-1H-pyrazole-5-carboxylate from methyl 4-iodo-1-methyl-3-[4-(trifluoromethyl)phenyl]-1H-pyrazole-5-carboxylate.

$^1$H-NMR (400 MHz, d$_6$-DMSO): δ=7.86 (d, 2H), 7.72 (d, 2H), 4.12 (s, 3H), 3.96 (s, 3H) ppm.

HPLC-MS: log P=4.14; mass (m/z)=353 [M+H]$^+$.

1-Methyl-4-(trifluoromethyl)-3-[4-(trifluoromethyl)phenyl]-1H-pyrazole-5-carboxylic acid

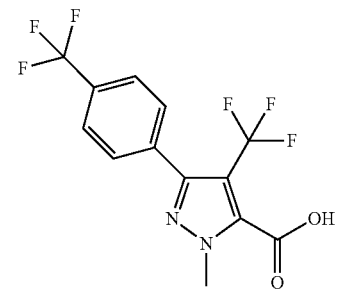 [SMILES: Cn1nc(-c2ccc(C(F)(F)F)cc2)c(C(F)(F)F)c1C(=O)O]

This compound is prepared analogously to the preparation of 3-(difluoromethoxy)-1-methyl-1H-pyrazole-5-carboxylic acid from methyl 1-methyl-4-(trifluoromethyl)-3-[4-(trifluoromethyl)phenyl]-1H-pyrazole-5-carboxylate.

$^1$H-NMR (400 MHz, d$_6$-DMSO): δ=7.85 (d, 2H), 7.71 (d, 2H), 4.09 (s, 3H) ppm.

HPLC-MS: log P=1.24; mass (m/z)=339 [M+H]$^+$.

5-(Benzylsulphanyl)-1-methyl-3-(pentafluoroethyl)-4-(trifluoromethyl)-1H-pyrazole

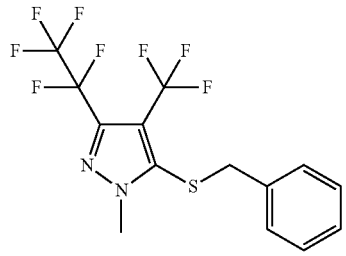 [SMILES: Cn1nc(C(F)(F)C(F)(F)F)c(C(F)(F)F)c1SCc1ccccc1]

A solution of 3.00 g (10.5 mmol) of 5-fluoro-1-methyl-3-(pentafluoroethyl)-4-(trifluoromethyl)-1H-pyrazole and 1.48 ml (12.6 mmol) of benzylmercaptan is initially introduced into 24 ml of acetonitrile at 0° C. 4.78 ml (34.3 mmol) of triethylamine are then added dropwise and the reaction mixture is stirred for two hours at between 0° C. and 10° C. Following concentration by evaporation in vacuo, the resulting oil is purified by chromatography on silica gel, giving 3.19 g of 5-(benzylsulphanyl)-1-methyl-3-(pentafluoroethyl)-4-(trifluoromethyl)-1H-pyrazole (78%).

$^1$H-NMR (400 MHz, d$_6$-DMSO): δ=7.27 (m, 3H), 7.08 (m, 2H), 4.13 (s, 2H), 3.68 (s, 3H) ppm.

HPLC-MS: log P=5.00; mass (m/z)=391 [M+H]$^+$.

1-Methyl-3-(pentafluoroethyl)-4-(trifluoromethyl)-1H-pyrazole-5-sulphonyl chloride

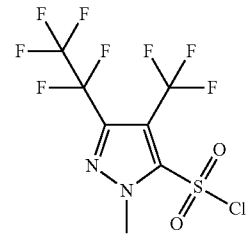 [SMILES: Cn1nc(C(F)(F)C(F)(F)F)c(C(F)(F)F)c1S(=O)(=O)Cl]

A solution of 1.00 g (2.49 mmol) of 5-(benzylsulphanyl)-1-methyl-3-(pentafluoroethyl)-4-(trifluoromethyl)-1H-pyrazole in 17 ml of dichloromethane is admixed with 20 ml of hydrochloric acid (16%) and 30 ml of sodium hypochloride solution (13%) and stirred at room temperature for 18 hours. After adding 10 ml of chlorine liquor and a further seven hours at room temperature, extraction is carried out several times with dichloromethane, and the organic phase is dried over magnesium sulphate, filtered and concentrated by evaporation in vacuo. The crude product is reacted without further purification to give the corresponding sulphonamides.

$^1$H NMR (400 MHz, d$_6$-DMSO): δ=4.10 (s, 3H) ppm.

Ethyl-3-(hydroxymethyl)-1-methyl-4-(trifluoromethyl)-1H-pyrazole-5-carboxylate

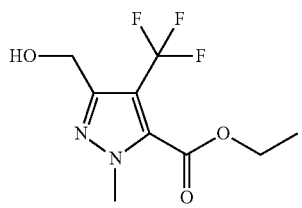 [SMILES: CCOC(=O)c1c(C(F)(F)F)c(CO)nn1C]

A solution of 6.00 g (20.4 mmol) of diethyl 1-methyl-4-(trifluoromethyl)-1H-pyrazole-3,5-dicarboxylate in 80 ml of tetrahydrofuran is admixed under argon at −78° C. with 38.9 ml (42.8 mmol) of a 1.1M solution of diisobutylaluminium hydride in cyclohexane and stirred overnight at this temperature. The reaction mixture is admixed with water and extracted twice with ethyl acetate. The organic phase is dried over sodium sulphate, filtered over silica gel and concentrated by evaporation in vacuo. Chromatographic purification on silica gel gives 4.10 g of ethyl 3-(hydroxymethyl)-1-methyl-4-(trifluoromethyl)-1H-pyrazole-5-carboxylate (80%).

$^1$H-NMR (400 MHz, $d_6$-DMSO): δ=5.03 (br. s, 1H), 4.49 (s, 2H), 4.37 (q, 2H), 4.02 (s, 3H), 1.32 (t, 3H) ppm.

HPLC-MS: log P=1.74; mass (m/z)=253 [M+H]$^+$.

Ethyl 3-formyl-1-methyl-4-(trifluoromethyl)-1H-pyrazole-5-carboxylate

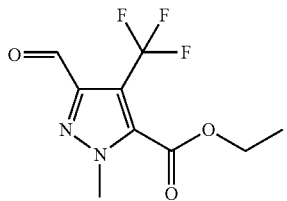 [SMILES: CCOC(=O)c1c(C(F)(F)F)c(C=O)nn1C]

A solution of 1.50 g (5.95 mmol) of ethyl 3-(hydroxymethyl)-1-methyl-4-(trifluoromethyl)-1H-pyrazole-5-carboxylate in 100 ml of dichloromethane is admixed with 4.14 g (47.6 mmol) of manganese(IV) oxide and heated under reflux for four hours. The cooled reaction mixture is filtered over Celite and concentrated by evaporation on a rotary evaporator. This gives 1.36 g of ethyl 3-formyl-1-methyl-4-(trifluoromethyl)-1H-pyrazole-5-carboxylate (91%).

$^1$H-NMR (400 MHz, $d_3$-acetonitrile): δ=9.99 (s, 1H), 4.44 (q, 2H), 4.11 (s, 3H), 1.37 (t, 3H) ppm.

HPLC-MS: log P=2.40; mass (m/z)=251 [M+H]$^+$.

Ethyl 3-(difluoromethyl)-1-methyl-4-(trifluoromethyl)-1H-pyrazole-5-carboxylate

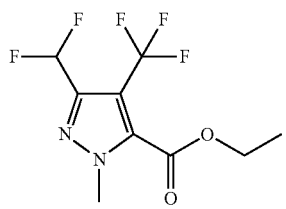 [SMILES: CCOC(=O)c1c(C(F)(F)F)c(C(F)F)nn1C]

A solution of 1.00 g (4.00 mmol) of ethyl 3-formyl-1-methyl-4-(trifluoromethyl)-1H-pyrazole-5-carboxylate in 40 ml of dichloromethane is cooled to −10° C. under argon and 1.11 ml (8.39 mmol) of diethylaminosulphur trifluoride are added dropwise over 10 minutes. The reaction mixture is stirred at −10° C. for one hour, and admixed firstly with solid sodium carbonate and then with saturated sodium carbonate solution. The aqueous phase is extracted twice with dichloromethane, and the organic phase is dried over sodium sulphate and concentrated by evaporation. Chromatographic purification on silica gel gives 585 mg of ethyl 3-(difluoromethyl)-1-methyl-4-(trifluoromethyl)-1H-pyrazole-5-carboxylate (54%).

$^1$H-NMR (400 MHz, $d_6$-DMSO): δ=7.11 (t, 1H), 4.41 (q, 2H), 4.11 (s, 3H), 1.33 (t, 3H) ppm.

HPLC-MS: log P=3.05; mass (m/z)=273 [M+H]$^+$.

3-(Difluoromethyl)-1-methyl-4-(trifluoromethyl)-1H-pyrazole-5-carboxylic acid

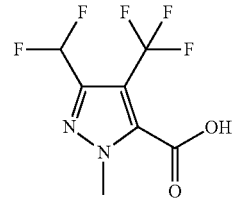 [SMILES: Cn1nc(C(F)F)c(C(F)(F)F)c1C(=O)O]

A solution of 600 mg (2.20 mmol) of ethyl 3-(difluoromethyl)-1-methyl-4-(trifluoromethyl)-1H-pyrazole-5-carboxylate in 10 ml of methanol is admixed with 331 mg (3.31 mmol) of 40% strength sodium hydroxide solution and stirred for three hours at room temperature. The reaction mixture is concentrated by evaporation, admixed with water and extracted with diethyl ether. The aqueous phase is acidified with dilute hydrochloric acid and extracted twice with diethyl acetate. The organic phase is dried over sodium sulphate and, after filtration, is concentrated by evaporation. This gives 452 mg of 3-(difluoromethyl)-1-methyl-4-(trifluoromethyl)-1H-pyrazole-5-carboxylic acid (84%).

$^1$H-NMR (400 MHz, $d_6$-DMSO): δ=7.07 (t, 1H), 4.09 (s, 3H) ppm.

HPLC-MS: log P=1.10; mass (m/z)=245 [M+H]$^+$.

Ethyl 3-[cyclopropyl(hydroxy)methyl]-1-methyl-4-(trifluoromethyl)-1H-pyrazole-5-carboxylate

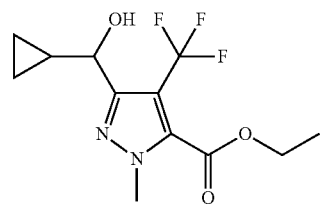 [SMILES: CCOC(=O)c1c(C(F)(F)F)c(C(O)C2CC2)nn1C]

A solution of 1.82 g (7.28 mmol) of ethyl 3-formyl-1-methyl-4-(trifluoromethyl)-1H-pyrazole-5-carboxylate in 80 ml of tetrahydrofuran is admixed under argon at −78° C. with 17.5 ml (8.73 mmol) of 0.5M cyclopropylmagnesium bromide solution in tetrahydrofuran, and stirred for 30 minutes at this temperature and then overnight at room temperature. The reaction solution is admixed with saturated ammonium chloride solution and extracted with ethyl acetate, and the organic phase is dried over sodium sulphate and concentrated by evaporation on a rotary evaporator. Chromatographic purification on silica gel gives 0.67 g of ethyl 3-[cyclopropyl(hydroxy)methyl]-1-methyl-4-(trifluoromethyl)-1H-pyrazole-5-carboxylate (31%).

$^1$H-NMR (400 MHz, $d_6$-DMSO): δ=5.08 (d, 1H), 4.37 (q, 2H), 4.06 (m, 1H), 4.01 (s, 3H), 1.31 (m, 4H), 0.52 (m, 1H), 0.43 (m, 2H), 0.18 (m, 1H) ppm.

HPLC-MS: log P=2.38; mass (m/z)=275 [M−H$_2$O+H]$^+$.

3-[Cyclopropyl(hydroxy)methyl]-1-methyl-4-(trifluoromethyl)-1H-pyrazole-5-carboxylic acid

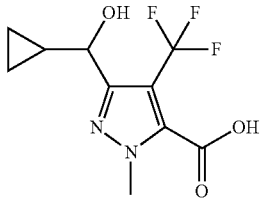 [SMILES: Cn1nc(C(O)C2CC2)c(C(F)(F)F)c1C(=O)O]

This compound is prepared analogously to the preparation of 3-(difluoromethyl)-1-methyl-4-(trifluoromethyl)-1H-pyrazole-5-carboxylic acid from ethyl 3-[cyclopropyl(hydroxy)methyl]-1-methyl-4-(trifluoromethyl)-1H-pyrazole-5-carboxylate.

$^1$H-NMR (400 MHz, d$_6$-DMSO): δ=3.88 (m, 1H), 3.83 (s, 3H), 1.16 (m, 1H), 1.01 (t, 3H), 0.33 (m, 1H), 0.25 (m, 2H), 0.02 (m, 1H) ppm.

HPLC-MS: log P=0.72; mass (m/z)=247 [M–H$_2$O+H]$^+$.

Ethyl 3-(2-hydroxypropan-2-yl)-1-methyl-4-(trifluoromethyl)-1H-pyrazole-5-carboxylate

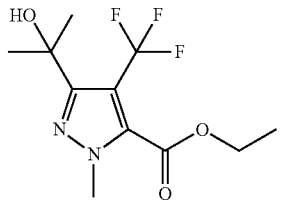 [SMILES: CCOC(=O)c1c(C(F)(F)F)c(C(C)(C)O)nn1C]

At –78° C., 4.76 ml (14.3 mmol) of a 3M methylmagnesium chloride in tetrahydrofuran are added dropwise over 10 minutes to a solution of 2.00 g (6.80 mmol) of ethyl 3-formyl-1-methyl-4-(trifluoromethyl)-1H-pyrazole-5-carboxylate in 30 ml of tetrahydrofuran. The reaction mixture is stirred for four hours at –78° C. and then added to saturated ammonium chloride solution and extracted three times with ethyl acetate. The organic phase is dried over sodium sulphate and concentrated by evaporation on a rotary evaporator. Chromatographic purification on silica gel gives 976 mg of ethyl 3-(2-hydroxypropan-2-yl)-1-methyl-4-(trifluoromethyl)-1H-pyrazole-5-carboxylate (51%).

$^1$H-NMR (400 MHz, d$_6$-DMSO): δ=4.88 (br. s, 1H), 4.38 (q, 2H), 3.88 (s, 3H), 1.48 (s, 6H), 1.31 (t, 3H) ppm.

HPLC-MS: log P=2.33; mass (m/z)=263 [M–H$_2$O+H]$^+$.

Ethyl 3-(2-fluoropropan-2-yl)-1-methyl-4-(trifluoromethyl)-1H-pyrazole-5-carboxylate

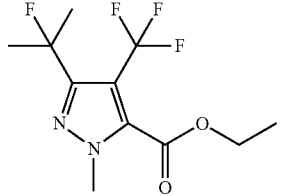 [SMILES: CCOC(=O)c1c(C(F)(F)F)c(C(C)(C)F)nn1C]

At –10° C., 0.52 ml (3.9 mmol) of diethylaminosulphur trifluoride is added dropwise to a solution of 1.00 g (3.57 mmol) of ethyl 3-(2-hydroxypropan-2-yl)-1-methyl-4-(trifluoromethyl)-1H-pyrazole-5-carboxylate in 20 ml of dichloromethane. The mixture is afterstirred for one hour at –10° C., sodium carbonate is added, and the mixture is stirred for 10 minutes at room temperature. After adding saturated sodium carbonate solution, extraction is carried out with dichloromethane, and the combined organic phases are dried over sodium sulphate and concentrated by evaporation in vacuo on a rotary evaporator. Purification by flash chromatography on silica gel (cyclohexane/ethyl acetate) gives 700 mg of ethyl 3-(2-fluoropropan-2-yl)-1-methyl-4-(trifluoromethyl)-1H-pyrazole-5-carboxylate (67%).

$^1$H-NMR (400 MHz, d$_6$-DMSO): δ=4.40 (q, 2H), 3.95 (s, 3H), 1.70 (d, 6H), 1.32 (t, 3H) ppm.

HPLC-MS: log P=3.55; mass (m/z)=283 [M+H]$^+$.

3-(2-Fluoropropan-2-yl)-1-methyl-4-(trifluoromethyl)-1H-pyrazole-5-carboxylic acid

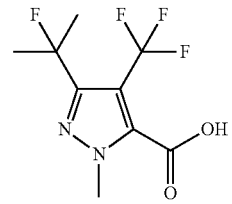 [SMILES: Cn1nc(C(C)(C)F)c(C(F)(F)F)c1C(=O)O]

A solution of 700 mg (2.48 mmol) of ethyl 3-(2-fluoropropan-2-yl)-1-methyl-4-(trifluoromethyl)-1H-pyrazole-5-carboxylate in 10 ml of methanol is admixed with 208 mg (3.72 mmol) of potassium hydroxide and 1 ml of water and heated at 50° C. for one hour. The reaction mixture is concentrated by evaporation, admixed with water and extracted with diethyl ether. The aqueous phase is acidified with dilute hydrochloric acid and extracted twice with ethyl acetate, and the organic phase is dried over sodium sulphate and, after filtration, is concentrated by evaporation. This gives 498 mg of 3-(2-fluoropropan-2-yl)-1-methyl-4-(trifluoromethyl)-1H-pyrazole-5-carboxylic acid (79%).

$^1$H-NMR (400 MHz, d$_6$-DMSO): δ=3.92 (s, 3H), 1.69 (d, 6H) ppm.

HPLC-MS: log P=1.43; mass (m/z)=255 [M+H]$^+$.

Ethyl 2-(pentafluoroethyl)-4-(trifluoromethyl)-1,3-thiazole-5-carboxylate

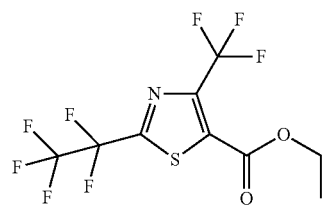 [SMILES: CCOC(=O)c1sc(C(F)(F)C(F)(F)F)nc1C(F)(F)F]

A mixture of 2.00 g (12.3 mmol) of 2,2,3,3,3-pentafluoropropanamide and 2.48 g (6.13 mmol) of Lawesson reagent are admixed with 20 ml of tetrahydrofuran and heated under reflux for 3.5 hours. Following concentration by evaporation in vacuo, the resulting 2,2,3,3,3-pentafluoropropanethioamide is purified by distillation (561 mg).

557 mg (3.10 mmol) of 2,2,3,3,3-pentafluoropropanethioamide and 746 mg (3.41 mmol) of ethyl 2-chloro-4,4,4-trifluoro-3-oxobutanoate (commercially available or can be prepared in accordance with *Journal of Fluorine Chemistry* 2004, 125, 1287-1290) are dissolved in 15 ml of acetonitrile, and 0.86 ml (6.19 mmol) of triethylamine is added dropwise. The reaction mixture is heated at reflux for 5 hours and then left at room temperature for two days. Chromatographic purification on silica gel gives 568 mg of ethyl 2-(pentafluoroethyl)-4-(trifluoromethyl)-1,3-thiazole-5-carboxylate (13%).

$^1$H-NMR (400 MHz, d$_6$-DMSO): δ=4.42 (q, 2H), 1.33 (t, 3H) ppm.

HPLC-MS: log P=4.36.

2-(Pentafluoroethyl)-4-(trifluoromethyl)-1,3-thiazole-5-carboxylic acid

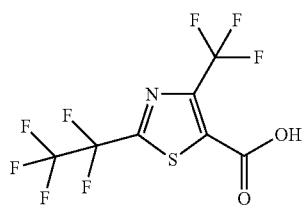 [SMILES: O=C(O)c1sc(C(F)(F)C(F)(F)F)nc1C(F)(F)F]

A solution of 540 mg (1.57 mmol) of ethyl 2-(pentafluoroethyl)-4-(trifluoromethyl)-1,3-thiazole-5-carboxylate in 3 ml of methanol and 1 ml of water is admixed with 94.4 mg (2.36 mmol) of sodium hydroxide solution and heated at 60° C. for two hours. The reaction mixture is acidified with conc. hydrochloric acid and extracted four times with dichloromethane, and the organic phase is washed with saturated sodium chloride solution, dried over magnesium sulphate and, after filtration, is concentrated by evaporation. This gives 417 mg (min. 50% strength, max. 82%) of 2-(pentafluoroethyl)-4-(trifluoromethyl)-1,3-thiazole-5-carboxylic acid.

HPLC-MS: log P=2.06; mass (m/z)=316 [M+H]$^+$.

2,2,2-Trifluoro-1-[1-methyl-4-(rifluoromethyl)-1H-imidazol-2-yl]ethanamine

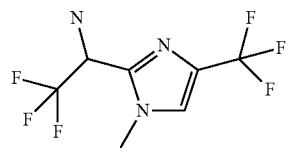 [SMILES: Cn1cc(C(F)(F)F)nc1C(N)C(F)(F)F]

2.0 g (8.12 mmol) of 2,2,2-trifluoro-1-[1-methyl-4-(trifluoromethyl)-1H-imidazol-2-yl]ethanone [preparation analogous to *Synthesis* 2008, 6, 948-956] are dissolved in 40 ml of toluene under a protective gas atmosphere and then admixed with 8.93 ml (8.93 mmol) of a 1M solution of lithium (bistrimethylsilyl)amide in toluene. The solution is then stirred for 1 h at room temperature. 8.12 ml (16.2 mmol) of a 2M solution of borane dimethylsulphide complex in tetrahydrofuran are then added and the mixture is stirred for a further 16 hours at room temperature. 6.0 ml of 2M sodium hydroxide solution are then added. The organic phase is dried over magnesium sulphate and then concentrated by evaporation under reduced pressure on a rotary evaporator. The product is purified by column chromatography on silica gel (dichloromethane:methanol=9:1). This gives 0.85 g of 2,2,2-trifluoro-1-[1-methyl-4-(trifluoromethyl)-1H-imidazole-2-yl]ethanamine (42%) as a yellow oil.

$^1$H-NMR (400 MHz, d$_3$-acetonitrile): δ=7.60 (s, 1H), 4.80 (m, 1H), 3.84 (s, 3H) ppm.

$^{13}$C-NMR (400 MHz, d$_3$-acetonitrile): δ=145.7, 130.5, 126.2, 123.9, 123.0, 51.0, 34.1 ppm.

TABLE 1

(Ia)

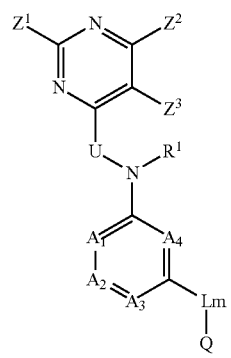

| Ex. No. | Process | $Z^1$ | $Z^2$ | $Z^3$ | $R^1$ | $A_4$ | $A_3$ | $A_2$ | $A_1$ | Lm | U | Q | logP | Mass [m/z]$^1$ |
|---|---|---|---|---|---|---|---|---|---|---|---|---|---|---|
| Ia-1 | F | CH$_3$ | CF$_2$CF$_3$ | CF$_3$ | H | C—H | C—Cl | C—H | C—H | CONH | CO | Cyclopropyl | 3.33$^{a)}$ | 517.0$^{a)}$ |

TABLE 2

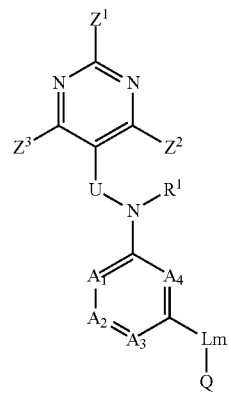
(Ib)

| Ex. No. | Process | $Z^1$ | $Z^2$ | $Z^3$ | $R^1$ | $A_4$ | $A_3$ | $A_2$ | $A_1$ | Lm | U | Q | logP | Mass $[m/z]^1$ |
|---|---|---|---|---|---|---|---|---|---|---|---|---|---|---|
| Ib-2 | D | $CF_3CH_2O$ | $CF_3$ | — | H | C—H | C—Cl | C—H | C—H | CONH | CO | Cyclopropyl | $2.76^{a)}$ | $483.0^{a)}$ |
| Ib-3 | A | $CF_3$ | $CF_3$ | — | H | C—H | C—Cl | C—H | C—H | CONH | CO | Cyclopropyl | $2.78^{a)}$ | $453.1^{a)}$ |
| Ib-4 |   | $CF_3$ | $CF_3$ | — | H | C—H | C—Cl | C—H | C—H | CONH | CO | 2,2,2-Trifluoroethyl | $3.14^{a)}$ | $495.0^{a)}$ |
| Ib-5 | A | $CF_3$ | $CF_3$ | — | H | C—H | C—Cl | C—H | C—H | CONH | CO | 3-Chloroprop-2-enyl | $3.19^{a)}$ | $487.0^{a)}$ |
| Ib-6 | A | $CF_3$ | $CF_3$ | — | H | C—H | C—Cl | C—H | C—H | CONH | CO | Benzyl | $3.39^{a)}$ | $503.1^{a)}$ |
| Ib-7 | A | $C_2F_5$ | $CF_3$ | — | H | C—H | C—Cl | C—H | C—H | CONH | CO | Cyclopropyl | $3.20^{a)}$ | $503.1^{a)}$ |
| Ib-8 | A | $C_2F_5$ | Me | Me | H | C—H | C—Cl | C—H | C—H | CONH | CO | Cyclopropyl | $2.82^{a)}$ | $463.1^{a)}$ |
| Ib-9 | A | $C_2F_5$ | $CF_3$ | — | H | C—H | C—Cl | C—H | C—H | CONH | CO | 2,2,2-Trifluoroethyl | $3.53^{a)}$ | $545.0^{a)}$ |
| Ib-10 | A | $C_2F_5$ | $CF_3$ | — | H | C—H | C—Cl | C—H | C—H | CONH | CO | 3-Chloroprop-2-enyl | $3.59^{a)}$ | $537.0^{a)}$ |
| Ib-11 | A | $C_2F_5$ | $CF_3$ | — | H | C—H | C—Cl | C—H | C—H | CONH | CO | Benzyl | $3.78^{a)}$ | $553.1^{a)}$ |
| Ib-12 | A | $C_2F_5$ | Me | Me | H | C—H | C—Cl | C—H | C—H | CONH | CO | 2,2,2-Trifluoroethyl | $3.22^{a)}$ | $505.1^{a)}$ |
| Ib-13 | A | $C_2F_5$ | Me | Me | H | C—H | C—Cl | C—H | C—H | CONH | CO | 3-Chloroprop-2-enyl | $3.26^{a)}$ | $497.1^{a)}$ |
| Ib-14 | A | $C_2F_5$ | Me | Me | H | C—H | C—Cl | C—H | C—H | CONH | CO | Benzyl | $3.49^{a)}$ | $513.1^{a)}$ |
| Ib-15 | A | $C_3F_7$ | $CF_3$ | — | H | C—H | C—Cl | C—H | C—H | CONH | CO | Cyclopropyl | $3.56^{a)}$ | $553.1^{a)}$ |
| Ib-16 | A | $C_3F_7$ | $CF_3$ | — | H | C—H | C—Cl | C—H | C—H | CONH | CO | 2,2,2-Trifluoroethyl | $3.88^{a)}$ | $595.0^{a)}$ |
| Ib-17 | A | $C_3F_7$ | $CF_3$ | — | H | C—H | C—Cl | C—H | C—H | CONH | CO | 3-Chloroprop-2-enyl | $3.92^{a)}$ | $587.0^{a)}$ |
| Ib-18 | A | $C_3F_7$ | $CF_3$ | — | H | C—H | C—Cl | C—H | C—H | CONH | CO | Benzyl | $4.13^{a)}$ | $603.1^{a)}$ |
| Ib-19 | A | $CF_3$ | Me | — | H | C—H | C—Cl | C—H | C—H | CONH | CO | Cyclopropyl | 2.24v | $399.0^{a)}$ |
| Ib-20 | A | $CF_3$ | Me | — | H | C—H | C—Cl | C—H | C—H | CONH | CO | 2,2,2-Trifluoroethyl | $2.65^{a)}$ | $441.0^{a)}$ |
| Ib-21 | A | $CF_3$ | Me | — | H | C—H | C—Cl | C—H | C—H | CONH | CO | 3-Chloroprop-2-enyl | $2.69^{a)}$ | $433.0^{a)}$ |
| Ib-22 | A | $CF_3$ | Me | — | H | C—H | C—Cl | C—H | C—H | CONH | CO | Benzyl | $2.94^{a)}$ | $449.0^{a)}$ |
| Ib-23 | A | $C_2F_5$ | Me | — | H | C—H | C—Cl | C—H | C—H | CONH | CO | Cyclopropyl | $2.76^{a)}$ | $449.0^{a)}$ |
| Ib-24 | A | $C_2F_5$ | Me | — | H | C—H | C—Cl | C—H | C—H | CONH | CO | 2,2,2-Trifluoroethyl | $3.16^{a)}$ | $491.0^{a)}$ |
| Ib-25 | A | $C_2F_5$ | Me | — | H | C—H | C—Cl | C—H | C—H | CONH | CO | 3-Chloroprop-2-enyl | $3.2^{a)}$ | $483.0^{a)}$ |
| Ib-26 | A | $C_2F_5$ | Me | — | H | C—H | C—Cl | C—H | C—H | CONH | CO | Benzyl | $3.43^{a)}$ | $499.0^{a)}$ |
| Ib-27 | A | $C_2F_5$ | $CHF_2$ | — | H | C—H | C—Cl | C—H | C—H | CONH | CO | Cyclopropyl | $2.92^{a)}$ | $485.1^{a)}$ |
| Ib-28 | A | $C_2F_5$ | $CHF_2$ | — | H | C—H | C—Cl | C—H | C—H | CONH | CO | 2,2,2-Trifluoroethyl | $3.27^{a)}$ | $527.0^{a)}$ |
| Ib-29 | A | $C_2F_5$ | $CHF_2$ | — | H | C—H | C—Cl | C—H | C—H | CONH | CO | Benzyl | $3.51^{a)}$ | $535.1^{a)}$ |
| Ib-30 | A | $C_2F_5$ | Cyclopropyl | — | H | C—H | C—Cl | C—H | C—H | CONH | CO | Cyclopropyl | $3.28^{a)}$ | $475.0^{a)}$ |
| Ib-31 | A | $C_2F_5$ | Cyclopropyl | — | H | C—H | C—Cl | C—H | C—H | CONH | CO | 2,2,2-Trifluoroethyl | $3.65^{a)}$ | $517.0^{a)}$ |
| Ib-32 | A | $CF_2CF_3$ | $CHF_2$ | H | H | C—H | C—Cl | C—H | C—H | CONH | CO | 3-chloroprop-2-enyl | $3.29^{a)}$ | $519.0^{a)}$ |
| Ib-33 | A | $CF_2CF_3$ | $CF_2CF_3$ | H | H | C—H | C—Cl | C—H | C—H | CONH | CO | Cyclopropyl | $3.64^{a)}$ | $553.0^{a)}$ |
| Ib-34 | A | $CF_2CF_3$ | $CF_2CF_3$ | H | H | C—H | C—Cl | C—H | C—H | CONH | CO | 2,2,2-trifluoromethyl | $3.94^{a)}$ | $595.0^{a)}$ |
| Ib-35 | A | $CF_2CF_3$ | $CF_2CF_3$ | H | H | C—H | C—Cl | C—H | C—H | CONH | CO | Benzyl | $4.20^{a)}$ | $603.0^{a)}$ |
| Ib-36 | A | $CF_2CF_3$ | $CF_3$ | H | H | C—H | C—Cl | C—Br | C—H | CONH | CO | Cyclopropyl | $3.62^{a)}$ | $582.9^{a)}$ |
| Ib-37 | A | $CF_2CF_3$ | $CF_3$ | H | H | C—H | C—Cl | C—H | C—H | CONH | CO | 1-Cyclopropylethyl | $3.76^{a)}$ | $531.1^{a)}$ |
| Ib-38 | A | $CF_2CF_3$ | $CF_3$ | H | CH3 | C—H | C—Cl | C—H | C—H | CONH | CO | Cyclopropyl | $3.23^{a)}$ | $517.1^{a)}$ |

Extraordinarily preferred are also compounds of the general formulae (Ib) which are produced from any desired combination of the radicals $Z^1$, $Z^2$, $Z^3$, $R^1$, $A_4$, $A_3$, $A_2$, $A_1$, $L_m$, U and Q listed in Table 2.

TABLE 3

(Ie)

| Ex. No. | Process | $Z^1$ | $Z^2$ | $R^1$ | $A_4$ | $A_3$ | $A_2$ | $A_1$ | $L_m$ | U | Q | logP | Mass [m/z]$^1$ |
|---|---|---|---|---|---|---|---|---|---|---|---|---|---|
| Ie-1 | A | $CF_3$ | Cl | H | C—H | C—Cl | C—H | C—H | CONH | CO | Cyclopropyl | 2.48$^{a)}$ | 418.0$^{a)}$ |
| Ie-2 | A | $CF_3$ | Cl | H | C—H | C—Cl | C—H | C—H | CONH | CO | 1-Methylethyl | 2.72$^{a)}$ | 420.0$^{a)}$ |
| Ie-3 | A | $CF_3$ | Cl | H | C—H | C—Cl | C—H | C—H | CONH | CO | 2,2,2-Trifluoroethyl | 2.88$^{a)}$ | 460.0$^{a)}$ |
| Ie-4 | A | $CF_3$ | Cl | H | C—H | C—Cl | C—H | C—H | CONH | CO | 3-Chloroprop-2-enyl | 2.92$^{a)}$ | 452.0$^{a)}$ |
| Ie-5 | A | $CF_3$ | Cl | H | C—H | C—Cl | C—H | C—H | CONH | CO | Benzyl | 3.16$^{a)}$ | 468.1$^{a)}$ |

Extraordinarily preferred are also compounds of the general formulae (Ie) which are produced from any desired combination of the radicals $Z^1$, $Z^2$, $R^1$, $A_4$, $A_3$, $A_2$, $A_1$, $L_m$, U and Q listed in Table 3.

TABLE 4

(Ii)

| Ex. No. | Process | $Z^1$ | $Z^2$ | $R^1$ | $A_4$ | $A_3$ | $A_2$ | $A_1$ | $L_m$ | U | Q | logP | Mass [m/z]$^1$ |
|---|---|---|---|---|---|---|---|---|---|---|---|---|---|
| Ii-1 | A | $CF_3$ | Cl | H | C—H | C—Cl | C—H | C—H | CONH | CO | Cyclopropyl | 2.46$^{a)}$ | 418.0$^{a)}$ |
| Ii-2 | A | $CF_3$ | Cl | H | C—H | C—Cl | C—H | C—H | CONH | CO | 1-Methylethyl | 2.73$^{a)}$ | 420.0$^{a)}$ |
| Ii-3 | A | $CF_3$ | Cl | H | C—H | C—Cl | C—H | C—H | CONH | CO | 2,2,2-Trifluoroethyl | 2.86$^{a)}$ | 460.0$^{a)}$ |
| Ii-4 | A | $CF_3$ | Cl | H | C—H | C—Cl | C—H | C—H | CONH | CO | 3-Chloroprop-2-enyl | 2.93$^{a)}$ | 451.9$^{a)}$ |
| Ii-5 | A | $CF_3$ | Cl | H | C—H | C—Cl | C—H | C—H | CONH | CO | Benzyl | 3.17$^{a)}$ | 468.0$^{a)}$ |

Extraordinarily preferred are also compounds of the general formulae (Ii) which are produced from any desired combination of the radicals $Z^1$, $Z^2$, $R^1$, $A_4$, $A_3$, $A_2$, $A_1$, $L_m$, U and Q listed in Table 4.

TABLE 5

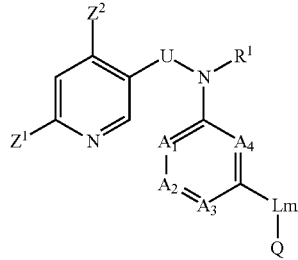

(Ij)

| Ex. No. | Process | $Z^1$ | $Z^2$ | $R^1$ | $A_4$ | $A_3$ | $A_2$ | $A_1$ | Lm | U | Q | logP | Mass [m/z][1] |
|---|---|---|---|---|---|---|---|---|---|---|---|---|---|
| Ij-1 | D | $CF_3CH_2O$ | $CF_3$ | H | C—H | C—Cl | C—H | C—H | CONH | CO | Cyclopropyl | 3.02[a] | 482.1[a] |
| Ij-2 | D | $CF_3CH(Me)O$ | $CF_3$ | H | C—H | C—Cl | C—H | C—H | CONH | CO | Cyclopropyl | 3.32[a] | 496.1[a] |
| Ij-3 | D | $C_2F_5CH_2O$ | $CF_3$ | H | C—H | C—Cl | C—H | C—H | CONH | CO | Cyclopropyl | 3.44[a] | 532.1[a] |
| Ij-4 | A | $(CF_3)_2CH_2O$ | $CF_3$ | H | C—H | C—Cl | C—H | C—H | CONH | CO | Cyclopropyl | 3.65[a] | 550.1[a] |

Extraordinarily preferred are also compounds of the general formulae (Ij) which are produced from any desired combination of the radicals $Z^1$, $Z^2$, $R^1$, $A_4$, $A_3$, $A_2$, $A_1$, $L_m$, U and Q listed in Table 5.

TABLE 6

(IK)

| Ex. No. | Process | Z¹ | Z² | Z³ | R¹ | A₄ | A₃ | A₂ | A₁ | Lm | U | Q | logP | Mass [m/z] |
|---|---|---|---|---|---|---|---|---|---|---|---|---|---|---|
| Ik-1 | A | C₂F₅ | CF₃ | CH₃ | H | C—H | C—Cl | C—H | C—H | CONH | CO | Cyclopropyl | 3.34[a] | 505.0[a] |
| Ik-2 | B | C₂F₅ | CF₃ | CH₃ | H | C—H | C—Cl | C—H | C—H | CONH | CO | H | 3.22[a] | 466.0[a] |
| Ik-3 | B | C₂F₅ | CF₃ | CH₃ | H | C—H | C—Cl | C—H | C—H | CONH | CO | Prop-2-ynyl | 3.11[b] | 502.9[b] |
| Ik-4 | C | C₂F₅ | I | CH3 | H | C—H | C—Cl | C—H | C—H | CONH | CO | Cyclopropyl | 3.15[a] | 562.9[a] |
| Ik-5 | C | C₂F₅ | Vinyl | CH₃ | H | C—H | C—Cl | C—H | C—H | CONH | CO | Cyclopropyl | 3.11[b] | 463.1[b] |
| Ik-6 | B | C₂F₅ | CF₃ | CH₃ | H | C—H | C—Cl | C—H | C—H | CONH | CO | 2,2-Difluorocyclopropyl | 3.33[b] | 541.1[b] |
| Ik-7 | A | C₂F₅ | CF₃ | CH₃ | H | C—H | C—Cl | C—Br | C—H | CONH | CO | Cyclopropyl | 3.81[a] | 582.9[a] |
| Ik-8 | B | C₂F₅ | CF₃ | CH₃ | H | C—H | C—Cl | C—H | C—H | CONH | CO | trans-2-Fluorocyclopropyl | 3.24[b] | 523.1[b] |
| Ik-9 | B | C₂F₅ | CF₃ | CH₃ | H | C—H | C—Cl | C—OCH₃ | C—H | CONH | CO | cis-2-Fluorocyclopropyl | 3.28[b] | 523.1[b] |
| Ik-10 | A | C₂F₅ | CF₃ | C₂H₅ | H | C—H | C—Cl | C—H | C—H | CONH | CO | Benzyl | 4.18[a] | 563.1[a] |
| Ik-11 | A | C₂F₅ | Br | CH₃ | H | C—H | C—Cl | CCONHcPr | C—H | CONH | CO | 1-Trifluoromethylethyl | 2.00[a] | 572.9[a] |
| Ik-12 | A | C₂F₅ | Br | CH₃ | H | C—H | C—Cl | C—H | C—H | CONH | CO | 1-Cyclopropylethyl | 3.84[a] | 543.0[a] |
| Ik-13 | A | C₂F₅ | CF₃ | CH₃ | H | C—H | C—H | C—H | C—H | CONH | CO | Cyclopropyl | 3.15[a] | 471.1[a] |
| Ik-14 | A | C₂F₅ | CF₃ | CH₃ | H | C—H | C—H | C—H | C—H | CONH | CO | Benzyl | 3.77[a] | 521.1[a] |
| Ik-15 | A | C₂F₅ | CF₃ | CH₃ | H | C—H | C—H | CCONHcPr | C—H | CONH | CO | Cyclopropyl | 2.74[a] | 554.2[a] |
| Ik-16 | A | CF₃CClF | Br | CH₃ | H | C—H | C—Cl | C—H | C—H | CONH | CO | Cyclopropyl | 3.35[a] | 530.9[a] |
| Ik-17 | A | C₂F₅ | H | CH₃ | H | C—H | C—Cl | C—H | C—H | CONH | CO | Cyclopropyl | 2.94[a] | 437.0[a] |
| Ik-18 | A | CF₃ | Cl | CH₃ | H | C—H | C—Cl | C—H | C—H | CONH | CO | Cyclopropyl | 2.77[a] | 421.1[a] |
| Ik-19 | A | CF₃ | Cl | CH₃ | H | C—H | C—Cl | C—H | C—H | CONH | CO | 3-Chloroprop-2-enyl | 3.22[a] | 455.0[a] |
| Ik-20 | A | CF₃ | Br | CH₃ | H | C—H | C—Cl | C—H | C—H | CONH | CO | Benzyl | 3.46[a] | 471.1[a] |
| Ik-21 | A | CF₃ | Br | CH₃ | H | C—H | C—Cl | C—H | C—H | CONH | CO | Cyclopropyl | 2.75[a] | 467.0[a] |
| Ik-22 | A | CF₃ | Br | CH₃ | H | C—H | C—Cl | C—H | C—H | CONH | CO | 3-Chloroprop-2-enyl | 3.20[a] | 501.0[a] |
| Ik-23 | A | CF₃ | Br | CH₃ | H | C—H | C—Cl | C—H | C—H | CONH | CO | Benzyl | 3.44[a] | 517.0[a] |
| Ik-24 | A | C₂F₅ | CF₃ | CH₃ | H | C—H | COCHF₂ | C—H | C—H | CONH | CO | Methylsulphonyl | 3.13[a] | 543.0[a] |
| Ik-25 | A | C₂F₅ | Br | CH₃ | H | C—H | C—Cl | C—H | C—H | CONH | CO | Cyclopropyl | 3.49[a] | 537.1[a] |
| Ik-26 | A | C₂F₅ | Br | CH₃ | H | C—H | C—Cl | C—H | C—H | CONH | CO | Cyclopropyl | 3.22[a] | 515.0[a] |
| Ik-27 | A | C₂F₅ | Br | CH₃ | H | C—H | C—Cl | C—H | C—H | CONH | CO | 1-Methylethyl | 3.49[a] | 517.0[a] |
| Ik-28 | A | C₂F₅ | Br | CH₃ | H | C—H | C—Cl | C—H | C—H | CONH | CO | 3-Chloroprop-2-enyl | 3.64[a] | 550.9[a] |
| Ik-29 | A | C₂F₅ | Br | CH₃ | H | C—H | C—Cl | C—H | C—H | CONH | CO | 1,2,4-Triazol-3-ylmethyl | 2.31[b] | 546.0[b] |
| Ik-30 | B | C₂F₅ | CF₃ | CH₃ | H | C—H | C—H | C—H | C—H | CONH | CO | Propyl | 3.23[b] | 507.0[b] |
| Ik-31 | B | C₂F₅ | CF₃ | CH₃ | H | C—H | C—H | C—H | C—H | CONCH₃ | CO | Cyclopropyl | 3.51[b] | 519.0[b] |

TABLE 6-continued (IK)

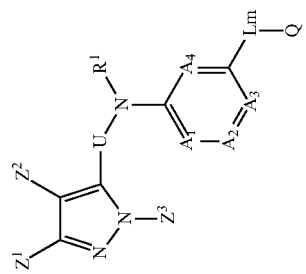

| Ex. No. | Process | $Z^1$ | $Z^3$ | $Z^2$ | $R^1$ | $A_4$ | $A_3$ | $A_2$ | $A_1$ | Lm | U | Q | logP | Mass [m/z]¹ |
|---|---|---|---|---|---|---|---|---|---|---|---|---|---|---|
| Ik-32 | B | $C_2F_5$ | $CF_3$ | $CH_3$ | H | C—H | C—Cl | C—H | C—H | CONH | CO | Oxetan-3-yl | 2.76[b] | 521.0[b] |
| Ik-33 | B | $C_2F_5$ | $CF_3$ | $CH_3$ | H | C—H | C—Cl | C—H | C—H | CONH | CO | 2-Hydroxypropyl | 2.65[b] | 523.0[b] |
| Ik-34 | B | $C_2F_5$ | $CF_3$ | $CH_3$ | H | C—H | C—Cl | C—H | C—H | CONH | CO | Methoxycarbonyl-methyl | 3.04[b] | 537.0[b] |
| Ik-35 | B | $C_2F_5$ | $CF_3$ | $CH_3$ | H | C—H | C—Cl | C—H | C—H | CONCH$_3$ | CO | 1-Methylethyl | 3.73[b] | 521.0[b] |
| Ik-36 | B | $C_2F_5$ | $CF_3$ | $CH_3$ | H | C—H | C—Cl | C—H | C—H | CONH | CO | Cyclobutyl | 3.53[b] | 519.0[b] |
| Ik-37 | B | $C_2F_5$ | $CF_3$ | $CH_3$ | H | C—H | C—Cl | C—H | C—H | CONH | CO | 2,6-Difluorophenylmethyl | 3.73[b] | 591.0[b] |
| Ik-38 | B | $C_2F_5$ | $CF_3$ | $CH_3$ | H | C—H | C—Cl | C—H | C—H | CONH | CO | 1-Phenylethyl | 3.89[b] | 569.0[b] |
| Ik-39 | B | $C_2F_5$ | $CF_3$ | $CH_3$ | H | C—H | C—Cl | C—H | C—H | CONH | CO | Cyclopentyl | 3.78[b] | 533.0[b] |
| Ik-40 | B | $C_2F_5$ | $CF_3$ | $CH_3$ | H | C—H | C—Cl | C—H | C—H | CONH | CO | 4-Chlorophenylethyl | 4.23[b] | 603.0[b] |
| Ik-42 | B | $C_2F_5$ | $CF_3$ | $CH_3$ | H | C—H | C—Cl | C—H | C—H | CONH | CO | 2,2-Dimethyl-3-fluoropropyl | 3.68[b] | 553.0[b] |
| Ik-43 | B | $C_2F_5$ | $CF_3$ | $CH_3$ | H | C—H | C—Cl | C—H | C—H | CONH | CO | Isoxazol-3-ylmethyl | 3.02[b] | 546.0[b] |
| Ik-44 | B | $C_2F_5$ | $CF_3$ | $CH_3$ | H | C—H | C—Cl | C—H | C—H | CONH | CO | 3,3-Dichloro-1,1-dimethylprop-2-enyl | 4.28[b] | 602.9[b] |
| Ik-45 | B | $C_2F_5$ | $CF_3$ | $CH_3$ | H | C—H | C—Cl | C—H | C—H | CONH | CO | 3-Methyloxetan-3-ylmethyl | 2.98[b] | 548.9[b] |
| Ik-46 | B | $C_2F_5$ | $CF_3$ | $CH_3$ | H | C—H | C—Cl | C—H | C—H | CONH | CO | 2,2-Dimethylcyclopropyl-methyl | 4.11[b] | 547.0[b] |
| Ik-47 | B | $C_2F_5$ | $CF_3$ | $CH_3$ | H | C—H | C—Cl | C—H | C—H | CONH | CO | 2-Phenylcyclopropyl | 4.00[b] | 581.0[b] |
| Ik-48 | B | $C_2F_5$ | $CF_3$ | $CH_3$ | H | C—H | C—Cl | C—H | C—H | CONH | CO | Cyanomethyl | 2.93[b] | 503.9[b] |
| Ik-49 | B | $C_2F_5$ | $CF_3$ | $CH_3$ | H | C—H | C—Cl | C—H | C—H | CONH | CO | 3-Fluorophenylmethyl | 3.78[b] | 573.0[b] |
| Ik-50 | B | $C_2F_5$ | $CF_3$ | $CH_3$ | H | C—H | C—Cl | C—H | C—H | CONH | CO | 2-Methylprop-2-enyl | 3.53[b] | 519.0[b] |
| Ik-52 | B | $C_2F_5$ | $CF_3$ | $CH_3$ | H | C—H | C—Cl | C—H | C—H | CONH | CO | 2-Fluorophenylmethyl | 3.73[b] | 573.0[b] |
| Ik-53 | B | $C_2F_5$ | $CF_3$ | $CH_3$ | H | C—H | C—Cl | C—H | C—H | CONH | CO | 2-Ethoxyethyl | 3.28[b] | 537.0[b] |
| Ik-54 | B | $C_2F_5$ | $CF_3$ | $CH_3$ | H | C—H | C—Cl | C—H | C—H | CONH | CO | 2,5-Difluorophenylmethyl | 3.84[b] | 591.0[b] |
| Ik-55 | B | $C_2F_5$ | $CF_3$ | $CH_3$ | H | C—H | C—Cl | C—H | C—H | CONH | CO | 2-Trifluoromethylphenylethyl | 4.28[b] | 637.0[b] |
| Ik-56 | B | $C_2F_5$ | $CF_3$ | $CH_3$ | H | C—H | C—Cl | C—H | C—H | CONH | CO | 2-Hydroxypropyl | 2.65[b] | 523.0[b] |
| Ik-57 | B | $C_2F_5$ | $CF_3$ | $CH_3$ | H | C—H | C—Cl | C—H | C—H | CONH | CO | 2-Methylbutyl | 4.00[b] | 535.0[b] |
| Ik-58 | B | $C_2F_5$ | $CF_3$ | $CH_3$ | H | C—H | C—Cl | C—H | C—H | CONH | CO | trans-4-Hydroxycyclohexyl | 2.69[b] | 563.0[b] |
| Ik-60 | B | $C_2F_5$ | $CF_3$ | $CH_3$ | H | C—H | C—Cl | C—H | C—H | CONCH$_3$ | CO | Propyl | 3.78[b] | 521.0[b] |
| Ik-61 | B | $C_2F_5$ | $CF_3$ | $CH_3$ | H | C—H | C—Cl | C—H | C—H | CONH | CO | Pyrimidin-2-ylmethyl | 2.84[b] | 557.0[b] |
| Ik-62 | B | $C_2F_5$ | $CF_3$ | $CH_3$ | H | C—H | C—Cl | C—H | C—H | CONH | CO | Dicyclopropylmethyl | 4.00[b] | 559.0[b] |
| Ik-63 | B | $C_2F_5$ | $CF_3$ | $CH_3$ | H | C—H | C—Cl | C—H | C—H | CONH | CO | 1-Cyclopropylethyl | 3.73[b] | 533.0[b] |
| Ik-64 | B | $C_2F_5$ | $CF_3$ | $CH_3$ | H | C—H | C—Cl | C—H | C—H | CONH | CO | 1-Trifluoromethylethyl | 3.68[b] | 533.0[b] |
| | | | | | | | | | | | | 2,2-Difluoropropyl | 3.37[b] | 561.0[b] |

TABLE 6-continued (IK)

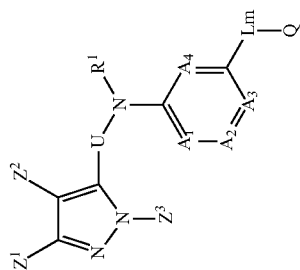

| Ex. No. | Process | $Z^1$ | $Z^3$ | $Z^2$ | $R^1$ | $A_4$ | $A_3$ | $A_2$ | $A_1$ | Lm | U | Q | logP | Mass [m/z]¹ |
|---|---|---|---|---|---|---|---|---|---|---|---|---|---|---|
| Ik-65 | B | $C_2F_5$ | $CF_3$ | $CH_3$ | H | C—H | C—Cl | C—H | C—H | CONH | CO | 4-Trifluoromethylcyclohexyl | 4.11[b] | 543.0[b] |
| Ik-66 | B | $C_2F_5$ | $CF_3$ | $CH_3$ | H | C—H | C—Cl | C—H | C—H | CONH | CO | Ethyl | 3.15[b] | 615.1[b] |
| Ik-67 | B | $C_2F_5$ | $CF_3$ | $CH_3$ | H | C—H | C—Cl | C—H | C—H | CONH | CO | 1,1-Dimethylethyl | 3.84[b] | 492.9[b] |
| Ik-68 | B | $C_2F_5$ | $CF_3$ | $CH_3$ | H | C—F | C—H | C—H | C—H | CONH | CO | 2-Cyanoethyl | 2.89[b] | 521.0[b] |
| Ik-69 | A | $C_2F_5$ | $CF_3$ | $CH_3$ | H | C—H | C—Cl | C—H | C—H | CONH | CO | 1-Methylethyl | 3.45[a] | 517.9[a] |
| Ik-70 | A | $CF_3$ | H | $CH_3$ | H | C—H | C—H | C—H | C—H | CONH | CO | 1-Methylethyl | 2.74[a] | 491.1[a] |
| Ik-71 | A | $CF_3$ | H | $CH_3$ | H | C—H | C—Cl | C—H | C—H | CONH | CO | Cyclopropyl | 2.48[a] | 389.1[a] |
| Ik-72 | A | $C_3F_7$ | Br | $CH_3$ | H | C—H | C—Cl | C—H | C—H | CONH | CO | 1-Methylethyl | 3.87[a] | 387.1[a] |
| Ik-73 | A | $C_3F_7$ | Br | $CH_3$ | H | C—H | C—Cl | C—H | C—H | CONH | CO | Cyclopropyl | 3.58[a] | 567.0[a] |
| Ik-74 | A | $C_2F_5$ | $CF_3$ | $CH_3$ | H | C—F | C—F | C—H | C—H | CONH | CO | 1-Methylethyl | 3.56[a] | 564.9[a] |
| Ik-75 | A | $C_2F_5$ | $CF_3$ | $CH_3$ | H | C—H | C—CH₃ | C—H | C—H | CONH | CO | 1-Methylethyl | 3.39[a] | 509.1[a] |
| Ik-76 | A | $C_2F_5$ | $CF_3$ | $CH_3$ | H | C—Cl | C—H | C—H | C—H | CONH | CO | 1-Methylethyl | 3.40[a] | 491.1[a] |
| Ik-77 | A | $C_2F_5$ | $CF_3$ | $CH_3$ | H | C—H | C—Cl | C—H | C—H | CONH | CO | 1-Methylethyl | 3.47[a] | 507.0[a] |
| Ik-78 | A | $C_2F_5$ | $CF_3$ | $CH_3$ | H | C—F | C—H | C—H | C—H | CONH | CO | 1-Pyridin-2-ylmethyl | 3.18[b] | 570.1[b] |
| Ik-79 | A | $C_2F_5$ | $CF_3$ | $CH_3$ | H | C—H | C—Cl | C—H | C—H | CONH | CO | Pyridin-2-ylmethyl | 2.80[a] | 556.1[a] |
| Ik-80 | A | $C_2F_5$ | $CF_3$ | $CH_3$ | H | C—H | C—Cl | C—H | C—H | CONH | CO | 5-Fluoropyridin-2-ylmethyl | 4.75[a] | 574.1[a] |
| Ik-81 | A | $C_2F_5$ | $CF_3$ | $CH_3$ | H | C—H | C—Cl | C—H | C—H | CONH | CO | 1,1-Dimethylbut-2-ynyl | 4.03[a] | 545.1[a] |
| Ik-82 | A | $C_2F_5$ | $CF_3$ | $CH_3$ | H | C—H | C—Cl | C—H | C—H | CONH | CO | 2-(Methylsulphanyl)-ethyl | 3.57[a] | 539.0[a] |
| Ik-83 | A | $C_2F_5$ | $CF_3$ | $CH_3$ | H | C—H | C—Cl | C—H | C—H | CONH | CO | 3-Chloroprop-2-enyl | 3.72[a] | 539.0[a] |
| Ik-84 | A | $C_2F_5$ | $CF_3$ | $CH_3$ | H | C—H | C—Cl | C—H | C—H | CONH | CO | Benzyl | 3.90[a] | 555.1[a] |
| Ik-85 | A | $C_2F_5$ | $CF_3$ | $CH_3$ | H | C—H | C—Cl | C—H | C—H | CONH | CO | CH3 | 3.04[a] | 479.0[a] |
| Ik-86 | A | $C_2F_5$ | $CF_3$ | $CH_3$ | H | C—H | C—Cl | C—H | C—H | CONH | CO | 2,2-Difluoroethyl | 3.41[a] | 529.0[a] |
| Ik-87 | A | $C_2F_5$ | $CF_3$ | $CH_3$ | H | C—H | C—Cl | C—H | C—H | CONH | CO | 2,2,2-Trifluoroethyl | 3.67[a] | 547.0[a] |
| Ik-88 | A | $C_2F_5$ | $CF_3$ | $CH_3$ | H | C—H | C—Cl | C—H | C—H | CONH | CO | 2-Fluoroethyl | 3.21[a] | 511.0[a] |
| Ik-89 | A | $C_2F_5$ | $CF_3$ | $CH_3$ | H | C—H | C—Cl | C—H | C—H | CONH | CO | 1-CH3-2-(ethylsulphanyl)ethyl | 4.09[a] | 567.0[a] |
| Ik-90 | A | $C_2F_5$ | $CF_3$ | $CH_3$ | H | C—H | C—Cl | C—H | C—H | CONH | CO | 1-Methylethyl | 3.60[a] | 507.1[a] |
| Ik-91 | A | $C_2F_5$ | $CF_3$ | $CH_3$ | H | C—H | C—Cl | C—H | C—H | CONH | CO | 1-Methylpropyl | 3.87[a] | 521.1[a] |
| Ik-92 | A | $C_2F_5$ | $CF_3$ | $CH_3$ | H | C—H | C—Cl | C—H | C—H | CONH | CO | 2-Methylpropyl | 3.90[a] | 521.1[a] |
| Ik-93 | A | $C_2F_5$ | $CF_3$ | $CH_3$ | H | C—H | C—Cl | C—Cl | C—H | CONH | CO | Prop-2-enyl | 3.44[a] | 505.1[a] |
| Ik-94 | A | $C_2F_5$ | H | $CH_3$ | H | C—H | C—Cl | C—H | C—H | CONH | CO | Prop-2-enyl | 2.62[a] | 387.1[a] |
| Ik-95 | A | $C_2F_5$ | $CF_3$ | $CH_3$ | H | C—H | C—Cl | C—H | C—H | CONH | CO | Cyclopropyl | 3.43[a] | 489.0[a] |
| Ik-96 | A | $C_2F_5$ | $CF_3$ | $CH_3$ | H | C—H | C—F | C—F | C—H | CONH | CO | Cyclopropyl | 3.71[a] | 503.0[a] |
| Ik-97 | A | $C_2F_5$ | $CF_3$ | $CH_3$ | H | C—H | C—Cl | C—H | C—H | CONH | CO | Benzyl | 4.19[a] | 557.1[a] |
| Ik-98 | A | $C_2F_5$ | I | $CH_3$ | H | C—H | C—Cl | C—H | C—H | CONH | CO | 3-Chloroprop-2-enyl | 3.54[a] | 569.9[a] |

TABLE 6-continued (IK)

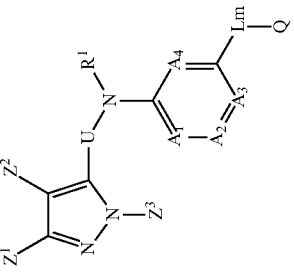

| Ex. No. | Process | $Z^1$ | $Z^3$ | $Z^2$ | $R^1$ | $A_4$ | $A_3$ | $A_2$ | $A_1$ | Lm | U | Q | logP | Mass [m/z][1] |
|---|---|---|---|---|---|---|---|---|---|---|---|---|---|---|
| Ik-99 | A | $C_2F_5$ | I | $CH_3$ | H | C—H | C—Cl | C—H | C—H | CONH | CO | 2,2,2-Trifluoroethyl | 3.52[a] | 604.9[a] |
| Ik-100 | A | $CHFCF_3$ | $CF_3$ | $CF(CH_3)_2$ | H | C—H | C—Cl | C—H | C—H | CONH | CO | Cyclopropyl | 3.39[a] | 531.1[a)2] |
| Ik-101 | A | $C_2F_5$ | $CF_3$ | $CH_3$ | H | C—H | C—Cl | C—H | C—H | CONH | CO | 3-Chloroprop-2-enyl | 3.80[a] | 539.0[a] |
| Ik-102 | A | $C_2F_5$ | $CF_3$ | $CH_3$ | H | C—H | C—Cl | C—H | C—H | CONH | CO | Cyclopropyl | 3.38[a] | 505.0[a] |
| Ik-103 | A | $C_2F_5$ | $CF_3$ | $CH_3$ | H | C—H | C—Cl | C—H | C—H | C(O)O | CO | Ethyl | 4.42[a] | 494.1[a] |
| Ik-104 | A | $C_2F_5$ | $CF_3$ | $CH_3$ | H | C—H | C—OCHF$_2$ | C—H | C—H | C(O)O | CO | H | 3.23[a] | 496.1[a)2] |
| Ik-105 | A | $C_2F_5$ | $CF_3$ | $CH_3$ | H | C—H | Bond to Q | C—H | C—F | C(O)O | CO | —CH$_2$— [Bond to A$_3$] | 3.27[a] | 462.0[a] |
| Ik-106 | A | $C_2F_5$ | $CF_3$ | $CH_3$ | H | C—H | Bond to Q | C—H | C—H | C(O)O | CO | —CH$_2$— [Bond to A$_3$] | 3.20[a] | 444.0[a] |
| Ik-107 | E | $C_2F_5$ | $CF_3$ | $CH_3$ | H | C—H | C—Cl | C—H | C—H | C(O)OCH$_2$C(O) | CO | Methoxy | 4.03[a] | 555.0[a] |
| Ik-108 | E | $C_2F_5$ | $CF_3$ | $CH_3$ | H | C—H | C—Cl | C—H | C—H | C(O)OCH$_2$C(O) | CO | N,N-Dimethylamino | 3.57[a] | 551.1[a] |
| Ik-109 | E | $C_2F_5$ | $CF_3$ | $CH_3$ | H | C—H | C—Cl | C—H | C—H | C(O)OCH$_2$C(O) | CO | N,N-Diethylamino | 4.11[a] | 579.1[a] |
| Ik-110 | E | $C_2F_5$ | $CF_3$ | $CH_3$ | H | C—H | C—Cl | C—H | C—H | C(O)OCH$_2$C(O)NHC(O) | CO | NH$_2$ | 3.10[a] | 566.1[a] |
| Ik-112 | E | $C_2F_5$ | $CF_3$ | $CH_3$ | H | C—H | C—Cl | C—H | C—H | C(O)OCH$_2$C(O) | CO | N-Allylamino | 3.66[a] | 581.2[a] |
| Ik-113 | E | $C_2F_5$ | $CF_3$ | $CH_3$ | H | C—H | C—Cl | C—H | C—H | C(O)OCH$_2$C(O)NH | CO | Methoxycarbonyl | 3.60[a] | 567.2[a] |
| Ik-114 | E | $C_2F_5$ | $CF_3$ | $CH_3$ | H | C—H | C—Cl | C—H | C—H | C(O)OCH$_2$C(O)NMe | CO | Methoxy | 3.87[a] | 551.2[a)2] |
| Ik-115 | E | $C_2F_5$ | $CF_3$ | $CH_3$ | H | C—H | C—Cl | C—H | C—H | C(O)OCH$_2$C(O)NH | CO | Hydroxymethyl | 2.93[a] | 551.2[a] |
| Ik-116 | E | $C_2F_5$ | $CF_3$ | $CH_3$ | H | C—H | C—Cl | C—H | C—H | C(O)OCH$_2$C(O)NH | CO | N-Ethylamino | 3.52[a] | 646.9[a] |
| Ik-117 | A | $CF_3OC_2F_4OCF_2$ | Br | $CH_3$ | H | C—H | C—Cl | C—H | C—H | CONH | CO | Cyclopropyl | 4.31[a] | 690.9[a] |
| Ik-118 | E | $CF_3OC_2F_4OCF_2$ | Br | $CH_3$ | H | C—H | C—Cl | C—H | C—H | CONH | CO | 2,2,2-Trifluoroethyl | 4.61[a] | 682.9[a] |
| Ik-119 | A | $CF_3OC_2F_4OCF_2$ | Br | $CH_3$ | H | C—H | C—Cl | C—H | C—H | CONH | CO | 3-Chloroprop-2-enyl | 4.66[a] | 615.0[a] |
| Ik-120 | A | $C_4F_9$ | Br | $CH_3$ | H | C—H | C—Cl | C—H | C—H | CONH | CO | Cyclopropyl | 3.99[a] | 654.9[a)2] |
| Ik-121 | A | $C_4F_9$ | Br | $CH_3$ | H | C—H | C—Cl | C—H | C—H | CONH | CO | 2,2,2-Trifluoroethyl | 4.29[a] | 648.9[a)2] |
| Ik-122 | A | $C_2F_5$ | Br | $CH_3$ | H | C—H | C—Cl | C—H | C—H | CONH | CO | 3-Chloroprop-2-enyl | 4.35[a] | 531.1[a] |
| Ik-123 | C | $C_2F_5$ | 4-Fluoro-phenyl | $CH_3$ | H | C—H | C—Cl | C—H | C—H | CONH | CO | Cyclopropyl | 3.60[a] | 444.0[a] |
| Ik-124 | A | $CF_2CF_3$ | $CF_3$ | H | H | C—H | C—Cl | C—H | C—H | CONH | CO | 2,2,2-Trifluoroethyl | 3.26[a] | 533.0[a] |
| Ik-125 | A | $CF_3$ | $CF_3$ | $CH_3$ | H | C—H | C—Cl | C—H | C—H | CONH | CO | 2,2,2-Trifluoroethyl | 3.25[a] | 497.0[a] |
| Ik-126 | C | $OCHF_2$ | $CF_3$ | $CH_3$ | H | C—H | C—Cl | C—H | C—H | CONH | CO | 2,2,2-Trifluoroethyl | 3.01[a] | 495.0[a] |
| Ik-127 | B | $CF_2CF_3$ | $CF_3$ | $CH_3$ | H | C—H | C—Br | C—H | C—H | CONH | CO | (1S,2R)-2-Fluoro-cyclopropyl | 3.29[a] | 568.0[a] |
| Ik-128 | B | $CF_2CF_3$ | $CF_3$ | $CH_3$ | H | C—H | C—Br | C—H | N | CONH | CO | (1S,2R)-2-Fluoro-cyclopropyl | 3.19[a] | 568.0[a] |

TABLE 6-continued

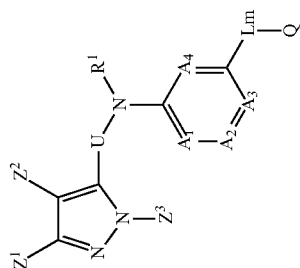

(IK)

| Ex. No. | Process | $Z^1$ | $Z^3$ | $Z^2$ | $R^1$ | $A_4$ | $A_3$ | $A_2$ | $A_1$ | Lm | U | Q | logP | Mass [m/z] |
|---|---|---|---|---|---|---|---|---|---|---|---|---|---|---|
| Ik-129 | B | $CF_2CF_3$ | $CF_3$ | $CH_3$ | H | C—H | C—Cl | C—H | N | COO | CO | H | 2.82[a] | 467.0[a] |
| Ik-130 | B | $CF_2CF_3$ | $CF_3$ | $CH_3$ | H | C—H | N | C—H | C—H | CONH | CO | 2,2-Difluoro-cyclopropyl | 3.59[a] | 508.0[a] |
| Ik-131 | B | $CF_2CF_3$ | $CF_3$ | $CH_3$ | H | C—H | C—Cl | C—H | C—H | CONH | CO | H | 2.77[a] | 467.0[a] |
| Ik-132 | A | $CF_2CF_3$ | $CF_3$ | $CH_3$ | $CH_3$ | C—H | C—Cl | N | C—H | CONH | CO | Cyclopropyl | 3.30[a] | 519.1[a] |
| Ik-133 | A | $CF_2CF_3$ | $CF_3$ | $CH_3$ | $CH_3$ | C—H | C—Cl | C—H | C—H | CONH | CO | 2,2,2-Trifluoroethyl | 3.66[a] | 561.0[a] |
| Ik-134 | A | $CF_2CF_3$ | $CF_3$ | $CH_3$ | $CH_2OCH_3$ | C—H | C—Cl | C—H | C—H | CONH | CO | Benzyl | 3.94[a] | 569.1[a] |
| Ik-135 | A | $CF_2CF_3$ | $CF_3$ | $CH_3$ | Ethyl | C—H | C—Cl | C—H | C—H | CONH | CO | Cyclopropyl | 3.51[a] | 549.1[a] |
| Ik-136 | A | $CF_2CF_3$ | $CF_3$ | $CH_3$ | 1-Methylethyl | C—H | C—Cl | C—H | C—H | CONH | CO | Cyclopropyl | 3.55[a] | 533.1[a] |
| Ik-137 | A | $CF_2CF_3$ | $CF_3$ | $CH_3$ | 1-Methylethyl | C—H | C—Cl | C—H | C—H | CONH | CO | Cyclopropyl | 3.74[a] | 547.1[a] |
| Ik-138 | A | $CF_2CF_3$ | $CF_3$ | $CH_3$ | Ethyl | C—H | C—Cl | C—H | C—H | CONH | CO | 2,2,2-Trifluoroethyl | 3.81[a] | 575.1[a] |
| Ik-139 | A | $CF_2CF_3$ | $CF_3$ | $CH_3$ | 1-Methylethyl | C—H | C—Cl | C—H | C—H | CONH | CO | 2,2,2-Trifluoroethyl | 4.02[a] | 589.1[a] |
| Ik-140 | A | $CF_2CF_3$ | $CF_3$ | $CH_3$ | H | C—H | C—F | C—F | C—H | CONH | CO | Cyclopropyl | 3.60[a] | 507.1[a] |
| Ik-141 | A | $CF_2CF_3$ | $CF_3$ | $CH_3$ | H | C—H | C—F | C—F | C—H | CONH | CO | 2,2,2-Trifluoroethyl | 3.89[a] | 549.1[a] |
| Ik-142 | A | $CF_2CF_3$ | $CF_3$ | $CH_3$ | H | C—H | C—F | C—F | C—H | CONH | CO | Benzyl | 4.00[a] | 573.0[a] |
| Ik-143 | A | $CF_2CF_3$ | $CF_3$ | $CH_3$ | H | C—H | C—Cl | C—F | C—H | CONH | CO | Cyclopropyl | 3.39[a] | 523.0[a] |
| Ik-144 | A | $CF_2CF_3$ | $CF_3$ | $CH_3$ | H | C—H | C—Cl | C—F | C—H | CONH | CO | 2,2,2-Trifluoroethyl | 3.73[a] | 565.0[a] |
| Ik-145 | A | $CF_2CF_3$ | $CF_3$ | $CH_3$ | H | C—H | C—F | C—Cl | C—H | CONH | CO | Cyclopropyl | 3.32[a] | 507.1[a] |
| Ik-146 | A | $CF_2CF_3$ | $CF_3$ | $CH_3$ | H | C—H | C—F | C—Cl | C—H | CONH | CO | 2,2,2-Trifluoroethyl | 3.64[a] | 549.0[a] |
| Ik-147 | A | $CF_2CF_3$ | $CF_3$ | $CH_3$ | H | C—H | C—Cl | C—H | C—H | CONH | CO | Cyclopropyl | 3.61[a] | 539.0[a] |
| Ik-148 | A | $CF_2CF_3$ | $CF_3$ | $CH_3$ | H | C—H | C—F | C—H | C—H | CONH | CO | Cyclopropyl | 3.53[a] | 523.2[a] |
| Ik-149 | A | $CF_2CF_3$ | $CF_3$ | $CH_3$ | H | C—Cl | C—F | C—H | C—H | CONH | CO | Benzyl | 4.33[a] | 589.2[a] |
| Ik-150 | A | $CF_2CF_3$ | $CF_3$ | $CH_3$ | H | C—H | C—Cl | C—H | C—H | CONH | CO | Benzyl | 4.23[a] | 589.0[a] |
| Ik-151 | A | $CF_2CF_3$ | $CF_3$ | $CH_3$ | H | C—H | C—Cl | C—H | C—H | CONH | CO | 2,2,2-Trifluoroethyl | 3.83[a] | 565.2[a] |
| Ik-152 | B | $CF_3$ | Cl | $CH_3$ | H | C—H | C—Cl | C—H | C—H | CONH | CO | $CH(CH_3)CF_3$ | 3.44[a] | 477.0[a] |
| Ik-153 | B | $CF_3$ | Cl | $CH_3$ | H | C—H | C—Cl | C—H | C—H | CONH | CO | 2-Fluorocyclopropyl | 2.86[a] | 439.0[a] |
| Ik-154 | A | $CF_2CF_3$ | $CF_3$ | $CH_3$ | H | C—H | C—Cl | C—H | C—H | CONH | CO | 2,2,2-Trifluoroethyl | 3.20[a] | 463.0[a] |
| Ik-155 | A | $CF_2CF_3$ | $CF_3$ | $CH_3$ | H | C—H | C—Cl | C—H | C—H | CONH | CO | Cyclopropyl | 3.31[a] | 489.1[a] |
| Ik-156 | A | $CF_2CF_3$ | $CF_3$ | $CH_3$ | H | C—H | C—Cl | C—H | C—H | CONH | CO | 2,2,2-Trifluoroethyl | 3.66[a] | 531.1[a] |
| Ik-157 | A | $CF_2CF_3$ | $CF_3$ | $CH_3$ | H | C—H | C—Cl | C—H | C—H | CONH | CO | Benzyl | 3.95[a] | 537.0[a] |
| Ik-158 | B | $CF_3$ | Br | $CH_3$ | H | C—H | C—Cl | C—H | C—H | CONH | CO | 1-Trifluoromethylethyl | 3.40[a] | 522.9[a] |
| Ik-159 | B | $CF_3$ | Br | $CH_3$ | H | C—H | C—Cl | C—H | C—H | CONH | CO | 2-Fluorocyclopropyl | 2.82[a] | 485.0[a] |

TABLE 6-continued (IK)

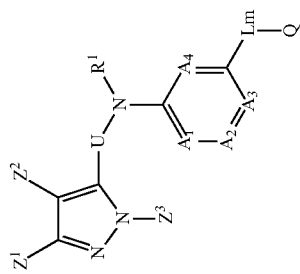

| Ex. No. | Process | $Z^1$ | $Z^2$ | $Z^3$ | $R^1$ | $A_4$ | $A_3$ | $A_2$ | $A_1$ | Lm | U | Q | logP | Mass [m/z]$^1$ |
|---|---|---|---|---|---|---|---|---|---|---|---|---|---|---|
| Ik-160 | B | $CF_3$ | Br | $CH_3$ | H | C—H | C—Cl | C—H | C—H | CONH | CO | 2,2,2-Trifluoroethyl | 3.17$^{(a)}$ | 508.9$^{(a)}$ |
| Ik-161 | B | $CF_2CF_3$ | $CF_3$ | $CH_3$ | H | C—H | C—F | C—H | C—H | CONH | CO | $CH(CH_3)CF_3$ | 3.89$^{(a)}$ | 545.1$^{(a)}$ |
| Ik-162 | B | $CF_2CF_3$ | $CF_3$ | $CH_3$ | H | C—H | C—H | C—F | C—H | CONH | CO | Benzyl | 4.05$^{(a)}$ | 537.2$^{(a)}$ |
| Ik-163 | B | $CF_2CF_3$ | $CF_3$ | $CH_3$ | H | C—H | C—Cl | C—H | C—H | CONH | CO | H | 2.83$^{(a)}$ | 465.1$^{(a)}$ |
| Ik-164 | A | $CF_2CF_3$ | $CF_3$ | $CH_3$ | H | C—H | C—Cl | C—Cl | C—H | CONH | CO | 1-Trifluoromethylethyl | 5.44$^{(a)}$ | 595.0$^{(a)}$ |
| Ik-165 | A | $CF_2CF_3$ | $CF_3$ | $CH_3$ | H | C—H | C—Cl | C—H | C—$CH_3$ | CONH | CO | Cyclopropyl | 3.96$^{(a)}$ | 573.0$^{(a)}$ |
| Ik-166 | B | $CF_2CF_3$ | $CF_3$ | $CH_3$ | H | C—H | C—Cl | C—H | C—H | CONH | CO | Cyclopropyl | 3.43$^{(a)}$ | 519.2$^{(a)}$ |
| Ik-167 | B | $CF_2CF_3$ | $CF_3$ | $C(CH_3)_3$ | H | C—H | C—Cl | C—H | C—H | CONH | CO | Cyclopropyl | 4.17$^{(a)}$ | 547.1$^{(a)}$ |
| Ik-168 | A | $CF_2CF_3$ | $CF_3$ | $CH_3$ | H | C—H | C—F | C—H | C—H | CONH | CO | 2-Fluorocyclopropyl | 3.35$^{(a)}$ | 507.0$^{(a)}$ |
| Ik-169 | A | $CF_2CF_3$ | $CF_3$ | $CH_3$ | H | C—F | C—H | C—H | C—H | CONH | CO | Cyclopropyl | 3.53$^{(a)}$ | 525.1$^{(a)}$ |
| Ik-170 | A | $CF_2CF_3$ | $CF_3$ | $CH_3$ | H | C—Cl | C—H | C—Cl | C—H | CONH | CO | Cyclopropyl | 3.78$^{(a)}$ | 538.9$^{(a)}$ |
| Ik-171 | A | $CF_2CF_3$ | $CF_3$ | $CH_3$ | H | C—H | C—Br | C—H | C—H | CONH | CO | 2,2,2-Trifluoroethyl | 3.97$^{(a)}$ | 581.0$^{(a)}$ |
| Ik-172 | A | $CF_2CF_3$ | $CF_3$ | $CH_3$ | H | C—H | C—Br | C—H | C—H | CONH | CO | Benzyl | 4.03$^{(a)}$ | 599.0$^{(a)}$ |
| Ik-173 | A | $CF_2CF_3$ | $CF_3$ | $CH_3$ | H | C—H | C—Br | C—H | C—H | CONH | CO | 2,2,2-Trifluoroethyl | 3.77$^{(a)}$ | 592.9$^{(a)}$ |
| Ik-174 | A | $CF_2CF_3$ | $CF_3$ | $CH_3$ | H | C—H | C—Cl | C—Br | C—H | CONH | CO | 1-Trifluoromethylethyl | 3.95$^{(a)}$ | 604.9$^{(a)}$ |
| Ik-175 | A | $CF_2CF_3$ | $CF_3$ | $CH_3$ | H | C—H | C—Cl | C—H | C—H | CONH | CO | Cyclopropyl | 3.39$^{(a)}$ | 549.0$^{(a)}$ |
| Ik-176 | A | $CF_2CF_3$ | $CF_3$ | $CH_3$ | H | C—H | C—Cl | C—Br | C—H | CONH | CO | Cyclopropyl | 4.00$^{(a)}$ | 567.0$^{(a)}$ |
| Ik-177 | B | $CF_2CF_3$ | $CF_3$ | Phenyl | H | C—H | C—Cl | C—H | C—H | CONH | CO | Benzyl | 4.42$^{(a)}$ | 635.0$^{(a)}$ |
| Ik-178 | B | $CF_2CF_3$ | $CF_3$ | $CH_3$ | H | C—H | C—Cl | C—H | C—H | CONH | CO | 2,2,2-Trifluoroethyl | 4.14$^{(a)}$ | 626.9$^{(a)}$ |
| Ik-179 | A | $CF_2CF_3$ | $CF_3$ | H | H | C—H | C—$NO_2$ | C—H | C—H | CONH | CO | Cyclopropyl | 2.95$^{(a)}$ | 491.0$^{(a)}$ |
| Ik-180 | B | $CF_2CF_3$ | $CF_3$ | $CH_3$ | H | C—H | C—$NO_2$ | C—H | C—H | CONH | CO | Cyclopropyl | 3.27$^{(a)}$ | 516.0$^{(a)}$ |
| Ik-181 | B | $CF_2CF_3$ | $CF_3$ | $CH_3$ | H | C—H | C—I | C—H | C—H | CONH | CO | 2,2,2-Trifluoroethyl | 3.58$^{(a)}$ | 557.9$^{(a)}$ |
| Ik-182 | A | $CF_3$ | I | $CH_3$ | H | C—H | C—I | C—H | C—H | CONH | CO | Cyclopropyl | 2.70$^{(a)}$ | 513.0$^{(a)}$ |
| Ik-183 | B | $CF_2CF_3$ | $CF_3$ | $CH_3$ | H | C—H | C—$OCH_3$ | C—H | C—H | CONH | CO | Cyclopropyl | 3.45$^{(a)}$ | 597.0$^{(a)}$ |
| Ik-184 | B | $CF_2CF_3$ | $CF_3$ | $CH_3$ | H | C—H | C—Cl | C—H | C—H | CONH | CO | Benzyl | 4.07$^{(a)}$ | 647.0$^{(a)}$ |
| Ik-185 | B | $CF_2CF_3$ | $CF_3$ | $CH_3$ | H | C—H | C—Cl | C—Cyano | C—H | CONH | CO | Cyclopropyl | 3.32$^{(a)}$ | 501.1$^{(a)}$ |
| Ik-186 | B | $CF_2CF_3$ | $CF_3$ | $CH_3$ | H | C—H | C—Cl | C—F | C—H | CONH | CO | 3,3-Dichloroprop-2-en-1-yl | 4.09$^{(a)}$ | 572.9$^{(a)}$ |
| Ik-187 | B | $CF_2CF_3$ | $CF_3$ | $CH_3$ | H | C—H | C—Cl | C—F | C—H | CONH | CO | Cyclopropyl | 3.40$^{(a)}$ | 530.0$^{(a)}$ |
| Ik-188 | B | $CF_2CF_3$ | $CF_3$ | $CH_3$ | H | C—H | C—Cl | C—F | C—H | CONH | CO | Cyclopropyl | 3.59$^{(a)}$ | 523.1$^{(a)}$ |
| Ik-189 | B | $CF_2CF_3$ | $CF_3$ | $CH_3$ | H | C—H | C—Cl | C—F | C—H | CONH | CO | Benzyl | 4.14$^{(a)}$ | 573.1$^{(a)}$ |
| Ik-190 | B | $CF_2CF_3$ | $CF_3$ | $CH_3$ | H | C—H | C—$SCH_3$ | C—F | C—H | CONH | CO | 2,2,2-Trifluoroethyl | 3.91$^{(a)}$ | 565.0$^{(a)}$ |
| Ik-191 | B | $CF_2CF_3$ | $CF_3$ | $CH_3$ | H | C—H | C—$SCH_3$ | C—F | C—H | CONH | CO | Cyclopropyl | 3.57$^{(a)}$ | 535.1$^{(a)}$ |
| Ik-192 | B | $CF_2CF_3$ | $CF_3$ | $CH_3$ | H | C—H | C—$SCH_3$ | C—F | C—H | CONH | CO | Benzyl | 4.15$^{(a)}$ | 585.1$^{(a)}$ |
| Ik-193 | B | $CF_2CF_3$ | $CF_3$ | $CH_3$ | H | C—H | C—$SCH_3$ | C—F | C—H | CONH | CO | 2,2,2-Trifluoroethyl | 3.90$^{(a)}$ | 577.0$^{(a)}$ |

TABLE 6-continued (IK)

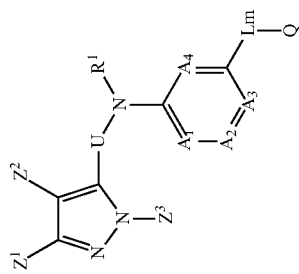

| Ex. No. | Process | $Z^1$ | $Z^3$ | $Z^2$ | $R^1$ | $A_4$ | $A_3$ | $A_2$ | $A_1$ | Lm | U | Q | logP | Mass [m/z]¹ |
|---|---|---|---|---|---|---|---|---|---|---|---|---|---|---|
| Ik-194 | B | $CF_2CF_3$ | $CF_3$ | $CH_3$ | H | C—H | C—$SO_2CH_3$ | C—F | C—H | CONH | CO | Cyclopropyl | 2.92$^{(a)}$ | 567.1$^{(a)}$ |
| Ik-195 | A | $CF_3$ | $CF_3$ | $CH_3$ | H | C—H | C—Cl | C—H | C—H | CONH | CO | Cyclopropyl | 2.89$^{(a)}$ | 455.1$^{(a)}$ |
| Ik-196 | A | $CF_3$ | $CF_3$ | $CH_3$ | H | C—H | C—Cl | C—H | C—H | CONH | CO | 3-Chloroprop-2-enyl | 3.28$^{(a)}$ | 489.1$^{(a)}$ |
| Ik-197 | A | $CF_3$ | $CF_3$ | H | H | C—H | C—Cl | C—H | C—H | CONH | CO | Cyclopropyl | 2.55$^{(a)}$ | 441.1$^{(a)}$ |
| Ik-198 | B | $CF_2CF_3$ | $CF_3$ | $CH_3$ | H | C—H | C—$SCH_3$ | C—Br | C—H | CONH | CO | Cyclopropyl | 3.87$^{(a)}$ | 596.9$^{(a)}$ |
| Ik-199 | B | $CF_2CF_3$ | $CF_3$ | $CH_3$ | H | C—H | C—$SCH_3$ | C—Br | C—H | CONH | CO | Benzyl | 4.43$^{(a)}$ | 647.0$^{(a)}$ |
| Ik-200 | B | $CF_2CF_3$ | $CF_3$ | $CH_3$ | H | C—H | C—$SCH_3$ | C—Br | C—H | CONH | CO | 2,2,2-Trifluoroethyl | 4.22$^{(a)}$ | 639.0$^{(a)}$ |
| Ik-201 | B | $CF_2CF_3$ | $CF_3$ | $CH_3$ | H | C—H | C—$SCH_3$ | C—Cl | C—H | CONH | CO | Cyclopropyl | 3.80$^{(a)}$ | 551.0$^{(a)}$ |
| Ik-202 | B | $CF_2CF_3$ | $CF_3$ | $CH_3$ | H | C—H | C—$SCH_3$ | C—Cl | C—H | CONH | CO | Benzyl | 4.39$^{(a)}$ | 601.0$^{(a)}$ |
| Ik-203 | B | $CF_2CF_3$ | $CF_3$ | $CH_3$ | H | C—H | C—$SCH_3$ | C—Cl | C—H | CONH | CO | 2,2,2-Trifluoroethyl | 4.15$^{(a)}$ | 593.0$^{(a)}$ |
| Ik-204 | B | $CF_2CF_3$ | $CF_3$ | $CH_3$ | H | C—H | C—I | C—Cl | C—H | CONH | CO | Cyclopropyl | 3.84$^{(a)}$ | 630.9$^{(a)}$ |
| Ik-205 | B | $CF_2CF_3$ | $CF_3$ | $CH_3$ | H | C—H | C—I | C—Cl | C—H | CONH | CO | Benzyl | 4.45$^{(a)}$ | 681.0$^{(a)}$ |
| Ik-206 | B | $CF_2CF_3$ | $CF_3$ | $CH_3$ | H | C—H | C—I | C—Cl | C—H | CONH | CO | 2,2,2-Trifluoroethyl | 4.18$^{(a)}$ | 672.9$^{(a)}$ |
| Ik-207 | B | $CF_2CF_3$ | $CF_3$ | $CH_3$ | H | C—H | C—Br | C—Br | C—H | CONH | CO | Cyclopropyl | 3.84$^{(a)}$ | 628.8$^{(a)}$ |
| Ik-208 | B | $CF_2CF_3$ | $CF_3$ | $CH_3$ | H | C—H | C—Br | C—Br | C—H | CONH | CO | Benzyl | 4.42$^{(a)}$ | 678.9$^{(a)}$ |
| Ik-209 | B | $CF_2CF_3$ | $CF_3$ | $CH_3$ | H | C—H | C—Br | C—Br | C—H | CONH | CO | 2,2,2-Trifluoroethyl | 4.18$^{(a)}$ | 670.9$^{(a)}$ |
| Ik-210 | B | $CF_2CF_3$ | $CF_3$ | $CH_3$ | H | C—H | C—I | C—Br | C—H | CONH | CO | Cyclopropyl | 3.92$^{(a)}$ | 676.9$^{(a)}$ |
| Ik-211 | B | $CF_2CF_3$ | $CF_3$ | $CH_3$ | H | C—H | C—I | C—Br | C—H | CONH | CO | Benzyl | 4.49$^{(a)}$ | 726.9$^{(a)}$ |
| Ik-212 | B | $CF_2CF_3$ | $CF_3$ | $CH_3$ | H | C—H | C—I | C—Br | C—H | CONH | CO | 2,2,2-Trifluoroethyl | 4.15$^{(a)}$ | 718.9$^{(a)}$ |
| Ik-213 | B | $CF_2CF_3$ | $CF_3$ | $CH_3$ | H | C—H | C—Br | C—Cl | C—H | CONH | CO | Cyclopropyl | 3.81$^{(a)}$ | 584.9$^{(a)}$ |
| Ik-214 | B | $CF_2CF_3$ | $CF_3$ | $CH_3$ | H | C—H | C—Br | C—Cl | C—H | CONH | CO | Benzyl | 4.42$^{(a)}$ | 635.0$^{(a)}$ |
| Ik-215 | B | $CF_2CF_3$ | $CF_3$ | $CH_3$ | H | C—H | C—Br | C—Cl | C—H | CONH | CO | 2,2,2-Trifluoroethyl | 4.14$^{(a)}$ | 627.0$^{(a)}$ |
| Ik-216 | B | $CF_2CF_3$ | $CF_3$ | Ethyl | H | C—H | C—Cl | C—H | C—H | CONH | CO | 2,2,2-Trifluoroethyl | 3.93$^{(a)}$ | 561.1$^{(a)}$ |
| Ik-217 | A | $CF_2CF_3$ | $CF_3$ | Ethyl | H | C—H | C—Cl | C—H | C—H | CONH | CO | Cyclopropyl | 3.63$^{(a)}$ | 519.1$^{(a)}$ |
| Ik-218 | A | $CF_2CF_3$ | $CF_3$ | 1-Methyl-ethyl | H | C—H | C—Cl | C—H | C—H | CONH | CO | Cyclopropyl | 4.02$^{(a)}$ | 533.1$^{(a)}$ |
| Ik-219 | A | $CF_2CF_3$ | $CF_3$ | $CH_2OCH_3$ | H | C—H | C—Cl | C—H | C—H | CONH | CO | Cyclopropyl | 3.50$^{(a)}$ | 535.1$^{(a)}$ |
| Ik-220 | A | $CF_2CF_3$ | $CF_3$ | $CH_2OCH_3$ | H | C—H | C—Cl | C—H | C—H | CONH | CO | 2,2,2-Trifluoroethyl | 3.82$^{(a)}$ | 577.1$^{(a)}$ |
| Ik-221 | A | $CF_2CF_3$ | $CF_3$ | $CH_3$ | H | C—H | C—H | C—Br | C—H | CONH | CO | Cyclopropyl | 3.74$^{(a)}$ | 551.0$^{(a)}$ |
| Ik-222 | A | $CF_2CF_3$ | $CF_3$ | $CH_3$ | H | C—H | C—H | C—Br | C—H | CONH | CO | Benzyl | 4.35$^{(a)}$ | 601.1$^{(a)}$ |
| Ik-223 | B | $CF_2CF_3$ | $CF_3$ | $CH_3$ | H | C—H | C—Br | C—Br | C—H | CONH | CO | 2,2,2-Trifluoroethyl | 4.09$^{(a)}$ | 593.0$^{(a)}$ |
| Ik-224 | B | $CF_2CF_3$ | $CF_3$ | $CH_3$ | H | C—H | C—I | C—F | C—H | CONH | CO | 3-Chloroprop-2-enyl | 3.99$^{(a)}$ | 649.0$^{(a)}$ |
| Ik-225 | B | $CF_2CF_3$ | $CF_3$ | $CH_3$ | H | C—H | C—I | C—F | C—H | CONH | CO | Cyclopropyl | 3.63$^{(a)}$ | 615.0$^{(a)}$ |
| Ik-226 | B | $CF_2CF_3$ | $CF_3$ | $CH_3$ | H | C—H | C—I | C—F | C—H | CONH | CO | 2,2,2-Trifluoroethyl | 3.95$^{(a)}$ | 657.0$^{(a)}$ |

TABLE 6-continued (IK)

| Ex. No. | Process | Z¹ | Z³ | Z² | R¹ | A₄ | A₃ | A₂ | A₁ | Lm | U | Q | logP | Mass [m/z]¹ |
|---|---|---|---|---|---|---|---|---|---|---|---|---|---|---|
| Ik-227 | B | CF₂CF₃ | CF₃ | CH₃ | H | C—H | C—I | C—F | C—H | CONH | CO | Benzyl | 4.20[a] | 665.0[a] |
| Ik-228 | B | CF₂CF₃ | CF₃ | CH₃ | H | C—H | C—Br | C—F | C—H | CONH | CO | 2,2,2-Trifluoroethyl | 3.88[a] | 611.0[a] |
| Ik-229 | B | CF₂CF₃ | CF₃ | CH₃ | H | C—H | C—Br | C—F | C—H | CONH | CO | Benzyl | 4.14[a] | 619.0[a] |
| Ik-230 | A | CF(CH₃)₂ | CF₃ | CH₃ | H | C—H | C—Cl | C—H | C—H | CONH | CO | Cyclopropyl | 2.70 [M − F][a] | 427.0[a] |
| Ik-231 | A | CHF2 | CF₃ | CH₃ | H | C—H | C—Cl | C—H | C—H | CONH | CO | Cyclopropyl | 2.46[a] | 437.0[a] |
| Ik-232 | A | CHF2 | CF₃ | CH₃ | H | C—H | C—Cl | C—H | C—H | CONH | CO | 3-Chloroprop-2-enyl | 2.92[a] | 471.0[a] |
| Ik-234 | A | OCHF₂ | H | CH₃ | H | C—H | C—Cl | C—H | C—H | CONH | CO | Cyclopropyl | 2.17[a] | 385.1[a] |
| Ik-235 | A | Cyclopropyl | Br | CH₃ | H | C—H | C—Cl | C—H | C—H | CONH | CO | Cyclopropyl | 2.60[a] | 437.0[a] |
| Ik-236 | A | OCHF₂ | Br | CH₃ | H | C—H | C—Cl | C—H | C—H | CONH | CO | 2,2,2-Trifluoroethyl | 2.88[a] | 505.0[a] |
| Ik-237 | A | OCHF₂ | Br | CH₃ | H | C—H | C—Cl | C—H | C—H | CONH | CO | Cyclopropyl | 2.51[a] | 462.9[a] |
| Ik-238 | A | OCHF₂ | Cl | CH₃ | H | C—H | C—Cl | C—H | C—H | CONH | CO | Cyclopropyl | 2.52[a] | 419.0[a] |
| Ik-239 | A | OCHF₂ | Cl | CH₃ | H | C—H | C—Cl | C—H | C—H | CONH | CO | 2,2,2-Trifluoroethyl | 2.89[a] | 460.9[a] |
| Ik-240 | A | OCHF₂ | I | CH₃ | H | C—H | C—Cl | C—H | C—H | CONH | CO | Cyclopropyl | 2.54[a] | 511.0[a] |
| Ik-241 | A | OCHF₂ | I | CH₃ | H | C—H | C—Cl | C—H | C—H | CONH | CO | 2,2,2-Trifluoroethyl | 2.92[a] | 553.0[a] |
| Ik-242 | A | CF₃CH₂O | Cl | CH₃ | H | C—H | C—Cl | C—H | C—H | CONH | CO | Cyclopropyl | 2.89[a] | 451.0[a] |
| Ik-243 | A | CF₃CH₂O | Cl | CH₃ | H | C—H | C—Cl | C—H | C—H | CONH | CO | 2,2,2-Trifluoroethyl | 3.27[a] | 492.9[a] |
| Ik-244 | A | CF₃CH₂O | I | CH₃ | H | C—H | C—Cl | C—H | C—H | CONH | CO | 2,2,2-Trifluoroethyl | 3.24[a] | 584.9[a] |
| Ik-245 | A | CF₃CH₂O | I | CH₃ | H | C—H | C—Cl | C—H | C—H | CONH | CO | Cyclopropyl | 2.85[a] | 542.9[a] |
| Ik-246 | A | CF₃CH₂O | H | CH₃ | H | C—H | C—Cl | C—H | C—H | CONH | CO | 2,2,2-Trifluoroethyl | 2.92[a] | 459.0[a] |
| Ik-247 | A | CF₃CH₂O | H | CH₃ | H | C—H | C—Cl | C—H | C—H | CONH | CO | Cyclopropyl | 2.55[a] | 417.1[a] |
| Ik-248 | A | 4-Fluorophenyl | Br | CH₃ | H | C—H | C—Cl | C—H | C—H | CONH | CO | Cyclopropyl | 3.04[a] | 492.9[a] |
| Ik-249 | A | 4-(Trifluoromethyl)phenyl | Br | CH₃ | H | C—H | C—Cl | C—H | C—H | CONH | CO | Cyclopropyl | 3.63[a] | 543.1[a] |
| Ik-250 | A | 2,4-Dichlorophenyl | Br | CH₃ | H | C—H | C—Cl | C—H | C—H | CONH | CO | Cyclopropyl | 3.59[a] | 543.0[a] |
| Ik-251 | A | 4-(Trifluoromethoxy)phenyl | Br | CH₃ | H | C—H | C—Cl | C—H | C—H | CONH | CO | Cyclopropyl | 3.76[a] | 557.0[a] |
| Ik-252 | A | 2-Chlorophenyl | Br | CH₃ | H | C—H | C—Cl | C—H | C—H | CONH | CO | 2,2,2-Trifluoroethyl | 3.41[a] | 549.0[a] |
| Ik-253 | A | 4-(Trifluoromethyl)phenyl | Br | CH₃ | H | C—H | C—Cl | C—H | C—H | CONH | CO | 2,2,2-Trifluoroethyl | 3.99[a] | 585.0[a] |
| Ik-254 | A | 2,4-Dichlorophenyl | Br | CH₃ | H | C—H | C—Cl | C—H | C—H | CONH | CO | 2,2,2-Trifluoroethyl | 4.04[a] | 585.0[a] |
| Ik-255 | A | 4-(Trifluoromethoxy)phenyl | Br | CH₃ | H | C—H | C—Cl | C—H | C—H | CONH | CO | 2,2,2-Trifluoroethyl | 4.15[a] | 601.0[a] |
| Ik-256 | A | CF₃CH₂O | Br | CH₃ | H | C—H | C—Cl | C—H | C—H | CONH | CO | Cyclopropyl | 2.87[a] | 497.0[a] |

TABLE 6-continued (IK)

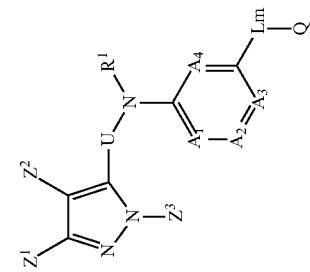

| Ex. No. | Process | $Z^1$ | $Z^3$ | $Z^2$ | $R^1$ | $A_4$ | $A_3$ | $A_2$ | $A_1$ | Lm | U | Q | logP | Mass [m/z]¹ |
|---|---|---|---|---|---|---|---|---|---|---|---|---|---|---|
| Ik-257 | A | $CF_3CH_2O$ | Br | $CH_3$ | H | C—H | C—Cl | C—H | C—H | CONH | CO | 2,2,2-Trifluoroethyl | 3.26[a] | 538.9[a] |
| Ik-258 | A | 3,5-Bis(trifluoro-methyl)phenyl | $CF_3$ | $CH_3$ | H | C—H | C—Cl | C—H | C—H | CONH | CO | 2,2,2-Trifluoroethyl | 4.46[a] | 641.0[a] |
| Ik-259 | A | 3,5-Bis(trifluoro-methyl)phenyl | $CF_3$ | $CH_3$ | H | C—H | C—Cl | C—H | C—H | CONH | CO | Cyclopropyl | 4.19[a] | 599.1[a] |
| Ik-260 | A | $CF_3CH_2O$ | F | $CH_3$ | H | C—H | C—Cl | C—H | C—H | CONH | CO | Cyclopropyl | 2.75[a] | 435.1[a] |
| Ik-261 | A | Cyclopropyl | $CF_3$ | $CH_3$ | H | C—H | C—Cl | C—H | C—H | CONH | CO | Cyclopropyl | 2.78[a] | 427.1[a] |
| Ik-262 | C | $CF_2CF_3$ | Prop-2-enyl | $CH_3$ | H | C—H | C—Cl | C—H | C—H | CONH | CO | Cyclopropyl | 3.37[a] | 475.2[a] |
| Ik-263 | C | $CF_2CF_3$ | Ethyl | $CH_3$ | H | C—H | C—H | C—H | C—H | CONH | CO | Cyclopropyl | 3.05[a] | 431.1[a] |
| Ik-264 | C | $CF_3OC_2F_4OCF_2$ | I | $CH_3$ | H | C—H | C—Cl | C—H | C—H | CONH | CO | Cyclopropyl | 3.66[a] | 694.8[a] |
| Ik-265 | C | C4F9 | I | $CH_3$ | H | C—H | C—Cl | C—H | C—H | CONH | CO | Cyclopropyl | 3.90[a] | 663.0[a] |
| Ik-266 | A | C4F9 | H | $CH_3$ | H | C—H | C—Cl | C—H | C—H | CONH | CO | Cyclopropyl | 3.74[a] | 536.8[a] |
| Ik-267 | C | C4F9 | I | $CH_3$ | H | C—H | C—Cl | C—H | C—H | CONH | CO | 1-Cyclopropylethyl | 4.38[a] | 691.0[a] |
| Ik-268 | C | C4F9 | I | $CH_3$ | H | C—H | C—Cl | C—H | C—H | CONH | CO | Cyclobutyl | 4.16[a] | 676.9[a] |
| Ik-269 | C | C4F9 | I | $CH_3$ | H | C—H | C—Cl | C—H | C—H | CONH | CO | 3-Chloroprop-2-enyl | 4.27[a] | 696.9[a] |
| Ik-270 | B | $CF_2CF_3$ | $CF_3$ | $CH_3$ | H | C—H | C—Cl | C—H | C—H | CONH | CO | 1-(Pyridin-3-yl)methyl | 2.27[b] | 570.1[b] |
| Ik-271 | B | $CF_2CF_3$ | $CH_3$ | $CH_3$ | H | C—H | C—Cl | C—H | C—H | CONH | CO | Benzyl | 3.42[b] | 501.0[b] |
| Ik-272 | B | $CF_2CF_3$ | Ethyl | $CH_3$ | H | C—H | C—Cl | C—H | C—H | CONH | CO | Benzyl | 3.68[b] | 515.0[b] |
| Ik-273 | B | $CF_2CF_3$ | $CF_3$ | $CH_3$ | H | C—H | C—Cl | C—H | C—H | CONH | CO | [4-(Trifluoromethyl)-1,3-thiazol-2-yl]methyl | 3.75[b] | 629.9[b] |
| Ik-274 | B | $CF_2CF_3$ | $CF_3$ | $CH_3$ | H | C—H | C—Cl | C—H | C—H | CONH | CO | 2-Cyanopropan-2-yl | 3.37[b] | 531.9[b] |
| Ik-275 | B | $CF_2CF_3$ | $CF_3$ | $CH_3$ | H | C—H | C—Cl | C—H | C—H | CONH | CO | 2-Cyano-1-methoxy-propan-2-yl | 3.37[b] | 562.0[b] |
| Ik-276 | B | $CF_2CF_3$ | $CF_3$ | $CH_3$ | H | C—H | C—Cl | C—H | C—H | CONH | CO | 2,2,2-Trifluoro-1-[1-methyl-4-(trifluoromethyl)-1H-imidazol-2-yl]ethyl | 4.00[b] | 695.1[b] |
| Ik-277 | B | $CF_2CF_3$ | $CF_3$ | $CH_3$ | H | C—H | C—Cl | C—H | C—H | CONH | CO | 2,2,2-Trifluoro-1-(4-methyl-1,3-thiazol-2-yl)ethyl | 4.00[b] | 644.1[b] |
| Ik-278 | B | $CF_2CF_3$ | $CF_3$ | $CH_3$ | H | C—H | C—Cl | C—H | C—H | CONH | CO | 1,1-Dioxido-2,3-dihydrothiophen-3-yl | 2.80[b] | 581.0[b] |
| Ik-279 | B | $CF_2CF_3$ | $CF_3$ | $CH_3$ | H | C—H | C—Cl | C—H | C—H | CONH | CO | (1R,2S)-2-Methyl-cyclopropyl | 3.37[b] | 519.0[b] |
| Ik-280 | B | $CF_2CF_3$ | $CF_3$ | $CH_3$ | H | C—H | C—Cl | C—H | C—H | CONH | CO | (1R,2S)-2-Methyl- | 3.46[b] | 519.0[b] |

TABLE 6-continued (IK)

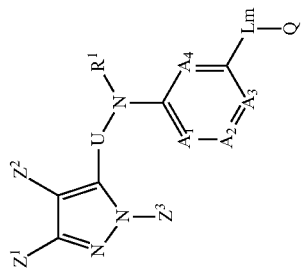

| Ex. No. | Process | $Z^1$ | $Z^3$ | $Z^2$ | $R^1$ | $A_4$ | $A_3$ | $A_2$ | $A_1$ | Lm | U | Q | logP | Mass [m/z][1] |
|---|---|---|---|---|---|---|---|---|---|---|---|---|---|---|
| Ik-281 | B | $CF_2CF_3$ | $CF_3$ | $CH_3$ | H | C—H | C—Cl | C—H | C—H | CONH | CO | cyclopropyl 2-(2,2,2-Trifluoro-ethoxy)ethyl | 3.53[b] | 591.1[b] |
| Ik-282 | B | $CF_2CF_3$ | $CF_3$ | $CH_3$ | H | C—H | C—Cl | C—H | C—H | CONH | CO | 2-Chlorobenzyl | 4.05[b] | 589.1[b] |
| Ik-283 | B | $CF_2CF_3$ | $CF_3$ | $CH_3$ | H | C—H | C—Cl | C—H | C—H | CONH | CO | 4-Chlorobenzyl | 4.05[b] | 589.1[b] |
| Ik-284 | B | $CF_2CF_3$ | $CF_3$ | $CH_3$ | H | C—H | C—Cl | C—H | C—H | CONH | CO | 1-(2-Fluorophenyl)-ethyl | 4.00[b] | 587.1[b] |
| Ik-285 | B | $CF_2CF_3$ | $CF_3$ | $CH_3$ | H | C—H | C—Cl | C—H | C—H | CONH | CO | Tetrahydro-2H-pyran-4-yl | 3.06[b] | 549.1[b] |
| Ik-286 | B | $CF_2CF_3$ | $CF_3$ | $CH_3$ | H | C—H | C—Cl | C—H | C—H | CONH | CO | 2-Ethylcyclopropyl | 3.84[b] | 533.1[b] |
| Ik-287 | B | $CF_2CF_3$ | $CF_3$ | $CH_3$ | H | C—H | C—Cl | C—H | C—H | CONH | CO | Cyclopent-3-en-1-yl | 3.63[b] | 531.1[b] |
| Ik-288 | B | $CF_2CF_3$ | $CF_3$ | $CH_3$ | H | C—H | C—Cl | C—H | C—H | CONH | CO | 1-(1-Chlorocyclo-propyl)ethyl | 4.05[b] | 567.0[b] |
| Ik-289 | B | $CF_2CF_3$ | $CF_3$ | $CH_3$ | H | C—H | C—Cl | C—H | C—H | CONH | CO | 2-Methyl-1-(methylsulphanyl)propan-2-yl | 4.05[b] | 567.1[b] |
| Ik-290 | B | $CF_2CF_3$ | $CF_3$ | $CH_3$ | H | C—H | C—Cl | C—H | C—H | CONH | CO | 1-Fluoropropan-2-yl | 3.28[b] | 525.1[b] |
| Ik-291 | B | $CF_2CF_3$ | $CF_3$ | $CH_3$ | H | C—H | C—Cl | C—H | C—H | CONH | CO | 3,3,3-Trifluoropropyl | 3.53[b] | 561.0[b] |
| Ik-292 | B | $CF_2CF_3$ | $CF_3$ | $CH_3$ | H | C—H | C—Cl | C—H | C—H | CONH | CO | 1-Cyanoethyl | 3.02[b] | 517.9[b] |
| Ik-293 | B | $CF_2CF_3$ | $CF_3$ | $CH_3$ | H | C—H | C—Cl | C—H | C—H | CONH | CO | But-3-yn-2-yl | 3.28[b] | 516.9[b] |
| Ik-294 | B | $CF_2CF_3$ | $CF_3$ | $CH_3$ | H | C—H | C—Cl | C—H | C—H | CONH | CO | (2S)-1,1,1-Trifluoropropan-2-yl | 3.63[b] | 561.1[b] |
| Ik-295 | B | $CF_2CF_3$ | $CF_3$ | $CH_3$ | H | C—H | C—Cl | C—H | C—H | CONH | CO | (2Z)-3-Chlorobut-2-en-1-yl | 3.73[b] | 553.1[b] |
| Ik-296 | B | $CF_2CF_3$ | $CF_3$ | $CH_3$ | H | C—H | C—Cl | C—H | C—H | CONH | CO | 1-(Trifluoromethyl)-cyclopropyl | 3.58[b] | 573.1[b] |
| Ik-297 | B | $CF_2CF_3$ | $CF_3$ | $CH_3$ | H | C—H | C—Cl | C—H | C—H | CONH | CO | 1,1,1-Trifluorobutan-2-yl | 3.89[b] | 575.1[b] |
| Ik-298 | B | $CF_2CF_3$ | $CF_3$ | $CH_3$ | H | C—H | C—Cl | C—H | C—H | CONH | CO | 1,1,1-Trifluoropentan-2-yl | 4.11[b] | 589.1[b] |
| Ik-299 | B | $CF_2CF_3$ | $CF_3$ | $CH_3$ | H | C—H | C—Cl | C—H | C—H | CONH | CO | 4,4,4-Trifluorobutan-2-yl | 3.63[b] | 575.1[b] |
| Ik-300 | B | $CF_2CF_3$ | $CF_3$ | $CH_3$ | H | C—H | C—Cl | C—H | C—H | CONH | CO | 4,4,4-Trifluoro-2-methylbutan-2-yl | 4.00[b] | 589.1[b] |
| Ik-301 | B | $CF_2CF_3$ | $CF_3$ | $CH_3$ | H | C—H | C—Cl | C—H | C—H | CONH | CO | 2-Methyl-1-(methyl-sulphonyl)propan-2-yl | 3.02[b] | 599.1[b] |
| Ik-302 | B | $CF_2CF_3$ | $CF_3$ | $CH_3$ | H | C—H | C—Cl | C—H | C—H | CONH | CO | 2,2,3,3,3-Penta-fluoropropyl | 3.78[b] | 597.1[b] |
| Ik-303 | B | $CF_2CF_3$ | $CF_3$ | $CH_3$ | H | C—H | C—Cl | C—H | C—H | CONH | CO | 1-(3-Fluoro-phenyl)ethyl | 3.89[b] | 587.1[b] |
| Ik-304 | B | $CF_2CF_3$ | $CF_3$ | $CH_3$ | H | C—H | C—Cl | C—H | C—H | CONH | CO | 3-Methylbenzyl | 3.94[b] | 569.1[b] |

TABLE 6-continued (IK)

| Ex. No. | Process | $Z^1$ | $Z^3$ | $Z^2$ | $R^1$ | $A_4$ | $A_3$ | $A_2$ | $A_1$ | Lm | U | Q | logP | Mass [m/z][1] |
|---|---|---|---|---|---|---|---|---|---|---|---|---|---|---|
| Ik-305 | B | $CF_2CF_3$ | $CF_3$ | $CH_3$ | H | C—H | C—Cl | C—H | C—H | CONH | CO | 2-Methylbenzyl | 3.89[b] | 569.1[b] |
| Ik-306 | B | $CF_2CF_3$ | $CF_3$ | $CH_3$ | H | C—H | C—Cl | C—H | C—H | CONH | CO | 4-Methylbenzyl | 3.94[b] | 569.1[b] |
| Ik-307 | B | $CF_2CF_3$ | $CF_3$ | $CH_3$ | H | C—H | C—Cl | C—H | C—H | CONH | CO | (2R)-1,1,1-Trifluoro-propan-2-yl | 3.78[b] | 561.0[b] |
| Ik-308 | B | $CF_2CF_3$ | $CF_3$ | $CH_3$ | H | C—H | C—Cl | C—H | C—H | CONH | CO | 2,4-Difluorobenzyl | 3.94[b] | 591.0[b] |
| Ik-309 | B | $CF_2CF_3$ | $CF_3$ | $CH_3$ | H | C—H | C—Cl | C—H | C—H | CONH | CO | 3,4-Difluorobenzyl | 3.94[b] | 591.1[b] |
| Ik-310 | B | $CF_2CF_3$ | $CF_3$ | $CH_3$ | H | C—H | C—Cl | C—H | C—H | CONH | CO | (2S)-1,1,1-Trifluoro-3-methylbutan-2-yl | 3.89[b] | 589.1[b] |
| Ik-311 | B | $CF_2CF_3$ | $CF_3$ | $CH_3$ | H | C—H | C—Cl | C—H | C—H | CONH | CO | (1S,2R)-2-Fluoro-cyclopropyl | 3.28[b] | 523.1[b] |
| Ik-312 | B | $CF_2CF_3$ | $CF_3$ | $CH_3$ | H | C—H | C—Cl | C—H | C—H | CONH | CO | 4-Fluorobenzyl | 3.73[b] | 573.0[b] |
| Ik-313 | B | $CF_2CF_3$ | $CF_3$ | $CH_3$ | H | C—H | C—Cl | C—H | C—H | CONH | CO | Pyridin-4-ylmethyl | 1.93[b] | 555.9[b] |
| Ik-314 | B | $CF_2CF_3$ | $CF_3$ | $CH_3$ | H | C—H | C—Cl | C—Br | N | CONH | CO | (1S,2R)-2-Fluoro-cyclopropyl | 3.14[a] | 524.1[a] |
| Ik-315 | B | $CF_2CF_3$ | $CF_3$ | $CH_3$ | H | C—H | C—Cl | C—H | N | CONH | CO | Prop-2-enyl | 3.42[a] | 552.0[a] |
| Ik-316 | B | $CF_2CF_3$ | $CF_3$ | $CH_3$ | H | C—H | C—Cl | C—H | N | CONH | CO | Prop-2-enyl | 3.38[a] | 506.1[a] |
| Ik-317 | B | $CF_2CF_3$ | $CF_3$ | $CH_3$ | H | C—H | C—Cl | C—H | N | CONH | CO | 2,2,2-Trifluoroethyl | 3.61[a] | 548.1[a] |
| Ik-318 | B | $CF_2CF_3$ | $CF_3$ | $CH_3$ | H | C—H | C—Cl | C—H | N | CONH | CO | Cyclopropyl | 3.24[a] | 506.1[a] |
| Ik-319 | B | $CF_2CF_3$ | $CF_3$ | $CH_3$ | H | C—H | C—Cl | N | C—H | CONH | CO | (1S,2R)-2-Fluoro-cyclopropyl | 2.98[a] | 524.1[a] |
| Ik-320 | B | $CF_2CF_3$ | $CF_3$ | $CH_3$ | H | C—H | C—Cl | N | C—H | CONH | CO | 2,2,2-Trifluoroethyl | 3.37[a] | 548.0[a] |
| Ik-321 | B | $CF_2CF_3$ | $CF_3$ | $CH_3$ | H | C—H | C—Cl | N | C—H | CONH | CO | Prop-2-enyl | 3.15[a] | 506.0[a] |
| Ik-322 | B | $CF_2CF_3$ | $CF_3$ | $CH_3$ | H | C—H | C—Cl | N | C—H | CONH | CO | Cyclopropyl | 3.03[a] | 506.1[a] |
| Ik-323 | B | $CF_2CF_3$ | $CF_3$ | $CH_3$ | H | C—H | C—Cl | N | C—H | CONH | CO | 2,2-Difluoro-cyclopropyl | 3.22[a] | 542.0[a] |
| Ik-324 | B | $CF_2CF_3$ | $CF_3$ | $CH_3$ | H | C—H | C—Cl | N | C—H | CONH | CO | Propyl | 3.33[a] | 508.0[a] |
| Ik-325 | B | $CF_2CF_3$ | $CF_3$ | $CH_3$ | H | C—H | C—Cl | N | C—H | CONH | CO | 2-Methylcyclopropyl | 3.35[a] | 520.1[a] |
| Ik-326 | B | $CF_2CF_3$ | $CF_3$ | $CH_3$ | H | C—H | C—Cl | N | C—H | CONH | CO | 1-Methylethyl | 3.28[a] | 508.1[a] |
| Ik-327 | B | $CF_2CF_3$ | $CF_3$ | $CH_3$ | H | C—H | C—Cl | N | C—H | CONH | CO | (1S,2R)-2-Fluoro-cyclopropyl | 2.98[a] | 524.1[a] |
| Ik-328 | B | $CF_2CF_3$ | $CF_3$ | $CH_3$ | H | C—H | C—Cl | N | C—H | CONH | CO | 3-Chloroprop-2-enyl | 3.43[a] | 540.0[a] |
| Ik-329 | B | $CF_2CF_3$ | $CF_3$ | $CH_3$ | H | C—H | C—Cl | C—H | C—H | CONH | CO | 1-Trifluoromethylethyl | 3.62[a] | 562.1[a] |
| Ik-330 | B | $CF_2CF_3$ | $CF_3$ | $CH_3$ | H | N | C—H | C—H | C—H | CONH | CO | Cyclopropyl | n.d.[a] | 472.1[a] |
| Ik-331 | B | $CF_2CF_3$ | $CF_3$ | $CH_3$ | H | N | C—H | C—H | C—H | CONH | CO | 2-Fluorocyclopropyl | 3.46[a] | 490.1[a] |
| Ik-332 | B | $CF_2CF_3$ | $CF_3$ | $CH_3$ | H | N | C—Br | C—H | C—H | CONH | CO | 2-Fluorocyclopropyl | 3.65[a] | 568.0[a] |

TABLE 6-continued

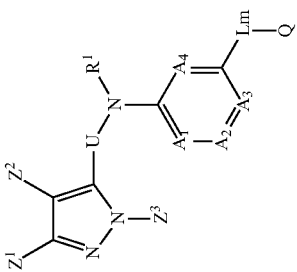

(IK)

| Ex. No. | Process | $Z^1$ | $Z^2$ | $Z^3$ | $R^1$ | $A_4$ | $A_3$ | $A_2$ | $A_1$ | Lm | U | Q | logP | Mass [m/z]¹ |
|---|---|---|---|---|---|---|---|---|---|---|---|---|---|---|
| Ik-333 | B | $CF_2CF_3$ | $CF_3$ | $CH_3$ | H | N | C—Br | C—H | C—H | CONH | CO | 2,2,2-Trifluoroethyl | 3.97[a] | 592.0[a] |
| Ik-334 | B | $CF_2CF_3$ | $CF_3$ | $CH_3$ | H | N | C—Br | C—H | C—H | CONH | CO | 1-Trifluoromethylethyl | 4.23[a] | 606.0[a] |
| Ik-335 | B | $CF_2CF_3$ | $CF_3$ | $CH_3$ | H | N | C—Br | C—H | C—H | CONH | CO | 2-Methyl-1-(methyl-sulphanyl)propan-2-yl | 4.50[a] | 613.9[a] |
| Ik-336 | B | $CF_2CF_3$ | $CF_3$ | $CH_3$ | H | N | C—Br | C—H | C—H | CONH | CO | Propyl | 3.82[a] | 552.0[a] |
| Ik-337 | B | $CF_2CF_3$ | $CF_3$ | $CH_3$ | H | N | C—Br | C—H | C—H | CONH | CO | 1-Cyclopropylethyl | 4.14[a] | 578.0[a] |
| Ik-338 | B | $CF_2CF_3$ | $CF_3$ | $CH_3$ | H | N | C—Br | C—H | C—H | CONH | CO | Prop-2-enyl | 3.73[a] | 549.9[a] |
| Ik-339 | B | $CF_2CF_3$ | $CF_3$ | $CH_3$ | H | C—H | C—I | C—H | C—H | $CON(CH_2CH_3)$ | CO | Cyclopropyl | 4.37[a] | 643.1[a] |
| Ik-340 | B | $CF_2CF_3$ | $CF_3$ | $CH_3$ | H | C—H | C—Cl | C—F | C—H | $CON(CH_3)$ | CO | 2,2,2-Trifluoroethyl | 3.84[b] | 561.0[b] |
| Ik-341 | B | $CF_2CF_3$ | $CF_3$ | $CH_3$ | H | C—H | C—Cl | C—H | C—H | $CON(CH_3)$ | CO | 2,2-Difluoroethyl | 3.53[b] | 543.0[b] |
| Ik-342 | B | $CF_2CF_3$ | $CF_3$ | $CH_3$ | H | C—H | C—Cl | C—H | C—H | CON(Cyclopropyl) | CO | Pyridin-2-ylmethyl | 3.47[b] | 596.1[b] |
| Ik-343 | B | $CF_2CF_3$ | $CF_3$ | $CH_3$ | H | C—H | C—Cl | C—H | C—H | $CON(CH_3)$ | CO | 3,3-Difluoroazetidin-1-yl | 3.58[b] | 541.0[b] |
| Ik-344 | B | $CF_2CF_3$ | $CF_3$ | $CH_3$ | H | C—H | C—Cl | C—H | C—H | $CONH(CH_2CH_3)$ | CO | Cyclopropyl | 3.84[b] | 533.1[b] |
| Ik-345 | B | $CF_2CF_3$ | $CF_3$ | $CH_3$ | H | C—H | C—Cl | C—H | C—H | CO | CO | 4-(Trifluoromethyl)-piperidin-1-yl | 3.94[a] | 601.1[b] |
| Ik-346 | B | $CF_2CF_3$ | $CF_3$ | $CH_3$ | H | C—H | C—Cl | C—H | C—H | CON(Cyclopropyl) | CO | Cyclopropyl(tetrahydro-2H-pyran-4-yl)amino | 3.77[b] | 589.1[b] |
| Ik-347 | A | $CF_2CF_3$ | $CF_3$ | $CH_3$ | H | C—H | C—Cl | C—H | C—H | CONH | $SO_2$ | Cyclopropyl | 3.38[a] | 541.0[a] |
| Ik-348 | A | $CF_2CF_3$ | $CF_3$ | $CH_3$ | H | C—H | C—Cl | C—H | C—H | CONH | $SO_2$ | 1-Cyclopropylethyl | 4.08[a] | 569.1[a] |

Extraordinarily preferred are also compounds of the general formulae (Ik) which are produced from any desired combination of the radicals $Z^1$, $Z^2$, $Z^3$, $R^1$, $A_4$, $A_3$, $A_2$, $A_1$, $L_m$, U and Q listed in Table 6.

TABLE 7

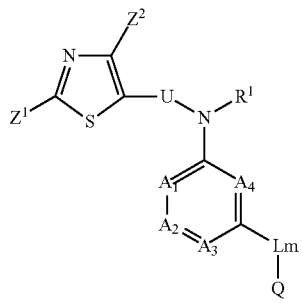

(II)

| Ex. No. | Process | $Z^1$ | $Z^2$ | $R^1$ | $A_4$ | $A_3$ | $A_2$ | $A_1$ | Lm | U | Q | logP | Mass [m/z][1] |
|---|---|---|---|---|---|---|---|---|---|---|---|---|---|
| II-1 | A | $CF_2CF_3$ | $CF_3$ | H | C—H | C—Cl | C—H | C—H | CONH | CO | Cyclopropyl | 337[a] | 508.0[a] |

TABLE 8

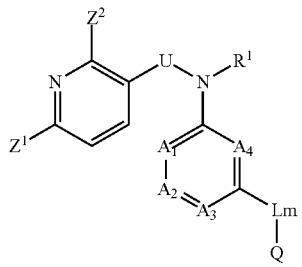

(Ir)

| Ex No. | Process | $Z^1$ | $Z^2$ | R1 | A4 | A3 | A2 | A1 | L | U | Q | logP | Mass [m/z][1] |
|---|---|---|---|---|---|---|---|---|---|---|---|---|---|
| Ir-1 | A | $CF_3$ | Cl | H | C—H | C—Cl | C—H | C—H | CONH | CO | Cyclopropyl | 2.48[a] | 418.0[a] |
| Ir-2 | A | $CF_3$ | Me | H | C—H | C—Cl | C—H | C—H | CONH | CO | Cyclopropyl | 2.27[a] | 398.0[a] |
| Ir-3 | A | $CF_3$ | Cl | H | C—H | C—Cl | C—H | C—H | CONH | CO | 1-Methylethyl | 2.68[a] | 420.0[a] |
| Ir-4 | A | $CF_3$ | Me | H | C—H | C—Cl | C—H | C—H | CONH | CO | 1-Methylethyl | 2.53[a] | 400.1[a] |
| Ir-5 | A | $CF_3$ | Me | Fl | C—H | C—Cl | C—H | C—H | CONH | CO | Methyl | 1.97[a] | 372.0[a] |
| Ir-6 | A | $CF_3$ | Cl | H | C—H | C—Cl | C—H | C—H | CONH | CO | Methyl | 2.16[a] | 392.0[a] |
| Ir-7 | A | $CF_3$ | Cl | H | C—H | C—Cl | C—H | C—Me | CONH | CO | Prop-2-enyl | 2.68[a] | 432.0[a] |
| Ir-8 | A | $CF_3$ | Me | H | C—H | C—Cl | C—H | C—Me | CONH | CO | Prop-2-enyl | 2.45[a] | 412.1[a] |
| Ir-9 | A | $CF_3$ | Cl | H | C—H | C—Cl | C—H | C—H | CONH | CO | 2,2,2-Trifluoroethyl | 2.82[a] | 460.0[a] |
| Ir-10 | A | $CF_3$ | Cl | H | C—H | C—Cl | C—H | C—H | CONH | CO | 3-Chloroprop-2-enyl | 2.86[a] | 453.0[a] |
| Ir-11 | A | $CF_3$ | $CH_3$ | H | C—H | C—Cl | C—H | C—H | CONH | CO | 2,2,2-Trifluoroethyl | 2.67[a] | 440.0[a] |

Extraordinarily preferred are also compounds of the general formulae (Ir) which are produced from any desired combination of the radicals $Z^1$, $Z^2$, $R^1$, $A_4$, $A_3$, $A_2$, $A_1$, $L_m$, U and Q listed in Table 8.
[1] The stated mass is the peak of the isotope pattern of the [M + H]⁺ ion with the highest intensity; if the [M − H]⁻ ion has been detected, the mass specified is indicated by [2].
[2] The stated mass is the peak of the isotope pattern of the [M − H]⁻ ion with the highest intensity.

[a] Note regarding the determination of the logP values and mass detection: The logP values given were determined in accordance with EEC Directive 79/831 Annex V.A8 by HPLC (High Performance Liquid Chromatography) on a phase inversion column (C18). Agilent 1100 LC system; 50*4.6 Zorbax Eclipse Plus C18 1.8 micron; eluent A: acetonitrile (0.1% formic acid); eluent B: water (0.09% formic acid); linear gradient from 10% acetonitrile to 95% acetonitrile in 4.25 min, then 95% acetonitrile for a further 1.25 min; oven temperature 55° C.; flow: 2.0 ml/min. The mass detection is carried out via an Agilend MSD system.
[b] Note regarding the determination of the logP values and mass detection: The logP values given were determined in accordance with EEC Directive 79/831 Annex V.A8 by HPLC (High Performance Liquid Chromatography) on a phase inversion column (C18). HP1100; 50*4.6 Zorbax Eclipse Plus C18 1.8 micron; eluent A: acetonitrile (0.1% formic acid); eluent B: water (0.08% formic acid); linear gradient from 5% acetonitrile to 95% acetonitrile in 1.70 min, then 95% acetonitrile for a further 1.00 min; oven temperature 55° C.; flow: 2.0 ml/min. The mass detection is carried out via the mass detector Micromass ZQ2000 from Waters.

TABLE 9

| Ex. No. | NMR data |
|---|---|
| Ia-1 | ¹H-NMR (400 MHz, d₃-acetonitrile): δ = 9.31 (bs, 1H), 7.73-7-68 (m, 2H), 7.45 (d, 1H), 6.90 (bs, 1H), 2.86 (s, 3H), 2.85-2.81 (m, 1H), 0.81-0.74 (m, 2H), 0.60-0.56 (m, 2H) ppm. |

TABLE 9-continued

| Ex. No. | NMR data |
|---|---|
| Ib-1 | $^1$H-NMR (400 MHz, d$_6$-DMSO): δ = 10.85 (s, 1H), 9.35 (s, 1H), 8.32 (d, 1H), 7.66-7.64 (m, 2H), 7.48-7.46 (m, 1H), 2.86-2.80 (m, 1H), 0.72-0.67 (m, 2H), 0.55-0.51 (m, 2H) ppm. |
| Ib-2 | $^1$H-NMR (400 MHz, d$_6$-DMSO): δ = 10.78 (s, 1H), 9.22 (s, 1H), 8.31 (d, 1H), 7.67-7.65 (m, 2H), 7.47-7.45 (m, 1H), 5.21-5.14 (q, 2H), 2.85-2.81 (m, 1H), 0.72-0.67 (m, 2H), 0.55-0.51 (m, 2H) ppm. |
| Ib-3 | $^1$H-NMR (400 MHz, d$_6$-DMSO): δ = 10.91 (s, 1H), 9.66 (s, 1H), 8.33 (d, 1H), 7.66-7.64 (m, 2H), 7.50-7.48 (m, 1H), 2.86-2.81 (m, 1H), 0.72-0.67 (m, 2H), 0.56-0.52 (m, 2H) ppm. |
| Ib-4 | $^1$H-NMR (400 MHz, d$_6$-DMSO): δ = 10.97 (s, 1H), 9.67 (s, 1H), 9.05-9.02 (m, 1H), 7.73-7.71 (m, 2H), 7.55-7.53 (m, 1H), 4.11-4.04 (m, 2H) ppm. |
| Ib-5 | $^1$H-NMR (400 MHz, d$_6$-DMSO): δ = 10.94 (s, 1H), 9.66 (s, 1H), 8.61-8.55 (m, 1H), 7.72-7.65 (m, 2H), 7.51 (d, 1H), 6.43-6.37 (m, 1H), 6.06-5.96 (m, 1H), 4.06-4.01 (m, 1H), 3.92-3.89 (m, 1H) ppm. |
| Ib-9 | $^1$H-NMR (400 MHz, d$_6$-DMSO): δ = 10.97 (s, 1H), 9.70 (s, 1H), 9.04 (t, 1H), 7.73-7.71 (m, 2H), 7.56-7.53 (m, 1H), 4.11-4.02 (m, 2H) ppm. |
| Ib-14 | $^1$H-NMR (400 MHz, d$_6$-DMSO): δ = 10.80 (s, 1H), 8.81 (s, 1H), 7.77-7.72 (m, 2H), 7.50 (d, 1H), 7.38-7.31 (m, 3H), 7.26-7.24 (m, 1H), 4.46 (d, 2H), 2.57 (s, 6H) ppm. |
| Ib-16 | $^1$H-NMR (400 MHz, d$_3$-acetonitrile): δ = 9.49 (bs, 1H), 9.40 (s, 1H), 7.82 (d, 1H), 7.73-7.70 (m, 1H), 7.50 (d, 1H), 7.38-7.36 (m, 1H), 4.13-4.03 (m, 2H) ppm. |
| Ib-19 | $^1$H-NMR (400 MHz, d$_6$-DMSO): δ = 10.73 (s, 1H), 9.12 (s, 1H), 8.30 (d, 1H), 7.73-7.70 (m, 2H), 7.46 (d, 1H), 2.86-2.81 (m, 1H), 2.69 (s, 3H), 0.72-0.68 (m, 2H), 0.56-0.52 (m, 2H) ppm. |
| Ib-24 | $^1$H-NMR (400 MHz, d$_6$-DMSO): δ = 10.80 (s, 1H), 9.15 (s, 1H), 9.00 (t, 1H), 7.80-7.76 (m, 2H), 7.52 (d, 1H), 4.11-4.02 (m, 2H), 2.70 (s, 3H) ppm. |
| Ib-27 | $^1$H-NMR (400 MHz, d$_6$-DMSO): δ = 10.91 (s, 1H), 9.56 (s, 1H), 8.33 (m, 1H), 7.70-7.67 (m, 2H), 7.48 (d, 1H), 7.33 (t, 1H), 2.87-2.80 (m, 1H), 0.72-0.68 (m, 2H), 0.56-0.52 (m, 2H) ppm. |
| Ib-30 | $^1$H-NMR (400 MHz, d$_6$-DMSO): δ = 10.85 (s, 1H), 9.04 (s, 1H), 8.30 (d, 1H), 7.76-7.70 (m, 2H), 7.6 (d, 1H), 2.86-2.80 (m, 1H), 2.53-2.45 (m, 1H), 1.39-1.21 (m, 2H), 1.20-1.16 (m, 2H), 0.72-0.68 (m, 2H), 0.56-0.52 (m, 2H) ppm. |
| Ib-33 | $^1$H-NMR (400 MHz, d$_3$-acetonitrile): δ = 9.39 (s, 1H), 9.06 (bs, 1H), 7.78 (d, 1H), 7.68-7.66 (m, 2H), 7.50 (d, 1H), 7.35 (bs, 1H), 4.13-4.04 (m, 2H) ppm. |
| Ib-34 | $^1$H-NMR (400 MHz, d$_3$-acetonitrile): δ = 9.39 (s, 1H), 9.06 (bs, 1H), 7.78 (d, 1H), 7.68-7.66 (m, 2H), 7.50 (d, 1H), 7.35 (bs, 1H), 4.13-4.04 (m, 2H) ppm. |
| Ib-35 | $^1$H-NMR (400 MHz, d$_3$-acetonitrile): δ = 9.38 (s, 1H), 9.06 (bs, 1H), 7.75 (d, 1H), 7.67-7.64 (m, 1H), 7.47 (d, 1H), 7.40-7.28 (m, 6H), 4.53 (d, 2H) ppm. |
| Ib-36 | $^1$H-NMR (400 MHz, d$_6$-DMSO): δ = 11.06 (s, 1H), 9.70 (bs, 1H), 8.44 (d, 1H), 8.10 (d, 1H), 7.54 (d, 1H), 2.85-2.78 (m, 1H), 0.73-0.68 (m, 2H), 0.55-0.51 (m, 2H) ppm. |
| Ib-37 | $^1$H-NMR (400 MHz, d$_3$-acetonitrile): δ = 9.39 (s, 1H), 9.16 (bs, 1H), 7.70 (d, 1H), 7.65 (dd, 1H), 7.46 (d, 1H), 6.84 (d, 1H), 3.55-3.49 (m, 1H), 1.26 (d, 3H), 0.96-0.92 (m, 1H), 0.52-0.43 (m, 2H), 0.38-0.27 (m, 2H) ppm. |
| Ie-1 | $^1$H-NMR (400 MHz, d$_6$-DMSO): δ = 10.83 (s, 1H), 8.87 (s, 1H), 8.31 (d, 1H), 8.02 (d, 1H), 7.75-7.71 (m, 2H), 7.46 (d, 1H), 2.86-2.81 (m, 1H), 0.72-0.67 (m, 2H), 0.56-0.52 (m, 2H) ppm. |
| Ii-1 | $^1$H-NMR (400 MHz, d$_6$-DMSO): δ = 10.83 (s, 1H), 8.87 (s, 1H), 8.32 (d, 1H), 8.02 (d, 1H), 7.75-7.71 (m, 2H), 7.46 (d, 1H), 2.86-2.81 (m, 1H), 0.72-0.67 (m, 2H), 0.56-0.52 (m, 2H) ppm. |
| Ij-1 | $^1$H-NMR (400 MHz, d$_6$-DMSO): δ = 10.69 (s, 1H), 8.62 (s, 1H), 8.30 (d, 1H), 7.69-7.66 (m, 2H), 7.47-7.42 (m, 2H), 5.17-5.10 (q, 2H), 2.85-2.80 (m, 1H), 0.72-0.67 (m, 2H), 0.55-0.51 (m, 2H) ppm. |
| Ij-2 | $^1$H-NMR (400 MHz, d$_6$-DMSO): δ = 10.68 (s, 1H), 8.62 (s, 1H), 8.30 (d, 1H), 7.69-7.66 (m, 2H), 7.44-7.41 (m, 2H), 6.02-5.95 (m, 1H), 2.85-2.80 (m, 1H), 1.52 (d, 3H), 0.72-0.67 (m, 2H), 0.55-0.51 (m, 2H) ppm. |
| Ij-4 | $^1$H-NMR (400 MHz, d$_3$-acetonitrile) δ = 9.01 (bs, 1H), 8.58 (s, 1H), 7.70 (m, 1H), 7.48 (s, 1H), 7.42 (d, 1H), 6.91-6.82 (m, 2H), 2.84-2.80 (m, 1H), 0.78-0.73 (m, 2H), 0.59-0.55 (m, 2H) ppm. |
| Ik-1 | $^1$H-NMR (400 MHz, d$_3$-acetonitrile): δ = 9.45 (bs, 1H), 7.71 (d, 1H), 7.65 (dd, 1H), 7.45 (d, 1H), 6.94 (bs, 1H), 3.98 (s, 3H), 2.79-2.85 (m, 1H), 0.72-0.79 (m, 2H), 0.57-0.60 (m, 2H) ppm. |
| Ik-2 | $^1$H-NMR (400 MHz, d$_3$-acetonitrile): δ = 9.16 (bs, 1H), 8.11 (d, 1H), 7.74 (dd, 1H), 7.52 (d, 1H), 3.98 (s, 3H) ppm. |
| Ik-3 | $^1$H-NMR (d$_6$-DMSO) 11.24 (s, 1H), 8.49 (1H, t, J = 2 Hz, NH), 7.71 (1H, d, J = 2.5 Hz), 7.68 (1H, dd; J = 9.2 Hz), 7.50 (1H, d, J = 9 Hz), 4.05 (2H, dd, J = 5.5, 2.5 Hz), 4.00 (3H, s), 3.87 (1H, s) ppm. |
| Ik-6 | $^1$H-NMR (d$_3$-d$_3$-acetonitrile) 9.40 (s, 1H, br), 7.77 (d, 1H), 7.67 (dd, 1H), 7.48 (d, 1H), 7.25 (s, 1H, br), 3.98 (s, 3H), 3.45 (m, 1H), 1.90 (m, 1H), 1.55 (m, 1H) ppm. |
| Ik-7 | $^1$H-NMR (400 MHz, d$_3$-acetonitrile): δ = 9.21 (bs, 1H), 8.08 (d, 1H), 7.57 (d, 1H), 6.93 (bs, 1H), 3.98 (s, 3H), 2.79-2.84 (m, 1H), 0.73-0.79 (m, 2H), 0.58-0.61 (m, 2H) ppm. |
| Ik-9 | $^1$H-NMR (d$_6$-DMSO) 8.49 (1H, d, J = 4 Hz, NH), 7.70 (1H, dd, J = 8, 2.5 Hz), 7.68 (1H, s), 7.50 (1H, d, J = 8 Hz), 4.7 (1H, ddd, J = 62, 4.4 Hz), 4.00 (3H, s), 2.85 (1H, m), 1.15 (1H, m), 1.05 (1H, m) ppm. |
| Ik-18 | $^1$H-NMR (400 MHz, d$_3$-acetonitrile): δ = 8.80 (bs, 1H), 7.73 (d, 1H), 7.67 (dd, 1H), 7.43 (d, 1H), 6.79 (bs, 1H), 4.07 (s, 3H), 2.81-2.87 (m, 1H), 0.74-0.79 (m, 2H), 0.57-0.62 (m, 2H) ppm. |
| Ik-25 | $^1$H-NMR (400 MHz, d$_3$-acetonitrile): δ = 9.23 (bs, 1H), 7.92 (d, 1H), 7.76 (dd, 1H), 7.25 (d, 1H), 7.08 (bs, 1H), 6.78 (t, 1H), 3.98 (s, 3H), 2.81-2.86 (m, 1H), 0.74-0.79 (m, 2H), 0.55-0.60 (m, 2H) ppm. |
| Ik-43 | $^1$H-NMR (d$_6$-DMSO) 11.43 (s, 1H), 9.12 (t, 1H), 8.86 (s, 1H), 7.75-7.70 (m, 2H), 7.56 (d, 1H), 4.53 (d, 2H), 4.02 (s, 3H) ppm. |
| Ik-47 | $^1$H-NMR (d$_6$-DMSO) 11.42 (s, 1H), 11.30 (s, 1H, isomer), 8.78 (d, 1H, NH), 8.44 (d, 1H, isomer), 7.72 (d, 1H), 7.70 (dd, 1H), 7.52 (d, 1H), 7.40 (d, 1H), 7.30-7.10 (m, 4H), 4.02 (s, 3H), 3.00 (m, 1H), 2.05 (m, 1H), 1.30-1.20 (m, 4H) ppm. |
| Ik-51 | $^1$H-NMR (d$_6$-DMSO) 11.23 (s, 1H), 8.40 (1H, s, NH), 7.70 (1H, s), 7.65 (1H, dd, J = 8, 2.5 Hz), 7.50 (1H, d, J = 8 Hz), 4.7 (1H, ddd, J = 62, 4.4 Hz), 4.00 (3H, s), 2.50 (1H, m), 1.40 (1H, m), 1.00 (1H, m) ppm. |
| Ik-52 | $^1$H-NMR (d$_6$-DMSO) 11.20 (s, 1H), 8.82 (t, 1H, NH), 7.70 (m, 2H), 7.52 (d, 1H), 7.45 (dd, 1H), 7.35-7.30 (m, 1H), 7.15 (m, 1H), 4.49 (d, 2H), 4.00 (s, 3H) ppm. |
| Ik-59 | $^1$H-NMR (d$_6$-DMSO) 11.23 (s, 1H), 7.65-7.60 (m, 2H), 7.50 (d, 1H), 4.01 (6H, m), 1.55 (m, 2H), 0.95 (t, 3H), 0.70 (t, 2H) ppm. |
| Ik-60 | $^1$H-NMR (d$_6$-DMSO) 11.44 (s, 1H), 9.00 (t, 1H), 8.79 (d, 2H), 7.87 (d, 1H), 7.75 (dd, 1H), 7.55 (d, 1H), 7.41 (t, 1H), 4.62 (d, 2H), 4.03 (s, 3H) ppm. |
| Ik-62 | $^1$H-NMR (d$_6$-DMSO) 11.42 (s, 1H), 8.44 (d, 1H, NH), 7.70 (dd, 1H), 7.68 (s, 1H), 7.53 (d, 1H), 4.00 (s, 3H), 3.50 (m, 1H), 1.20 (d, 3H), 0.90 (m, 1H), 0.50-0.25 (m, 3H) ppm. |
| Ik-63 | $^1$H-NMR (d$_6$-DMSO) 11.25 (s, 1H), 8.95 (d, 1H, NH), 7.72 (dd, 1H), 7.68 (m, 1H), 7.53 (d, 1H), 4.75 (m, 1H), 4.00 (s, 3H), 1.33 (d, 3H) ppm. |

TABLE 9-continued

| Ex. No. | NMR data |
|---|---|
| Ik-64 | $^1$H-NMR (d$_6$-DMSO) 11.25 (s, 1H), 8.72 (t, 1H, NH), 7.70 (m, 2H), 7.50 (d, 1H), 4.00 (s, 3H), 3.72-3.65 (ddd, 2H), 1.65 (t, 3H, J(H, F) = 18 Hz) ppm. |
| Ik-83 | $^1$H-NMR (400 MHz, d$_3$-acetonitrile): δ = 9.18 (bs, 1H), 7.75 (s, 1H), 7.65 (dd, 1H), 7.46 (d, 1H), 6.94 (bs, 1H), 6.25-6.36 (m, 1H), 5.95-6.09 (m, 1H), 3.98 (s, 3H) ppm. (mixture of E/Z isomers) |
| Ik-84 | $^1$H-NMR (400 MHz, d$_3$-acetonitrile): δ = 9.29 (bs, 1H), 7.78 (d, 1H), 7.67 (dd, 1H), 7.48 (d, 1H), 7.21-7.52 (m, 6H), 4.54 (d, 2H), 3.97 (s, 3H) ppm. |
| Ik-87 | $^1$H-NMR (400 MHz, d$_3$-acetonitrile): δ = 9.23 (bs, 1H), 7.78 (d, 1H), 7.67 (dd, 1H), 7.49 (d, 1H), 7.24 (bs, 1H), 4.02-4.12 (m, 1H), 3.98 (s, 3H) ppm. |
| Ik-90 | $^1$H-NMR (400 MHz, d$_3$-acetonitrile): δ = 9.46 (bs, 1H), 7.71 (d, 1H), 7.65 (dd, 1H), 7.45 (d, 1H), 6.73 (bs, 1H), 4.09-4.16 (m, 1H), 3.98 (s, 3H), 1.21 (d, 6H) ppm. |
| Ik-93 | $^1$H-NMR (400 MHz, d$_3$-acetonitrile): δ = 9.19 (bs, 1H), 7.80 (d, 1H), 7.74 (dd, 1H), 7.37 (d, 1H), 6.92 (bs, 1H), 5.90-5.99 (m, 1H), 5.23 (dd, 1H), 5.13 (dd, 1H), 3.98 (s, 3H) ppm. |
| Ik-100 | $^1$H-NMR (400 MHz, d$_3$-acetonitrile): δ = 9.28 (bs, 1H), 7.57-7.62 (m, 2H), 7.43 (d, 1H), 6.92 (bs, H), 6.18 (dq, 1H), 2.78-2.83 (m, 1H), 1.98 (d, 1H), 0.73-0.79 (m, 2H), 0.57-0.60 (m, 2H) ppm. |
| Ik-107 | $^1$H-NMR (400 MHz, d$_3$-acetonitrile): δ = 9.19 (bs, 1H), 8.22 (d, 1H), 7.76 (dd, 1H), 7.55 (d, 1H), 4.86 (s, 2H), 3.98 (s, 3H), 3.76 (s, 3H) ppm. |
| Ik-117 | (d$_6$-DMSO) 0.45 (m, 2H), 0.72 (m, 2H), 2.82 (m, 1H) 4.21 (s, 3H), 7.46 (m, 1H), 7.50 (s, 1H), 7.75 (m, 1H), 8.30 (br. s, 1H). |
| Ik-118 | (d$_3$-acetonitrile) 3.38 (m, 1H) 4.07 (s, 3H), 7.44 (m, 1H), 7.51 (s, 1H), 7.76 (m, 1H), 8.87 (br. s, 1H). |
| Ik-123 | (d$_3$-acetonitrile) 0.45 (m, 2H), 0.72 (m, 2H), 2.79 (m, 1H) 4.11 (s, 3H), 7.15-7.25 (m, 3H), 7.3-7.4 (m, 2H), 7.4-7.5 (m, 2H), 7.91 (br. s, 1H). |
| Ik-132 | $^1$H-NMR (400 MHz, d$_3$-acetonitrile; mixture of cis and trans configured amides): δ = 6.55-7.63 (m, 4H), 3.98 & 3.84 (2 s, together 3H), 3.45 & 3.21 (2 s, together 3H), 2.77-2.90 (m, 1H), 0.72-0.81 (m 2 H), 0.51-0.63 (m, 2H) ppm. |
| Ik-137 | $^1$H-NMR (400 MHz, d$_3$-acetonitrile; mixture of cis and trans configured amides): δ = 7.58 & 7.39 (2 d, together 1H), 7.16-7.31 (m, 2H), 6.77 & 6.99 (2 bs, together 1H), 4.90-4.98 (m, 1H), 3.86 & 3.98 (2 s, together 3H), 2.76-2.82 (m, 1H), 1.17-1.23 (m, 6H), 0.73-0.80 (m, 2H), 0.53-0.58 (m, 2H) ppm. |
| Ik-138 | $^1$H-NMR (400 MHz, d$_3$-acetonitrile): δ = 7.38-7.50 (m, 1H), 7.28 (d, 1H), 7.19 (dd, 1H), 7.10 (bs, 1H), 3.84-4.12 (m, 7H), 1.24 (t, 3H) ppm. |
| Ik-142 | $^1$H-NMR (400 MHz, d$_3$-acetonitrile): δ = 9.16 (bs, 1H), 8.26 (d, 1H), 7.27-7.42 (m, 6H), 4.54 (d, 2H), 3.98 (s, 3H) ppm. |
| Ik-146 | $^1$H-NMR (400 MHz, d$_3$-acetonitrile): δ = 9.08 (bs, 1H), 8.52 (dd, 1H), 7.43 (bs, 1H), 7.22 (t, 1H), 4.08-4.16 (m, 2H), 4.00 (s, 3H) ppm. |
| Ik-147 | $^1$H-NMR (400 MHz, d$_3$-acetonitrile): δ = 9.00 (bs, 1H), 8.11 (s, 1H), 7.64 (s, 1H), 6.98 (bs, 1H), 4.01 (s, 3H), 2.80-2.85 (m. 1H), 0.74-0.79 (m, 2H), 0.58-0.62 (m, 2H) ppm. |
| Ik-149 | $^1$H-NMR (400 MHz, d$_3$-acetonitrile): δ = 9.30 (bs, 1H), 7.90-7.93 (m, 1H), 7.65-7.66 (m, 1H), 7.57-7.61 (m, 1H), 7.23-7.35 (m, 5H), 4.54 (d, 2H), 3.98 (s, 3H) ppm. |
| Ik-151 | $^1$H-NMR (400 MHz, d$_3$-acetonitrile): δ = 8.99 (bs, 1H), 8.44 (d, 1H), 7.49 (d, 1H), 7.45 (bs, 1H), 4.07-4.16 (m, 2H), 4.03 (s, 3H) ppm. |
| Ik-154 | $^1$H-NMR (400 MHz, d$_3$-acetonitrile): δ = 8.83 (bs, 1H), 7.81 (d, 1H), 7.71 (dd, 1H), 7.48 (d, 1H), 7.21 (bs, 1H), 4.02-4.12 (m, 2H), 4.07 (s, 3H) ppm. |
| Ik-155 | $^1$H-NMR (400 MHz, d$_3$-acetonitrile): δ = 9.11 (bs, 1H), 7.97-8.00 (m, 1H), 7.70-7.76 (m, 1H), 7.20 (dd, 1H), 6.92 (bs, 1H), 3.98 (s, 3H), 2.85-2.90 (m, 1H), 0.75-0.79 (m, 2H), 0.59-0.63 (m, 2H) ppm. |
| Ik-156 | $^1$H-NMR (400 MHz, d$_3$-acetonitrile): δ = 9.13 (bs, 1H), 8.04-8.07 (m, 1H), 7.76-7.82 (m, 1H), 7.35 (bs, 1H), 7.26 (dd, 1H), 4.05-4.16 (m, 1H), 3.98 (s, 3H) ppm. |
| Ik-158 | $^1$H-NMR (400 MHz, d$_3$-acetonitrile): δ = 8.84 (bs, 1H), 7.77 (d, 1H), 7.70 (dd, 1H), 7.47 (d, 1H), 7.10 (bs, 1H), 4.79-4.88 (m, 1H), 4.07 (s, 3H), 1.39 (d, 3H) ppm. |
| Ik-161 | $^1$H-NMR (400 MHz, d$_3$-acetonitrile): δ = 9.18 (bs, 1H), 7.99 (dd, 1H), 7.75-7.80 (m, 1H), 7.25 (dd, 1H), 7.10 (bs, 1H), 4.85-4.93 (m, 1H), 3.98 (s, 3H), 1.41 (d, 3H) ppm. |
| Ik-162 | $^1$H-NMR (400 MHz, d$_3$-acetonitrile): δ = 9.26 (bs, 1H), 7.95 (s, 1H), 7.65-7.70 (m, 1H), 7.24-7.48 (m, 7H), 4.54 (d, 2H), 3.98 (s, 3H) ppm. |
| Ik-167 | $^1$H-NMR (400 MHz, d$_3$-acetonitrile): δ = 9.40 (bs, 1H), 7.64 (d, 1H), 7.61 (dd, 1H), 7.44 (d, 1H), 6.93 (bs, 1H), 2.79-2.84 (m, 1H), 1.66 (s, 9H), 0.73-0.78 (m, 2H), 0.56-0.60 (m, 2H) ppm. |
| Ik-169 | $^1$H-NMR (400 MHz, d$_3$-acetonitrile): δ = 9.17 (bs, 1H), 8.12-8.19 (m, 1H), 7.61 (dd, 1H), 7.16 (bs, 1H), 3.98 (s, 3H), 2.81-2.87 (m, 1H), 0.73-0.80 (m, 2H), 0.53-0.59 (m, 2H) ppm. |
| Ik-170 | $^1$H-NMR (400 MHz, d$_3$-acetonitrile): δ = 8.93 (bs, 1H), 8.15 (d, 1H), 7.34 (d, 1H), 6.79 (bs, 1H), 4.01 (s, 3H), 2.78-2.85 (m, 1H), 0.73-0.79 (m, 2H), 0.54-0.59 (m, 2H) ppm. |
| Ik-172 | $^1$H-NMR (400 MHz, d$_3$-acetonitrile): δ = 9.13 (bs, 1H), 7.70-7.71 (m, 1H), 7.63 (d, 1H), 7.54-7.58 (m, 1H), 7.26-7.42 (m, 5H), 7.13 (bs, 1H), 4.54 (d, 2H), 3.97 (s, 3H) ppm. |
| Ik-173 | $^1$H-NMR (400 MHz, d$_3$-acetonitrile): δ = 9.16 (bs, 1H), 7.72 (d, 1H), 7.66 (d, 1H), 7.55-7.60 (m, 1H), 7.20 (bs, 1H), 4.02-4.11 (m 2H), 3.97 (s, 3H) ppm. |
| Ik-174 | $^1$H-NMR (400 MHz, d$_3$-acetonitrile): δ = 9.14 (bs, 1H), 7.68-7.77 (m, 1H), 7.65 (d, 1H), 7.58 (dd, 1H), 7.07 (bs, 1H), 4.78-4.88 (m, 2H), 3.97 (s, 3H) ppm. |
| Ik-175 | $^1$H-NMR (400 MHz, d$_3$-acetonitrile): δ = 9.25 (bs, 1H), 7.53-7.65 (m, 3H), 6.77 (bs, 1H), 3.98 (s, 3H), 2.79-2.86 (m, 1H), 0.73-0.79 (m, 2H), 0.60-0.62 (m, 2H) ppm. |
| Ik-178 | $^1$H-NMR (400 MHz, d$_6$-DMSO): δ = 11.40 (s, 1H), 9.15 (t, 1H), 8.17 (d, 3H), 7.63 (d, 1H), 4.01-4.12 (m, 5H) ppm. |
| Ik-179 | $^1$H-NMR (400 MHz, d$_3$-acetonitrile): δ = 9.15 (bs, 1H), 7.70-7.72 (m, 1H), 7.65 (dd, 1H), 7.42 (d, 1H), 6.79 (bs, 1H), 2.81-2.89 (m, 1H), 0.72-0.81 (m 2 H), 0.51-0.64 (m, 2H) ppm. |
| Ik-181 | $^1$H-NMR (400 MHz, d$_3$-acetonitrile): δ = 9.51 (bs, 1H), 8.14 (d, 1H), 7.86 (dd, 1H), 7.82 (d, 1H), 7.32 (bs, 1H), 4.04-4.14 (m, 1H), 3.99 (s, 3H) ppm. |
| Ik-183 | $^1$H-NMR (400 MHz, d$_3$-acetonitrile): δ = 9.11 (bs, 1H), 7.86 (d, 1H), 7.58 (d, 1H), 7.38 (dd, 1H), 6.68 (bs, 1H), 3.97 (s, 3H), 2.79-2.85 (m, 1H), 0.73-0.79 (m, 2H), 0.62-0.65 (m, 2H) ppm. |
| Ik-187 | $^1$H-NMR (400 MHz, d$_3$-acetonitrile): δ = 9.33 (bs, 1H), 8.09 (d, 1H), 7.85 (d, 1H), 6.88 (bs, 1H), 3.97 (s, 3H), 2.82-2.87 (m, 1H), 0.75-0.81 (m, 2H), 0.58-0.63 (m, 2H) ppm. |
| Ik-189 | $^1$H-NMR (400 MHz, d$_3$-acetonitrile): δ = 7.78 (d, 1H), 7.49 (d, 1H), 7.24-7.42 (m, 6H), 4.54 (d, 2H), 3.97 (s, 3H) ppm. |

TABLE 9-continued

| Ex. No. | NMR data |
|---|---|
| Ik-192 | $^1$H-NMR (400 MHz, d$_3$-acetonitrile): δ = 9.26 (bs, 1H), 7.63 (dd, 1H), 7.22-7.46 (m, 7H), 4.55 (d, 2H), 3.97 (s, 3H), 2.38 (s, 3H) ppm. |
| Ik-194 | $^1$H-NMR (400 MHz, d$_3$-acetonitrile): δ = 9.44 (bs, 1H), 7.74 (dd, 1H), 7.34 (s, 1H), 6.76 (bs, 1H), 3.97 (s, 3H), 3.24 (s, 3H), 2.72-2.78 (m, 1H), 0.70-0.76 (m, 2H), 0.58-0.62 (m, 2H) ppm. |
| Ik-197 | $^1$H-NMR (400 MHz, d$_3$-acetonitrile): δ = 9.08 (bs, 1H), 7.71 (d, 1H), 7.67 (dd, 1H), 7.42 (d, 1H), 6.78 (bs, 1H), 3.95 (s, 3H), 2.82-2.88 (m, 1H), 0.73-0.80 (m, 2H), 0.54-0.61 (m, 2H) ppm. |
| Ik-199 | $^1$H-NMR (400 MHz, d$_3$-acetonitrile): δ = 9.38 (bs, 1H), 8.08 (d, 1H), 7.57 (d, 1H), 7.43 (dd, 2H), 7.38 (dt, 2H), 7.27-7.31 (m, 2H), 4.54 (d, 2H), 3.97 (s, 3H), 2.36 (s, 3H) ppm. |
| Ik-203 | $^1$H-NMR (400 MHz, d$_3$-acetonitrile): δ = 9.35 (bs, 1H), 7.92 (d, 1H), 7.54 (d, 1H), 7.33 (bs, 1H), 4.07-4.11 (m, 1H), 3.98 (s, 3H), 2.38 (s, 3H) ppm. |
| Ik-204 | $^1$H-NMR (400 MHz, d$_3$-acetonitrile): δ = 9.25 (bs, 1H), 7.88 (d, 1H), 7.40 (d, 1H), 6.71 (bs, 1H), 3.97 (s, 3H), 2.79-2.86 (m, 1H), 0.73-0.81 (m, 2H), 0.58-0.64 (m, 2H) ppm. |
| Ik-208 | $^1$H-NMR (400 MHz, d$_3$-acetonitrile): δ = 9.25 (bs, 1H), 8.07 (d, 1H), 7.58 (d, 1H), 7.26-7.41 (m, 5H), 7.14 (bs, 1H), 4.54 (d, 2H), 3.97 (s, 3H) ppm. |
| Ik-213 | $^1$H-NMR (400 MHz, d$_3$-acetonitrile): δ = 9.24 (bs, 1H), 7.90 (d, 1H), 7.48 (d, 1H), 6.75 (bs, 1H), 3.97 (s, 3H), 2.76-2.89 (m, 1H), 0.73-0.80 (m, 2H), 0.58-0.62 (m, 2H) ppm. |
| Ik-216 | $^1$H-NMR (400 MHz, d$_3$-acetonitrile): δ = 9.18 (bs, 1H), 7.76 (d, 1H), 7.66 (dd, 1H), 7.49 (d, 1H), 7.22 (bs, 1H), 4.30 (q, 2H), 4.03-4.13 (m, 2H), 1.43-1.48 (m, 3H) ppm. |
| Ik-218 | $^1$H-NMR (400 MHz, d$_3$-acetonitrile): δ = 9.19 (bs, 1H), 7.68 (d, 1H), 7.62 (dd, 1H), 7.44 (d, H), 6.78 (bs, 1H), 4.66-4.75 (m, 1H), 2.81-2.87 (m, 1H), 1.49 (d, 6H), 0.72-0.79 (m, 2H), 0.58-0.62 (m, 2H) ppm. |
| Ik-220 | $^1$H-NMR (400 MHz, d$_3$-acetonitrile): δ = 9.20 (bs, 1H), 7.75 (d, 1H), 7.65 (dd, 1H), 7.49 (d, H), 7.23 (bs, 1H), 5.55 (s, 2H), 4.02-4.11 (m, 2H), 3.37 (s, 3H) ppm. |
| Ik-222 | $^1$H-NMR (400 MHz, d$_3$-acetonitrile): δ = 9.33 (bs, 1H), 8.05 (t, 1H), 7.97 (t, 1H), 7.80 (t, H), 7.62 (bs, 1H), 7.24-7.48 (m, 5H), 4.54 (d, 2H), 3.98 (s, 3H) ppm. |
| Ik-229 | $^1$H-NMR (400 MHz, d$_3$-acetonitrile): δ = 9.54 (bs, 1H), 7.74 (dd, 1H), 7.27-7.44 (m, 7H), 4.54 (d, 2H), 3.97 (s, 3H) ppm. |
| Ik-230 | $^1$H-NMR (400 MHz, d$_6$-DMSO): δ = 11.09 (br. s, 1H), 8.32 (br. d, 1H), 7.65-7.68 (m, 2H), 7.45-7.47 (m, 1H), 3.83 (s, 3H), 2.82-2.83 (m, 1H), 1.74 (d, 6H), 0.68-0.71 (m, 2H), 0.51-0.55 (m, 2H) ppm. |
| Ik-231 | $^1$H-NMR (400 MHz, d$_6$-DMSO): δ = 11.38 (s, 1H), 8.57 (d, 1H), 7.69-7.74 (m, 2H), 7.55 (d, 1H), 7.24 (t, 1H), 4.00 (s, 3H), 2.83-2.88 (m, 1H), 0.71-0.74 (m, 2H), 0.53-0.56 (m, 2H) ppm. |
| Ik-235 | $^1$H-NMR (400 MHz, d$_6$-DMSO): δ = 10.53 (s, 1H), 8.30 (d, 1H), 7.72 (m, 2H), 7.45 (d, 1H), 3.73 (s, 3H), 2.84 (m, 1 H), 1.85 (m, 1H), 0.92 (m, 2H), 0.80 (m, 2H), 0.69 (m, 2H), 0.53 (m, 2H) ppm. |
| Ik-236 | $^1$H-NMR (400 MHz, d$_6$-DMSO): δ = 10.79 (s, 1H), 9.03 (m, 1H), 7.80 (m, 1H), 7.76 (m, 1H), 7.52 (m, 1H), 7.27 (t, 1H), 4.06 (m, 2H), 3.87 (s, 3H) ppm. |
| Ik-239 | $^1$H-NMR (400 MHz, d$_6$-DMSO): δ = 10.84 (s, 1H), 9.02 (m, 1H), 7.78 (m, 1H), 7.76 (m, 1H), 7.51 (d, 1H), 7.27 (t, 1H), 4.06 (m, 2H), 3.88 (s 1H) ppm. |
| Ik-240 | $^1$H-NMR (400 MHz, d$_6$-DMSO): δ = 10.65 (s, 1H), 8.32 (m, 1H), 7.73 (m, 1H), 7.69 (m, 1H), 7.47 (d, 1H), 7.24 (t, 1H), 3.87 (s, 3H), 2.83 (m, 1H), 0.69 (m, 2H), 0.53 (m, 2H) ppm. |
| Ik-243 | $^1$H-NMR (400 MHz, d$_6$-DMSO): δ = 10.68 (s, 1H), 9.01 (m, 1H), 7.78 (m, 2H), 7.51 (d, 1H), 4.06 (m, 2H), 3.82 (s, 3H) ppm. |
| Ik-245 | $^1$H-NMR (400 MHz, d$_6$-DMSO): δ = 10.60 (s, 1H), 8.32 (m, 1H), 7.72 (m, 1H), 7.68 (m, 1H), 7.45 (d, 1H), 4.85 (m, 2H), 3.81 (sm 3H), 2.84 (m, 1H), 0.70 (m, 2H), 0.53 (m, 2H) ppm. |
| Ik-246 | $^1$H-NMR (400 MHz, d$_6$-DMSO): δ = 10.40 (s, 1H), 7.83 (m, 2H), 7.52 (m, 1H), 6.59 (s, 1H), 4.82 (m, 2H), 4.08 (m, 2H), 3.96 (s, 3H) ppm. |
| Ik-248 | $^1$H-NMR (400 MHz, d$_6$-DMSO): δ = 10.94 (s, 1H), 8.51 (d, 1H), 7.87 (m, 2H), 7.74 (m, 2H), 7.50 (d, 1H), 7.34 (m, 2H), 3.98 (s, 3H), 2.83 (m, 1H), 0.70 (m, 2H), 0.52 (m, 2H) ppm. |
| Ik-249 | $^1$H-NMR (400 MHz, d$_6$-DMF): δ = 10.89 (s, 1H), 8.42 (m, 1H), 8.16 (d, 2H), 7.97 (m, 1H), 7.94 (d, 2H), 7.89 (m, 1H), 7.55 (m, 1H), 4.14 (s, 4H), 2.97 (m, 1H), 0.78 (m, 2H), 0.53 (m, 2H) ppm. |
| Ik-25 | $^1$H-NMR (400 MHz, d$_3$-acetonitrile): δ = 9.23 (bs, 1H), 7.92 (d, 1H), 7.76 (dd, 1H), 7.25 (d, 1H), 7.08 (bs, 1H), 6.78 (t, 1H), 3.98 (s, 3H), 2.81-2.86 (m, 1H), 0.74-0.79 (m, 2H), 0.55-0.60 (m, 2H) ppm. |
| Ik-253 | $^1$H-NMR (400 MHz, d$_6$-DMF): δ = 10.92 (s, 1H), 9.16 (t, 1H), 8.16 (d, 2H), 8.04 (m, 1H), 7.95 (m, 3H), 7.61 (d, 1H), 4.26 (m, 2H), 4.14 (s, 3H) ppm. |
| Ik-257 | $^1$H-NMR (400 MHz, d$_6$-DMSO): δ = 10.69 (s, 1H), 9.00 (m, 1H), 7.79 (m, 1H), 7.75 (m, 1H), 7.51 (d, 1H), 4.88 (m, 2H), 4.06 (m, 2H), 3.81 (s, 3H) ppm. |
| Ik-258 | $^1$H-NMR (400 MHz, d$_6$-DMSO): δ = 11.24 (s, 1H), 9.03 (m, 1H), 8.23 (s, 1H), 8.17 (s, 2H), 7.77 (m, 2H), 7.55 (d, 1H), 4.08 (m, 2H), 4.01 (s, 3H) ppm. |
| Ik-259 | $^1$H-NMR (400 MHz, d$_6$-DMSO): δ = 11.18 (s, 1H), 8.34 (m, 1H), 8.22 (s, 1H), 8.18 (s, 2H), 7.70 (m, 2H), 7.49 (d, 1H), 2.84 (m, 1H), 0.70 (m, 2H), 0.55 (m, 2H) ppm. |
| Ik-260 | $^1$H-NMR (400 MHz, d$_6$-DMSO): δ = 10.39 (s, 1H), 8.28 (m, 1H), 7.70 (m, 2H), 7.44 (m, 1H), 4.87 (m, 2H), 3.53 (s, 3H), 2.82 (m, 1H), 0.70 (m, 2H), 0.54 (m, 2H) ppm. |
| Ik-261 | $^1$H-NMR (400 MHz, d$_6$-DMSO): δ = 10.97 (s, 1H), 8.31 (m, 1H), 7.67 (m, 2H), 7.47 (d, 1H), 3.76 (s, 3H), 2.82 (m, 1H), 1.92 (m, 1H), 0.94 (m, 2H), 0.85 (m, 2H), 0.69 (m, 2H), 0.54 (m, 2H) ppm. |
| Ik-262 | (d$_3$-acetonitrile) 0.52 (m, 2H), 0.75 (m, 2H), 2.83 (m, 2H), 4.04 (s, 3H), 4.46 (m, 2H), 5.20 (m, 1H), 5.90 (m, 2H), 7.3-7.5 (m, 2H), 7.67-7.76 (m, 1H), 9.0 (brs, 1H). |
| Ik-263 | (d$_6$-DMSO) 0.45 (m, 2H), 0.70 (m, 2H), 1.10 (t, 3H), 2.67 (m, 2H), 2.85 (m, 1H) 3.96 (s, 3H), 7.42 (m, 1H), 7.55 (m, 1H), 7.80 (m, 1H), 8.10 (s, 1H), 8.26 (br. s, 1H). |
| Ik-264 | (d$_6$-DMSO) 0.46 (m, 2H), 0.72 (m, 2H), 2.87 (m, 1H) 4.17 (s, 3H), 7.44 (m, 1H), 7.55 (m, 1H), 7.77 (m, 1H), 8.30 (br. s, 1H). |
| Ik-265 | (d$_6$-DMSO) 0.47 (m, 2H), 0.73 (m, 2H), 2.83 (m, 1H) 4.19 (s, 3H), 7.46 (m, 1H), 7.52 (s, 1H), 7.77 (m, 1H), 8.30 (br. s, 1H). |
| Ik-269 | (d$_6$-DMSO) 3.93 (m, 2H) 4.03 (s, 3H), 6.01 (m, 1H), 6.40 (m, 1H), 7.50 (m, 1H), 7.70 (m, 1H), 7.78 (m, 1H), 8.59 (m, 1H). |
| Ik-270 | $^1$H-NMR (d$_3$-d$_3$-acetonitrile) 9.25 (s, 1H, br), 8.50 (s, 1H, br), 7.80 (m, 1H), 7.72 (d, 1H), 7.65 (m, 1H), 7.50 (m, 1H), 7.40-7.25 (m, 3H), 5.15 (m, 1H), 3.98 (s, 3H), 1.50 (d, 3H) ppm. |
| Ik-272 | $^1$H-NMR (d$_6$-DMSO) 10.94 (s, 1H), 9.00 (t, 1H), 7.81 (d, 1H), 7.77 (dd, 1H), 7.52 (d, 1H), 7.30 (m, 4H), 7.25 (m, 1H), 4.46 (d, 2H), 3.96 (s, 3H), 2.65 (q, 2H), 1.09 (t, 3H) ppm. |
| Ik-273 | $^1$H-NMR (d$_6$-DMSO) 11.46 (s, 1H), 9.52 (t, 1H), 8.46 (s, 1H), 7.73 (d, 1H), 7.70 (dd, 1H), 7.59 (d, 1H), 4.78 (d, 2H), 4.03 (s, 3H) ppm. |

TABLE 9-continued

| Ex. No. | NMR data |
|---|---|
| Ik-276 | $^1$H-NMR (d$_6$-DMSO) 11.43 (s, 1H), 9.96 (d, 1H), 7.94 (s, 1H), 7.78 (dd, 1H), 7.69 (d, 1H), 7.55 (d, 1H), 6.40 (m, 1H), 4.03 (s, 3H), 3.76 (s, 3H) ppm. |
| Ik-278 | $^1$H-NMR (d$_6$-DMSO) 11.44 (s, 1H), 9.23 (d, 1H), 7.79 (d, 1H), 7.70 (dd, 1H), 7.56 (d, 1H), 7.24 (dd, 1H), 6.90 (dd, 1H), 5.30 (m, 1H), 4.02 (s, 3H), 3.80 (dd, 1H), 3.15 (dd, 1H) ppm. |
| Ik-279 | $^1$H-NMR (d$_3$-d$_3$-acetonitrile) 9.28 (s, 1H, br), 7.72 (d, 1H), 7.65 (dd, 1H), 7.46 (d, 1H), 6.82 (s, 1H, br), 3.98 (s, 3H), 2.84 (m, 1H), 1.09 (d, 3H), 1.05 (m, 1H), 0.95 (m, 1H), 0.25 (m, 1H) ppm. |
| Ik-280 | $^1$H-NMR (d$_3$-d$_3$-acetonitrile) 9.27 (s, 1H, br), 7.68 (d, 1H), 7.64 (dd, 1H), 7.44 (d, 1H), 6.90 (s, 1H, br), 3.97 (s, 3H), 2.50 (m, 1H), 1.09 (d, 3H), 0.95 (m, 1H), 0.75 (m, 1H), 0.55 (m, 1H) ppm. |
| Ik-281 | $^1$H-NMR (d$_6$-DMSO) 11.43 (s, 1H), 8.60 (t, 1H), 7.73 (d, 1H), 7.67 (dd, 1H), 7.54 (d, 1H), 4.10 (q, 2H, J(H, F) = 9 Hz), 4.02 (s, 3H), 3.70 (t, 2H), 3.40 (m, 2H) ppm. |
| Ik-285 | $^1$H-NMR (d$_6$-DMSO) 11.40 (s, 1H), 8.49 (d, 1H), 7.70 (m, 2H), 7.52 (d, 1H), 4.02 (s, 3H), 3.95 (m, 1H), 3.82 (m, 4H), 1.75 (m, 2H), 1.50 (m, 2H) ppm. |
| Ik-287 | $^1$H-NMR (d$_6$-DMSO) 11.39 (s, 1H), 8.66 (d, 1H), 7.70-7.50 (m, 2H), 7.52 (d, 1H), 5.70 (s, 2H), 4.50 (m, 1H), 4.02 (s, 3H), 2.70 (m, 2H), 2.28 (m, 2H) ppm. |
| Ik-288 | $^1$H-NMR (d$_6$-DMSO) 11.41 (s, 1H), 8.62 (d, 1H), 7.72 (dd, 1H), 7.66 (d, 1H), 7.54 (d, 1H), 4.02 (s, 3H), 4.00 (m, 1H), 1.30 (d, 3H), 1.20 (m, 1H), 1.10-1.00 (m, 3H) ppm. |
| Ik-289 | $^1$H-NMR (d$_6$-DMSO) 11.39 (s, 1H), 8.20 (s, 1H), 7.72 (dd, 1H), 7.64 (d, 1H), 7.50 (d, 1H), 4.03 (s, 3H), 2.12 (s, 2H), 1.36 (s, 3H) ppm. |
| Ik-293 | $^1$H-NMR (d$_3$-d$_3$-acetonitrile) 9.30 (s, 1H, br), 7.72 (d, 1H), 7.65 (dd, 1H), 7.47 (d, 1H), 7.23 (d, 1H, br), 4.86 (m, 1H), 3.98 (s, 3H), 2.57 (s, 1H), 1.46 (d, 3H) ppm. |
| Ik-299 | $^1$H-NMR (d$_6$-DMSO) 11.44 (s, 1H), 8.62 (d, 1H), 7.74 (dd, 1H), 7.66 (d, 1H), 7.55 (d, 1H), 4.30 (m, 1H), 4.02 (s, 3H), 3.40 (m, 2H), 1.24 (d, 3H) ppm. |
| Ik-300 | $^1$H-NMR (d$_6$-DMSO) 11.39 (s, 1H), 8.40 (s, 1H), 7.73 (dd, 1H), 7.60 (d, 1H), 7.51 (d, 1H), 4.02 (s, 3H), 3.95 (q, 2H, J(H, F) = 13 Hz), 1.42 (s, 6H) ppm. |
| Ik-311 | $^1$H-NMR (d$_6$-DMSO) 8.49 (1H, d, J = 4 Hz, NH), 7.70 (1H, dd, J = 8, 2.5 Hz), 7.68 (1H, s), 7.50 (1H, d, J = 8 Hz), 4.7 (1H, ddd, J = 62, 4.4 Hz), 4.00 (3H, s), 2.85 (1H, m), 1.15 (1H, m), 1.05 (1H, m) ppm. |
| Ik-342 | $^1$H-NMR (d$_6$-DMSO) 11.41 (s, 1H), 8.55 (d, 1H), 7.86 (d, 1H), 7.80 (m, 2H), 7.65 (m, 1H), 7.54 (d, 1H), 7.38 (d, 1H), 7.30 (t, 1h), 4.75 (s, 2H, br), 4.04 (s, 3H), 2.70 (m, 1H), 0.65 (m, 2H), 0.45 (m, 2H) ppm. |
| Ik-345 | $^1$H-NMR (d$_6$-DMSO) 11.43 (s, 1H), 7.75-7.70 (m, 2H), 7.55 (m, 1H), 4.60 (m, 1H), 4.03 (s, 3H), 2.85 (m, 1H), 2.65 (m, 1H), 1.95 (m, 1H), 1.80 (m, 1H), 1.50-1.30 (m, 4H) ppm. |
| Ik-347 | $^1$H-NMR (400 MHz, d$_6$-DMSO): δ = 8.17 (m, 1H), 7.28 (m, 1H), 7.04 (m, 2H), 4.15 (s, 3H), 2.77 (m, 1H), 0.67 (m 2H), 0.49 (m, 2H) ppm. |
| Ik-348 | $^1$H-NMR (400 MHz, d$_6$-DMSO): δ = 8.40 (s, 1H), 8.10 (m, 1H), 7.42 (d, 1H), 7.15 (m, 1H), 7.11 (m, 1H), 4.18 (s, 3H), 3.48 (m, 1H), 1.17 (d, 3H), 0.90 (m, 1H), 0.43 (m, 1H), 0.33 (m, 2H), 0.22 (m, 1H) ppm. |
| Il-1 | $^1$H-NMR (400 MHz, d$_6$-DMSO): δ = 11.05 (br. m, 1H), 8.33 (br. d, 1H), 7.63-7.67 (m, 2H), 7.48 (d, 1H), 2.80-2.86 (m, 1H), 0.69-0.72 (m, 2H), 0.53-0.55 (m, 2H) ppm. |
| Ir-2 | $^1$H-NMR (400 MHz, d$_6$-DMSO): δ = 10.60 (s, 1H), 8.29 (d, 1H), 8.14 (d, 1H), 7.83 (d, 1H), 7.75-7.70 (m, 2H), 7.44 (d, 1H), 2.86-2.81 (m, 1H), 2.63 (s, 3H), 0.72-0.67 (m, 2H), 0.55-0.52 (m, 2H) ppm. |
| Ir-10 | $^1$H-NMR (400 MHz, d$_6$-DMSO): δ = 10.79 (s, 1H), 8.58-8.54 (m, 1H), 8.37 (d, 1H), 8.08 (d, 1H), 7.78-7.76 (m, 1H), 7.72-7.68 (m, 1H), 7.49 (d, 1H), 6.43-6.37 (m, 1H), 6.06-5.96 (m, 1H), 4.06-4.01 (m, 1H), 3.92-3.89 (m, 1H) ppm. |
| Ir-11 | $^1$H-NMR (400 MHz, d$_6$-DMSO): δ = 10.66 (s, 1H), 8.99 (m, 1H), 8.15 (d, 1H), 7.85-7.77 (m, 3H), 7.50 (d, 1H), 4.10-4.01 (m, 1H), 2.64 (s, 3H) ppm. |

Preparation of the Starting Compounds

Ethyl 4-(difluoromethyl)-2-(pentafluoroethyl)pyrimidine-5-carboxylate

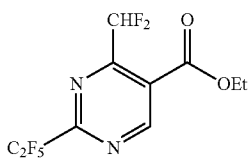

A mixture of 1.620 g (10 mmol) of 2,2,3,3,3-pentafluoropropanimidamide (commercially available) and 2.222 g (10 mmol) of ethyl (2Z)-2-(ethoxymethylidene)-4,4-difluoro-3-oxobutanoate (for preparation see WO 2005/123690) in 10 ml of absolute ethanol is stirred under reflux for 4 days after adding 0.680 g (10 mmol) of sodium methylate. The mixture is then concentrated by evaporation in vacuo and the residue is taken up in 10 ml of water and extracted twice with 10 ml of ethyl acetate. The organic phases are washed successively with 5 ml of water and 5 ml of saturated sodium chloride solution, dried over sodium sulphate, filtered and concentrated by evaporation in vacuo. Chromatographic purification with a mixture of cyclohexane and ethyl acetate gives 1.264 g (3.95 mM, 39.5% of theory) of ethyl 4-(difluoromethyl)-2-(pentafluoroethyl)pyrimidine-5-carboxylate as a white solid.

$^1$H-NMR (400 MHz, d$_6$-DMSO): δ=9.58 (s, 1H), 7.49 (t, 1H), 4.45 (q, 2H), 1.38 (t, 3H) ppm.

HPLC-MS$^{a)}$: log P=3.42 mass (m/z)=321 [M+H]$^+$.

The following were obtained in the same way:

Ethyl 2-(pentafluoroethyl)-4-(trifluoromethyl)pyrimidine-5-carboxylate from ethyl 2-(ethoxymethylidene)-4,4,4-trifluoro-3-oxobutanoate (commercially available) and 2,2,3,3,3-pentafluoropropanimidamide

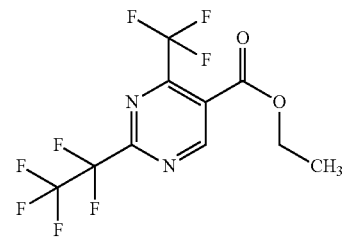 [SMILES: CCOC(=O)c1cnc(C(F)(F)C(F)(F)F)nc1C(F)(F)F]

¹H-NMR (400 MHz, d₆-DMSO): δ=9.66 (s, 1H), 4.45 (q, 2H), 1.36 (t, 3H) ppm.
HPLC-MS$^{a)}$: log P=3.86 mass (m/z)=339 [M+H]⁺.

Ethyl 2-(heptafluoropropyl)-4-(trifluoromethyl)pyrimidine-5-carboxylate from ethyl 2-(ethoxymethylidene)-4,4,4-trifluoro-3-oxobutanoate (commercially available) and 2,2,3,3,4,4,4-heptafluorobutanimidamide (commercially available or for preparation see Journal of Fluorine Chemistry, 2003, 122(2), 175-182)

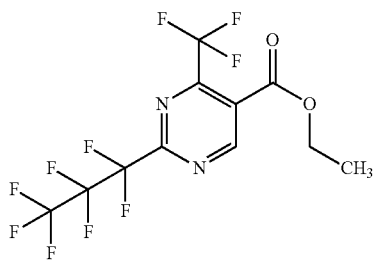 [SMILES: CCOC(=O)c1cnc(C(F)(F)C(F)(F)C(F)(F)F)nc1C(F)(F)F]

¹H-NMR (400 MHz, d₆-DMSO): δ=9.68 (s, 1H), 4.46 (q, 2H), 1.36 (t, 3H) ppm.
HPLC-MS$^{a)}$: log P=4.32 mass (m/z)=389 [M+H]⁺.

Ethyl 4,6-dimethyl-2-(pentafluoroethyl)pyrimidine-5-carboxylate from ethyl (2E)-2-acetyl-3-ethoxybut-2-enoate (for preparation see J. Med. Chem. 2006, 49, 6351) and 2,2,3,3,3-pentafluoropropanimidamide

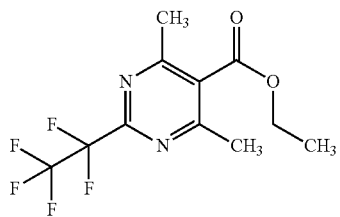 [SMILES: CCOC(=O)c1c(C)nc(C(F)(F)C(F)(F)F)nc1C]

¹H-NMR (400 MHz, d₆-DMSO): δ=4.46 (q, 2H), 3.1 (s, 6H), 1.36 (t, 3H) ppm.
HPLC-MS$^{a)}$: log P=3.68 mass (m/z)=299 [M+H]⁺.

Ethyl 4-methyl-2-(trifluoromethyl)pyrimidine-5-carboxylate is commercially available Ethyl 4-methyl-2-(pentafluoroethyl)pyrimidine-5-carboxylate can be synthesized analogously to the procedure Bioorg. Med. Chem. Letters, 2005, 15, 4898.

4-(Difluoromethyl)-2-(pentafluoroethyl)pyrimidine-5-carboxylic acid

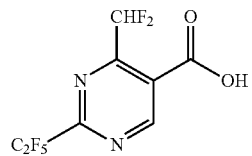

1.150 g (3.59 mM) of ethyl 4-(difluoromethyl)-2-(pentafluoroethyl)pyridimine-5-carboxylate are dissolved in 4 ml of absolute ethanol. 5.388 ml (10.77 mM) of 2N sodium hydroxide solution are added and the reaction mixture is stirred for 4 h at room temperature.

2N hydrochloric acid is added to adjust the pH to 2-3. The resulting solid is filtered off with suction, washed with a small amount of water and titrated with cyclohexane. This gives 0.870 g (2.98 mM, 82.9% of theory) of 4-(difluoromethyl)-2-(pentafluoroethyl)pyrimidine-5-carboxylic acid as white solid.

¹H-NMR (400 MHz, d₆-DMSO): δ=9.55 (s, 1H), 7.58 (t, 1H) ppm.
HPLC-MS$^{a)}$: log P=1.80 mass (m/z)=293 [M+H]⁺.

The following were obtained in the same way:

2-(Pentafluoroethyl)-4-(trifluoromethyl)pyrimidine-5-carboxylic acid from ethyl 2-(pentafluoroethyl)-4-(trifluoromethyl)pyrimidine-5-carboxylate

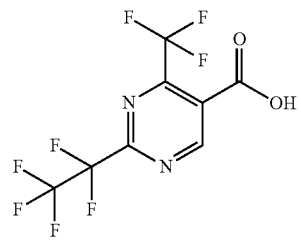 [SMILES: O=C(O)c1cnc(C(F)(F)C(F)(F)F)nc1C(F)(F)F]

¹H-NMR (400 MHz, d₆-DMSO): δ=9.40 (s, 1H) ppm.
HPLC-MS$^{a)}$: log P=1.80 mass (m/z)=311 [M+H]⁺.

2-(Heptafluoropropyl)-4-(trifluoromethyl)pyrimidine-5-carboxylic acid from ethyl 2-(heptafluoropropyl)-4-(trifluoromethyl)pyrimidine-5-carboxylate

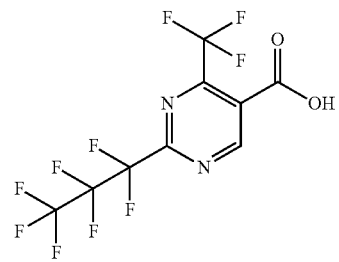

¹H-NMR (400 MHz, d₆-DMSO): δ=9.50 (s, 1H) ppm.
HPLC-MS$^{a)}$: log P=2.23 mass (m/z)=361 [M+H]⁺.

4-methyl-2-(trifluoromethyl)pyrimidine-5-carboxylic acid from ethyl 4-methyl-2-(trifluoromethyl)pyrimidine-5-carboxylate

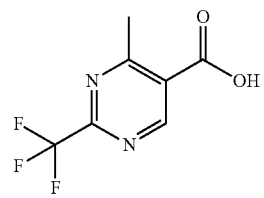

¹H-NMR (400 MHz, d₆-DMSO): δ=9.19 (s, 1H) ppm.
HPLC-MS$^{a)}$: log P=1.26 mass (m/z)=207 [M+H]⁺.

4-Methyl-2-(pentafluoroethyl)pyrimidine-5-carboxylic acid from ethyl 4-methyl-2-(pentafluoroethyl)pyrimidine-5-carboxylate

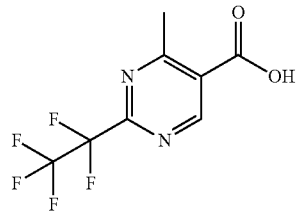 [SMILES: Cc1nc(C(F)(F)C(F)(F)F)ncc1C(=O)O]

$^1$H-NMR (400 MHz, d$_6$-DMSO): δ=9.25 (s, 1H) ppm.
HPLC-MS$^{a)}$: log P=1.97 mass (m/z)=257 [M+H]$^+$.

4,6-Dimethyl-2-(pentafluoroethyl)pyrimidine-5-carboxylic acid from ethyl 4,6-dimethyl-2-(pentafluoroethyl)pyrimidine-5-carboxylate

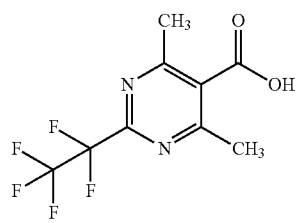 [SMILES: Cc1nc(C(F)(F)C(F)(F)F)nc(C)c1C(=O)O]

$^1$H-NMR (400 MHz, d$_6$-DMSO): δ=2.58 (s, 6H) ppm.
HPLC-MS$^{a)}$: log P=1.63 mass (m/z)=271 [M+H]$^+$.

4-Chloro-3-(trifluoromethyl)pyridine-2-carboxylic acid from 4-chloro-3-(trifluoromethyl)pyridine was prepared analogously to the literature source European Journal of Organic Chemistry 2004, 18, 3793 from 4-chloro-3-(trifluoromethyl)pyridine

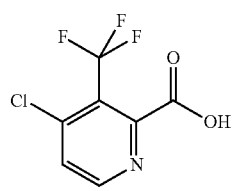 [SMILES: O=C(O)c1nccc(Cl)c1C(F)(F)F]

$^1$H-NMR (400 MHz, d$_6$-DMSO): δ=9.13 (d, 1H), 9.07 (d, 1H) ppm.
HPLC-MS: log P=1.16 mass (m/z)=226 [M+H]$^+$.

5-Cyano-1-methyl-3-pentafluoroethyl-4-trifluoromethyl-1H-pyrazole

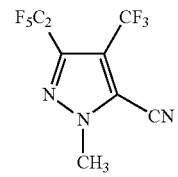

42.0 g (146.8 mM) of 5-fluoro-1-methyl-3-pentafluoroethyl-4-trifluoromethylpyrazole [for synthesis see Izvestiya Akademii Nauk SSSR, Seriya Khimicheskaya 1990, (11), 2583-9] and 11.5 g (234.9 mM) of sodium cyanide are suspended in 150 ml of acetonitrile p.A. and then heated under reflux temperature under a protective gas atmosphere. After cooling, the reaction mixture is poured onto a mixture of 300 ml of distilled water and 300 ml of diethyl ether. The aqueous phase is extracted three times with diethyl ether. The combined organic phases are washed twice with water and once with saturated aqueous sodium chloride solution. The organic phase is dried over sodium sulphate and then filtered. The solvent is removed under reduced pressure on a rotary evaporator and the resulting residue is subjected to fractional distillation in vacuo.

This gives 37.0 g (119.9 mM, 82% of theory) of 5-cyano-1-methyl-3-pentafluoroethyl-4-trifluoromethylpyrazole as colourless liquid (b.p. 74° C./10 mbar).

$^1$H-NMR (400 MHz, d$_3$-acetonitrile): δ=4.11 (s, 3H, CH$_3$) ppm

GC-MS: Retention time 2.67 min; mass (m/z): 224 (M)$^+$.

1-Methyl-3-pentafluoroethyl-4-trifluoromethyl-1H-pyrazole-5-carboxylic acid

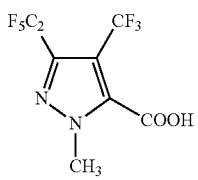

11.0 g (37.5 mM) of 5-cyano-1-methyl-3-pentafluoroethyl-4-trifluoromethylpyrazole, 22.0 ml of 50% strength sodium hydroxide solution and 7.0 ml of distilled water are heated in an oil bath until the solid has melted. The reaction mixture is then stirred overnight (oil bath temperature 100° C.). After cooling, the reaction mixture is poured onto a mixture of 150 ml of concentrated hydrochloric acid and 150 ml of ice. It is afterstirred for 0.5 h and the solid is filtered off. The solid is washed with a small amount of water and then dried in an oil pump vacuum.

This gives 11.2 g (35.7 mM, 95% of theory) of 1-methyl-3-pentafluoroethyl-4-trifluoromethylpyrazole-5-carboxylic acid as a white solid.

$^1$H-NMR (400 MHz, d$_3$-acetonitrile) δ=4.08 (s, 3H, CH$_3$) ppm;

HPLC-MS$^{a)}$: log P=1.86; mass (m/z): 313.0 (M+H)$^+$.

1-Methyl-3-pentafluoroethyl-1H-pyrazole

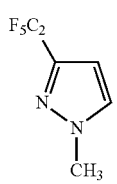

7.18 g (155.83 mmol) of methylhydrazine are added dropwise to a solution of 30.90 g (141.67 mmol) of (E)-5-ethoxy-1,1,1,2,2-pentafluoropent-4-en-3-one (preparation: Synthesis 2000, 5, 738-42) in 56 ml of methanol and the reaction mixture is heated under reflux for 18 hours. The majority of the methanol is distilled off at atmospheric pressure and the residue is added to ice. The aqueous phase is extracted three times with dichloromethane and the organic phase is then washed three times with saturated sodium chloride solution. After drying over sodium sulphate, the solvent is distilled off at reduced pressure on a rotary evaporator. This gives 15.81 g (52% of theory) of 1-methyl-3-pentafluoroethyl-1H-pyrazole as an oil.

$^1$H-NMR (400 MHz, d$_3$-acetonitrile) δ=3.89 (s, 3H, CH$_3$), 6.57 (m, 1H, CH), 7.61 (m, 1H, CH) ppm;

HPLC-MS$^{a)}$: log P=2.29; Mass (m/z): 201 (M+H)$^+$.

The following were obtained in the same way:

1-Methyl-3-(1-chloro-1,2,2,2-tetrafluoroethyl-1H-pyrazole from (E)-5-ethoxy-1-(1-chloro-1,1,2,2-tetrafluoropent-4-en-3-one

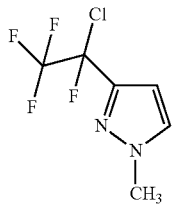

$^1$H-NMR (400 MHz, d$_3$-acetonitrile) δ=3.89 (s, 3H, CH$_3$), 6.54 (m, 1H, CH), 7.58 (m, 1H, CH) ppm;

HPLC-MS$^{a)}$: log P=2.46; mass (m/z): 217 (M+H)$^+$.

1-Methyl-3-heptafluoropropyl-1H-pyrazole from (E)-5-ethoxy-1,1,1,2,2,3,3-heptafluorohex-4-en-3-one

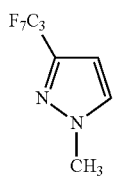

$^1$H-NMR (400 MHz, d$_3$-acetonitrile) δ=3.94 (s, 3H, CH$_3$), 6.65 (m, 1H, CH), 7.91 (m, 1H, CH) ppm;

HPLC-MS$^{a)}$: log P=2.84; mass (m/z): 251 (M+H)$^+$.

1-Methyl-3-nonafluorobutyl-1H-pyrazole from (E)-5-ethoxy-1,1,1,2,2,3,3,4,4-nonafluorohept-4-en-3-one

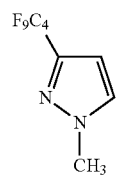

$^1$H-NMR (400 MHz, d$_3$-acetonitrile) δ=3.97 (s, 3H, CH$_3$), 6.57 (m, 1H, CH), 7.61 (m, 1H, CH) ppm;

HPLC-MS$^{a)}$: log P=3.38; mass (m/z): 301 (M+H)$^+$.

3-{[difluoro(trifluoromethoxy)methoxy](difluoro)methyl}-1-methyl-1H-pyrazole from (E)-5-ethoxy-3-{[difluoro(trifluoromethoxy)methoxy](difluoro)methyl}-4-en-3-one

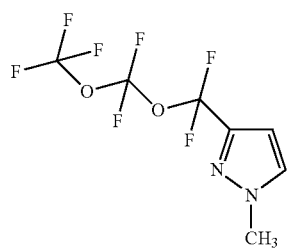 [SMILES: Cn1ccc(C(F)(F)OC(F)(F)OC(F)(F)F)n1]

$^1$H-NMR (400 MHz, d$_3$-acetonitrile) δ=3.90 (s, 3H, CH$_3$), 6.54 (m, 1H, CH), 7.58 (m, 1H, CH) ppm;

HPLC-MS$^{a)}$: log P=3.79; mass (m/z): 333 (M+H)$^+$.

4-Bromo-1-methyl-3-heptafluoropropyl-1H-pyrazole

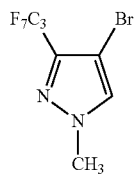

At 40° C., 3.27 g (20.45 mmol) of bromine are added dropwise to a solution of 4.65 g (18.59 mmol) of 1-methyl-3-heptafluoropropyl-1H-pyrazole in 18 ml of water and the reaction mixture is afterstirred firstly at 60° C. for 1 hour and then at room temperature for 18 hours. The aqueous phase is extracted three times with dichloromethane and the organic phase is dried over sodium sulphate. The dichloromethane is distilled off at reduced pressure on a rotary evaporator. This gives 5.75 g (77.85% of theory) of 1-methyl-3-heptafluoropropyl-4-bromo-1H-pyrazole as an oil.

$^1$H-NMR (400 MHz, d$_3$-acetonitrile) δ=3.90 (s, 3H, CH$_3$), 7.73 (m, 1H, CH) ppm;

HPLC-MS$^{a)}$: mass (m/z): 330 (M+H)$^+$.

The following were obtained in the same way:

4-Bromo-1-methyl-3-pentafluoroethyl-1H-pyrazole from 1-methyl-3-pentafluoroethyl-1H-pyrazole

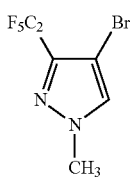

$^1$H-NMR (400 MHz, $d_3$-acetonitrile) δ=3.90 (s, 3H, CH$_3$), 7.77 (m, 1H, CH) ppm;
HPLC-MS$^{a)}$: log P=2.99; mass (m/z): 280 (M+H)$^+$.

4-Bromo-1-methyl-3-(1-chloro-1,2,2,2-tetrafluoroethyl-1H-pyrazole from 1-methyl-3-(1-chloro-1,2,2,2-tetrafluoroethyl-1H-pyrazole

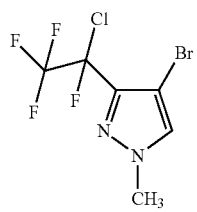

$^1$H-NMR (400 MHz, $d_3$-acetonitrile) δ=3.89 (s, 3H, CH$_3$), 7.75 (m, 1H, CH) ppm;
HPLC-MS$^{a)}$: log P=3.17; mass (m/z): 296 (M+H)$^+$.

1-Methyl-3-pentafluoroethyl-1H-pyrazole-5-carboxylic acid

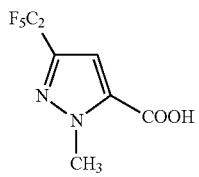

Under an argon atmosphere, 5.00 g (24.99 mmol) of 1-methyl-3-pentafluoroethyl-1H-pyrazole are initially introduced in diethyl ether and the solution is cooled to −78° C. 11.09 ml (27.73 mmol) of 2M lithium diisopropylamide solution in THF/heptane are added dropwise and, at −30° C. with vigorous stirring, 450 g of crushed dry ice are added. When the evolution of gas has finished, the reaction mixture is admixed with 235 ml of water and adjusted to a pH of 11 with 1N sodium hydroxide solution. The alkaline solution is extracted three times with ethyl acetate and then adjusted to pH 2 with 1N hydrochloric acid. The aqueous phase is extracted three times with ethyl acetate and the organic phase is dried over sodium sulphate. Distilling off the solvent on a rotary evaporator under reduced pressure gives 1.20 g (17.75% of theory) of 1-methyl-3-pentafluoroethyl-1H-pyrazole-5-carboxylic acid as a solid.

$^1$H-NMR (400 MHz, $d_3$-acetonitrile) δ=4.16 (s, 3H, CH$_3$), 7.14 (m, 1H, CH) ppm;
HPLC-MS$^{a)}$: log P=2.08; mass (m/z): 245 (M+H)$^+$.

The following were obtained in the same way:

4-Bromo-1-methyl-3-pentafluoroethyl-1H-pyrazole-5-carboxylic acid from 4-bromo-1-methyl-3-pentafluoroethyl-1H-pyrazole

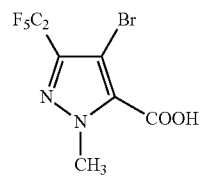

$^1$H-NMR (400 MHz, $d_3$-acetonitrile) δ=4.15 (s, 3H, CH$_3$), ppm;
HPLC-MS$^{a)}$: log P=4.69; mass (m/z): 324 (M+H)$^+$.

4-Bromo-1-methyl-3-heptafluoropropyl-1H-pyrazole-5-carboxylic acid from 4-bromo-1-methyl-3-heptafluoropropyl-1H-pyrazole

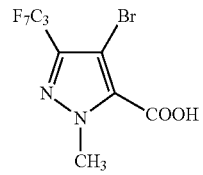

$^1$H-NMR (400 MHz, $d_3$-acetonitrile) δ=4.15 (s, 3H, CH$_3$), ppm;
HPLC-MS$^{a)}$: log P=2.26; mass (m/z): 374 (M+H)$^+$.

4-Bromo-1-methyl-3-(1-chloro-1,2,2,2-tetrafluoroethyl)-1H-pyrazole-5-carboxylic acid from 4-bromo-1-methyl-3-(1-chloro-1,2,2,2-tetrafluoroethyl-1H-pyrazole

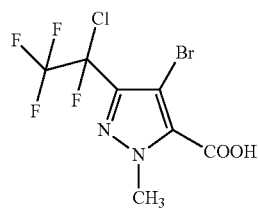

$^1$H-NMR (400 MHz, $d_3$-acetonitrile) δ=4.14 (s, 3H, CH$_3$), ppm;
HPLC-MS$^{a)}$: log P=2.43; mass (m/z): 340 (M+H)$^+$.

1-Methyl-3-nonafluorobutyl-1H-pyrazole-5-carboxylic acid from 1-methyl-3-nonafluorobutyl-1H-pyrazole

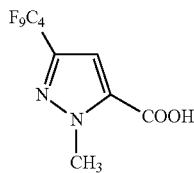

$^1$H-NMR (400 MHz, d$_3$-acetonitrile) δ=4.17 (s, 3H, CH$_3$), 7.14 (m, 1H, CH) ppm;
HPLC-MS$^{a)}$: log P=3.01; mass (m/z): 345 (M+H)$^+$.

3-{[Difluoro(trifluoromethoxy)methoxy](difluoro)methyl}-1-methyl-1H-pyrazole-5-carboxylic acid from 3-{[difluoro(trifluoromethoxy)methoxy](difluoro)methyl}-1-methyl-1H-pyrazole

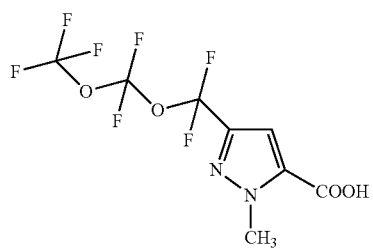 [SMILES: Cn1nc(C(F)(F)OC(F)(F)OC(F)(F)F)cc1C(=O)O]

$^1$H-NMR (400 MHz, d$_3$-acetonitrile) δ=4.16 (s, 3H, CH$_3$), 7.11 (m, 1H, CH) ppm;
HPLC-MS$^{a)}$: log P=3.38; mass (m/z): 377 (M+H)$^+$.

4-Bromo-1-methyl-3-nonafluorobutyl-1H-pyrazole-5-carboxylic acid

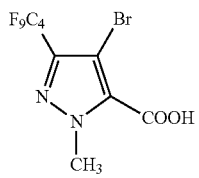

At 40° C., 0.255 g (1.60 mmol) of bromine is added dropwise to a solution of 0.50 g (1.45 mmol) of 1-methyl-3-nonafluorobutyl-1H-pyrazole in 3.5 ml of water and the reaction mixture is afterstirred firstly at 60° C. for 1 hour and then at room temperature for 3 days. The aqueous phase is extracted three times with dichloromethane and the organic phase is dried over sodium sulphate. The dichloromethane is distilled off at reduced pressure on a rotary evaporator. This gives 0.54 g (80.12% of theory) of 4-bromo-1-methyl-3-nonafluorobutyl-1H-pyrazolecarboxylic acid as an oil.

$^1$H-NMR (400 MHz, d$_3$-acetonitrile) δ=4.16 (s, 3H, CH$_3$), ppm;
HPLC-MS$^{a)}$: log P=3.17; mass (m/z): 424 (M+H)$^+$.

The following were obtained in the same way:

4-Bromo-3-{[difluoro(trifluoromethoxy)methoxy](difluoro)methyl}-1-methyl-1H-pyrazole-5-carboxylic acid from 3-{[difluoro(trifluoromethoxy)methoxy](difluoro)methyl}-1-methyl-1H-pyrazole-5-carboxylic acid

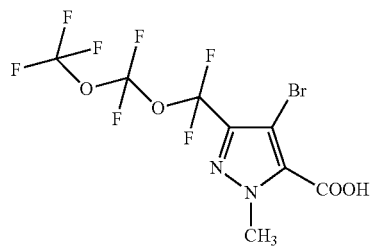 [SMILES: Cn1nc(C(F)(F)OC(F)(F)OC(F)(F)F)c(Br)c1C(=O)O]

$^1$H-NMR (400 MHz, d$_3$-acetonitrile) δ=4.14 (s, 3H, CH$_3$), ppm;
HPLC-MS$^{a)}$: log P=3.56; mass (m/z): 456 (M+H)$^+$.

1-Methyl-3-pentafluoroethyl-4-iodo-1H-pyrazole-5-carboxylic acid

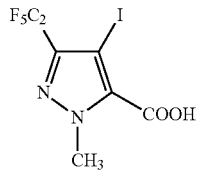

1.34 g (2.46 mmol) of ammonium cerium(IV) nitrate and then 0.75 g (2.95 mmol) of iodine are added to a solution of 1.20 g (4.91 mmol) of 1-methyl-3-pentafluoroethyl-1H-pyrazole in 4.3 ml of acetonitrile and the reaction mixture is heated under reflux for 18 hours. After adding 20 ml of dichloromethane, the mixture is washed firstly with water, with sodium disulphite solution and finally with saturated sodium chloride solution. The organic phase is dried over sodium sulphate and the solvent is distilled off at reduced pressure on a rotary evaporator. This gives 1.28 g (47% of theory) of 4-iodo-1-methyl-3-pentafluoroethyl-1H-pyrazolecarboxylic acid as an oil.

$^1$H-NMR (400 MHz, d$_3$-acetonitrile) δ=4.16 (s, 3H, CH$_3$), ppm;
HPLC-MS: log P=2.33; mass (m/z): 371 (M+H)$^+$.

BIOLOGICAL EXAMPLES

The effectiveness of the compounds according to the invention in respect of animal pests is illustrated by the following biological examples.

Example A

Phaedon Test

PHAECO Spray Treatment

| Solvents: | 78.0 parts by weight of acetone |
| --- | --- |
|  | 1.5 parts by weight of dimethylformamide |
| Emulsifier: | 0.5 part by weight of alkylaryl polyglycol ether |

To produce a suitable active ingredient preparation, part by weight of active ingredient is mixed with the stated amounts of solvents and emulsifier, and the concentrate is diluted to the desired concentration with emulsifier-containing water.

Discs of Chinese cabbage leaves (*Brassica pekinensis*) are sprayed with an active ingredient preparation of the desired concentration and, after drying, populated with larvae of the mustard beetle (*Phaedon cochleariae*).

After the desired time, the effect in % is determined. Here, 100% means that all of the beetle larvae have been killed; 0% means that no beetle larvae have been killed.

In this test, for example, the following compounds of the preparation examples exhibit, at an application rate of 500 g/ha, an effect of ≥80%:
Ex. No.: lak-93, lak-90, lak-1, lak-92, lak-89, lak-88, lak-87, lak-86, lak-85, lak-84, lak-83, lak-82, lak-81, lak-79, lak-80, lak-74, lak-75, lak-76, lak-77, lak-73, lar-2, lai-1, lai-4, lak-69, lae-1, lae-4, lak-35, lak-36, lak-37, lak-38, lak-39, lak-40, lak-41, lak-42, lak-43, lak-44, lak-45, lak-46, lak-47, lak-48, lak-49, lak-50, lak-51, lak-52, lak-53, lak-54, lak-55, lak-57, lak-3, lak-59, lak-60, lak-61, lak-62, lak-63, lak-64, lak-65, lak-66, lak-67, lak-68, lak-31, lak-30, lak-26, lak-27, lak-28, lab-1, lar-9, lar-10, lak-25, lab-2, lak-24, lak-18, lak-19, lak-20, lak-21, lak-22, lak-23, lak-16, lak-17, lak-15, lak-13, lak-14, laj-1, lab-3, lab-4, lab-5, lak-11, lak-12, lak-9, lak-7, lak-102, lak-6, lak-4, lak-98, lak-99, lak-100, lak-95, lak-96, lak-117, lak-118, lak-119, lak-120, lak-121, lak-122, lab-9, laj-3, lab-7, lab-10, laj-2, lak-5, lab-18, lab-15, lab-16, lab-17, lab-24, lab-31, lab-27, lab-28, lab-29, lab-30

Example B

Spodoptera frugiperda Test

SPODFR Spray Treatment

| Solvents: | 78.0 parts by weight of acetone |
| --- | --- |
|  | 1.5 parts by weight of dimethylformamide |
| Emulsifier: | 0.5 part by weight of alkylaryl polyglycol ether |

To produce a suitable active ingredient preparation, 1 part by weight of active ingredient is mixed with the stated amounts of solvents and emulsifier, and the concentrate is diluted to the desired concentration with emulsifier-containing water.

Discs of maize leaves (*Zea mays*) are sprayed with an active ingredient preparation of the desired concentration and, after drying, populated with caterpillars of the army worm (*Spodoptera frugiperda*).

After the desired time, the effect in % is determined. Here, 100% means that all of the caterpillars have been killed; 0% means that no caterpillars have been killed.

In this test, for example, the following compounds of the preparation examples exhibit, at an application rate of 500 g/ha, an effect of ≥80%:
Ex. No.: lak-93, lak-90, lak-1, lak-87, lak-86, lak-84, lak-83, lak-80, lak-75, lak-73, lak-35, lak-36, lak37, lak-38, lak-39, lak-40, lak-43, lak-44, lak-47, lak-49, lak-54, lak-57, lak-3, lak-59, lak-61, lak-62, lak-63, lak-64, lak-65, lak-66, lak-67, lak-68, lak-31, lak-30, lak-26, lak-28, lak-18, lak-19, lak-21, lak-22, lak-16, lak-13, lak-11, lak-9, lak-7, lak-6, lak-99, lak-95, lak-117, lak-118, lak-119, lak-120, lak-121, lak-122, lab-9, lab-15, lab-16, lab-17, lab-31, lab-29, lab-30

Example C

Myzus Test

MYZUPE Spray Treatment

| Solvents: | 78.0 parts by weight of acetone |
| --- | --- |
|  | 1.5 parts by weight of dimethylformamide |
| Emulsifier: | 0.5 part by weight of alkylaryl polyglycol ether |

To produce a suitable active ingredient preparation, 1 part by weight of active ingredient is mixed with the stated amounts of solvents and emulsifier, and the concentrate is diluted to the desired concentration with emulsifier-containing water.

Discs of Chinese cabbage leaves (*Brassica pekinensis*) which are infested by all stages of the green peach aphid (*Myzus persicae*) are sprayed with an active ingredient preparation of the desired concentration.

After the desired time, the effect in % is determined. Here, 100% means that all aphids have been killed; 0% means that no aphids have been killed.

In this test, for example, the following compounds of the preparation examples exhibit, at an application rate of 500 g/ha, an effect of ≥80%:
Ex. No.: lak-93, lak-90, lak-1, lak-88, lak-87, lak-86, lak-85, lak-83, lak-82, lak-2, lak-66, lak-33, lak-32, lak-30, lak-24, lak-22, lak-104, lab-3, lak-9, lak-6, lab-15, lak-108, lab-19, lab-20, lab-23, lab-24, lab-27, lab-30, lak-113, lak-34

Example D

Tetranychus Test, OP-Resistant

TETRUR Spray Treatment

| Solvents: | 78.0 parts by weight of acetone |
| --- | --- |
|  | 1.5 parts by weight of dimethylformamide |
| Emulsifier: | 0.5 part by weight of alkylaryl polyglycol ether |

To produce a suitable active ingredient preparation, 1 part by weight of active ingredient is mixed with the stated amounts of solvents and emulsifier, and the concentrate is diluted to the desired concentration with emulsifier-containing water.

Discs of bean leaves (*Phaseolus vulgaris*) which are infested by all stages of the greenhouse red spider mite (*Tetranychus urticae*) are sprayed with an active ingredient preparation of the desired concentration.

After the desired time, the effect in % is determined. Here, 100% means that all spider mites have been killed; 0% means that no spider mites have been killed.

In this test, for example, the following compounds of the preparation examples exhibit, at an application rate of 500 g/ha, an effect of ≥80%:
Ex. No.: lak-93, lak-92, lak-89, lak-88, lak-87, lak-86, lak-85, lak-84, lak-83, lak-82, lak-81, lak-78, lak-79, lak-80, lak-2, lak-36, lak-37, lak-38, lak-39, lak-40, lak-41, lak-42, lak-43, lak-44, lak-45, lak-46, lak-47, lak-48, lak-49, lak-50, lak-51, lak-52, lak-54, lak-53, lak-57, lak-3, lak-60, lak-61, lak-62, lak-63, lak-64, lak-66, lak-67, lak-68, lak-33, lak-32, lak-31, lak-30, lak-28, lab-2, lak-24, lak-18, lak-19, lak-20, lak-21, lak-22, lak-23, lak-16, lak-14, lab-3, lab-4, lab-5, lab-6, lak-12, lak-9, lak-7, lak-98, lak-117, lak-118, lak-119, lak-120, lak-122, lab-9, lab-7, lab-10, lab-8, lab-18, lab-13, lab-14, lab-15, lab-16, lab-17, lab-22, lab-27, lab-28, lab-29

In this test, for example, the following compounds of the preparation examples exhibit, at an application rate of 100 g/ha, an effect of ≥80%:
Ex. No.: lak-90, lak-1

Example E

Lucilia Cuprina Test

LUCICU

Solvent: dimethyl sulphoxide

To produce a suitable active ingredient preparation, 1 part by weight of active ingredient is mixed with the stated amount of solvent, and the concentrate is diluted to the desired concentration with water.

Vessels containing horsemeat which has been treated with the active ingredient preparation of the desired concentration are populated with Lucilia cuprina larvae.

After the desired time, the kill in % is determined. Here, 100% means that all larvae have been killed; 0% means that no larvae have been killed.

In this test, for example, the following compounds of the preparation examples exhibit, at an application rate of 100 ppm, an effect of ≥80%:
Ex. No.: lak-93, lak-90, lak-88, lak-87, lak-86, lak-85, lak-84, lak-83, lak-80, lak-37, lak-38, lak-39, lak-40, lak-43, lak-47, lak-49, lak-51, lak-3, lak-62, lak-63, lak-64, lak-67, lak-68, lak-32, lak-18, lak-19, lak-22

Example F

*Ctenocephalides felis*; Oral

CTECFE

Solvent: 1 part by weight of dimethyl sulphoxide

To produce a suitable active ingredient preparation, 2 parts by weight of active ingredient are mixed with the stated amount of solvent. Part of the concentrate is diluted with citrated cattle blood, and the desired concentration is prepared.

20 unfed adult fleas (*Ctenocephalides felis*) are placed into a chamber which is closed at the top and bottom with gauze. A metal cylinder whose bottom end is closed with parafilm is placed onto the chamber. The cylinder contains the blood/active ingredient preparation, which can be taken up by the fleas through the parafilm membrane.

After the desired time, the kill in % is determined. Here, 100% means that all of the fleas have been killed; 0% means that no fleas have been killed.

In this test, for example, the following compounds of the preparation examples exhibit, at an application rate of 100 ppm, an effect of 80%:
Ex. No.: lak-90, lak-88, lak-87, lak-86, lak-85, lak-83, lak-82, lak-39, lak-43, lak-47, lak-49, lak-51, lak-3, lak-62, lak-63, lak-64, lak-68, lak-18, lak-22

Example G

*Musca domestica* Test

MUSCDO

Solvent: dimethyl sulphoxide

To produce a suitable active ingredient preparation, 1 part by weight of active ingredient is mixed with the stated amount of solvent, and the concentrate is diluted to the desired concentration with water.

Vessels containing a sponge which has been treated with the active ingredient preparation of the desired concentration are populated with *Musca domestica* adults.

After the desired time, the kill in % is determined. Here, 100% means that all of the flies have been killed; 0% means that no flies have been killed.

In this test, for example, the following compounds of the preparation examples exhibit, at an application rate of 100 ppm, an effect of ≥80%:
Ex. No.: lak-90, lak-88, lak-87, lak-86, lak-39, lak-40, lak-51, lak-3, lak-62, lak-63, lak-64, lak-67

Example H

*Boophilus microplus* Test

BOOPMI Injection

Solvent: dimethyl sulphoxide

To produce a suitable active ingredient preparation, 1 part by weight of active ingredient is mixed with the stated amount of solvent, and the concentrate is diluted to the desired concentration with water.

The active ingredient solution is injected into the abdomen (*Boophilus microplus*), the animals are transferred to dishes and stored in a climatically controlled room. The effect is monitored by deposition of fertile eggs.

After the desired time, the effect in % is determined. Here, 100% means that no ticks have laid fertile eggs.

In this test, for example, the following compounds of the preparation examples exhibit good effectiveness at an application rate of 20 μg/animal: see table
Ex. No.: lak-93, lak-90, lak-88, lak-87, lak-86, lak-85, lak-84, lak-83, lak-82, lak-80, lak-37, lak-38, lak-39, lak-40, lak-43, lak-47, lak-49, lak-51, lak-3, lak-64, lak-68, lak-18, lak-19, lak-22

Example I

*Boophilus microplus* Test

BOOPMI Dip

Solvent: dimethyl sulphoxide

To produce a suitable active ingredient preparation, 1 part by weight of active ingredient is mixed with the stated amount of solvent, and the concentrate is diluted to the desired concentration with water.

Adult female ticks (*Boophilus microplus*) are placed in perforated plastic beakers and immersed in the desired concentration for one minute. The ticks are transferred on filter paper to dishes. The ticks are stored under climatically controlled conditions for 42 days and egg deposition is observed.

After the desired time, the effect in % is determined. Here, 100% means that no ticks have laid fertile eggs.

In this test, for example, the following compounds of the preparation examples exhibit, at an application rate of 100 ppm, an effect of ≥80%:
Ex. No.: Iak-93, Iak-88, Iak-87, Iak-86, Iak-85, Iak-83, Iak-51, Iak-3, Iak-62, Iak-63, Iak-64, Iak-67, Iak-19, Iak-22

Example J

*Amblyomma hebaraeum* Test

AMBYHE

Solvent: dimethyl sulphoxide

To produce a suitable active ingredient preparation, 1 part by weight of active ingredient is mixed with the stated amount of solvent, and the concentrate is diluted to the desired concentration with water.

Nymphs of ticks (*Amblyomma hebraeum*) are placed in perforated plastic beakers and immersed in the desired concentration for one minute. The ticks are transferred on filter paper to a Petri dish and stored in a climatically controlled cabinet for 42 days.

After the desired time, the kill in % is determined. Here, 100% means that all ticks have been killed; 0% means that no ticks have been killed.

In this test, for example, the following compounds of the preparation examples exhibit, at an application rate of 100 ppm, an effect of ≥80%:
Ex. No.: Iak-90, Iak-83

The invention claimed is:

1. A compound of formula (Ik), or a salt, or N-oxide thereof:

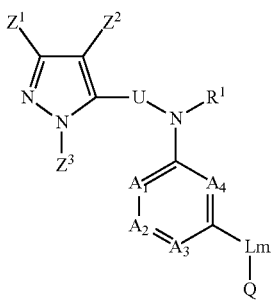

(Ik)

wherein

| Compound No. | $Z^1$ | $Z^2$ | $Z^3$ | $R^1$ | $A_1$ | $A_2$ |
|---|---|---|---|---|---|---|
| Ik-1 | $C_2F_5$ | $CF_3$ | $CH_3$ | H | C—H | C—H |
| Ik-17 | $C_2F_5$ | H | $CH_3$ | H | C—H | C—H |

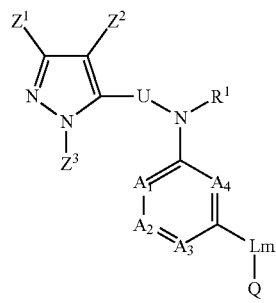

(Ik)

wherein

| | | | | | |
|---|---|---|---|---|---|
| Ik-70 | $CF_3$ | H | $CH_3$ | H | C—H | C—H |
| Ik-71 | $CF_3$ | H | $CH_3$ | H | C—H | C—H |
| IK-94 | $CF_3$ | H | $CH_3$ | H | C—H | C—H |
| Ik-124 | $CF_2CF_3$ | $CF_3$ | H | H | C—H | C—H |
| Ik-197 | $CF_3$ | $CF_3$ | H | H | C—H | C—H |
| Ik-234 | $OCHF_2$ | H | $CH_3$ | H | C—H | C—H |
| Ik-246 | $CF_3CH_2O$ | H | $CH_3$ | H | C—H | C—H |
| Ik-247 | $CF_3CH_2O$ | H | $CH_3$ | H | C—H | C—H |
| Ik-266 | $C_4F_9$ | H | $CH_3$ | H | C—H | C—H |
| Ik-84 | $C_2F_5$ | $CF_3$ | $CH_3$ | H | C—H | C—H |

| Compound No. | $A_3$ | $A_4$ | $L_m$ | U | Q |
|---|---|---|---|---|---|
| Ik-1 | C—Cl | C—H | CONH | CO | Cyclopropyl |
| Ik-17 | C—Cl | C—H | CONH | CO | Cyclopropyl |
| Ik-70 | C—Cl | C—H | CONH | CO | 1-Methylethyl |
| Ik-71 | C—Cl | C—H | CONH | CO | Cyclopropyl |
| IK-94 | C—Cl | C—H | CONH | CO | Prop-2-enyl |
| Ik-124 | C—Cl | C—H | CONH | CO | 2,2,2-Trifluoroethyl |
| Ik-197 | C—Cl | C—H | CONH | CO | Cyclopropyl |
| Ik-234 | C—Cl | C—H | CONH | CO | Cyclopropyl |
| Ik-246 | C—Cl | C—H | CONH | CO | 2,2,2-Trifluoroethyl |
| Ik-247 | C—Cl | C—H | CONH | CO | Cyclopropyl |
| Ik-266 | C—Cl | C—H | CONH | CO | Cyclopropyl |
| Ik-84 | C—Cl | C—H | CONH | CO | Benzyl. |

2. A medicament comprising a compound, or a salt, or N-oxide thereof according to claim 1.

3. A phamiaceutical composition comprising a compound, or a salt, or N-oxide thereof according to claim 1.

4. A crop protection composition comprising a compound, or a salt, or N-oxide thereof according to claim 1, and an extender and/or a surface-active substance.

5. The compound of claim 1, wherein $Z^1$ is $C_2F_5$, $Z^2$ is $CF_3$, $Z^3$ is $CH_3$, $R^1$ is H, $A_1$ is C—H, $A_2$ is C—H, $A_3$ is C—Cl, $A_4$ is C—H, $L_m$ is CONH, U is CO, and Q is benzyl.

* * * * *